(12) United States Patent
Ohsuki et al.

(10) Patent No.: US 8,158,638 B2
(45) Date of Patent: Apr. 17, 2012

(54) PYRAZOLOPYRIMIDINE DERIVATIVE

(75) Inventors: Satoru Ohsuki, Chiba (JP); Atsushi Tengeiji, Kanagawa (JP); Masahiro Ikeda, Tokyo (JP); Yoshihiro Shibata, Tokyo (JP); Chikahiro Nagata, Tokyo (JP); Takashi Shimada, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 332 days.

(21) Appl. No.: 12/442,094

(22) PCT Filed: Sep. 14, 2007

(86) PCT No.: PCT/JP2007/067933
§ 371 (c)(1),
(2), (4) Date: Apr. 13, 2009

(87) PCT Pub. No.: WO2008/035629
PCT Pub. Date: Mar. 27, 2008

(65) Prior Publication Data
US 2010/0113410 A1 May 6, 2010

(30) Foreign Application Priority Data
Sep. 19, 2006 (JP) ................................. 2006-253465

(51) Int. Cl.
A61K 31/505 (2006.01)
A61K 31/415 (2006.01)
C07D 491/00 (2006.01)
C07D 487/02 (2006.01)
(52) U.S. Cl. ...... 514/267; 514/406; 544/251; 548/359.5
(58) Field of Classification Search .................. 514/267, 514/406; 544/251; 548/359.5
See application file for complete search history.

(56) References Cited

FOREIGN PATENT DOCUMENTS

| WO | 98/43991 A1 | 10/1998 |
|---|---|---|
| WO | 2004/047755 A2 | 6/2004 |
| WO | 2005/028434 A2 | 3/2005 |
| WO | 2006/015263 A2 | 2/2006 |
| WO | 2005/021568 A2 | 5/2009 |

OTHER PUBLICATIONS

Calabresi P. and Chabner BA, "Section IX Chemotherapy of Neoplastic Diseases—Introduction," Goodman & Gilman's The Pharmacological Basis of Therapeutics 10th ed., 2001, Hardman JG, Limbird LE, and Gilman AG, Eds, McGraw-Hill, New York 2001, 1381-1388 (pp. 1381, 1383-1385, and 1388 provided).*
Heath EI, Hillman DW, Vaishampayan U, Sheng S, Sarkar F, Harper F, Gaskins M, Pitot HC, Tan W, Ivy SP, Pili R, Carducci MA, Erlichman C, Liu G. A phase II trial of 17-allylamino-17-demethoxygeldanamycin in patients with hormone-refractory metastatic prostate cancer. Clin Cancer Res. Dec. 1, 2008;14(23):7940-6.*
Vippagunta SR, Brittain HG, and Grant D J, "Crystalline solids," Advanced Drug Delivery Reviews, May 2001,48(1), 3-26.*
Akashi, S., "Investigation of Molecular Interaction Within Biological Macromolecular Complexes by Mass Spectrometry," Medicinal Research Reviews 26(3):339-368, May 2006.
Blagg B.S.J., and T.D. Kerr, "Hsp90 Inhibitors: Small Molecules That Transform the Hsp90 Protein Folding Machinery Into a Catalyst for Protein Degradation," Medicinal Research Reviews 26(3):310-338, May 2006.
Calderwood, S.K., et al., "Heat Shock Proteins in Cancer: Chaperones of Tumorigenesis," Trends in Biochemical Sciences 31(3):164-172, Mar. 2006.
Dymock B.W., et al., "Novel, Potent Small-Molecule Inhibitors of the Molecular Chaperone Hsp90 Discovered Through Structure-Based Design," Journal of Medicinal Chemistry 48(13):4212-4215, Jun. 2005.
Hammond, D.M., et al., "The Syntheses of Tricyclic Analogues of O6-Methylguanine," Organic & Biomolecular Chemistry 1(23):4166-4172, Dec. 2003.
He, H., et al., "Identification of Potent Water Soluble Purine-Scaffold Inhibitors of the Heat Shock Protein 90," Journal of Medicinal Chemistry 49(1):381-390, Jan. 2006.
Hornillo-Araujo, A.R., et al., "The Syntheses and Properties of Tricyclic Pyrrolo[2,3-d]pyrimidine Analogues of S6-Methylthioguanine and O6-Methylguanine," Organic & Biomolecular Chemistry 4(9):1723-1729, 2006.
Kamal, A., et al., "Therapeutic and Diagnostic Implications of Hsp90 Activation," Trends in Molecular Medicine 10(6):283-290, Jun. 2004. Sōti, C., et al., "Heat Shock Proteins as Emerging Therapeutic Targets," British Journal of Pharmacology 146(6):769-780, Nov. 2005.

* cited by examiner

Primary Examiner — San-Ming Hui
Assistant Examiner — Paul Zarek
(74) Attorney, Agent, or Firm — Christensen O'Connor Johnson Kindness PLLC

(57) ABSTRACT

Problem to be Solved
To provide a novel compound inhibiting the effect of HSP90, in particular a novel compound inhibiting the function of HSP90 as a chaperone protein and having antitumor activity.
Solution
The present invention provides a pyrazolopyrimidine compound represented by the formula (1) having various substituents which inhibits the ATPase activity of HSP90 and which has antitumor activity, an HSP90 inhibitor comprising the compound represented by the formula (1), a medicament comprising the compound represented by the formula (1), an anticancer agent comprising the compound represented by the formula (1), a pharmaceutical composition comprising the compound represented by the formula (1) and a method for treating cancer using the compound represented by the formula (1).

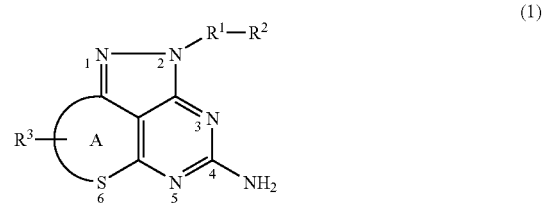

(1)

31 Claims, No Drawings

PYRAZOLOPYRIMIDINE DERIVATIVE

This application is the National Stage of International Application No. PCT/JP2007/067933, filed Sep. 14, 2007, which claims the benefit from Japanese Application No. 2006-253465, filed Sep. 19, 2006. Each application is incorporated herein by reference in its entirety.

TECHNICAL FIELD

The present invention relates to a tricyclic compound derived from pyrazolopyrimidine which inhibits the effect of heat shock protein 90 (HSP90).

BACKGROUND ART

HSP90 is a major intracellular chaperone protein. Chaperone proteins are proteins that bind to various proteins to assist in folding of the bound proteins. A group of proteins whose folding requires HSP90 are generally called HSP90 client proteins.

It is assumed that HSP90 as well as multiple proteins such as co-chaperones, partner proteins and immunophilins are involved in the mechanism of folding of client proteins by HSP90 and that they collaboratively assist in folding of HSP90 client proteins (Non-Patent Document 1); however, the details of the mechanism are still not sufficiently clear. It is assumed that HSP90 client proteins form a complex with HSP90, co-chaperones and the like and are then conformationally changed to mature proteins, and that the proteins are ubiquitinated and degraded by proteasomes when they are not folded normally by HSP90 and the like (Non-Patent Documents 1 to 4).

In recent years, HSP90 inhibitors have been expected as candidates for therapeutic agents for various diseases (for example, cancer, neurodegenerative diseases such as Alzheimer's disease, cardiovascular diseases, infections, autoimmune diseases, and diseases associated with apoptotic cell injury) (Non-Patent Document 2).

In particular, since many cancer-associated proteins including molecular targets for anticancer agents are HSP90 client proteins, HSP90 inhibitors have been expected as candidates for anticancer agents. For example, multiple proteins involved in the appearance and development of cancer such as Her2, Raf, Akt and telomerase are known as HSP90 client proteins (Non-Patent Document 1). It is assumed that these cancer-associated proteins are changed from immature proteins to mature proteins and act to cause malignant transformation of cells, by use of HSP90 as a chaperone protein. HSP90 is a protein that exists not only in cancer cells but also in normal cells, and it is reported that the affinity with a client protein and the ATPase activity necessary for its chaperone activity are higher in cancer cells than in normal cells (Non-Patent Documents 1 to 3). Therefore, HSP90 inhibitors are assumed to be capable of inactivating multiple cancer-associated proteins simultaneously in a cancer cell-specific manner, and have been expected as candidates for anticancer agents that are potent and have a broad antitumor spectrum.

Geldanamycin, herbimycin, 17-allylaminogeldanamycin (17-AAG) and the like are known as HSP90 inhibitors (Non-Patent Documents 1 to 4). These compounds bind to the ATP binding pocket at the N-terminal of HSP90 and inhibit binding of HSP90 to ATP in order to inhibit the function of HSP90 as a chaperone protein. Various compounds inhibiting HSP90 are reported in addition to the above compounds (Patent Document 1, Non-Patent Document 5 and Non-Patent Document 6).

[Patent Document 1] WO 2005/28434
[Non-Patent Document 1] Medicinal Research Reviews (2006) Vol. 26, No. 3, 310-338
[Non-Patent Document 2] TRENDS in Molecular Medicine (2004) Vol. 10, No. 6, 283-290
[Non-Patent Document 3] British Journal of Pharmacology (2005) 146, 769-780
[Non-Patent Document 4] TRENDS in Biochemical Sciences (2006) March, 31(3), 164-172
[Non-Patent Document 5] Journal of Medicinal Chemistry (2005) Vol. 48, No. 13, 4212-4215
[Non-Patent Document 6] Journal of Medicinal Chemistry (2006) Vol. 49, No. 1, 381-390

DISCLOSURE OF THE INVENTION

Problems to be Solved by the Invention

Although HSP90 inhibitors have been expected to be used as medicaments, in particular as anticancer agents as described above, an effective compound has not yet been obtained. Therefore, there is a need to develop a novel compound inhibiting the effect of HSP90, in particular a novel compound inhibiting the function of HSP90 as a chaperone protein and having antitumor activity.

Means for Solving the Problems

As a result of extensive studies to solve the above problems, the present inventors have found a tricyclic compound derived from pyrazolopyrimidine which is represented by the formula (1), as a novel compound inhibiting the ATPase activity of HSP90 and having antitumor activity. This finding has led to the completion of the present invention.

Specifically, the present invention provides:

[1] A compound represented by the formula (1), a salt of the compound, or a hydrate of the compound or the salt:

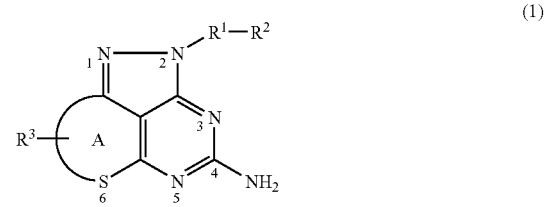

(1)

wherein in the formula (1),
$R^1$ represents a methylene group, an ethylene group or a propenylene group which may be substituted with 1 or 2 alkyl groups having 1 to 8 carbon atoms,
$R^2$ represents an aryl group which may have a substituent(s) or a heterocyclic group which may have a substituent(s),
Ring A represents a 5- to 8-membered ring (wherein the ring constituent atoms of Ring A other than the sulfur atom at the 6-position are carbon atoms), and
$R^3$ represents a hydrogen atom or 1 to 4 same or different substituents with which Ring A is substituted,
wherein
the same or different substituents
each independently represents a substituent selected from the group consisting of a halogen atom, a hydroxy group, a carboxy group, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an alkoxy group having 1 to 8 carbon atoms which may have a substituent(s), an alkoxycarbonyl group having 1 to 8 carbon atoms which may have a substituent(s), an alkanoyloxy group having 1 to 8 carbon atoms which may have a substituent(s), a carbamoyl group which may have a substituent(s), a carbamoyloxy group which may have a substituent(s), an alkylsulfonyloxy group having 1 to 8 carbon atoms which may have a substituent(s), an amino group which may have a substituent(s), a cyano group, an aryl group which may have a substituent(s), a heterocyclic group which may have a substituent(s), an oxo group and =NOR$^{31}$ (wherein R$^{31}$ represents a hydrogen atom or an alkyl group having 1 to 8 carbon atoms which may have a substituent(s)), and when there is a plurality of the same or different substituents, any two substituents of the same or different substituents together with the carbon atom(s) on which they are substituted may form a saturated or unsaturated, fused or spiro 3- to 8-membered ring which may have a substituent(s);

[2] The compound according to [1], a salt of the compound, or a hydrate of the compound or the salt, wherein R$^1$ in the formula (1) is a methylene group which may be substituted with 1 or 2 alkyl groups having 1 to 8 carbon atoms;

[3] The compound according to [1] or [2], a salt of the compound, or a hydrate of the compound or the salt, wherein R$^2$ in the formula (1) is a heterocyclic group which may have a substituent(s);

[4] The compound according to any one of [1] to [3], a salt of the compound, or a hydrate of the compound or the salt, wherein R$^2$ in the formula (1) is a pyridyl group which may have a substituent(s);

[5] The compound according to any one of [1] to [4], a salt of the compound, or a hydrate of the compound or the salt, wherein Ring A in the formula (1) is a 6- or 7-membered ring (wherein the ring constituent atoms of Ring A other than the sulfur atom at the 6-position are carbon atoms);

[6] The compound according to any one of [1] to [5], a salt of the compound, or a hydrate of the compound or the salt, wherein R$^3$ in the formula (1) is a hydrogen atom or 1 to 4 same or different substituents with which Ring A is substituted, wherein the same or different substituents are each independently a substituent selected from the group consisting of a hydroxy group, a carboxy group, an alkyl group having 1 to 8 carbon atoms which may have a substituent(s), an alkynyl group having 2 to 8 carbon atoms which may have a substituent(s), an alkoxy group having 1 to 8 carbon atoms which may have a substituent(s), a carbamoyl group which may have a substituent(s), a carbamoyloxy group which may have a substituent(s), an alkylsulfonyloxy group having 1 to 8 carbon atoms which may have a substituent(s), an amino group which may have a substituent(s), a cyano group, a heterocyclic group which may have a substituent(s) and an oxo group, and when there is a plurality of the same or different substituents, any two substituents of the same or different substituents together with the carbon atom(s) on which they are substituted may form a saturated or unsaturated, fused or spiro 3- to 8-membered ring which may have a substituent(s);

[7] The compound according to [1], a salt of the compound, or a hydrate of the compound or the salt, wherein the formula (1) is the following formula (1a):

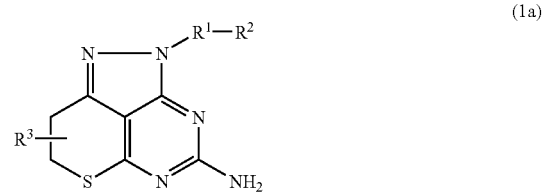

wherein in the formula (1a), R$^1$, R$^2$ and R$^3$ are as defined for R$^1$, R$^2$ and R$^3$ in [1], respectively;

[8] The compound according to [1], a salt of the compound, or a hydrate of the compound or the salt, wherein the formula (1) is the following formula (1b):

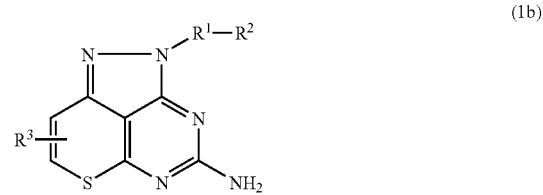

wherein in the formula (1b), R$^1$, R$^2$ and R$^3$ are as defined for R$^1$, R$^2$ and R$^3$ in [1], respectively;

[9] The compound according to [1], a salt of the compound, or a hydrate of the compound or the salt, wherein the formula (1) is the following formula (1c):

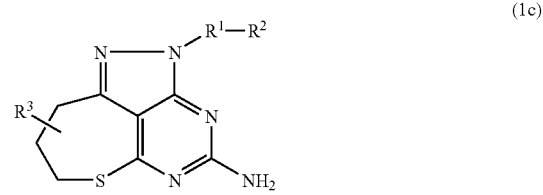

wherein in the formula (1c), R$^1$, R$^2$ and R$^3$ are as defined for R$^1$, R$^2$ and R$^3$ in [1], respectively;

[10] The compound according to [1], a salt of the compound, or a hydrate of the compound or the salt, wherein the formula (1) is the following formula (1d):

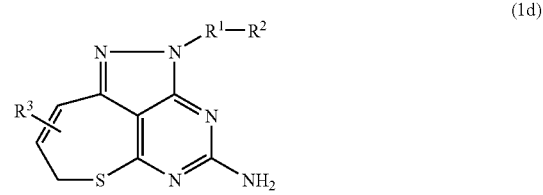

wherein in the formula (1d), R$^1$, R$^2$ and R$^3$ are as defined for R$^1$, R$^2$ and R$^3$ in [1], respectively;

[11] A compound represented by the formula (2), a salt of the compound, or a hydrate of the compound or the salt:

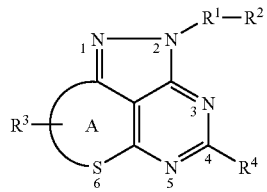

(2)

wherein in the formula (2), $R^1$ represents a methylene group, an ethylene group or a propenylene group which may be substituted with 1 or 2 alkyl groups having 1 to 8 carbon atoms, $R^2$ represents an aryl group which may have a substituent(s) or a heterocyclic group which may have a substituent(s), Ring A represents a 5- to 8-membered ring (wherein the ring constituent atoms of Ring A other than the sulfur atom at the 6-position are carbon atoms), $R^3$ represents a hydrogen atom or 1 to 4 same or different substituents with which Ring A is substituted, wherein the same or different substituents each independently represents a substituent selected from the group consisting of a halogen atom, a hydroxy group, a carboxy group, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an alkoxy group having 1 to 8 carbon atoms which may have a substituent(s), an alkoxycarbonyl group having 1 to 8 carbon atoms which may have a substituent(s), an alkanoyloxy group having 1 to 8 carbon atoms which may have a substituent(s), a carbamoyl group which may have a substituent(s), a carbamoyloxy group which may have a substituent(s), an alkylsulfonyloxy group having 1 to 8 carbon atoms which may have a substituent(s), an amino group which may have a substituent(s), a cyano group, an aryl group which may have a substituent(s), a heterocyclic group which may have a substituent(s), an oxo group and $=NOR^{31}$ (wherein $R^{31}$ represents a hydrogen atom or an alkyl group having 1 to 8 carbon atoms which may have a substituent(s)), and when there is a plurality of the same or different substituents, any two substituents of the same or different substituents together with the carbon atom(s) on which they are substituted may form a saturated or unsaturated, fused or spiro 3- to 8-membered ring which may have a substituent(s), and $R^4$ represents an amino group having a protecting group;

[12] A compound represented by the formula (3), a salt of the compound, or a hydrate of the compound or the salt:

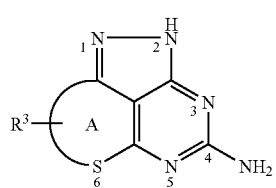

(3)

wherein in the formula (3),

Ring A represents a 5- to 8-membered ring (wherein the ring constituent atoms of Ring A other than the sulfur atom at the 6-position are carbon atoms), and $R^3$ represents a hydrogen atom or 1 to 4 same or different substituents with which Ring A is substituted, wherein the same or different substituents each independently represents a substituent selected from the group consisting of a halogen atom, a hydroxy group, a carboxy group, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an alkoxy group having 1 to 8 carbon atoms which may have a substituent(s), an alkoxycarbonyl group having 1 to 8 carbon atoms which may have a substituent(s), an alkanoyloxy group having 1 to 8 carbon atoms which may have a substituent(s), a carbamoyl group which may have a substituent(s), a carbamoyloxy group which may have a substituent(s), an alkylsulfonyloxy group having 1 to 8 carbon atoms which may have a substituent(s), an amino group which may have a substituent(s), a cyano group, an aryl group which may have a substituent(s), a heterocyclic group which may have a substituent(s), an oxo group and $=NOR^{31}$ (wherein $R^{31}$ represents a hydrogen atom or an alkyl group having 1 to 8 carbon atoms which may have a substituent(s)), and when there is a plurality of the same or different substituents, any two substituents of the same or different substituents together with the carbon atom(s) on which they are substituted may form a saturated or unsaturated, fused or spiro 3- to 8-membered ring which may have a substituent(s);

[13] An HSP90 inhibitor comprising the compound according to any one of [1] to [10], a salt of the compound, or a hydrate of the compound or the salt;

[14] An inhibitor of the ATPase activity of HSP90 comprising the compound according to any one of [1] to [10], a salt of the compound, or a hydrate of the compound or the salt;

[15] An inhibitor of binding of HSP90 to ATP comprising the compound according to any one of [1] to [10], a salt of the compound, or a hydrate of the compound or the salt;

[16] A medicament comprising the compound according to any one of [1] to [10], a salt of the compound, or a hydrate of the compound or the salt as an active ingredient;

[17] An anticancer agent comprising the compound according to any one of [1] to [10], a salt of the compound, or a hydrate of the compound or the salt as an active ingredient;

[18] A pharmaceutical composition comprising the compound according to any one of [1] to [10], a salt of the compound, or a hydrate of the compound or the salt, and a pharmaceutically acceptable carrier;

[19] A method for treating cancer comprising administering the compound according to any one of [1] to [10], a salt of the compound, or a hydrate of the compound or the salt; and

[20] Use of the compound according to any one of [1] to [12], a salt of the compound, or a hydrate of the compound or the salt for the manufacture of a medicament.

Advantages of the Invention

According to the present invention, there are provided a novel compound inhibiting an effect of HSP90, a therapeutic agent for a disease caused by an effect of HSP90 comprising the compound, a method for treating a disease caused by an effect of HSP90 using the compound. In particular, according to the present invention, there are provided a novel compound inhibiting the function of HSP90 as a chaperone protein and having antitumor activity, an anticancer agent comprising the compound, and a method for treating cancer using the compound.

BEST MODE FOR CARRYING OUT THE INVENTION

In the present invention, "heat shock protein 90" or "HSP90" refers to any or all of the HSP90 family unless otherwise specified. The HSP90 family includes HSP90α, HSP90β, 94 kDa glucose-regulated protein (GRP94) and Hsp75/tumor necrosis factor receptor associated protein 1 (TRAP1), for example.

In the present invention, "HSP90 inhibitor" refers to a compound or composition that partially or completely inhibits an effect of HSP90. Examples of the HSP90 inhibitor include a compound or composition that partially or completely inhibits the expression of HSP90 and a compound or composition that partially or completely inhibits the function of HSP90 as a chaperone protein.

Here, "function of HSP90 as a chaperone protein" refers to a function of HSP90 to assist folding of a client protein to convert the client protein to its functioning form, or a function of HSP90 to stabilize a client protein, for example.

Accordingly, specific examples of the HSP90 inhibitor include a compound inhibiting the expression of HSP90, a compound inhibiting binding of HSP90 to a client protein, a compound inhibiting binding of HSP90 to co-chaperones or immunophilins, a compound inhibiting binding of HSP90 to ATP, a compound inhibiting the ATPase activity of HSP90 and a compound inhibiting the conformational change of HSP90. The HSP90 inhibitor can be used as a therapeutic agent for a disease caused by an effect of HSP90.

In the present invention, examples of the "disease caused by an effect of HSP90" include cancer, neurodegenerative diseases such as Alzheimer's disease, cardiovascular diseases, infections, autoimmune diseases, and diseases associated with apoptotic cell injury.

Each substituent in the formulas (1) to (3) according to the present invention will be described below.

First, $R^1$ will be described.

$R^1$ represents a methylene group, an ethylene group or a propenylene group which may be substituted with 1 or 2 alkyl groups having 1 to 8 carbon atoms.

The "methylene group, ethylene group or propenylene group which may be substituted with 1 or 2 alkyl groups having 1 to 8 carbon atoms" refers to a methylene group, an ethylene group or a propenylene group which may be substituted with 1 or 2 linear, branched or cyclic alkyl groups having 1 to 8 carbon atoms. Examples of the alkyl group having 1 to 8 carbon atoms include a methyl group, an ethyl group, a propyl group, an isopropyl group, a cyclopropyl group, a cyclobutyl group, a cyclopentyl group and a cyclohexylethyl group.

Next, $R^2$ will be described.

$R^2$ represents an aryl group which may have a substituent(s) or a heterocyclic group which may have a substituent(s).

The aryl group in the "aryl group which may have a substituent(s)" refers to a group derived from a monocyclic or polycyclic aromatic hydrocarbon compound. The aryl group may be bonded at any position. Examples of the aryl group include a phenyl group, a naphthyl group and a fluorenyl group. These aryl groups may be substituted with one or the same or different 2 to 5 substituents selected from the group consisting of an alkyl group having 1 to 8 carbon atoms which may have a substituent(s) and c), d), f) to j) and l) to q) in the later-described Substituent Group.

Here, the alkyl group having 1 to 8 carbon atoms in the "alkyl group having 1 to 8 carbon atoms which may have a substituent(s)" refers to a linear, branched or cyclic alkyl group having 1 to 8 carbon atoms. Examples of the alkyl group having 1 to 8 carbon atoms include a methyl group, an ethyl group, a propyl group, an isopropyl group, a cyclopropyl group, a cyclobutyl group, a cyclopentyl group and a cyclohexylethyl group. These alkyl groups having 1 to 8 carbon atoms may be substituted with one or the same or different 2 or 3 substituents selected from c) to j) and l) to q) in the later-described Substituent Group. The alkyl group having 1 to 8 carbon atoms may be substituted on the same carbon atom or different carbon atoms with these substituents, insofar as it can be substituted.

The heterocyclic group in the "heterocyclic group which may have a substituent(s)" refers to a group derived from a saturated or unsaturated, monocyclic or condensed heterocyclic compound containing one or more oxygen, nitrogen or sulfur atoms as constituent atoms of the ring structure. The heterocyclic group may be bonded at any position. Examples of the saturated heterocyclic group include a group derived from azetidine, pyrrolidine, imidazolidine, triazolidine, tetrahydropyran, tetrahydrothiophene, oxazolidine, thiazolidine, piperidine, piperazine, tetrahydropyran, dioxane, tetrahydrothiopyran, morpholine, thiomorpholine, homomorpholine or homopiperazine. Examples of the unsaturated heterocyclic group include a group derived from pyrrole, pyrazole, imidazole, triazole, tetrazole, thiophene, furan, thiazole, oxazole, isothiazole, isoxazole, pyridine, dihydropyridine, pyridazine, pyrimidine, pyrazine, quinoline, isoquinoline, indole, 1,3-dioxaindan, benzothiazole, benzodioxole, benzodioxane or thiazolopyridine. These heterocyclic groups may be substituted with one or the same or different 2 to 5 substituents selected from the group consisting of an alkyl group having 1 to 8 carbon atoms which may have a substituent(s) and c), d), f) to j) and l) to q) in the later-described Substituent Group. Here, the "alkyl group having 1 to 8 carbon atoms which may have a substituent(s)" is as defined above.

Next, $R^3$ will be described.

$R^3$ represents a hydrogen atom or 1 to 4 same or different substituents with which Ring A is substituted (wherein the same or different substituents each independently represents a substituent selected from the group consisting of a halogen atom, a hydroxy group, a carboxy group, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an alkoxy group having 1 to 8 carbon atoms which may have a substituent(s), an alkoxycarbonyl group having 1 to 8 carbon atoms which may have a substituent(s), an alkanoyloxy group having 1 to 8 carbon atoms which may have a substituent(s), a carbamoyl group which may have a substituent(s), a carbamoyloxy group which may have a substituent(s), an alkylsulfonyloxy group having 1 to 8 carbon atoms which may have a substituent(s), an amino group which may have a substituent(s), a cyano group, an aryl group which may have a substituent(s), a heterocyclic group which may have a substituent(s), an oxo group and =NOR$^{31}$ (wherein R$^{31}$ represents a hydrogen atom or an alkyl group having 1 to 8 carbon atoms which may have a substituent(s)), and when there is a plurality of the same or different substituents, any two substituents of the same or different substituents together with the carbon atom(s) on which they are substituted may form a saturated or unsaturated, fused or spiro 3- to 8-membered ring which may have a substituent(s)).

When $R^3$ represents 2 to 4 same or different substituents, Ring A may be substituted on the same carbon atom or different carbon atoms with these substituents, insofar as it can be substituted.

The "alkyl group having 1 to 8 carbon atoms which may have a substituent(s)" is as defined for $R^2$ above.

The alkenyl group having 2 to 8 carbon atoms in the "alkenyl group having 2 to 8 carbon atoms which may have a substituent(s)" refers to a linear, branched or cyclic alkenyl group having 2 to 8 carbon atoms. Examples of the alkenyl group having 2 to 8 carbon atoms include a vinyl group, an allyl group, a 1-propenyl group, a 3-methyl-2-pentenyl group, a 1-butenyl group, a cyclopentenyl group and a cyclohexenylethyl group. These alkenyl groups having 2 to 8 carbon atoms may be substituted with one or the same or different 2 or 3 substituents selected from c) to j) and l) to q) in the later-described Substituent Group. The alkenyl group having 2 to 8 carbon atoms may be substituted on the same carbon atom or different carbon atoms with these substituents, insofar as it can be substituted.

The alkynyl group having 2 to 8 carbon atoms in the "alkynyl group having 2 to 8 carbon atoms which may have a substituent(s)" refers to a linear or branched alkynyl group having 2 to 8 carbon atoms. Examples of the alkynyl group having 2 to 8 carbon atoms include an ethynyl group, a 1-propynyl group, a 2-propynyl group, a 1-butynyl group, a 3-butynyl group and a 4-pentynyl group. These alkynyl groups having 2 to 8 carbon atoms may be substituted with one or the same or different 2 or 3 substituents selected from c) to j) and l) to q) in the later-described Substituent Group. The alkynyl group having 2 to 8 carbon atoms may be substituted on the same carbon atom or different carbon atoms with these substituents, insofar as it can be substituted.

The alkoxy group having 1 to 8 carbon atoms in the "alkoxy group having 1 to 8 carbon atoms which may have a substituent(s)" refers to an alkoxy group containing an alkyl group having 1 to 8 carbon atoms as described above in its structure. Examples of the alkoxy group having 1 to 8 carbon atoms include a methoxy group, an ethoxy group, an n-propyloxy group, an isopropyloxy group, an isobutyloxy group, a cyclopropylmethyloxy group and a cyclopentylmethyloxy group. These alkoxy groups having 1 to 8 carbon atoms may be substituted with one or the same or different 2 or 3 substituents selected from c) to j) and l) to q) in the later-described Substituent Group. The alkoxy group having 1 to 8 carbon atoms may be substituted on the same carbon atom or different carbon atoms with these substituents, insofar as it can be substituted.

The alkoxycarbonyl group having 1 to 8 carbon atoms in the "alkoxycarbonyl group having 1 to 8 carbon atoms which may have a substituent(s)" refers to an alkoxycarbonyl group containing an alkoxy group having 1 to 8 carbon atoms as described above in its structure. Examples of the alkoxycarbonyl group having 1 to 8 carbon atoms include a methoxycarbonyl group, an ethoxycarbonyl group, an n-propyloxycarbonyl group, an isopropyloxycarbonyl group, an isobutyloxycarbonyl group, a cyclopropylmethyloxycarbonyl group and a cyclopentylmethyloxycarbonyl group. These alkoxycarbonyl groups having 1 to 8 carbon atoms may be substituted with one or the same or different 2 or 3 substituents selected from c) to j) and l) to q) in the later-described Substituent Group. The alkoxycarbonyl group having 1 to 8 carbon atoms may be substituted on the same carbon atom or different carbon atoms with these substituents, insofar as it can be substituted.

The alkanoyloxy group having 1 to 8 carbon atoms in the "alkanoyloxy group having 1 to 8 carbon atoms which may have a substituent(s)" refers to an alkanoyloxy group containing an alkanoyl group having 1 to 8 carbon atoms in its structure. The "alkanoyl group having 1 to 8 carbon atoms" refers to a linear, branched or cyclic alkanoyl group having 1 to 8 carbon atoms. Examples of the group include a formyl group, an acetyl group, an n-propionyl group, an n-butyryl group, an isobutyryl group, a cyclopropanecarbonyl group and a cyclohexanecarbonyl group. Accordingly, examples of the alkanoyloxy group having 1 to 8 carbon atoms include a formyloxy group, an acetyloxy group, an n-propionyloxy group, an n-butyryloxy group, an isobutyryloxy group, a cyclopropanecarbonyloxy group and a cyclohexanecarbonyloxy group. These alkanoyloxy groups having 1 to 8 carbon atoms may be substituted with one or the same or different 2 or 3 substituents selected from c) to j) and l) to q) in the later-described Substituent Group. The alkanoyloxy group may be substituted on the same carbon atom or different carbon atoms with these substituents, insofar as it can be substituted.

The "carbamoyl group which may have a substituent(s)" refers to a carbamoyl group having a substituent(s) or a 4- to 7-membered saturated nitrogen-containing heterocyclic carbonyl group which may have a substituent(s), in addition to a carbamoyl group.

Here, the carbamoyl group having a substituent(s) refers to a carbamoyl group substituted with one or the same or different two substituents selected from the group consisting of an alkyl group having 1 to 8 carbon atoms which may have a substituent(s) as defined above, an alkenyl group having 2 to 8 carbon atoms which may have a substituent(s) as defined above, an alkynyl group having 2 to 8 carbon atoms which may have a substituent(s) as defined above, an aryl group which may have a substituent(s) as defined for $R^2$ above and a heterocyclic group which may have a substituent(s) as defined for $R^2$ above.

Examples of the 4- to 7-membered saturated nitrogen-containing heterocyclic carbonyl group include an azetidinocarbonyl group, a pyrrolidinocarbonyl group, a morpholinocarbonyl group and a piperazinocarbonyl group. The 4- to 7-membered saturated nitrogen-containing heterocyclic carbonyl group may be substituted with one or the same or different 2 or 3 substituents or atoms selected from an alkyl group which may have a substituent(s) as defined above and c) to j) and l) to q) in the later-described Substituent Group. The saturated nitrogen-containing heterocyclic carbonyl group may be substituted on the same carbon atom or different carbon atoms with these substituents, insofar as it can be substituted. When the saturated nitrogen-containing heterocyclic carbonyl group contains as a constituent atom a nitrogen atom other than the nitrogen atom bonded to the carbonyl group, as a piperadinocarbonyl group or the like does, the nitrogen atom other than the nitrogen atom bonded to the carbonyl group may be substituted with a substituent selected from a), b), j), k), n), p) and q) in the later-described Substituent Group.

The "carbamoyloxy group which may have a substituent(s)" refers to a carbamoyloxy group containing a carbamoyl group which may have a substituent(s) as defined above in its structure. Examples of the carbamoyloxy group include a carbamoyloxy group, a methylcarbamoyloxy group, an ethylcarbamoyloxy group, a cyclopropylmethylcarbamoyloxy group, an N,N-dimethylcarbamoyloxy group, an N-ethyl-N-methylcarbamoyloxy group, a pyrrolidinocarboxy group, a morpholinocarboxy group and a 4-methylpiperazinocarboxy group.

The "alkylsulfonyloxy group which may have a substituent(s)" refers to an alkylsulfonyloxy group containing an alkyl group having 1 to 8 carbon atoms which may have a substituent(s) as defined above in its structure. Examples of the alkylsulfonyloxy group having 1 to 8 carbon atoms which may have a substituent(s) include a methanesulfonyloxy group which may have a substituent(s), an ethanesulfonyloxy group which may have a substituent(s), an isopropylsulfonyloxy group which may have a substituent(s), a cyclopropanesulfonyloxy group which may have a substituent(s), a cyclopentanesulfonyloxy group which may have a substituent(s) and a cyclopentylmethanesulfonyloxy group which may have a substituent(s).

The "amino group which may have a substituent(s)" refers to an amino group substituted with one or the same or different two substituents, in addition to an amino group. The substituent for the amino group is selected from the group consisting of an alkyl group having 1 to 8 carbon atoms which may have a substituent(s) as defined above, an alkenyl group having 2 to 8 carbon atoms which may have a substituent(s) as defined above, an alkynyl group having 2 to 8 carbon atoms which may have a substituent(s) as defined above, an alkoxycarbonyl group having 1 to 8 carbon atoms which may have a substituent(s) as defined above, an alkanoyl group having 1 to 8 carbon atoms which may have a substituent(s) as defined above, a carbamoyl group which may have a substituent(s) as defined above, an aryl group which may have a substituent(s) as defined for $R^2$ above, a heterocyclic group which may have a substituent(s) as defined for $R^2$ above, an arylcarbonyl group which may have a substituent(s), a heterocyclic carbonyl group which may have a substituent(s), an alkylsulfonyl group having 1 to 8 carbon atoms which may have a substituent(s), an arylsulfonyl group which may have a substituent(s) and a heterocyclic sulfonyl group which may have a substituent(s).

Here, the "arylcarbonyl group which may have a substituent(s)" refers to an arylcarbonyl group containing an aryl group which may have a substituent(s) as defined for $R^2$ above in its structure. Examples of the arylcarbonyl group which may have a substituent(s) include a phenylcarbonyl group which may have a substituent(s), a naphthylcarbonyl group which may have a substituent(s) and a fluorenylcarbonyl group which may have a substituent(s).

The "heterocyclic carbonyl group which may have a substituent(s)" refers to a heterocyclic carbonyl group containing a heterocyclic group which may have a substituent(s) as defined for $R^2$ above in its structure. Examples of the heterocyclic carbonyl group which may have a substituent(s) include a furoyl group which may have a substituent(s), a tetrahydrofuroyl group which may have a substituent(s), a tetrahydropyrancarbonyl group which may have a substituent(s), a pyrrolidinecarbonyl group which may have a substituent(s), a pipecolinoyl group which may have a substituent(s), a morpholinecarbonyl group which may have a substituent(s), a piperazinecarbonyl group which may have a substituent(s), a picolinoyl group which may have a substituent(s), a nicotinoyl group which may have a substituent(s), an imidazolecarbonyl group which may have a substituent(s) and a thiazolecarbonyl group which may have a substituent(s).

The "alkylsulfonyl group having 1 to 8 carbon atoms which may have a substituent(s)" refers to an alkylsulfonyl group containing an alkyl group having 1 to 8 carbon atoms which may have a substituent(s) as defined above in its structure. Examples of the alkylsulfonyl group having 1 to 8 carbon atoms which may have a substituent(s) include a methanesulfonyl group which may have a substituent(s), an ethanesulfonyl group which may have a substituent(s), an isopropylsulfonyl group which may have a substituent(s), a cyclopropanesulfonyl group which may have a substituent(s), a cyclopentanesulfonyl group which may have a substituent(s) and a cyclopentylmethanesulfonyl group which may have a substituent(s).

The "arylsulfonyl group which may have a substituent(s)" refers to an arylsulfonyl group containing an aryl group which may have a substituent(s) as defined for $R^2$ above in its structure. Examples of the arylsulfonyl group which may have a substituent(s) include a phenylsulfonyl group which may have a substituent(s), a naphthylsulfonyl group which may have a substituent(s) and a fluorenylsulfonyl group which may have a substituent(s).

The "heterocyclic sulfonyl group which may have a substituent(s)" refers to a heterocyclic sulfonyl group containing a heterocyclic group which may have a substituent(s) as defined for $R^2$ above in its structure. Examples of the heterocyclic sulfonyl group which may have a substituent(s) include a tetrahydropyransulfonyl group which may have a substituent(s), a thiophenesulfonyl group which may have a substituent(s), a furansulfonyl group which may have a substituent(s), an isoxazolesulfonyl group which may have a substituent(s), a thiazolesulfonyl group which may have a substituent(s), an imidazolesulfonyl group which may have a substituent(s), a pyrazolesulfonyl group which may have a substituent(s) and a pyridinesulfonyl group which may have a substituent(s).

The "aryl group which may have a substituent(s)" is as defined for $R^2$ above.

The "heterocyclic group which may have a substituent(s)" is as defined for $R^2$ above.

The phrase "when there is a plurality of the same or different substituents, any two substituents of the same or different substituents together with the carbon atom(s) on which they are substituted may form a saturated or unsaturated, fused or spiro 3- to 8-membered ring which may have a substituent(s)" refers to the fact that a 3- to 8-membered ring which may have a substituent(s) is bonded to Ring A in the formula (1) in a fused or spiro manner. The 3- to 8-membered ring may be a saturated ring or an unsaturated ring, and may contain a nitrogen atom, an oxygen atom or a sulfur atom as a ring constituent atom other than a carbon atom. The 3- to 8-membered ring may be substituted with one or the same or different 2 or 3 substituents selected from a) to q) in the above Substituent Group. The 3- to 8-membered ring may be substituted on the same carbon atom or different carbon atoms with these substituents, insofar as it can be substituted.

The "alkyl group having 1 to 8 carbon atoms which may have a substituent(s)" in $R^{31}$ is as defined for $R^3$ above.

Next, $R^4$ will be described.

$R^4$ represents an amino group having a protecting group.

The protecting group in the "amino group having a protecting group" is not particularly limited insofar as it is a protecting group used in a common organic chemistry reactions. Examples of the amino group having a protecting group include an alkanoylamino group having 1 to 6 carbon atoms, a tert-butoxycarbonylamino group, a di(tert-butoxycarbonyl)amino group, a benzyloxycarbonylamino group, a di(benzyloxycarbonyl)amino group, a p-methoxybenzylamino group, a di(p-methoxybenzyl)amino group, a 2,4-dimethoxybenzylamino group, a di(2,4-dimethoxybenzyl)amino group and an N-(tert-butoxycarbonyl)-N-(2,4-dimethoxybenzyl)amino group.

Next, Ring A will be described.

Ring A represents a 5- to 8-membered ring. Ring A is, as represented by the formula (1):

$$\text{(1)}$$

a 5- to 8-membered heterocyclic group containing as a ring constituent atom one sulfur atom at the 6-position of the compound of the formula (1). The ring constituent atoms of Ring A other than the sulfur atom are formed by carbon atoms. Ring A may have a double bond therein.

[Substituent Group]

a) an alkyl group having 1 to 8 carbon atoms

The "alkyl group having 1 to 8 carbon atoms" refers to a linear, branched or cyclic alkyl group having 1 to 8 carbon atoms. Examples of the alkyl group having 1 to 8 carbon atoms include a methyl group, an ethyl group, a propyl group, an isopropyl group, a cyclopropyl group, a cyclobutyl group, a cyclopentyl group and a cyclohexylethyl group.

b) a halogenated alkyl group having 1 to 8 carbon atoms

The "halogenated alkyl group having 1 to 8 carbon atoms" refers to an alkyl group as defined in a) above which is substituted with one or the same or different 2 to 4 halogen atoms. The group may be substituted on the same carbon atom or different carbon atoms with the halogen atoms.

c) a halogen atom d) a hydroxy group e) an oxo group f) a cyano group g) a carboxy group h) an alkoxy group having 1 to 8 carbon atoms The "alkoxy group having 1 to 8 carbon atoms" refers to an alkoxy group containing an alkyl group having 1 to 8 carbon atoms as defined in a) above in its structure.

i) a halogenated alkoxy group having 1 to 8 carbon atoms

The "halogenated alkoxy group having 1 to 8 carbon atoms" refers to an alkoxy group containing a halogenated alkyl group having 1 to 8 carbon atoms as defined in b) above in its structure.

j) an alkoxycarbonyl group having 1 to 8 carbon atoms

The "alkoxycarbonyl group having 1 to 8 carbon atoms" refers to an alkoxycarbonyl group containing an alkoxy group having 1 to 8 carbon atoms as defined in h) above in its structure.

k) an alkanoyl group having 1 to 8 carbon atoms

The "alkanoyl group having 1 to 8 carbon atoms" refers to a linear, branched or cyclic alkanoyl group having 1 to 8 carbon atoms. Examples of the alkanoyl group having 1 to 8 carbon atoms include a formyl group, an acetyl group, an n-propionyl group, an n-butyryl group, an isobutyryl group, a cyclopropylcarbonyl group and a cyclohexylacetyl group.

l) an alkanoyloxy group having 1 to 8 carbon atoms

The "alkanoyloxy group having 1 to 8 carbon atoms" refers to an alkanoyloxy group containing an alkanoyl group having 1 to 8 carbon atoms as defined in k) above in its structure. Examples of the alkanoyloxy group having 1 to 8 carbon atoms include a formyloxy group, an acetyloxy group, an n-propionyloxy group, an n-butyryloxy group, an isobutyryloxy group, a cyclopropylcarbonyloxy group and a cyclohexylacetyloxy group.

m) an amino group which may be substituted with one or the same or different two alkyl groups having 1 to 8 carbon atoms The "amino group which may be substituted with one or the same or different two alkyl groups having 1 to 8 carbon atoms" refers to an unsubstituted amino group or an amino group substituted with 1 or 2 alkyl groups having 1 to 8 carbon atoms as defined in a) above.

n) a carbamoyl group which may be substituted with one or the same or different two alkyl groups having 1 to 8 carbon atoms The "carbamoyl group which may be substituted with one or the same or different two alkyl groups having 1 to 8 carbon atoms" refers to an unsubstituted carbamoyl group or a carbamoyl group substituted with 1 or 2 alkyl groups having 1 to 8 carbon atoms as defined in a) above.

o) an alkanoylamino group having 1 to 8 carbon atoms

The "alkanoylamino group having 1 to 8 carbon atoms" refers to an alkanoylamino group containing an alkanoyl group having 1 to 8 carbon atoms as defined in k) above in its structure.

p) a phenyl group which may be substituted with one or the same or different 2 or 3 substituents selected from the Substituent Group consisting of a) to d) and f) to o) above.

q) a saturated or unsaturated 4- to 7-membered monocyclic heterocyclic group which may be substituted with one or the same or different 2 or 3 substituents selected from the Substituent Group consisting of a) to d) and f) to o) above.

Examples of the saturated 4- to 7-membered monocyclic heterocyclic group include a group derived from azetidine, pyrrolidine, imidazolidine, triazolidine, tetrahydrofuran, tetrahydrothiophene, oxazolidine, thiazolidine, piperidine, piperazine, tetrahydropyran, dioxane, tetrahydrothiopyran, morpholine, thiomorpholine, homomorpholine or homopiperazine. Examples of the unsaturated 4- to 7-membered monocyclic heterocyclic group include a group derived from pyrrole, pyrazole, imidazole, triazole, tetrazole, thiophene, furan, thiazole, oxazole, isothiazole, isoxazole, pyridine, dihydropyridine, pyridazine, pyrimidine, quinoline, isoquinoline, indole, 1,3-dioxaindan, benzothiazole or thiazolopyridine.

In an embodiment of the present invention, $R^1$ is preferably a methylene group which may have 1 or 2 alkyl groups having 1 to 8 carbon atoms, and more preferably an unsubstituted methylene group.

$R^2$ is preferably a heterocyclic group which may have a substituent(s). The heterocyclic group is preferably a pyridyl group, a pyridazinyl group, a pyrimidinyl group, a pyrazinyl group, a benzothiazole group or a thiazolopyridyl group. The substituent with which the heterocyclic group may be substituted is preferably a halogen atom, an alkyl group, a halogenated alkyl group, an alkoxy group or a halogenated alkoxy group.

$R^3$ is preferably a hydrogen atom or 1 to 4 same or different substituents with which Ring A is substituted (wherein the same or different substituents each independently represents a substituent selected from the group consisting of a hydroxy group, a carboxy group, an alkyl group having 1 to 8 carbon atoms which may have a substituent(s), an alkynyl group having 2 to 8 carbon atoms which may have a substituent(s), an alkoxy group having 1 to 8 carbon atoms which may have a substituent(s), a carbamoyl group which may have a substituent(s), a carbamoyloxy group which may have a substituent(s), an amino group which may have a substituent(s), a cyano group, a heterocyclic group which may have a substituent(s) and an oxo group, or when there is a plurality of the same or different substituents, any two substituents of the same or different substituents together with the carbon atom(s) on which they are substituted form a saturated or unsaturated, fused or spiro 3- to 8-membered ring which may have a substituent(s)), and more preferably a hydrogen atom or 1 to 4 same or different substituents with which Ring A is substituted (wherein the same or different substituents are each independently selected from the group consisting of an alkyl group having 1 to 8 carbon atoms which may have a substituent(s), an alkynyl group having 2 to 8 carbon atoms which may have a substituent(s), a carbamoyl group which may have a substituent(s) and an amino group which may have a substituent(s)). The number of the same or different substituents is preferably 1 or 2.

$R^4$ is preferably a di(tert-butoxycarbonyl)amino group or a di(p-methoxybenzyl)amino group, and more preferably a di(tert-butoxycarbonyl)amino group.

Ring A is preferably a 6- or 7-membered ring. Specifically, Ring A is preferably a corresponding partial structure in a compound represented by any of the following formulas (1a) to (1d):

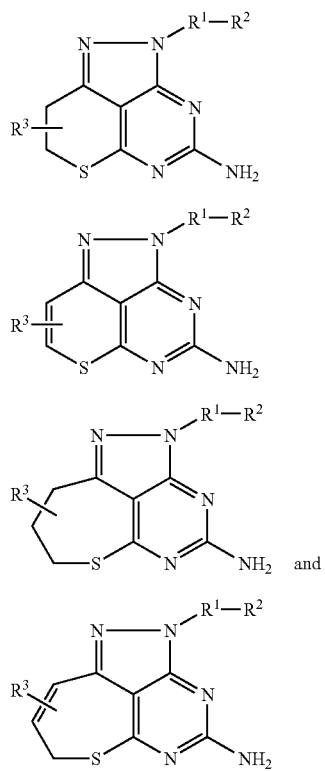

wherein in the formulas (1a) to (1d), $R^1$, $R^2$ and $R^3$ are as defined for $R^1$, $R^2$ and $R^3$ in the formula (1), respectively.

The compound represented by the formula (1) according to the present invention may be present as a stereoisomer or an optical isomer derived from an asymmetric carbon atom. The stereoisomer, the optical isomer and a mixture thereof are all included in the present invention.

The compound represented by the formula (1) according to the present invention is a novel tricyclic compound derived from pyrazolopyrimidine. The compound represented by the formula (1) according to the present invention inhibits the ATPase activity of HSP90 and is useful as an HSP inhibitor. Further, the compound represented by the formula (1) according to the present invention has antitumor activity to various tumor cells and is useful as an anticancer agent inhibiting HSP90. Moreover, the compound represented by the formula (1) according to the present invention is excellent, because the compound does not have a highly reactive substituent (for example, a halogen atom such as a chlorine atom) and therefore there is only a small risk of reduced activity by reaction with molecules in vivo (for example, reaction with the SH group of glutathione in vivo).

In another embodiment of the present invention, the compound represented by the formula (2):

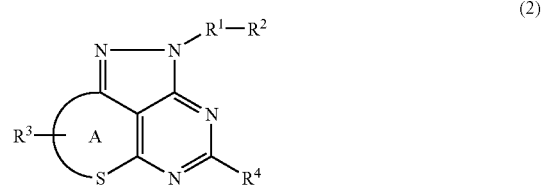

wherein in the formula (2), $R^1$, $R^2$, $R^3$ and Ring A are as defined for $R^1$, $R^2$, $R^3$ and Ring A in the formula (1), respectively, and $R^4$ represents an amino group having a protecting group, is important as a production intermediate for the compound represented by formula (1).

In another embodiment of the present invention, the compound represented by the formula (3):

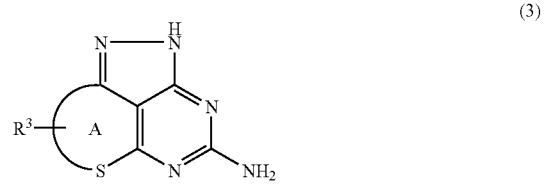

wherein in the formula (3), $R^3$ and Ring A are as defined for $R^3$ and Ring A in the formula (1), respectively, is important as a production intermediate for the compound represented by formula (1).

The tricyclic pyrazolopyrimidine derivative of the present invention may remain in a free form or may be in the form of a salt or a solvate.

The salt of the compound represented by the general formula (1) according to the present invention is not particularly limited so long as it is a medically acceptable salt. Examples of the salt include acid addition salts and salts of carboxy groups. Examples of the acid addition salts include inorganic acid salts such as hydrochlorides, sulfates, nitrates, hydrobromides, hydroiodides and phosphates, and organic acid salts such as acetates, methanesulfonates, benzenesulfonates, toluenesulfonates, citrates, maleates, fumarates and lactates. Examples of the salts of carboxy groups include any of inorganic salts or organic salts such as alkali metal salts such as lithium salts, sodium salts and potassium salts, alkali earth metal salts such as magnesium salts and calcium salts, ammonium salts, triethylamine salts, N-methylglucamine salts and tris-(hydroxylmethyl)aminomethane salts.

The solvate is not particularly limited so long as it is medically acceptable. Specific examples of the solvate include hydrates and alcoholates.

Next, a typical method for producing the compound represented by the formula (1) will be described. In each reaction, appropriate protecting group(s) may be used and conversion(s) desired in common organic chemistry reactions may be used, as necessary. The type of the protecting group(s) and the order of conversion of the respective substituents are not particularly limited.

(I) Main Steps

The compound (1) can be produced according to the following Scheme 1, for example.

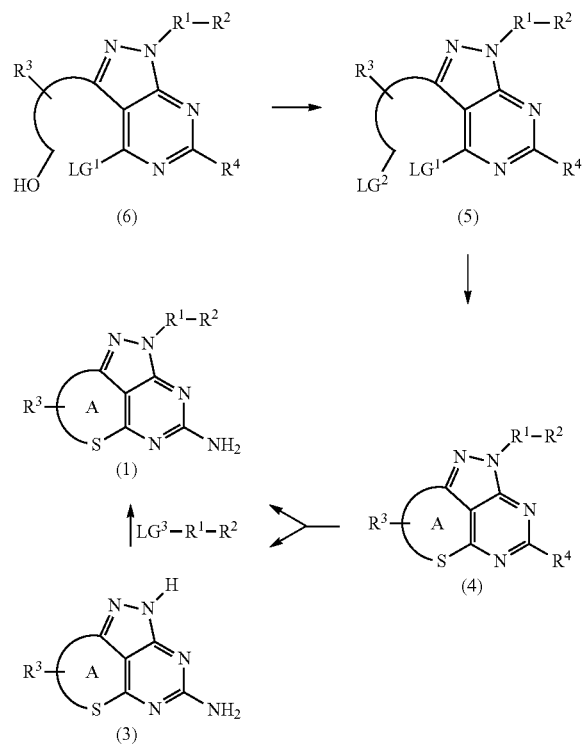

In each formula, $R^1$, $R^2$, $R^3$, $R^4$ and Ring A are as defined above, respectively, and $LG^1$, $LG^2$ and $LG^3$ represent leaving groups.

Examples of the leaving groups $LG^1$, $LG^2$ and $LG^3$ include a halogen atom, a toluenesulfonyloxy group, a methanesulfonyloxy group and a trifluoromethanesulfonyloxy group. $LG^1$ is preferably a chloro group. $LG^2$ is preferably a bromo group, a toluenesulfonyloxy group or a methanesulfonyloxy group. $LG^3$ is preferably a chloro group, a bromo group or an iodo group.

As described in Scheme 1, a compound (5) can be obtained by converting the hydroxyl group of a compound (6) to a leaving group $LG^2$ such as a halogen atom, a toluenesulfonyloxy group, a methanesulfonyloxy group or a trifluoromethanesulfonyloxy group by treatment with thionyl chloride, thionyl bromide, toluenesulfonyl chloride, methanesulfonyl chloride or trifluoromethanesulfonyl chloride in the presence of a base, for example, based on common knowledge in organic chemistry.

A compound (4) can be obtained by reacting the compound (5) with sodium bisulfide in N,N-dimethylformamide and then treating with a base. The compound (4) can also be obtained by reacting the compound (5) with potassium thioacetate in N,N-dimethylformamide. Examples of the base include potassium carbonate and potassium bicarbonate. The base is preferably potassium carbonate. The reaction temperature is suitably −10° C. to 70° C., and preferably −10° C. to 30° C.

The compound (4) can be converted to the compound (3) by acid treatment or hydrolysis and subsequent treatment under deprotection reaction conditions suitable for the protecting group in the amino group having a protecting group ($R^4$), when its $R^1$-$R^2$ group is a protecting group such as a 4-methoxybenzyl group. A typical example of the deprotection reaction conditions suitable for the protecting group will be described below. For example, when the amino group substituted with a protecting group is an alkanoylamino group or an aroylamino group, the group can be converted to an amino group by hydrolysis using an aqueous solution of sodium hydroxide, potassium hydroxide, ammonia or the like. When the amino group substituted with a protecting group is a tert-butoxycarbonylamino group or a di-tert-butoxycarbonylamino group, the group can be converted to an amino group by treatment with an acid such as hydrochloric acid or trifluoroacetic acid.

The compound (3) can be converted to the compound (1) by treatment with $LG^3$-$R^1$-$R^2$ in a solvent in the presence of a base. Examples of the solvent include N,N-dimethylformamide, N-methylpyrrolidone, tetrahydrofuran and dimethylsulfoxide. Examples of the base include sodium hydride, sodium ethoxide, potassium tert-butoxide, potassium hydroxide, potassium carbonate and cesium carbonate. The reaction temperature is suitably 0° C. to 100° C. The reaction time is suitably 1 to 48 hours.

On the other hand, when the —$R^1$-$R^2$ group of the compound (4) is not a protecting group, the compound (1) can be obtained by treating the amino group having a protecting group ($R^4$) under the above deprotection reaction conditions.

(II) Steps of Conversion of Substituent $R^3$ on Ring A

The substituent $R^3$ on Ring A of the compound (1) or (4) obtained in the above Scheme 1 can be converted to another substituent based on common knowledge in organic chemistry, as shown in the following Scheme 2.

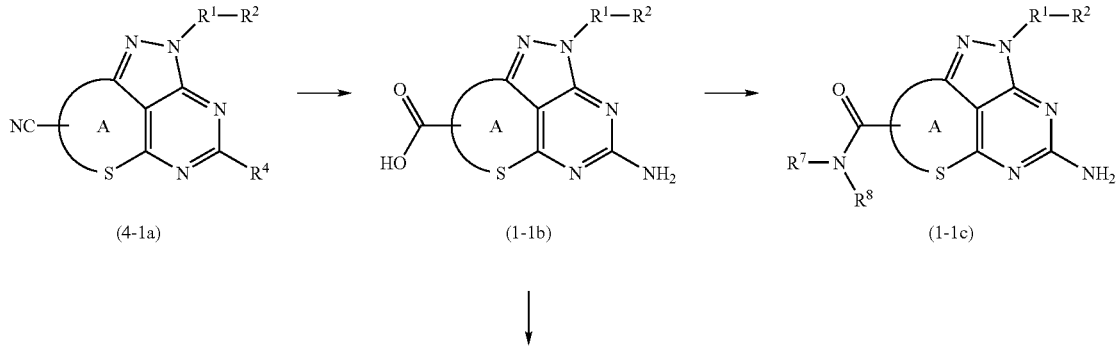

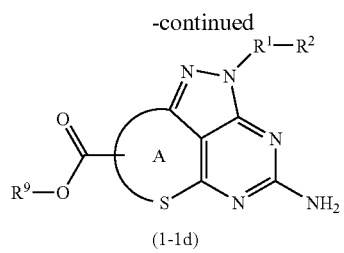

(1-1d)

In each formula, $R^1$, $R^2$, $R^4$ and Ring A are as defined above, respectively, $R^7R^8$NCO represents a carbamoyl group which may have a substituent(s) (wherein the carbamoyl group which may have a substituent(s) is as defined for $R^3$ above), and $R^9$ represents an alkyl group having 1 to 8 carbon atoms which may have a substituent(s) (wherein the alkyl group having 1 to 8 carbon atoms which may have a substituent(s) is as defined for $R^3$ above).

As shown in Scheme 2, a carboxylic acid derivative (1-1b) can be obtained by hydrolyzing a cyano derivative (4-1a) where $R^3$ in the compound (4) is a cyano group under acidic conditions, for example. In this case, the amino group having a protecting group ($R^4$) is deprotected and converted to an amino group by hydrolysis under acidic conditions.

The carboxylic acid derivative (1-1b) can be converted to an amide derivative (1-1c) by condensation reaction with various amines. A method generally used as a peptide synthesis method may be suitably used in the condensation reaction with amines. Examples of the peptide synthesis method include an azide method, an acid chloride method, a DCC (dicyclohexylcarbodiimide) method, an active ester method, a carbonyldiimidazole method, a method using a water-soluble carbodiimide and a method using diethyl cyanophosphate. These methods are described in M. Bondansky, Y. S. Klausner and M. A. Ondetti, "Peptide Synthesis" (A Wiley-interscience publication, New York, 1976), G. R. Pettit, "Synthetic Peptides" (Elsevier Scientific Publication Company, New York, 1976), The Chemical Society of Japan (ed.), "Jikken Kagaku Koza (Courses in Experimental Chemistry), 4th edition, Vol. 22, Yuki Gosei (Organic Synthesis) IV" (Maruzen Co., Ltd., 1992) or the like. Examples of the solvent used in the condensation reaction include N,N-dimethylformamide, N-methylpyrrolidone, pyridine, chloroform, methylene chloride, tetrahydrofuran, dioxane, acetonitrile and mixed solvents thereof. The reaction temperature is suitably $-20°$ C. to $50°$ C., and preferably $-10°$ C. to $30°$ C. As such an amine, there may be used a commercially available compound, or a compound produced by a method described in a document or a method described in Examples, or a method similar to these methods.

The carboxylic acid derivative (1-1b) can be converted to an ester derivative (1-1d) by condensation reaction with various alcohols ($R^9$—OH) or substitution reaction with various alkyl halides. As the condensation reaction of the carboxylic acid derivative (1-1b) with various alcohols, condensation reaction in the presence of an acid catalyst such as hydrochloric acid or sulfuric acid, Mitsunobu reaction or the like may be suitably used. In the substitution reaction with various alkyl halides, alkylation of a carboxyl group may be suitably performed using an appropriate base in a solvent.

When $R^3$ in the compound (4) is a hydroxyl group, for example, corresponding compounds (1-1f), (1-1g), (1-1h) or (1-1i) can be obtained, respectively, by converting the hydroxyl group to an alkoxy group, a carbamoyloxy group, an alkanoyloxy group or an oxo group, and then treating under appropriate deprotection reaction conditions suitable for the protecting group, as described in Scheme 3.

Scheme 3

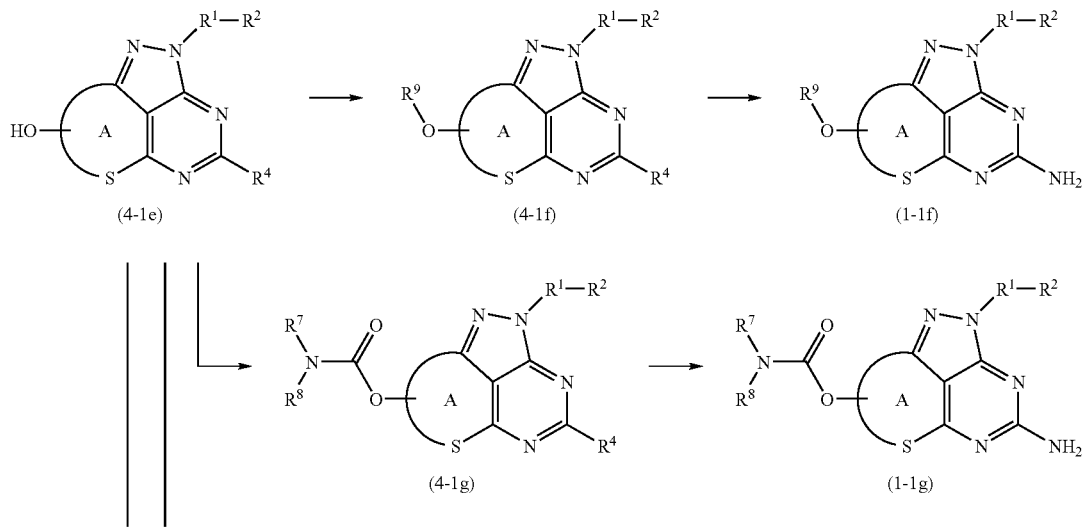

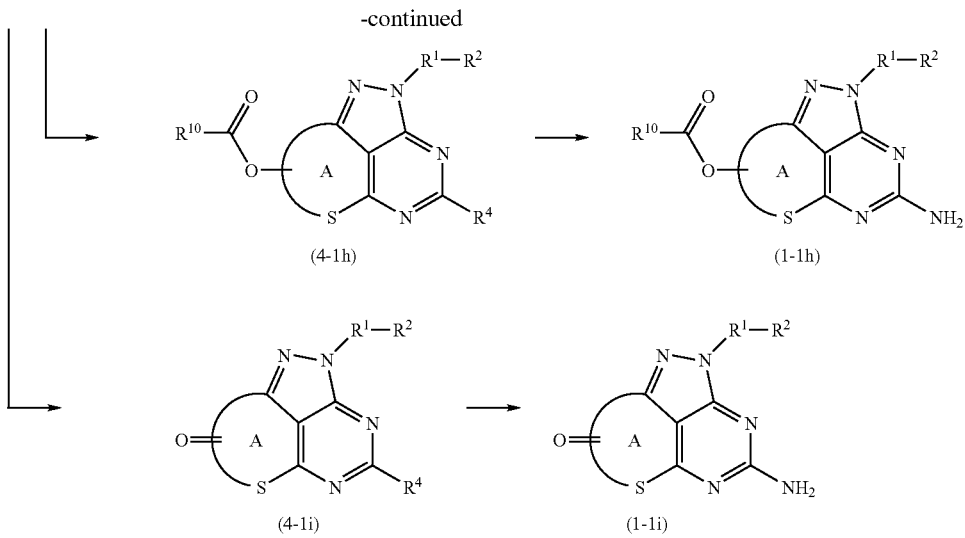

In each formula, $R^1$, $R^2$, $R^4$, $R^9$, $R^7R^8NCO$ and Ring A are as defined above, respectively, and $R^{10}$ represents a hydrogen atom or an alkyl group having 1 to 8 carbon atoms which may have a substituent(s) (wherein the alkyl group having 1 to 8 carbon atoms which may have a substituent(s) is as defined for $R^3$ above).

In the conversion of the hydroxyl group to an alkoxy group (conversion of a compound (4-1e) to a compound (4-1f)), a method generally used as ether synthesis method may be suitably used. For example, the alcohol derivative (4-1e) may be suitably treated with an alkyl halide in a solvent in the presence of a base. Examples of the solvent include N,N-dimethylformamide, N-methylpyrrolidone, diethyl ether, tetrahydrofuran and toluene. Examples of the base include sodium hydride, potassium hydride, sodium hydroxide, potassium hydroxide, potassium carbonate, sodium tert-butoxide, potassium tert-butoxide, pyridine, DBU and diisopropylethylamine. The base is preferably sodium hydride. The reaction temperature is suitably −80° C. to 150° C., and preferably 0° C. to 100° C. The reaction time is suitably 15 minutes to 72 hours. The method is described in The Chemical Society of Japan (ed.), "Jikken Kagaku Koza (Courses in Experimental Chemistry), 4th edition, Vol. 20, Yuki Gosei (Organic Synthesis) II" (Maruzen Co., Ltd., 1992) or the like.

In the conversion of the hydroxyl group to a carbamoyloxy group (conversion of the compound (4-1e) to a compound (4-1g)), a method generally used as carbamoylation reaction may be suitably used. Examples of the method include a method of treating the alcohol derivative (4-1e) with an isocyanate derivative in a solvent and a method of treating the alcohol derivative (4-1e) with 1,1′-carbonyldiimidazole or phosgene in a solvent and then adding an amine.

In the conversion of the hydroxyl group to an alkanoyloxy group (conversion of the compound (4-1e) to a compound (4-1h)), a method generally used as alkanoylation reaction may be suitably used. Examples of the method include an azide method, an acid chloride method, a DCC (dicyclohexylcarbodiimide) method, an active ester method, a carbonyldiimidazole method, a method using a water-soluble carbodiimide and a method using diethyl cyanophosphate.

Examples of the method for conversion of the hydroxyl group to an oxo group (conversion of the compound (4-1e) to a compound (4-1i)) include Mukaiyama oxidation, and Swern oxidation or oxidation reaction as its modification using DCC, trifluoroacetic anhydride, acetic anhydride or a sulfur trioxide-pyridine complex instead of oxalyl chloride. The method is described in The Chemical Society of Japan (ed.), "Jikken Kagaku Koza (Courses in Experimental Chemistry), 4th edition, Vol. 23, Yuki Gosei (Organic Synthesis) V" (Maruzen Co., Ltd., 1992) or the like.

The compounds (4-1f), (4-1g), (4-1h) and (4-1i) produced by the above methods can be converted to compounds (1-1f), (1-1g), (1-1h) and (1-1i) by treatment under deprotection reaction conditions suitable for the protecting group in the amino group having a protecting group ($R^4$).

Further, when $R^3$ in the compound (4) is an oxo group, the ketone derivative (4-1i) as a raw material can be converted to an amine derivative (4-1j) by reductive amination reaction with various amines, and then the amine derivative (4-1j) can be converted to an amine derivative (1-1j) by treatment under appropriate deprotection reaction conditions suitable for the protecting group, as described in Scheme 4, for example.

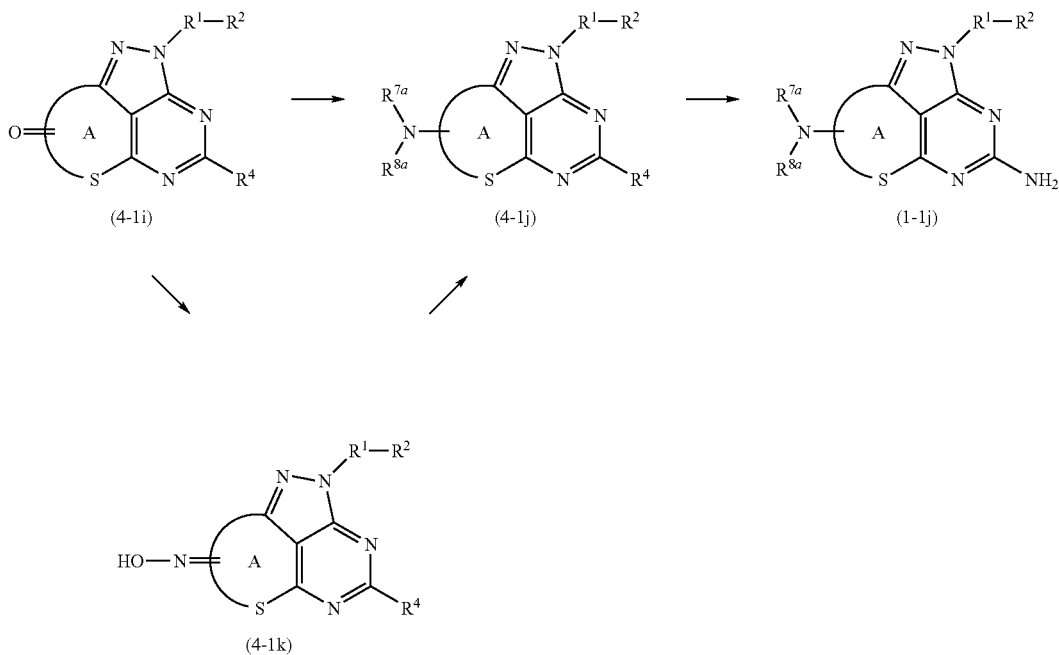

In each formula, $R^1$, $R^2$, $R^4$ and Ring A are as defined above, respectively, and $R^{7a}R^{8a}N$ represents an amino group which may have a substituent(s) (wherein the amino group which may have a substituent(s) is as defined for $R^3$ above).

Examples of the reducing agent used in the reductive amination reaction include sodium borohydride, sodium cyanoborohydride and sodium triacetoxyborohydride. Such a method is described in The Chemical Society of Japan (ed.), "Jikken Kagaku Koza (Courses in Experimental Chemistry), 4th edition, Vol. 20, Yuki Gosei (Organic Synthesis) II" (Maruzen Co., Ltd., 1992) or the like.

The amine derivative (4-1j), wherein both $R^{7a}$ and $R^{8a}$ are hydrogen atoms, can also be obtained by reducing an oxime derivative (4-1k) which can be obtained by condensation reaction of the ketone derivative (4-1i) with hydroxylamine.

Further, the amine derivative (4-1j), wherein both $R^{7a}$ and $R^{8a}$ are hydrogen atoms or any one of $R^{7a}$ and $R^{8a}$ is a hydrogen atom, can be further chemically modified as described in Scheme 5. For example, corresponding compounds (1-1l), (1-1m), (1-1n) and (1-1o) can be obtained, respectively, by producing a compound having an alkoxycarbonylamino group (4-1l), a compound having a carbamoylamino group (4-1m), a compound having an alkanoylamino group (4-1n) or a compound having an alkylsulfonylamino group, an arylsulfonylamino group or a heterocyclic sulfonylamino group (4-1o) from an amine derivative (4-1ja) and then converting $R^4$ to an amino group by treatment under appropriate deprotection reaction conditions suitable for the protecting group.

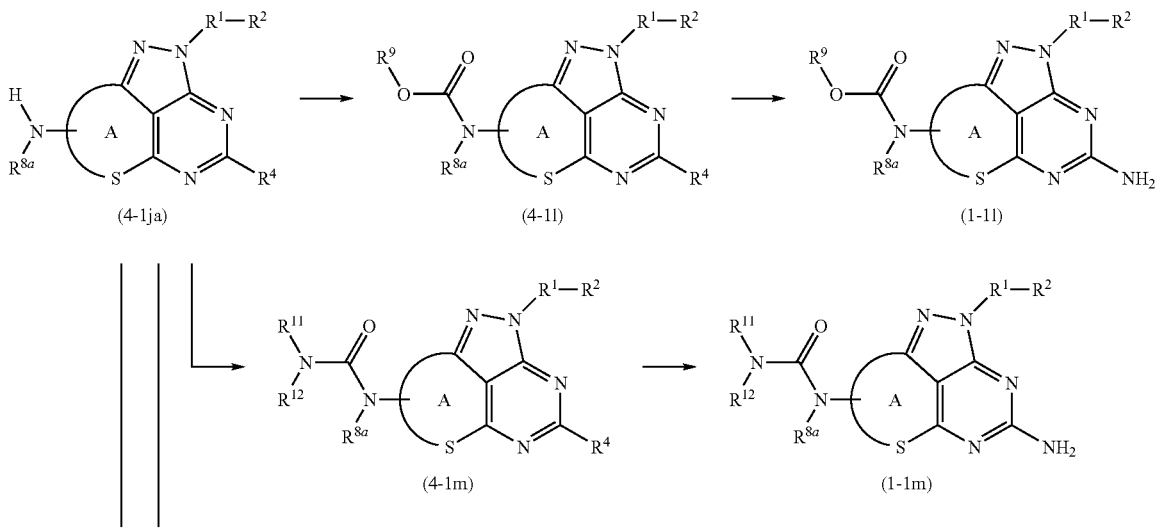

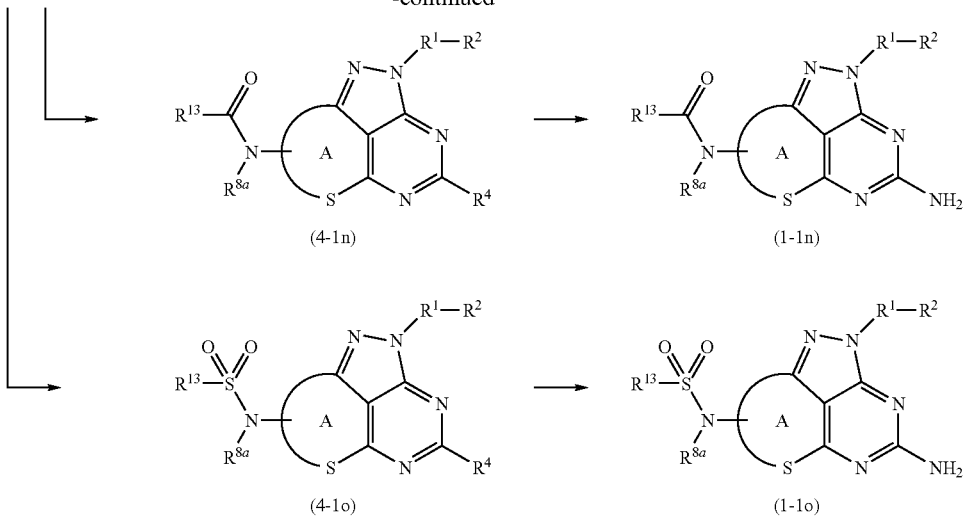

(4-1n) (1-1n)

(4-1o) (1-1o)

In each formula, $R^1$, $R^2$, $R^4$ and Ring A are as defined above, respectively, $R^{8a}$ represents a hydrogen atom, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an aryl group which may have a substituent(s) or a heterocyclic group which may have a substituent(s), $R^9$ represents an alkyl group having 1 to 8 carbon atoms which may have a substituent(s), $R^{11}$ and $R^{12}$ each independently represent a hydrogen atom, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an aryl group which may have a substituent(s) or a heterocyclic group which may have a substituent(s), and $R^{13}$ represents a hydrogen atom, an alkyl group having 1 to 8 carbon atoms which may have a substituent(s), an aryl group which may have a substituent(s) or a heterocyclic group which may have a substituent(s) (wherein the alkyl group having 1 to 8 carbon atoms which may have a substituent(s) in $R^{8a}$, $R^9$, $R^{11}$, $R^{12}$ and $R^{13}$ is as defined for $R^3$ above, the alkenyl group having 2 to 8 carbon atoms which may have a substituent(s) in $R^{8a}$, $R^{11}$ and $R^{12}$ is as defined for $R^3$ above, the alkynyl group having 2 to 8 carbon atoms which may have a substituent(s) in $R^{8a}$, $R^{11}$ and $R^{12}$ is as defined for $R^3$ above, the aryl group which may have a substituent(s) in $R^{8a}$, $R^{11}$, $R^{12}$ and $R^{13}$ is as defined for $R^3$ above, and the heterocyclic group which may have a substituent(s) in $R^{8a}$, $R^{11}$, $R^{12}$ and $R^{13}$ is as defined for $R^3$ above).

Examples of the conversion of the amino group to an alkoxycarbonylamino group (conversion of the amine derivative (4-1ja) to the compound having an alkoxycarbonylamino group (4-1l)) include a method of condensing the amine derivative (4-1jb) with a carbonate derivative such as alkoxycarbonyl chloride under basic conditions. Such a method is described in The Chemical Society of Japan (ed.), "Jikken Kagaku Koza (Courses in Experimental Chemistry), 4th edition, Vol. 20, Yuki Gosei (Organic Synthesis) II" (Maruzen Co., Ltd., 1992) or the like.

Examples of the conversion of the amino group to a carbamoylamino group (conversion of the amine derivative (4-1ja) to the compound having a carbamoylamino group (4-1m)) include addition reaction of the amine derivative (4-1ja) to cyanic acid or an isocyanate, and a method of previously treating any one of the amine derivative (4-1ja) and an introduced amine ($R^{11}$—NH—$R^{12}$) with 1,1'-carbonyldiimidazole or phosgene in a solvent and then adding the other remaining amine.

Examples of the conversion of the amino group to an amide (conversion of the amine derivative (4-1ja) to the amide (4-1n)) include condensation reaction of the amine derivative (4-1ja) with various carboxylic acids. A method generally used as the peptide reaction described above may be suitably used in the condensation reaction.

Examples of the conversion of the amino group to an alkylsulfonylamino group, an arylsulfonylamino group or a heterocyclic sulfonylamino group (conversion of the amine derivative (4-1ja) to the compound having an alkylsulfonylamino group, an arylsulfonylamino group or a heterocyclic sulfonylamino group (4-1o)) include condensation reaction of the amine derivative (4-1ja) with various alkylsulfonyl chlorides, arylsulfonyl chlorides or heterocyclic sulfonyl chlorides under basic conditions.

Further, when the substituent on Ring A of the compound (4) is a hydroxyl group, a compound containing a double bond in Ring A can be produced, as shown in Scheme 6.

Scheme 6

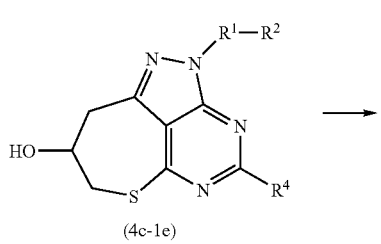

(4c-1e)

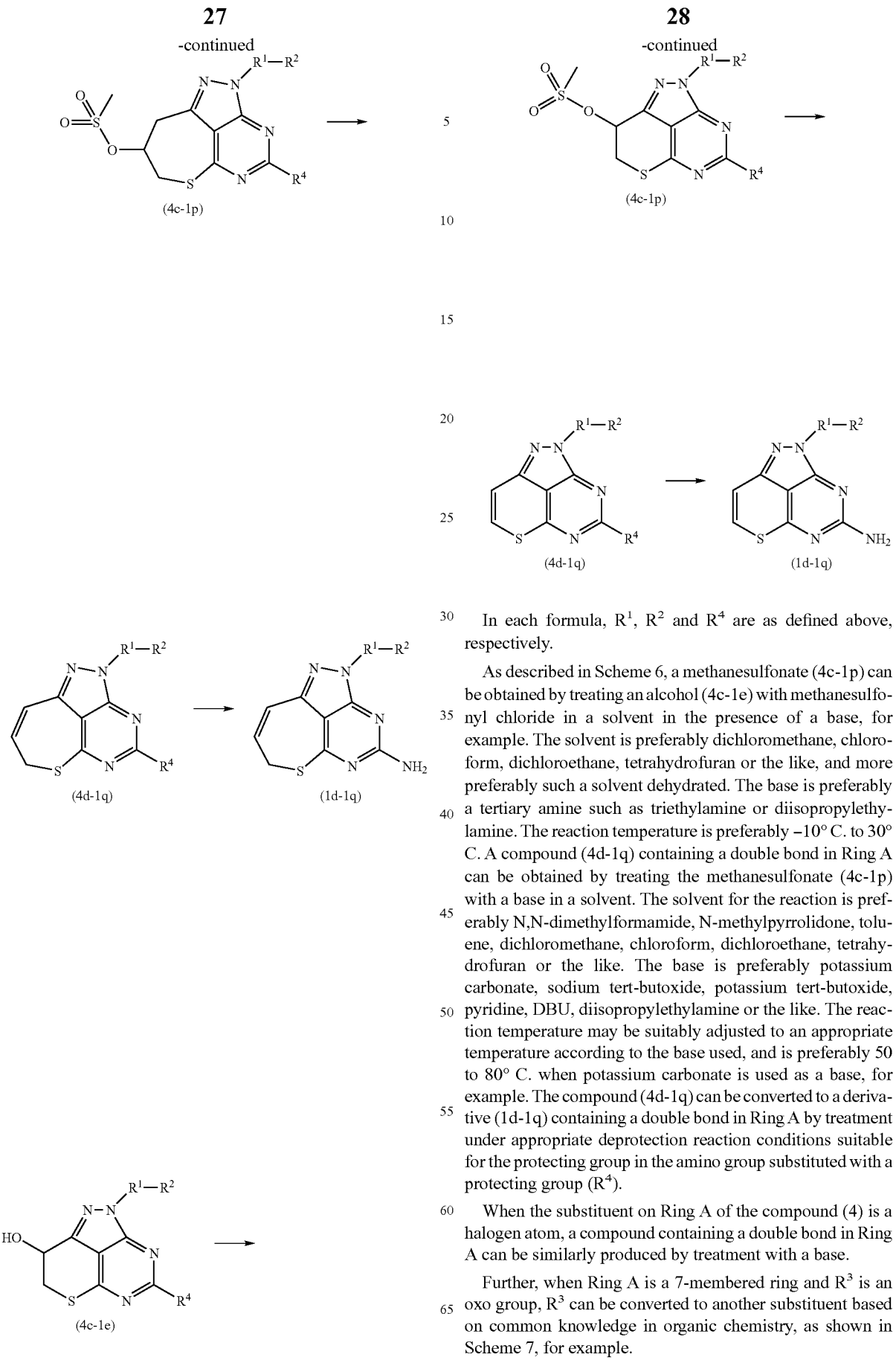

In each formula, $R^1$, $R^2$ and $R^4$ are as defined above, respectively.

As described in Scheme 6, a methanesulfonate (4c-1p) can be obtained by treating an alcohol (4c-1e) with methanesulfonyl chloride in a solvent in the presence of a base, for example. The solvent is preferably dichloromethane, chloroform, dichloroethane, tetrahydrofuran or the like, and more preferably such a solvent dehydrated. The base is preferably a tertiary amine such as triethylamine or diisopropylethylamine. The reaction temperature is preferably −10° C. to 30° C. A compound (4d-1q) containing a double bond in Ring A can be obtained by treating the methanesulfonate (4c-1p) with a base in a solvent. The solvent for the reaction is preferably N,N-dimethylformamide, N-methylpyrrolidone, toluene, dichloromethane, chloroform, dichloroethane, tetrahydrofuran or the like. The base is preferably potassium carbonate, sodium tert-butoxide, potassium tert-butoxide, pyridine, DBU, diisopropylethylamine or the like. The reaction temperature may be suitably adjusted to an appropriate temperature according to the base used, and is preferably 50 to 80° C. when potassium carbonate is used as a base, for example. The compound (4d-1q) can be converted to a derivative (1d-1q) containing a double bond in Ring A by treatment under appropriate deprotection reaction conditions suitable for the protecting group in the amino group substituted with a protecting group ($R^4$).

When the substituent on Ring A of the compound (4) is a halogen atom, a compound containing a double bond in Ring A can be similarly produced by treatment with a base.

Further, when Ring A is a 7-membered ring and $R^3$ is an oxo group, $R^3$ can be converted to another substituent based on common knowledge in organic chemistry, as shown in Scheme 7, for example.

Scheme 7
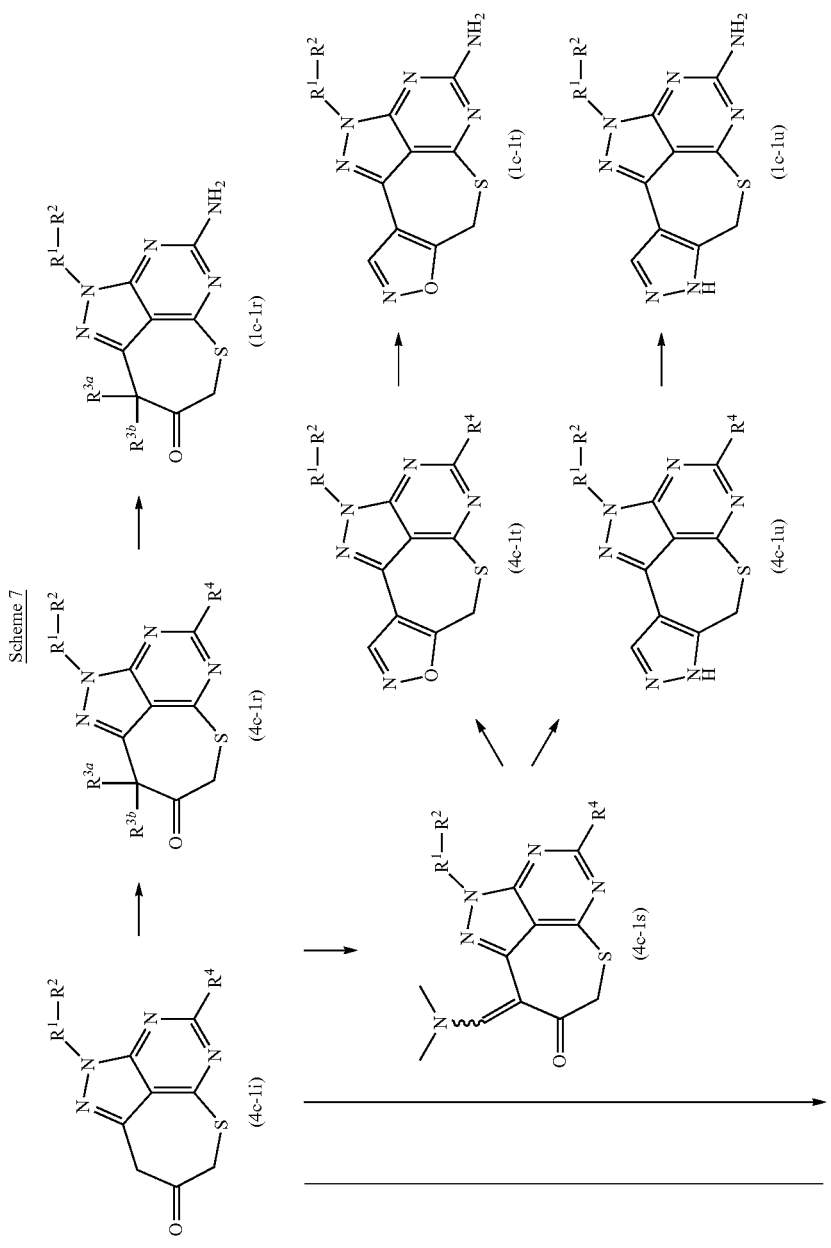

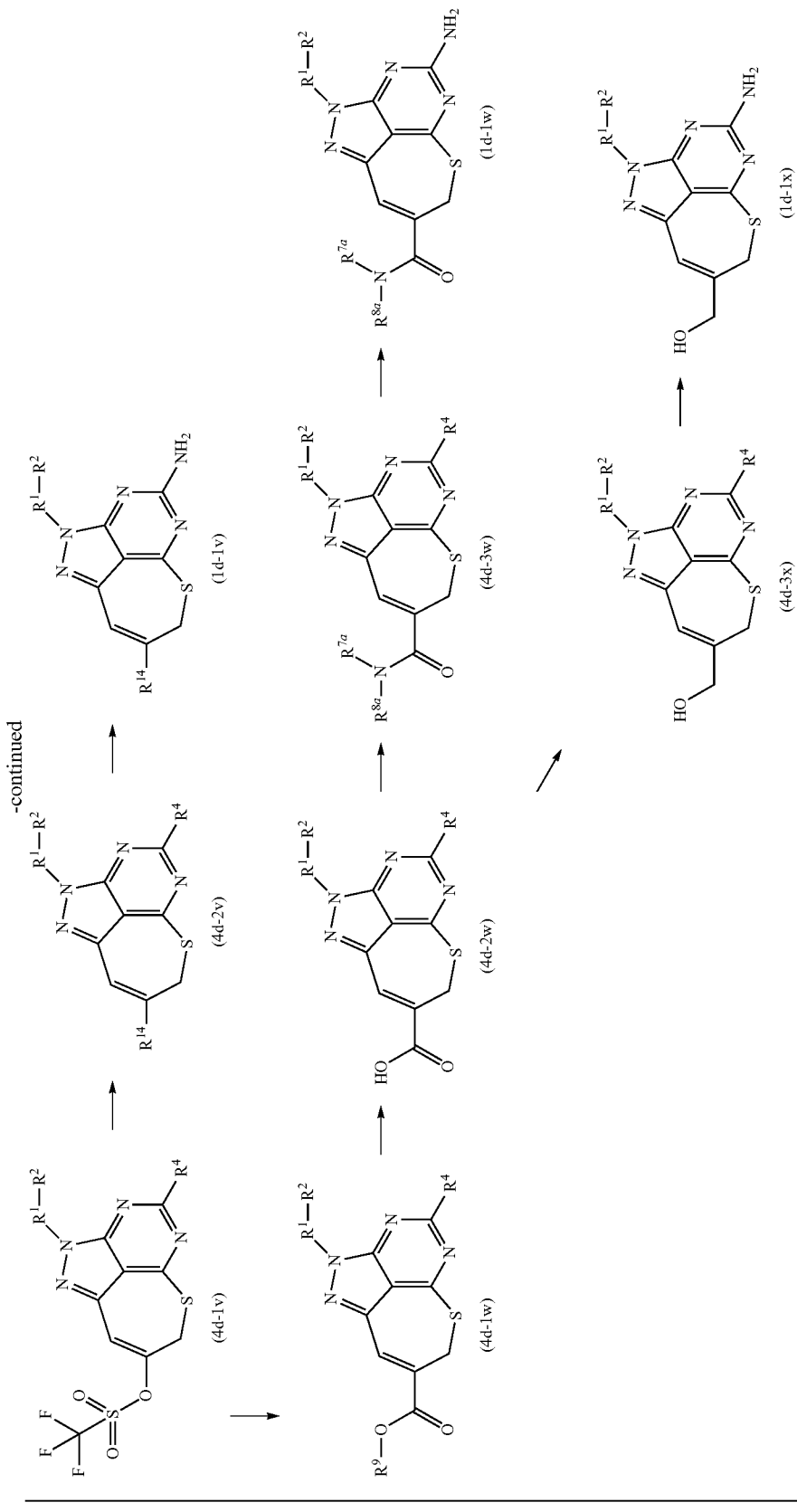

-continued
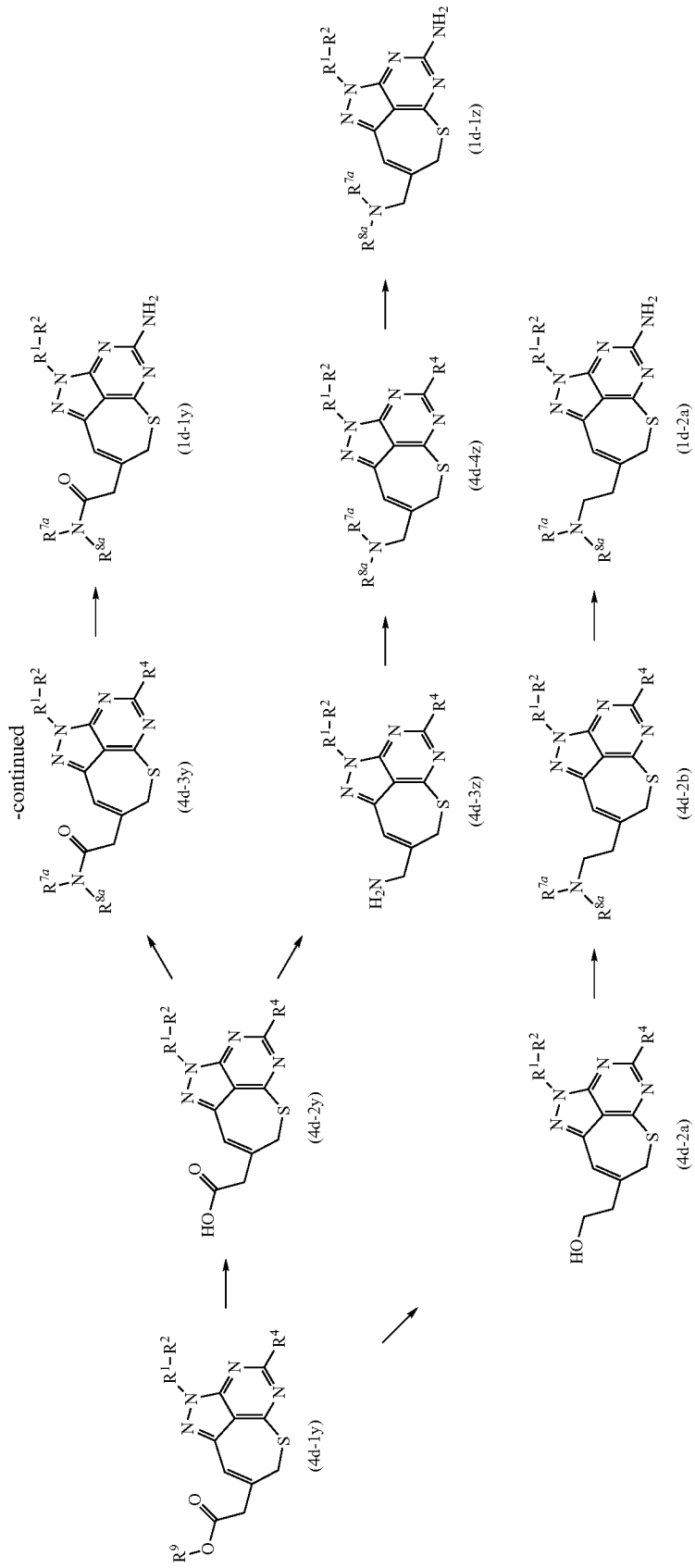

In each formula, $R^1$, $R^2$, $R^4$, $R^{7a}R^{8a}N$ and $R^9$ are as defined above, $R^{3a}$ and $R^{3b}$ represent any of the plurality of substituents of $R^3$ above, and $R^{14}$ represents a vinyl group which may have a substituent(s) or an aryl group which may have a substituent(s).

A ketone derivative (4c-1i) can be converted to a monosubstituted alkyl compound ($R^{3a}$=H, 4c-1r) by treatment with 0.5 to 1.5 molar equivalents of a halogenoalkane relative to the ketone derivative in a solvent in the presence of a base and a disubstituted alkyl compound (4c-1r) by treatment with 2 to 3 molar equivalents of a halogenoalkane relative to the ketone derivative in the presence of a base, and in particular can be converted to a spirocycloalkane derivative (4c-1r) by treatment with a dihaloethane such as dibromoethane in the presence of a base. The derivative can be converted to a mono- or difluoro compound (4c-1r) by treatment with N-fluorobenzenesulfonimide or the like in the presence of a base in the same manner as above. Examples of the solvent include tetrahydrofuran, N,N-dimethylformamide, N-methylpyrrolidone and dimethyl sulfoxide. The solvent is more preferably dimethyl sulfoxide or N,N-dimethylformamide. Examples of the base include sodium hydride, sodium tert-butoxide, potassium tert-butoxide, potassium carbonate and sodium carbonate. The base is preferably potassium carbonate or sodium hydride. The reaction temperature may be suitably adjusted to an appropriate temperature according to the base used. The reaction temperature is preferably 0° C. to 80° C., and more preferably 20° C. to 40° C. when the base is potassium carbonate, and is preferably −78° C. to 80° C., and more preferably −10° C. to 40° C. when the base is sodium hydride, for example. Various derivatives can be synthesized by treating the ketone derivative (4c-1r) in the same manner as in Schemes 4 and 5.

A β-ketoaldehyde equivalent (4c-1s) can be obtained by heating the ketone derivative (4c-1i) and N,N-dimethylformamide dimethyl acetal in a solvent such as toluene or benzene. It is reported that β-ketoaldehyde equivalent such as the equivalent (4c-1s) can be converted to a pyridone derivative, a pyrimidine derivative, a pyrazole derivative, an oxazole derivative or the like (see Bioorganic & Medicinal Chemistry (2003) Vol. 11, No. 22, 4749-4759, for example, for the method for converting a β-ketoaldehyde equivalent to a pyridone derivative; see Journal of Medicinal Chemistry (1978) Vol. 21, No. 7, 623-628 for the method for converting a β-ketoaldehyde equivalent to a pyrimidine derivative; see Journal of Heterocyclic Chemistry (1982) Vol. 19, No. 6, 1355-1361 for the method for converting β-ketoaldehyde equivalent to a pyrazole derivative; see Journal of Heterocyclic Chemistry (1983), Vol. 20, No. 3, 645-648 for the method for converting a β-ketoaldehyde equivalent to an oxazole derivative). For example, the equivalent (4c-1s) can be converted to an oxazole derivative (4d-1t) by treatment with hydroxylamine hydrochloride. The equivalent (4c-1s) can also be converted to a pyrazole derivative (4d-1u) by treatment with hydrazine.

The ketone derivative (4c-1i) can also be converted to a triflate compound (4-1v) by treatment with trifluoromethanesulfonic anhydride in the presence of a base. Examples of the solvent include methylene chloride, acetonitrile, tetrahydrofuran and N,N-dimethylformamide. The solvent is preferably methylene chloride. Examples of the base include sodium hydride, potassium hydride, sodium hydroxide, potassium hydroxide, potassium carbonate, sodium tert-butoxide, potassium tert-butoxide, pyridine, triethylamine, DBU and diisopropylethylamine. The base is preferably triethylamine. The reaction temperature is suitably −80° C. to 150° C., and preferably −10° C. to 40° C. Then, a vinyl or aryl derivative (4d-2v) can be produced from the triflate compound (4d-1v) by coupling reaction with an organoboronic acid derivative in the presence of a metal catalyst and a base. An appropriate additive may be used in the coupling reaction to promote the reaction. The organoboronic acid derivative is commercially available or can be produced by a known method. A reference on the method for producing an organoboronic acid derivative and the coupling reaction is Chemical Reviews, 1995, 95, 2457-2483.

The organoboronic acid derivative is preferably used in an amount of 1 to 2 molar equivalents relative to the triflate compound (4d-1v). The metal catalyst is preferably a palladium catalyst. Examples of the palladium catalyst include a [1,1'-bis(diphenylphosphino)ferrocene]dichloropalladium (II)/dichloromethane complex (1:1), dichlorobis(triphenylphosphine)palladium (II) and tetrakis(triphenylphosphine)palladium (0). The metal catalyst is preferably used in an amount of 0.01 to 0.2 molar equivalent relative to the triflate compound (4d-1v). Examples of the base include inorganic bases such as tripotassium phosphate, potassium carbonate, sodium carbonate and cesium carbonate. The base is preferably tripotassium phosphate, sodium carbonate or the like. The base is preferably used in an amount of 1 to 100 molar equivalents relative to the triflate compound (4d-1v). Examples of the additive include organophosphorus compounds such as 1,1'-bis(diphenylphosphino)ferrocene (dppf) and triphenylphosphine. The additive is preferably used in an amount of 0.05 to 0.2 molar equivalent relative to the triflate compound (4d-1v).

The solvent for the coupling reaction is not particularly limited so long as it does not inhibit the reaction and dissolves the starting material to a certain extent. Preferred examples of the solvent include ether solvents such as 1,4-dioxane and 1,2-dimethoxyethane, amide solvents such as N,N-dimethylformamide and N-methyl-2-pyrrolidone, hydrocarbon solvents such as toluene and benzene, alcohol solvents such as methanol and ethanol, and polar solvents such as acetonitrile and water. These solvents may be used as a mixed solvent of two or more. The reaction temperature is 10° C. to the boiling point of the solvent, and preferably room temperature to 100° C. The reaction time is usually about 1 to 50 hours.

The triflate compound (4d-1v) can be converted to an ester compound (4d-1w) by reaction under the above reaction conditions without using an organoboronic acid derivative in an alcohol as a solvent in a carbon monoxide atmosphere. The alcohol is preferably methanol or ethanol.

A carboxylic acid derivative (4d-2w) can be produced by hydrolysis reaction of the ester derivative compound (4d-1w). The hydrolysis reaction is preferably a known alkali hydrolysis. A reference is Jikken Kagaku Koza (Courses in Experimental Chemistry) (4th edition, Vol. 22, edited by The Chemical Society of Japan, Maruzen Co., Ltd.) "Yuki Gosei (Organic Synthesis) IV: San, Aminosan, Peputido (Acids, Amino Acids, Peptides)", pp. 6-11. An amide derivative (4d-3w) can be produced in the same manner as in Scheme 2.

An alcohol derivative (4d-3x) can be produced by reducing the carboxylic acid derivative (4d-2w). The reduction reaction is preferably a known reduction reaction. A reference is Jikken Kagaku Koza (Courses in Experimental Chemistry) (3rd edition, Vol. 14, edited by The Chemical Society of Japan, Maruzen Co., Ltd.) "Yuki Kagobutsu No Hannou To Gohsei (Reaction and Synthesis of Organic Compounds) [1]", pp. 477-478.

An acetic acid ester derivative (4d-1y) can be produced from the ketone derivative (4c-1i) by a homologation typified by Wittig reaction. The homologation is preferably a known reaction, and may be one described in Jikken Kagaku Koza (Courses in Experimental Chemistry) (4th edition, Vol. 22, edited by The Chemical Society of Japan, Maruzen Co., Ltd.) "Yuki Gosei (Organic Synthesis) I: Tankasuiso, Harogen Kagobutsu (Hydrocarbons, Halogen Compounds)", pp. 57-69. An acetic acid derivative (4d-2y) can be produced from the acetic acid ester derivative (4d-1y) by the same hydrolysis reaction as above. An acetic acid amide derivative (4d-3y) can be produced in the same manner as in Scheme 2.

An amine derivative (4d-3z) can be produced by rearrangement reaction of the carboxylic acid derivative (4d-2y). The rearrangement reaction is preferably a known rearrangement reaction. A reference is Jikken Kagaku Koza (Courses in Experimental Chemistry) (4th edition, Vol. 22, edited by The Chemical Society of Japan, Maruzen Co., Ltd.) "Yuki Gosei (Organic Synthesis) II: Arukoru, Amin (Alcohols, Amines)", pp. 302-308. An amine derivative (4d-4-z) can be produced by modification by the same method as shown in Scheme 5.

An ethanol derivative (4d-2a) can be produced by reducing the acetic acid ester derivative (4d-1y). The reduction reaction is preferably a known reduction reaction. A reference is Jikken Kagaku Koza (Courses in Experimental Chemistry) (3rd edition, Vol. 14, edited by The Chemical Society of Japan, Maruzen Co., Ltd.) "Yuki Kagobutsu No Hannou To Gohsei (Reaction and Synthesis of Organic Compounds) [1]", pp. 474-477. An ethylamine derivative (4d-2b) can be produced by substitution reaction. The substitution reaction is preferably a known reaction, and may be one described in Jikken Kagaku Koza (Courses in Experimental Chemistry) (4th edition, Vol. 22, edited by The Chemical Society of Japan, Maruzen Co., Ltd.) "Yuki Gosei (Organic Synthesis) II: Arukoru, Amin Kagobutsu (Alcohols, Amine Compounds)", pp. 284-290.

The compounds (4c-1r), (4d-1t), (4d-1u), (4d-2v), (4d-3w), (4d-3x), (4d-3y), (4d-4-z) and (4d-2b) can be converted to corresponding amine derivatives (1c-1r), (1d-1t), (1d-1u), (1d-1v), (1d-1w), (1d-1x), (1d-1y), (1d-1z) and (1d-2a), respectively, by treatment under appropriate deprotection reaction conditions suitable for the protecting group.

(III) Raw Material Production Steps

The compound (6) shown in Scheme 1 can be produced according to the method described below, for example, based on common knowledge in organic chemistry with reference to documents related to production of various 1H-pyrazolo [3,4-d]pyrimidine derivatives (for example, Synthesis, Vol. 10, pp. 645-647, 1975; Tetrahedron, Vol. 48, pp. 8089-8100, 1992; WO 2005/28434; or WO 98/4399) and the like.

A compound (6a) which is a synthetic raw material for the compound of the general formula (1), wherein Ring A is a 7- or 8-membered ring, can be produced according to Scheme 8, for example.

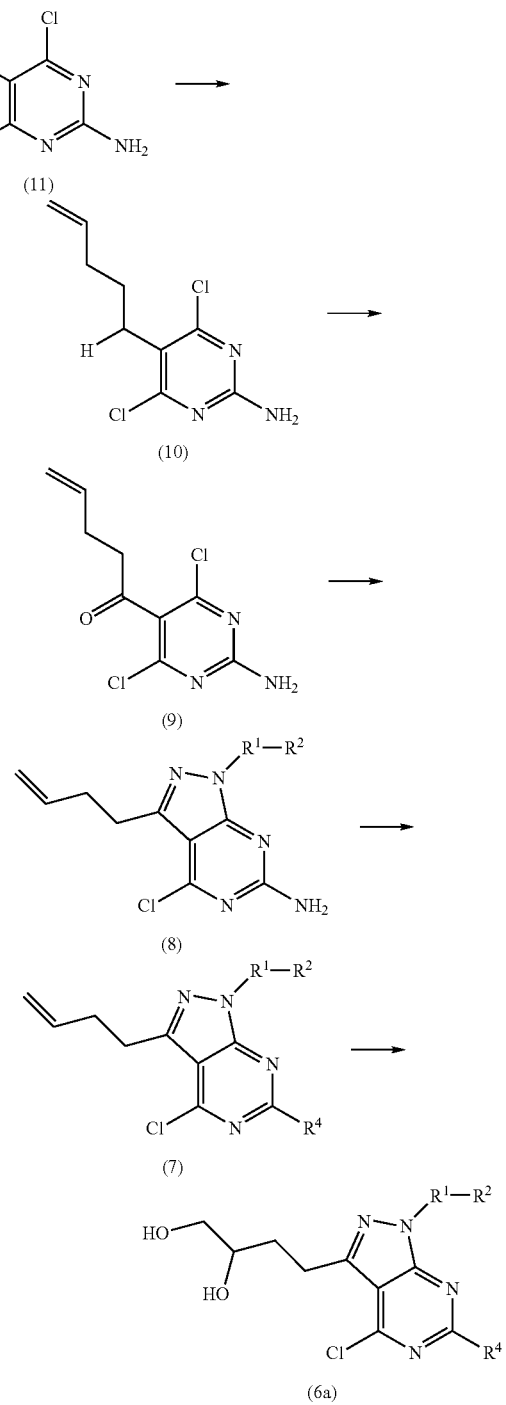

Scheme 8

In each formula, $R^1$, $R^2$ and $R^4$ are as defined above, respectively.

A compound (10) can be obtained by treating an aldehyde derivative (11) with 3-butenylmagnesium bromide in a solvent. Examples of the solvent used in this reaction include toluene, benzene, diethyl ether and tetrahydrofuran. The solvent is preferably tetrahydrofuran. The reaction temperature is suitably −78° C. to 50° C., and preferably −20° C. to 30° C.

The compound (10) can be converted to a ketone derivative (9) by treatment under appropriate oxidation reaction conditions. Examples of the oxidation reaction in that case include Mukaiyama oxidation; Swern oxidation or oxidation reaction as its modification using DCC, trifluoroacetic anhydride, acetic anhydride or a sulfur trioxide-pyridine complex instead of oxalyl chloride; and oxidation reaction using manganese dioxide.

The ketone derivative (9) can be converted to a compound (8) by treatment with $R^2$—$R^1$—$NHNH_2$ in a solvent. Examples of the solvent used in this reaction include alcohols, methylene chloride, tetrahydrofuran, dioxane and mixed solvents thereof. The reaction temperature is suitably −20° C. to 50° C., and preferably −10° C. to 30° C. When $R^2$—$R^1$—$NHNH_2$ is replaced with its salt, an equivalent or excess of a base relative to the salt may be suitably used. Examples of the base include triethylamine.

A diol derivative (6a) can be obtained by protecting the amino group at the 6-position of the compound (8) with an appropriate protecting group to convert it to a compound (7) and then performing 1,2-dihydroxylation. Examples of the dihydroxylation of an alkene include reaction using potassium permanganate in the presence of an alkali, water addition reaction in the presence of mercury salt (Kucherov-Deniges method), osmium oxidation reaction using a catalytic amount of osmium tetroxide and an amine oxide as a co-oxidant, and dihydroxylation reaction using iodine (Prevoat method or Woodward method).

The diol derivative (6a) can be converted to the compound (5) described in Scheme 1 by protecting its primary hydroxyl group with a bulky protecting group such as a tert-butyldiphenylsilyl group and then converting its secondary hydroxyl group to a leaving group $LG^2$ (such as a p-toluenesulfonyloxy group or a methanesulfonyloxy group), and then the compound (5) can be converted to the compound (4), wherein Ring A is a 7-membered ring, by subjecting the compound to cyclization reaction.

Alternatively, the diol derivative (6a) can be converted to the compound (5) described in Scheme 1 by selectively converting its primary hydroxyl group to a leaving group $LG^2$ (such as a p-toluenesulfonyloxy group or a methanesulfonyloxy group), and then the compound (5) can be converted to the compound (4), wherein Ring A is an 8-membered ring, by subjecting the compound to cyclization reaction.

In the reaction of producing the compound (10) from the compound (11) as described in Scheme 8, the following diol derivative (6b) which is a raw material for the compound (1), wherein Ring A is an 8-membered ring, can be obtained by performing the same reaction using 3-butenylmagnesium bromide instead of 4-pentenylmagnesium bromide.

In the formula, $R^1$, $R^2$ and $R^4$ are as defined above, respectively.

The diol derivative (6b) can be converted to the compound (5) described in Scheme 1 by protecting its primary hydroxyl group with a bulky protecting group such as a tert-butyldiphenylsilyl group and then converting its secondary hydroxyl group to a leaving group $LG^2$ (such as a p-toluenesulfonyloxy group or a methanesulfonyloxy group), and then the compound (5) can be converted to the compound (4), wherein Ring A is an 8-membered ring, by subjecting the compound to cyclization reaction.

The compound of the general formula (1), wherein Ring A is a 6- or 7-membered ring, can be produced from a diol derivative (6c), for example. The diol derivative (6c) can be produced according to Scheme 9.

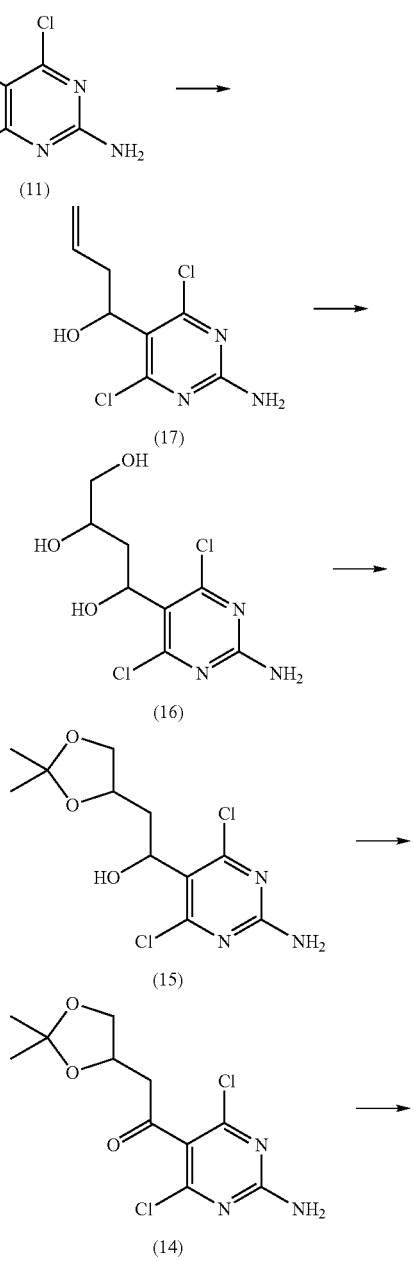

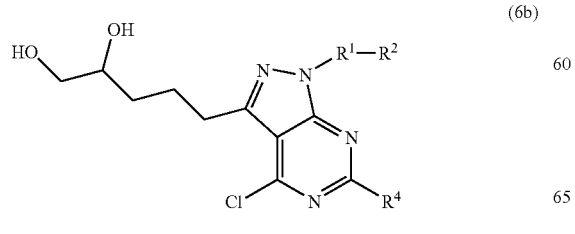

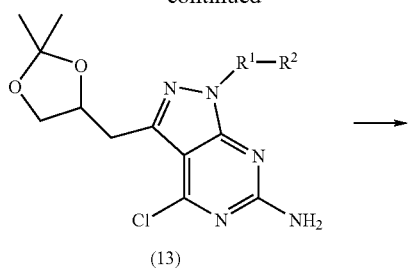

(13)

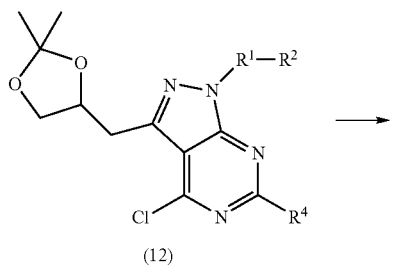

(12)

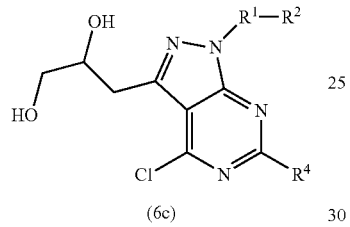

(6c)

Scheme 10

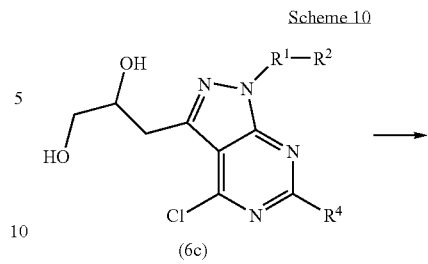

(6c)

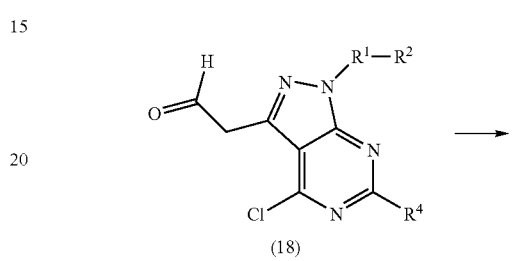

(18)

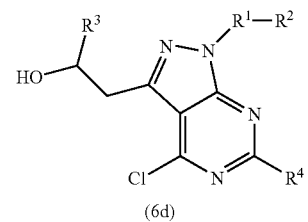

(6d)

In each formula, $R^1$, $R^2$ and $R^4$ are as defined above, respectively.

A compound (17) can be obtained by treating the aldehyde derivative (11) with allyl bromide and indium powder in a solvent. The alkene derivative (17) can also be obtained by Grignard reaction using the aldehyde derivative (11) and allylmagnesium bromide. A triol derivative (16) can be obtained by the aforementioned 1,2-dihydroxylation of the alkene derivative (17). The triol derivative (16) can be converted to an acetal derivative (15) by treatment with 2,2-dimethoxypropane and a catalytic amount of an acid in a solvent, or by treatment with an acid catalyst in acetone. Examples of the acid catalyst include p-toluenesulfonic acid. The acetal derivative (15) can be converted to an acetal derivative (12) through a compound (14) and a compound (13) by the same three-step treatment as in the conversion from the compound (10) to the compound (7) in Scheme 8 as described above. The diol derivative (6c) can be obtained by treating the acetal derivative (12) with a catalytic amount of an acid in an alcohol.

The diol derivative (6c) can be converted to the compound (4), wherein Ring A is a 6- or 7-membered ring, by the same method as the aforementioned method of converting the diol derivative (6a) to the compound (4), wherein Ring A is a 7- or 8-membered ring.

An alcohol derivative (6d) can be obtained by further converting the diol derivative (6c) according to the method described in Scheme 10. The alcohol derivative (6d) can be used as the starting compound (6) when Ring A of the compound (1) in Scheme 1 is a 6-membered ring.

In each formula, $R^1$, $R^2$, $R^3$ and $R^4$ are as defined above, respectively.

An aldehyde derivative (18) can be obtained by oxidation reaction of the diol derivative (6c) with sodium periodate. The alcohol derivative (6d) can be obtained by reacting the aldehyde derivative (18) with various nucleophilic reagents in a solvent. Trimethylsilyl cyanide, various Grignard reagents, organolithium reagents or organozinc reagents and the like can be used as a nucleophilic reagent. This reaction makes it possible to obtain the alcohol derivative (6d), wherein the substituent $R^3$ is a cyano group, an alkyl group having 1 to 8 carbon atoms which may have a substituent(s), an alkenyl group having 2 to 8 carbon atoms which may have a substituent(s), an alkynyl group having 2 to 8 carbon atoms which may have a substituent(s), an aryl group which may have a substituent(s), a heterocyclic group which may have a substituent(s), or the like.

An alcohol derivative (6e) or an alcohol derivative (6f) can be obtained, respectively, by performing the same reaction described in Scheme 9 using the diol derivative (6a) or the diol derivative (6b) instead of the diol derivative (6c). The alcohol derivative (6e) can be used as the starting compound (6) when Ring A of the compound (1) in Scheme 1 is a 7-membered ring. The alcohol derivative (6f) can be used as the starting compound (6) when Ring A of the compound (1) in Scheme 1 is an 8-membered ring.

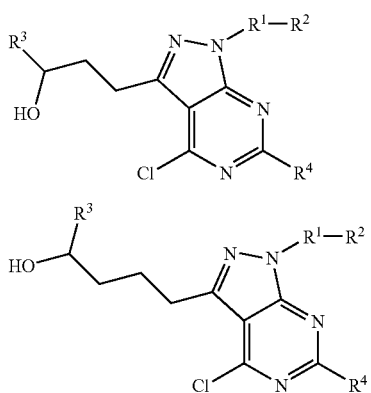

In each formula, $R^1$, $R^2$, $R^3$ and $R^4$ are as defined above, respectively.

The ATPase activity of HSP90 can be examined by an ATPase assay commonly used by a person skilled in the art. For example, the ATPase activity of HSP90 can be detected using a recombinant HSP90 protein and ATP in the presence or absence of the test compound, as described in Test Example 2 below. Alternatively, in an ATPase assay, the method described in Analytical Biochemistry 327, 176-183 (2004) or Nature 425, 407-410 (2003) may be suitably performed, for example.

Inhibition of the expression of HSP90 can be examined by Northern blotting, Western blotting, ELISA or the like commonly used by a person skilled in the art. For example, mRNA is recovered from cells cultured in the presence or absence of the test compound to perform Northern blotting. When the amount of HSP90 mRNA in mRNA recovered from the cells cultured in the presence of the test compound is reduced from that in mRNA recovered from the cells cultured in the absence of the test compound, the test compound is identified as a compound inhibiting the expression of HSP90. Alternatively, the amount of HSP90 protein may be suitably examined by performing Western blotting using the method described in Cancer. Res. 65, 6401-6408 (2005), for example.

Inhibition of binding of HSP90 to a client protein can be examined by immunoprecipitation and Western blotting commonly used by a person skilled in the art, for example. In immunoprecipitation and Western blotting, the method described in J. Biol. Chem. 277, 10346-10353 (2002) may be suitably performed, for example.

The compound inhibiting binding of HSP90 to co-chaperones or immunophilins can be examined by immunoprecipitation and Western blotting commonly used by a person skilled in the art, for example. Binding of HSP90 to co-chaperones or immunophilins may be suitably examined in the presence or absence of the test compound by performing the method described in Nature 425, 407-410 (2003), for example.

Inhibition of binding of HSP90 to ATP can be examined by a test for binding of labeled ATP to HSP90, for example. Binding of HSP90 to labeled ATP may be suitably examined in the presence or absence of the test compound by performing the method described in J. Biol. Chem. 272, 18608-18613 (1997), for example.

Inhibition of the conformational change of HSP90 can be examined by a conformational assay using bis-ANS (1,1'-bis (4-anilino-5-naphthalenesulfonic acid)), for example. In the conformational assay, the method described in J. Med. Chem. 47, 3865-3873 (2004) may be suitably performed, for example.

The compound of the present invention can be used for treatment of various cancers such as lung cancer, gastrointestinal cancer, ovarian cancer, uterine cancer, breast cancer, liver cancer, head and neck cancer, blood cancer, renal cancer and testicular neoplasm, for example.

The pharmaceutical composition comprising the compound of the present invention can be administered as various injections for intravenous injection, intramuscular injection, subcutaneous injection and the like, or by various methods such as oral administration and transdermal administration. Among these administration methods, intravenous administration and oral administration using an aqueous formulation are preferable. The aqueous formulation can be prepared by forming an acid adduct with a pharmacologically acceptable acid or forming a salt of an alkali metal such as sodium. In the case of oral administration, the aqueous formulation may be either a free form or a salt form.

Appropriate formulations can be selected according to the administration method and prepared by a method for preparing various formulations commonly used. Examples of oral formulations among dosage forms of the antitumor agent of the present invention include tablets, powders, granules, capsules, solutions, syrups, elixirs and oily or aqueous suspensions. When the formulation is an injection, a stabilizer, a preservative, a solubilizer or the like can also be used in the formulation. The injection may be provided as a formulation to be prepared before use by storing a solution which may contain such an adjuvant or the like in a container and then converting it to a solid formulation by lyophilization or the like. One dose may be stored in one container, or multiple doses may be stored in one container.

Examples of solid formulations include tablets, capsules, granules, pills, troches and powders. These solid formulations may contain a pharmaceutically acceptable additive together with the compound of the present invention. Examples of the additive include fillers, bulking agents, binders, disintegrants, solubilizers, wetting agents and lubricants. These can be selectively mixed as necessary to provide a formulation.

Examples of liquid formulations include solutions, elixirs, syrups, suspensions and emulsions. These liquid formulations may contain a pharmaceutically acceptable additive together with the compound of the present invention. Examples of the additive include suspending agents and emulsifiers. These can be selectively mixed as necessary to provide a formulation.

The compound of the present invention can be used for treating cancer of mammals, in particular humans. The dose and the dosage interval may be appropriately selected based on the judgment of the physician according to the site of disease and the body height, body weight, sex or medical history of the patient. When the compound of the present invention is administered to a human, the dose range is about 0.01 mg/kg body weight to 100 mg/kg body weight, preferably about 0.05 mg/kg body weight to 50 mg/kg body weight, and more preferably 0.1 mg/kg body weight to 10 mg/kg body weight per day. When the compound is administered to a human, the compound is preferably administered in one dose or two to four separate doses per day, and the administration is preferably repeated at appropriate intervals. The daily dose may exceed the aforementioned dose if necessary, based on the judgment of the physician.

The present invention will be specifically described with reference to Examples shown below; however, the present invention is not limited thereto, and they should not be construed as limitative in any sense. Reagents, solvents and starting materials not specifically described herein are readily available from commercial sources.

EXAMPLES

Example 1

Di-tert-butyl {2-[(4-methoxy-3,5-dimethylpyridin-2-yl)methyl]-7,8-dihydro-2H-6-thia-1,2,3,5-tetraazaacenaphthylen-4-yl}imidodicarbonate 1) 1-(2-Amino-4,6-dichloropyrimidin-5-yl)-3-buten-1-ol

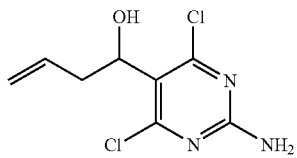

Indium powder (45.81 g) was added to a mixture composed of 2-amino-4,6-dichloropyrimidine-5-carboaldehyde (63.83 g) and N,N-dimethylformamide (500 mL). Then, sodium iodide (99.66 g) was added at an internal temperature of 10° C. under cooling in an ice bath. Allyl bromide (67.5 mL) was added to the resulting mixture over 20 minutes. After confirming that the internal temperature once increased was decreased, the ice bath was removed and the mixture was stirred for two hours. The reaction mixture was concentrated to about 200 mL under reduced pressure. Then, ethyl acetate (1.5 L) and a saturated sodium bicarbonate solution (1 L) were added to the residue, followed by stirring. The mixture was filtered through Celite and the filtrate was separated. Then, the organic layer was sequentially washed with water and brine. The organic layer was dried over anhydrous sodium sulfate and filtered. Then, the filtrate was concentrated to about 150 mL under reduced pressure. Hexane was added to the resulting residue, followed by stirring. Then, the solid was collected by filtration to obtain the title compound (57.24 g, 74%) as a solid.

¹H-NMR (CDCl₃) δ: 2.46 (1H, d), 2.66 (1H, ddd), 2.82 (1H, ddd), 5.13 (1H, d), 5.16 (1H, d), 5.27 (1H, dd), 5.33 (2H, br.s), 5.75-5.85 (1H, m).

2) 1-(2-Amino-4,6-dichloropyrimidin-5-yl)-2-(2,2-dimethyl-[1,3]dioxolan-4-yl)ethan-1-ol

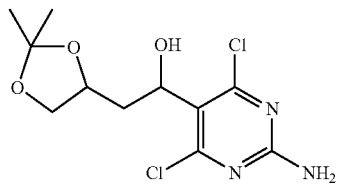

A mixture composed of the above 1-(2-amino-4,6-dichloropyrimidin-5-yl)-3-buten-1-ol (57.24 g), N-methylmorpholine-N-oxide (147.6 g), tetrahydrofuran (500 mL), acetone (500 mL), water (500 mL) and osmium tetroxide (62 mg) was stirred at room temperature for two days. After confirming that the raw material disappeared, a saturated sodium thiosulfate solution (1 L) was added, and the reaction mixture was concentrated to about 1.5 L under reduced pressure. The residue was saturated with sodium chloride, followed by extraction with tetrahydrofuran. The organic layer was dried over anhydrous sodium sulfate and filtered. Then, the filtrate was concentrated under reduced pressure to evaporate the solvent. N,N-Dimethylformamide (500 mL), 2,2-dimethoxypropane (210 mL) and p-toluenesulfonic acid monohydrate (18.61 g) were added to the resulting residue, and the mixture was stirred at room temperature for 14 hours. A saturated sodium bicarbonate solution (1 L) and water (1 L) were added to the reaction mixture, followed by extraction with ethyl acetate. The organic layer was sequentially washed with water and brine and dried over anhydrous sodium sulfate. After filtration, the filtrate was concentrated to about 100 mL under reduced pressure. Hexane was added to the residue, followed by stirring. The precipitated crystals were collected by filtration to obtain the title compound (53.88 g, 77%) as a solid.

3) 1-(2-Amino-4,6-dichloropyrimidin-5-yl)-2-(2,2-dimethyl-[1,3]dioxolan-4-yl)ethan-1-one

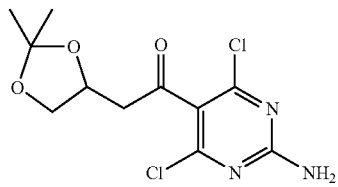

Triethylamine (5.25 mL) and a sulfur trioxide-pyridine complex (2.45 g) were added to a mixture composed of the above 1-(2-amino-4,6-dichloropyrimidin-5-yl)-2-(2,2-dimethyl-[1,3]dioxolan-4-yl)ethan-1-ol (2.32 g) and dimethyl sulfoxide (30 mL) under cooling in an ice bath. The ice bath was removed and the mixture was stirred for two hours. The reaction mixture was added dropwise to a 0.5 N hydrochloric acid solution (300 mL), followed by extraction with ethyl acetate. The organic layer was sequentially washed with water and brine and then dried over anhydrous magnesium sulfate. After filtration, the filtrate was concentrated under reduced pressure and the solvent was evaporated to obtain a crude product of the title compound (2.08 g, 90%) as a solid. The resulting compound was directly used for the next reaction without purification.

ESI-MS m/z: 270 (M+H)$^+$.

4) [(4-Methoxy-3,5-dimethylpyridin-2-yl)methyl]-hydrazine hydrochloride

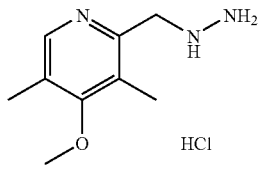

2-(Chloromethyl)-4-methoxy-3,5-dimethylpyridine (125.95 g) was added to a mixture of hydrazine monohydrate (360 ml) and methanol (3.3 L) under cooling in an ice bath, and the mixture was stirred for 30 minutes. Then, the ice bath was removed and the mixture was heated with stirring at 60° C. for 2.5 hours. After cooling to room temperature, water (1.5 L) was added to the reaction mixture, and about 3.5 L of the solvent was evaporated under reduced pressure. A 2 N sodium hydroxide solution (1 L) and sodium chloride (300 g) were added to the resulting concentrated residue, followed by extraction with dichloromethane. The organic layer was dried over anhydrous sodium sulfate and filtered. Then, the filtrate was concentrated under reduced pressure. The resulting residue was dissolved in dichloromethane (1.5 L). A 4 N solution of hydrochloric acid in dioxane (550 ml) was added under cooling in an ice bath, and then the mixture was stirred at −2° C. for 13 hours. The precipitated solid was collected by filtration, sequentially washed with dichloromethane, isopropyl ether and dichloromethane, and then dried to obtain the title compound (112.6 g, 68%).

$^1$H-NMR (DMSO-d$_6$) δ: 2.32 (3H, s), 2.38 (3H, s), 3.98 (2H, s), 4.41 (2H, s), 8.57 (1H, s).

5) 4-Chloro-3-[(2,2-dimethyl-1,3-dioxolan-4-yl)methyl]-1-[(4-methoxy-3,5-dimethylpyridin-2-yl)methyl]-1H-pyrazolo[3,4-d]pyrimidin-6-amine

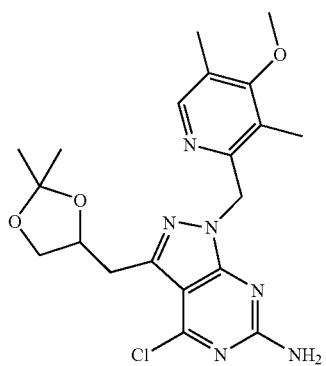

A solution of triethylamine (3.44 mL) in dehydrated dichloromethane was added to a mixture composed of 1-(2-amino-4,6-dichloropyrimidin-5-yl)-2-(2,2-dimethyl-[1,3]dioxolan-4-yl)ethan-1-one of 3) above (1.68 g), [(4-methoxy-3,5-dimethylpyridin-2-yl)methyl]-hydrazine hydrochloride of 4) above (2.87 g) and dehydrated dichloromethane (60 mL) under cooling in an ice bath over 20 minutes. The ice bath was removed, followed by stirring for two hours. Then, the reaction mixture was separated with chloroform and water. The organic layer was washed with water and then dried over anhydrous magnesium sulfate. After filtration, the filtrate was concentrated under reduced pressure. The resulting residue was purified by silica gel column chromatography (ethyl acetate-chloroform) to obtain the title compound (1.79 g, 75%) as a solid.

$^1$H-NMR (CDCl$_3$) δ: 1.35 (3H, s), 1.41 (3H, s), 2.22 (3H, s), 2.29 (3H, s), 3.10 (1H, dd), 3.44 (1H, dd), 3.71-3.74 (1H, m), 3.74 (3H, s), 4.02 (1H, dd), 4.55-4.60 (1H, m), 5.21 (2H, br.s), 5.47 (2H, s), 8.15 (1H, s).

ESI-MS m/z: 433 (M+H)$^+$.

6) Di-tert-butyl {4-chloro-3-[(2,2-dimethyl-1,3-dioxolan-4-yl)methyl]-1-[(4-methoxy-3,5-dimethylpyridin-2-yl)methyl]-1H-pyrazolo[3,4-d]pyrimidin-6-yl}imidodicarbonate

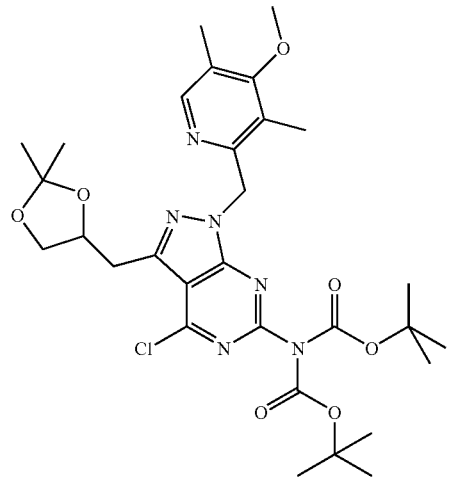

4-Dimethylaminopyridine (36 mg) and di-tert-butyl dicarbonate (3.90 g) were added to a mixture composed of 4-chloro-3-[(2,2-dimethyl-1,3-dioxolan-4-yl)methyl]-1-[(4-methoxy-3,5-dimethylpyridin-2-yl)methyl]-1H-pyrazolo[3,4-d]pyrimidin-amine of 5) above (1.29 g) and dehydrated tetrahydrofuran (50 mL), and the mixture was stirred at room temperature for 12 hours. The reaction mixture was filtered and then the filtrate was concentrated under reduced pressure. The resulting residue was purified by silica gel column chromatography (ethyl acetate-hexane) to obtain the title compound (1.63 g, 86%) as an oil.

$^1$H-NMR (CDCl$_3$) δ: 1.35 (3H, s), 1.38 (3H, s), 1.42 (18H, s), 2.20 (3H, s), 2.26 (3H, s), 3.27 (1H, dd), 3.53 (1H, dd), 3.74 (3H, s), 3.76 (1H, dd), 4.04 (1H, dd), 4.57-4.64 (1H, m), 5.65 (1H, dd), 8.07 (1H, s).

ESI-MS m/z: 633 (M+H)$^+$.

7) Di-tert-butyl {4-chloro-3-(2,3-dihydroxypropyl)-1-[(4-methoxy-3,5-dimethylpyridin-2-yl)methyl]-1H-pyrazolo[3,4-d]pyrimidin-6-yl}imidodicarbonate

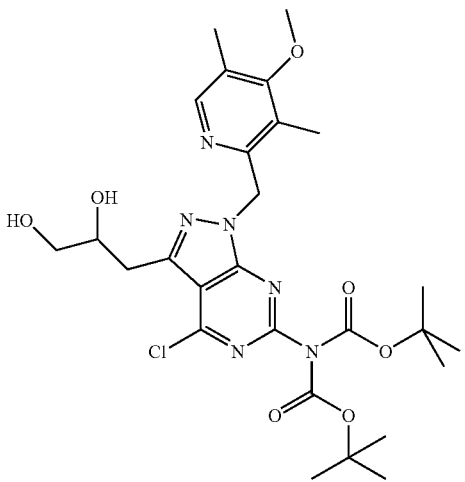

p-Toluenesulfonic acid monohydrate (3.76 g) was added to a solution of di-tert-butyl {4-chloro-3-[(2,2-dimethyl-1,3-dioxolan-4-yl)methyl]-1-[(4-methoxy-3,5-dimethylpyridin-2-yl)methyl]-1H-pyrazolo[3,4-d]pyrimidin-6-yl}imidodicarbonate of 6) above (12.52 g) in methanol (250 mL), and the mixture was stirred at room temperature for seven hours. The reaction mixture was poured into brine, followed by extraction with ethyl acetate. The organic layer was washed with brine, and then dried over anhydrous sodium sulfate. After filtration, the filtrate was concentrated under reduced pressure. The resulting residue was purified by silica gel column chromatography (ethyl acetate-methanol) to obtain the title compound (9.64 g, 82%) as an amorphous substance.

$^1$H-NMR (CDCl$_3$) δ: 1.42 (18H, s), 2.20 (3H, s), 2.29 (3H, s), 2.77-2.80 (1H, m), 3.31-3.33 (2H, m), 3.51-3.54 (1H, m), 3.64-3.67 (1H, m), 3.74 (3H, s) 3.76-3.79 (1H, m) 4.24-4.30 (1H, m) 5.66 (2H, s), 8.03 (1H, s).

ESI-MS m/z: 593 (M+H)$^+$.

8) Di-tert-butyl {4-chloro-3-(2-hydroxyethyl)-1-[(4-methoxy-3,5-dimethylpyridin-2-yl)methyl]-1H-pyrazolo[3,4-d]pyrimidin-6-yl}imidodicarbonate

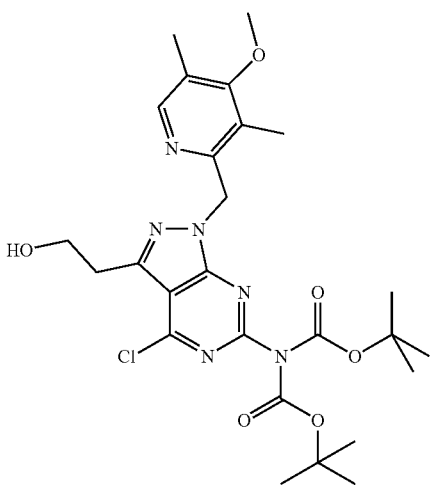

Sodium periodate (278 mg) was added to a mixture composed of di-tert-butyl{4-chloro-3-[(2,3-dihydroxypropyl-1-[(4-methoxy-3,5-dimethylpyridin-2-yl)methyl]-1H-pyrazolo[3,4-d]pyrimidin-6-yl}imidodicarbonate of 7) above (154 mg), tetrahydrofuran (1 mL), methanol (1 mL) and water (1 mL) under cooling in an ice bath. The ice bath was removed and the mixture was stirred for one hour. The reaction mixture was separated with a saturated sodium bicarbonate solution (40 mL) and ethyl acetate (40 mL). The organic layer was washed with brine, and then dried over anhydrous sodium sulfate and filtered. Then, the filtrate was concentrated under reduced pressure. Methanol (4 mL) was added to the resulting residue. Sodium borohydride (25 mg) was added in small portions under cooling in an ice bath, and the mixture was stirred for one hour. The reaction mixture was diluted with ethyl acetate and then sequentially washed with a 0.1 N hydrochloric acid solution and brine. The organic layer was dried over anhydrous sodium sulfate and filtered. Then, the filtrate was concentrated under reduced pressure and the solvent was evaporated to obtain a crude product of the title compound (129 mg, 88%) as an oil. The resulting compound was directly used for the next reaction without purification.

$^1$H-NMR (CDCl$_3$) δ: 1.43 (18H, s), 2.21 (3H, s), 2.28 (3H, s), 3.36 (2H, t), 3.75 (3H, s), 4.07 (2H, t), 5.66 (2H, s), 8.07 (1H, s).

ESI-MS m/z: 563 (M+H)$^+$.

9) 2-{6-[Bis(tert-butoxycarbonyl)amino]-4-chloro-1-[(4-methoxy-3,5-dimethylpyridin-2-yl)methyl]-1H-pyrazolo[3,4-d]pyrimidin-3-yl}ethyl 4-methylbenzenesulfonate

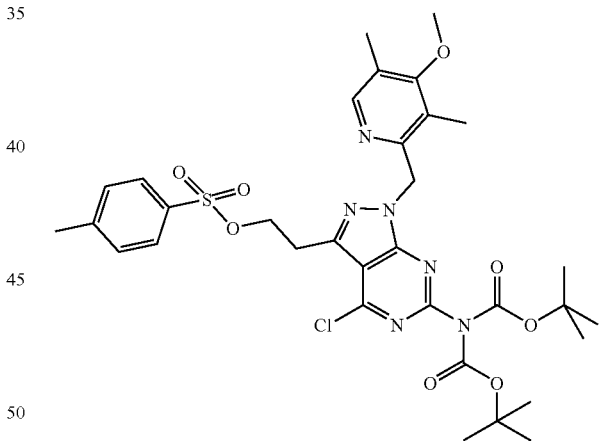

Triethylamine (0.048 mL), p-toluenesulfonyl chloride (43 mg) and 4-dimethylaminopyridine (0.7 mg) were added to a mixture composed of di-tert-butyl{4-chloro-3-(2-hydroxyethyl)-1-[(4-methoxy-3,5-dimethylpyridin-2-yl)methyl]-1H-pyrazolo[3,4-d]pyrimidin-6-yl}imidodicarbonate of 8) above (64 mg) and dehydrated dichloromethane (1 mL) under cooling in an ice bath. The ice bath was removed and the mixture was stirred for 12 hours. The reaction mixture was diluted with ethyl acetate and sequentially washed with water and brine. The organic layer was dried over anhydrous sodium sulfate and filtered, and then the filtrate was concentrated under reduced pressure. The resulting residue was purified by silica gel column chromatography (ethyl acetate-hexane) to obtain the title compound (74 mg, 91%) as an amorphous substance.

ESI-MS m/z: 717 (M+H)$^+$.

10) Di-tert-butyl {2-[(4-methoxy-3,5-dimethylpyridin-2-yl)methyl]-7,8-dihydro-2H-6-thia-1,2,3,5-tetraazaacenaphthylen-4-yl}imidodicarbonate

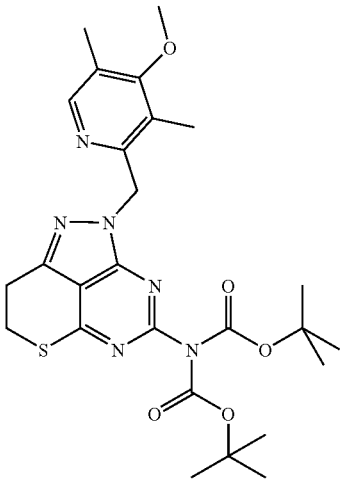

A mixture composed of 2-{6-[bis(tert-butoxycarbonyl)amino]-4-chloro-1-[4-methoxy-3,5-dimethylpyridin-2-yl]methyl]-1H-pyrazolo[3,4-d]pyrimidin-3-yl}ethyl 4-methylbenzenesulfonate of 9) above (74 mg), N,N-dimethylformamide (1 mL) and potassium thioacetate (19 mg) under cooling in an ice bath for two hours. Then, the ice bath was removed and the mixture was stirred for 1.5 hours. The reaction mixture was diluted with ethyl acetate and sequentially washed with water and brine. The organic layer was dried over anhydrous sodium sulfate and filtered. Then, the filtrate was concentrated under reduced pressure and the solvent was evaporated to obtain a crude product of the title compound (59 mg) as an oil. The resulting compound was directly used for the next reaction without purification.

ESI-MS m/z: 543 (M+H)$^+$.

Example 2

2-[(4-Methoxy-3,5-dimethylpyridin-2-yl)methyl]-7,8-dihydro-2H-6-thia-1,2,3,5-tetraazaacenaphthylen-4-amine

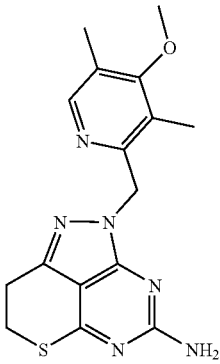

Trifluoroacetic acid (0.5 mL) was added to a mixture composed of di-tert-butyl {2-[(4-methoxy-3,5-dimethylpyridin-2-yl)methyl]-7,8-dihydro-2H-6-thia-1,2,3,5-tetraazaacenaphthylen-4-yl}imidodicarbonate of Step 10) of Example 1 (59 mg) and dichloromethane (2 mL) under cooling in an ice bath. Then, the ice bath was removed and the mixture was stirred for two hours. The reaction solution was concentrated under reduced pressure. Then, the resulting residue was dissolved in ethyl acetate and sequentially washed with a saturated sodium bicarbonate solution and brine. The organic layer was dried over anhydrous magnesium sulfate and filtered. Then, the filtrate was concentrated under reduced pressure. The resulting residue was purified by silica gel column chromatography (ethyl acetate-methanol) to obtain the title compound (26 mg, 85%) as a solid.

$^1$H-NMR (CDCl$_3$) δ: 2.22 (3H, s), 2.28 (3H, s), 3.12 (2H, t), 3.43 (2H, t), 3.74 (3H, s), 5.22 (2H, br.s), 5.44 (2H, s), 8.21 (1H, s).

ESI-MS m/z: 343 (M+H)$^+$.

Example 3

Di-tert-butyl {7-cyano-2-[(4-methoxy-3,5-dimethylpyridin-2-yl)methyl]-7,8-dihydro-2H-6-thia-1,2,3,5-tetraazaacenaphthylen-4-yl}imidodicarbonate 1) Di-tert-butyl {4-chloro-1-[(4-methoxy-3,5-dimethylpyridin-2-yl)methyl]-3-(2-oxoethyl)-1H-pyrazolo[3,4-d]pyrimidin-6-yl}imidodicarbonate

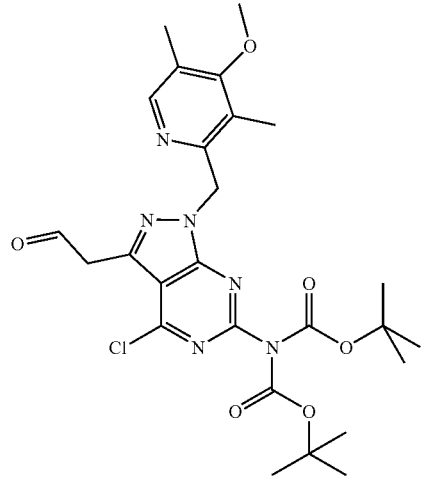

Sodium periodate (1.95 g) was added to a mixture composed of di-tert-butyl {4-chloro-3-(2,3-dihydroxypropyl)-1-[(4-methoxy-3,5-dimethylpyridin-2-yl)methyl]-1H-pyrazolo[3,4-d]pyrimidin-6-yl}imidodicarbonate shown in Step 7) of Example 1 (1.34 g), tetrahydrofuran (15 mL), methanol (15 mL) and water (15 mL) in small portions under cooling in an ice bath. The ice bath was removed and the mixture was stirred for one hour. Ethyl acetate (40 mL) was added to the reaction mixture, followed by filtration. The filtrate was separated, and the organic layer was sequentially washed with water and brine. The organic layer was dried over anhydrous magnesium sulfate and then filtered. The filtrate was concentrated under reduced pressure and the solvent was evaporated to obtain a crude product of the title compound (1.32 g, 104%) as an amorphous substance. The resulting compound was directly used for the next reaction without purification.

$^1$H-NMR (CDCl$_3$) δ: 1.44 (18H, s), 2.22 (3H, s), 2.28 (3H, s), 3.75 (3H, s), 4.21 (1H, d), 5.70 (2H, s), 8.12 (1H, s), 9.90 (1H, t).

2) Di-tert-butyl {4-chloro-3-(2-cyano-2-hydroxy-ethyl)-1-[(4-methoxy-3,5-dimethylpyridin-2-yl)methyl]-1H-pyrazolo[3,4-d]pyrimidin-6-yl}imidodicarbonate

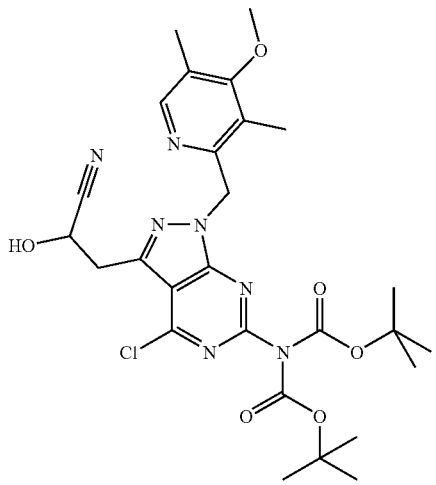

Trimethylsilyl cyanide (0.219 mL) and triethylamine (0.198 mL) were added to a mixture composed of the above di-tert-butyl {4-chloro-1-[(4-methoxy-3,5-dimethylpyridin-2-yl)methyl]-3-(2-oxoethyl)-1H-pyrazolo[3,4-d]pyrimidin-6-yl}imidodicarbonate (796 mg) and dichloromethane (10 mL) under cooling in an ice bath. Then, the ice bath was removed and the mixture was stirred for 16 hours. Chloroform (80 mL) and a 0.5 N hydrochloric acid solution (100 mL) were added to the reaction mixture, followed by separation. The organic layer was dried over anhydrous magnesium sulfate and filtered. Then, the filtrate was concentrated under reduced pressure. The resulting residue was dissolved in acetonitrile (20 mL). A 1 N hydrochloric acid solution (10 mL) was added and the mixture was stirred at room temperature for 30 minutes. A saturated sodium bicarbonate solution (80 mL) was added to the reaction mixture, followed by extraction with ethyl acetate. The organic layer was washed with brine, dried over anhydrous sodium sulfate and then filtered. The filtrate was concentrated under reduced pressure and the solvent was evaporated to obtain a crude product of the title compound (788 mg, 94%). The resulting compound was directly used for the next reaction without purification.

ESI-MS m/z: 588 (M+H)$^+$.

3) 2-{6-[Bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-cyanoethyl 4-methylbenzenesulfonate

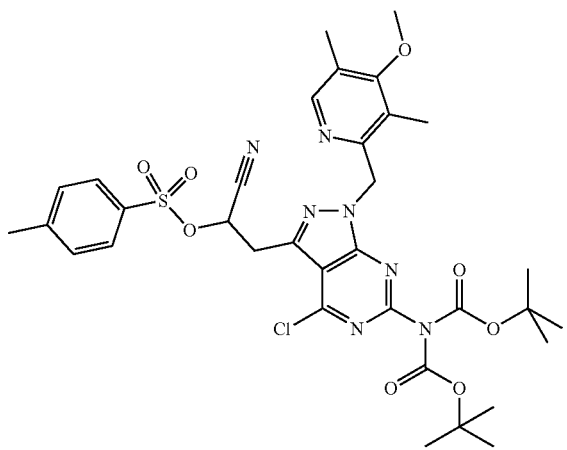

p-Toluenesulfonyl chloride (511 mg) was added to a mixture composed of the above crude di-tert-butyl {4-chloro-3-(2-cyano-2-hydroxyethyl)-1-[(4-methoxy-3,5-dimethylpyridin-2-yl)methyl]-1H-pyrazolo[3,4-d]pyrimidin-6-yl}imidodicarbonate (788 mg) and dehydrated dichloromethane (12 mL), followed by dropwise addition of triethylamine (0.56 mL). Then, 4-dimethylaminopyridine (16 mg) was added and the mixture was stirred at room temperature for three hours. The reaction mixture was diluted with chloroform and washed with water. The organic layer was dried over anhydrous sodium sulfate and then filtered, and the filtrate was concentrated under reduced pressure. The resulting residue was purified by silica gel column chromatography (ethyl acetate-hexane) to obtain the title compound (450 mg, 45%) as a solid.

$^1$H-NMR (CDCl$_3$) δ: 1.45 (18H, s), 2.21 (3H, s), 2.28 (3H, s), 2.44 (3H, s), 3.68-3.80 (5H, m), 5.51 (1H, dd), 5.60 (2H, d), 5.65 (1H, d), 7.28 (2H, d), 7.67 (2H, d), 8.09 (1H, s).

ESI-MS m/z: 742 (M+H)$^+$.

4) Di-tert-butyl {7-cyano-2-[(4-methoxy-3,5-dimethylpyridin-2-yl)methyl]-7,8-dihydro-2H-6-thia-1,2,3,5-tetraazaacenaphthylen-4-yl}imidodicarbonate

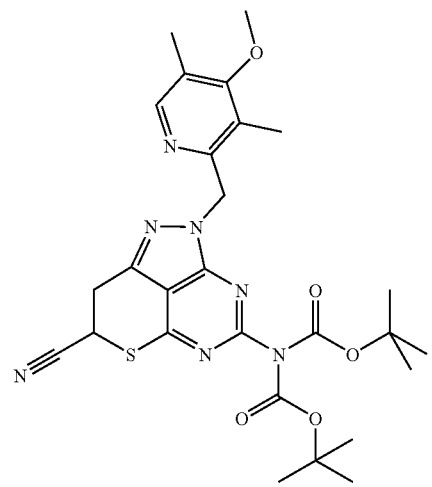

Sodium bisulfide monohydrate (58 mg) was added to a mixture composed of the above 2-{6-[bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-cyanoethyl 4-methylbenzenesulfonate (450 mg) and dehydrated N,N-dimethylformamide (8 mL) under cooling in an ice bath. Then, the ice bath was removed and the mixture was stirred for one hour. Potassium carbonate (84 mg) was added to the reaction mixture, followed by further stirring for 30 minutes. Water (100 mL) was added to the reaction mixture, followed by extraction with ethyl acetate. The organic layer was washed with brine, and then dried over anhydrous sodium sulfate. After filtration, the filtrate was concentrated under reduced pressure. The resulting residue was purified by silica gel column chromatography (ethyl acetate-hexane) to obtain the title compound (277 mg, 81%) as an oil.

$^1$H-NMR (CDCl$_3$) δ: 1.45 (18H, s), 2.22 (3H, s), 2.28 (3H, s), 3.55 (1H, dd), 3.64 (1H, dd), 3.74 (3H, s), 4.58 (1H, dd), 5.66 (2H, s), 8.16 (1H, s).

ESI-MS m/z: 568 (M+H)$^+$.

Example 4

4-Amino-2-[(4-methoxy-3,5-dimethylpyridin-2-yl)methyl]-7,8-dihydro-2H-6-thia-1,2,3,5-tetraazaacenaphthylene-7-carbonitrile

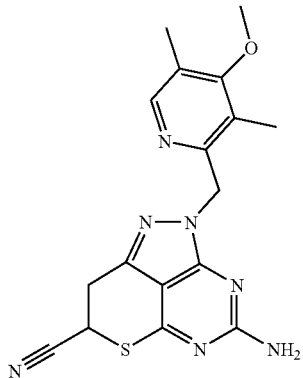

Trifluoroacetic acid (0.25 mL) was added to a mixture composed of di-tert-butyl {7-cyano-2-[(4-methoxy-3,5-dimethylpyridin-2-yl)methyl]-7,8-dihydro-2H-6-thia-1,2,3,5-tetraazaacenaphthylen-4-yl}imidodicarbonate of Step 4) of Example 3 (30 mg) and dichloromethane (1 mL). Then, the ice bath was removed and the mixture was stirred for one hour. After confirming that the raw material disappeared, the reaction mixture was concentrated under reduced pressure. A saturated sodium bicarbonate solution was added to the resulting residue. The precipitated solid was collected by filtration and washed with water. The resulting solid was dried to obtain the title compound (13.8 mg, 71%).

$^1$H-NMR (DMSO-d$_6$) δ: 2.18 (3H, s), 2.22 (3H, s), 3.35 (2H, dd), 3.47 (1H, dd), 3.72 (3H, s), 5.34 (1H, t), 5.37 (2H, s), 7.16 (2H, s), 8.09 (1H, s).
ESI-MS m/z: 368 (M+H)$^+$.

Example 5

2-[(4-Methoxy-3,5-dimethylpyridin-2-yl)methyl]-7-methyl-7,8-dihydro-2H-6-thia-1,2,3,5-tetraazaacenaphthylen-4-amine 1) Di-tert-butyl {4-chloro-3-(2-hydroxypropyl)-1-[(4-methoxy-3,5-dimethylpyridin-2-yl)methyl]-1H-pyrazolo[3,4-d]pyrimidin-6-yl}imidodicarbonate

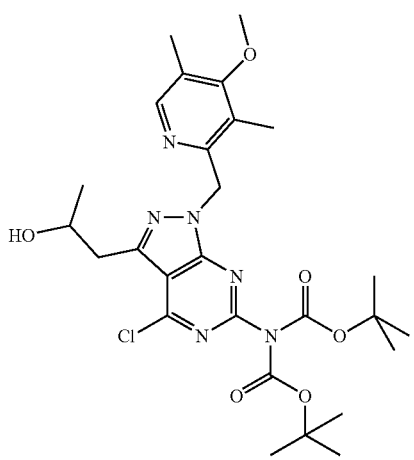

A 3 N solution of methylmagnesium bromide in diethyl ether (0.15 mL) was added dropwise to a mixture of di-tert-butyl {4-chloro-1-[(4-methoxy-3,5-dimethylpyridin-2-yl)methyl]-3-(2-oxoethyl)-1H-pyrazolo[3,4-d]pyrimidin-6-yl}imidodicarbonate of Step 1) of Example 3 (120 mg) and dehydrated tetrahydrofuran (1 mL) under cooling in a dry ice-acetone bath, and then the mixture was stirred for one hour. A saturated ammonium chloride solution (1 mL) was added dropwise to the reaction mixture, and then the dry ice-acetone bath was removed. The reaction mixture was separated with ethyl acetate (30 mL) and water (30 mL). Then, the organic layer was washed with brine and dried over anhydrous magnesium sulfate. After filtration, the filtrate was concentrated under reduced pressure. The resulting residue was purified by silica gel thin-layer chromatography (ethyl acetate-hexane) to obtain the title compound (52 mg, 42%) as an oil.
ESI-MS m/z: 577 (M+H)$^+$.

2) 2-{6-[Bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-methylethyl 4-methylbenzenesulfonate

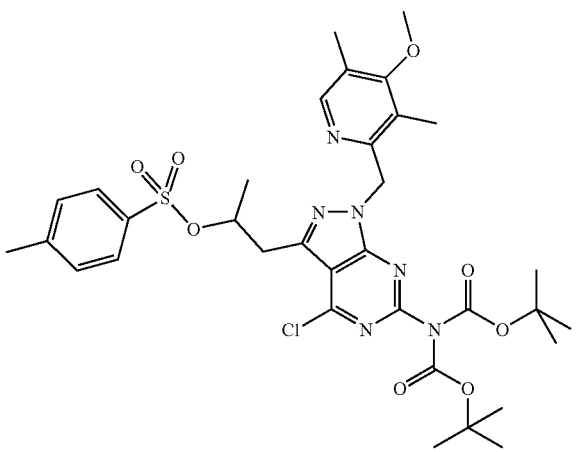

A crude product of the title compound (29 mg, 44%) was obtained as an oil by the same method as in Step 3) of Example 3 using the above di-tert-butyl {4-chloro-3-(2-hydroxypropyl)-1-[(4-methoxy-3,5-dimethylpyridin-2-yl)methyl]-1H-pyrazolo[3,4-d]pyrimidin-6-yl}imidodicarbonate (52 mg) and p-toluenesulfonyl chloride (86 mg). The resulting compound was directly used for the next reaction without purification.
ESI-MS m/z: 731 (M+H)$^+$.

3) 2-[(4-Methoxy-3,5-dimethylpyridin-2-yl)methyl]-7-methyl-7,8-dihydro-2H-6-thia-1,2,3,5-tetraazaacenaphthylen-4-amine

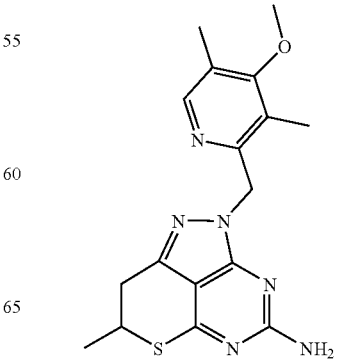

Sodium bisulfide monohydrate (3.8 mg) was added to a mixture of the above 2-{6-[bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-methylethyl 4-methylbenzenesulfonate (29 mg) and N,N-dimethylformamide (1 mL) under cooling in an ice bath, and the mixture was stirred for 20 minutes. Then, potassium carbonate (8.2 mg) was added and the ice bath was removed, followed by stirring for 10 hours. The reaction mixture was diluted with ethyl acetate and then sequentially washed with water and brine. The organic layer was dried over anhydrous sodium sulfate and then filtered, and the filtrate was concentrated under reduced pressure. The resulting residue was dissolved in dichloromethane (2 mL). Then, trifluoroacetic acid (0.5 mL) was added and the mixture was stirred for two hours. The reaction mixture was concentrated under reduced pressure. Then, the resulting residue was dissolved in chloroform and sequentially washed with a saturated sodium bicarbonate solution and water. The organic layer was dried over anhydrous sodium sulfate and then filtered, and the filtrate was concentrated under reduced pressure. The resulting residue was purified by silica gel thin-layer chromatography (chloroform-methanol) to obtain the title compound (8.9 mg, 63%) as a solid.

$^1$H-NMR (CDCl$_3$) δ: 1.56 (3H, d), 2.22 (3H, s), 2.28 (3H, s), 2.84 (1H, dd), 3.20 (1H, dd), 3.74 (3H, s), 3.84-3.93 (1H, m), 5.26 (2H, br.s), 5.44 (2H, s), 8.21 (1H, s).

ESI-MS m/z: 357 (M+H)$^+$.

Example 6

2-[(4-Methoxy-3,5-dimethylpyridin-2-yl)methyl]-7-prop-1-yn-1-yl-7,8-dihydro-2H-6-thia-1,2,3,5-tetraazaacenaphthylen-4-amine 1) 1-({6-[Bis(tert-butoxycarbonyl)amino]-4-chloro-1-[(4-methoxy-3,5-dimethylpyridin-2-yl)methyl]-1H-pyrazolo[3,4-d]pyrimidin-3-yl}methyl)but-2-yn-1-yl methanesulfonate

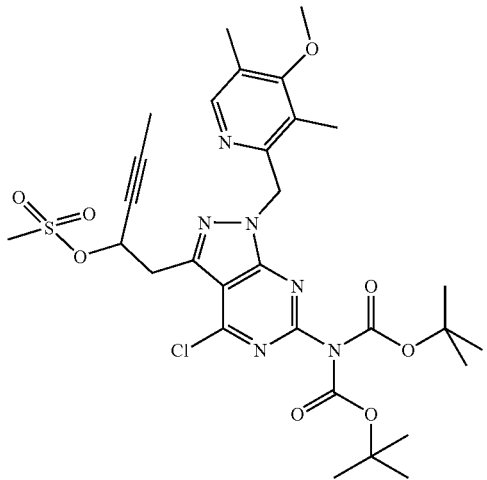

A 0.5 N solution of 1-propynylmagnesium bromide in tetrahydrofuran (0.60 mL) was added dropwise to a mixture of di-tert-butyl {4-chloro-1-[(4-methoxy-3,5-dimethylpyridin-2-yl)methyl]-3-(2-oxoethyl)-1H-pyrazolo[3,4-d]pyrimidin-6-yl}imidodicarbonate of Step 1) of Example 3 (120 mg) and dehydrated tetrahydrofuran under cooling in a dry ice-acetone bath, and then the mixture was stirred for one hour. A saturated ammonium chloride solution (1 mL) was added dropwise to the reaction mixture, and then the dry ice-acetone bath was removed. The reaction mixture was separated with ethyl acetate (30 mL) and water (30 mL). Then, the organic layer was washed with brine and dried over anhydrous magnesium sulfate. After filtration, the filtrate was concentrated under reduced pressure, and the resulting residue was dissolved in dichloromethane (6 mL). Methanesulfonyl chloride (46 μL) was added under cooling in an ice bath, and then a solution of triethylamine (96 μL) in dichloromethane was added dropwise. The ice bath was removed and the mixture was stirred for three hours. Then, the reaction mixture was diluted with dichloromethane and sequentially washed with water and brine. The organic layer was dried over anhydrous sodium sulfate and then filtered, and the filtrate was concentrated under reduced pressure. The resulting residue was purified by silica gel thin-layer chromatography (chloroform-methanol) to obtain the title compound (46 mg, 35%) as an oil.

ESI-MS m/z: 679 (M+H)$^+$.

2) 2-[(4-Methoxy-3,5-dimethylpyridin-2-yl)methyl]-7-prop-1-yn-1-yl-7,8-dihydro-2H-6-thia-1,2,3,5-tetraazaacenaphthylen-4-amine

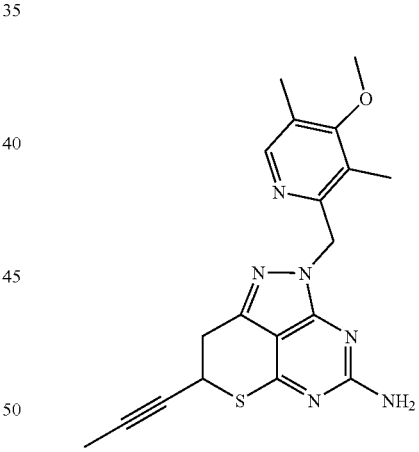

The title compound (7.2 mg, 28%) was obtained as a solid by the same method as in Step 3) of Example 5 using the above 1-({6-[bis(tert-butoxycarbonyl)amino]-4-chloro-1-[(4-methoxy-3,5-dimethylpyridin-2-yl)methyl]-1H-pyrazolo[3,4-d]pyrimidin-3-yl}methyl)but-2-yn-1-yl methanesulfonate (46 mg) and sodium bisulfide monohydrate (6.5 mg).

$^1$H-NMR (CDCl$_3$) δ: 1.85 (3H, d), 2.23 (3H, s), 2.27 (3H, s), 3.16 (1H, dd), 3.36 (1H, dd), 3.75 (3H, s), 4.48-4.53 (1H, m), 5.44 (2H, s), 8.19 (1H, s).

ESI-MS m/z: 381 (M+H)$^+$.

Example 7

4-Amino-2-[(4-methoxy-3,5-dimethylpyridin-2-yl)methyl]-7,8-dihydro-2H-6-thia-1,2,3,5-tetraazaacenaphthylene-7-carboxamide

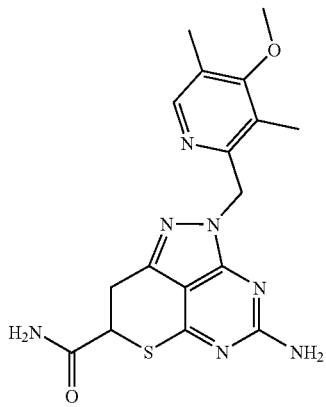

A mixture composed of di-tert-butyl {7-cyano-2-[(4-methoxy-3,5-dimethylpyridin-2-yl)methyl]-7,8-dihydro-2H-6-thia-1,2,3,5-tetraazaacenaphthylen-4-yl}imidodicarbonate of Step 4) of Example 3 (30 mg) and concentrated hydrochloric acid (1 mL) was stirred at room temperature for 1.5 hours. The reaction mixture was diluted with water and neutralized with a saturated sodium bicarbonate solution. The precipitate was collected by filtration and sequentially washed with a saturated sodium bicarbonate solution and water. Then, the resulting solid was dried to obtain the title compound (18.5 mg, 91%).

$^1$H-NMR (DMSO-$d_6$) δ: 2.17 (3H, s), 2.21 (3H, s), 3.09 (1H, dd), 3.26 (1H, dd), 3.71 (3H, s), 4.56 (1H, dd), 5.32 (2H, s), 6.94 (2H, s), 7.42 (1H, s), 7.75 (1H, s), 8.08 (1H, s).

ESI-MS m/z: 386 (M+H)$^+$.

Example 8

4-Amino-2-[(4-methoxy-3,5-dimethylpyridin-2-yl)methyl]-7,8-dihydro-2H-6-thia-1,2,3,5-tetraazaacenaphthylene-7-carboxylic acid

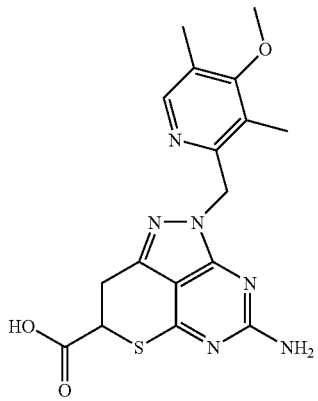

A mixture composed of di-tert-butyl {7-cyano-2-[(4-methoxy-3,5-dimethylpyridin-2-yl)methyl]-7,8-dihydro-2H-6-thia-1,2,3,5-tetraazaacenaphthylen-4-yl}imidodicarbonate of Step 4) of Example 3 (210 mg) and concentrated hydrochloric acid (6 mL) was stirred at room temperature for three days. The reaction mixture was concentrated under reduced pressure and the solvent was evaporated. Diethyl ether was added to the residue and the solid was powdered, followed by collection by filtration to obtain a hydrochloride of the title compound (171 mg). The resulting hydrochloride crude product (42 mg) was purified by reversed phase liquid chromatography to obtain the title compound (6.1 mg, 17%) as a solid.

$^1$H-NMR (DMSO-$d_6$) δ: 2.17 (3H, s), 2.21 (3H, s), 3.13 (1H, dd), 3.26 (2H, dd), 3.71 (3H, s), 4.71-4.80 (1H, m), 5.32 (2H, s), 6.94 (2H, s), 8.08 (1H, s).

ESI-MS m/z: 387 (M+H)$^+$.

Example 9

4-Amino-2-[(4-methoxy-3,5-dimethylpyridin-2-yl)methyl]-N-methyl-7,8-dihydro-2H-6-thia-1,2,3,5-tetraazaacenaphthylene-7-carboxamide

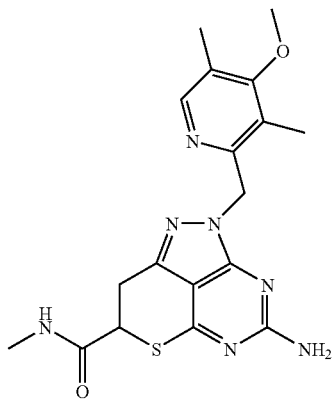

A mixture composed of 4-amino-2-[(4-methoxy-3,5-dimethylpyridin-2-yl)methyl]-7,8-dihydro-2H-6-thia-1,2,3,5-tetraazaacenaphthylene-7-carboxylic acid hydrochloride of Example 8 (42 mg), methylamine hydrochloride (13 mg), 1-hydroxybenzotriazole monohydrate (14 mg), 1-(3-dimethylaminopropyl)-3-ethylcarbodiimide hydrochloride (35 mg), diisopropylethylamine (79 μL) and dehydrated N,N-dimethylformamide (1 mL) was stirred at room temperature for 48 hours. A 0.5 N sodium hydroxide solution was added to the reaction mixture, and the solid was collected by filtration. The solid collected by filtration was dissolved in a mixed solvent of chloroform-methanol, followed by purification by silica gel thin-layer chromatography (chloroform-methanol) to obtain the title compound (17.9 mg, 49%) as a solid.

$^1$H-NMR (CDCl$_3$) δ: 2.23 (3H, s), 2.28 (3H, s), 2.78 (3H, d), 3.25 (1H, dd), 3.66 (1H, dd), 3.75 (3H, s), 4.33 (1H, dd), 5.38-5.46 (3H, m), 6.94 (1H, d), 8.15 (1H, s).

ESI-MS m/z: 400 (M+H)$^+$.

Example 10

4-Amino-2-[(4-methoxy-3,5-dimethylpyridin-2-yl)methyl]-N-ethyl-7,8-dihydro-2H-6-thia-1,2,3,5-tetraazaacenaphthylene-7-carboxamide

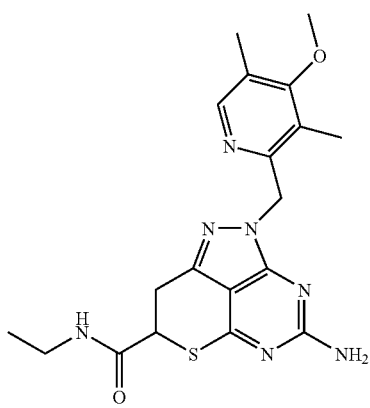

The title compound (16.0 mg, 42%) was obtained as a solid by the same method as in Example 9 using 4-amino-2-[(4-methoxy-3,5-dimethylpyridin-2-yl)methyl]-7,8-dihydro-2H-6-thia-1,2,3,5-tetraazaacenaphthylene-7-carboxylic acid hydrochloride of Example 8 (42 mg) and ethylamine hydrochloride (16 mg).

$^1$H-NMR (CDCl$_3$) δ: 1.08 (3H, t), 2.21 (3H, s), 2.28 (3H, s), 3.15-3.35 (2H, m), 3.69 (2H, dd), 3.74 (3H, s), 4.29 (1H, dd), 5.38-5.46 (5H, m), 6.60 (1H, br.s), 8.17 (1H, s).
ESI-MS m/z: 414 (M+H)$^+$.

Example 11

4-Amino-2-[(4-methoxy-3,5-dimethylpyridin-2-yl)methyl]-N,N-dimethyl-7,8-dihydro-2H-6-thia-1,2,3,5-tetraazaacenaphthylene-7-carboxamide

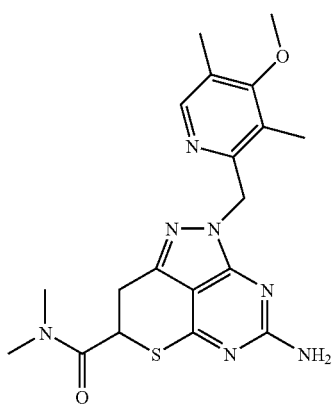

The title compound (5.9 mg, 16%) was obtained as a solid by the same method as in Example 9 using 4-amino-2-[(4-methoxy-3,5-dimethylpyridin-2-yl)methyl]-7,8-dihydro-2H-6-thia-1,2,3,5-tetraazaacenaphthylene-7-carboxylic acid hydrochloride of Example 8 (42 mg) and dimethylamine hydrochloride (16 mg).

$^1$H-NMR (CDCl$_3$) δ: 2.22 (3H, s), 2.29 (3H, s), 3.03 (3H, s), 3.17 (3H, s), 3.23 (1H, dd), 3.48 (1H, dd), 3.74 (3H, s), 4.73 (1H, dd), 5.26 (2H, s), 5.45 (2H, s), 8.20 (1H, s).
ESI-MS m/z: 414 (M+H)$^+$.

Example 12

4-Amino-N-cyclopropyl-2-[(4-methoxy-3,5-dimethylpyridin-2-yl)methyl]-7,8-dihydro-2H-6-thia-1,2,3,5-tetraazaacenaphthylene-7-carboxamide

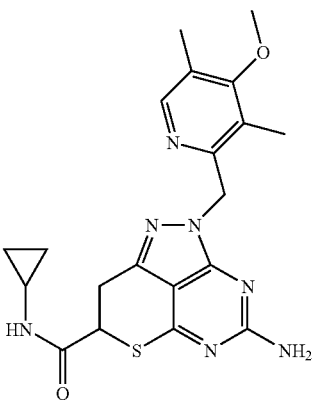

A mixture composed of 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (80 mg), cyclopropylamine (0.029 mL), 1-hydroxybenzotriazole monohydrate (32 mg), 1-(3-dimethylaminopropyl)-3-ethyl-carbodiimide hydrochloride (80 mg) and dehydrated N,N-dimethylformamide (10 mL) was stirred at room temperature for 16 hours. The reaction mixture was concentrated under reduced pressure. The resulting residue was diluted with ethyl acetate and sequentially washed with a saturated sodium bicarbonate solution and brine. The organic layer was dried over anhydrous magnesium sulfate and filtered. Then, the filtrate was concentrated under reduced pressure. The resulting residue was purified by NH silica gel column chromatography (dichloromethane-methanol) to obtain the title compound (30 mg, 34%) as a solid.

$^1$H-NMR (CDCl$_3$) δ: 0.42-0.49 (2H, m), 0.74-0.76 (2H, m), 2.22 (3H, s), 2.29 (3H, s), 2.65-2.67 (1H, m), 3.24 (1H, dd), 3.70 (1H, dd), 3.75 (3H, s), 4.24 (1H, dd), 5.24 (2H, s), 5.43 (2H, s), 6.60 (1H, s), 8.18 (1H, s).
ESI-MS m/z: 426 (M+H)$^+$.

Example 13

4-Amino-2-[(4-methoxy-3,5-dimethylpyridin-2-yl)methyl]-N-prop-2-yn-1-yl-7,8-dihydro-2H-6-thia-1,2,3,5-tetraazaacenaphthylene-7-carboxamide

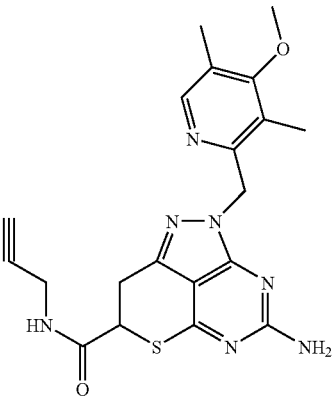

The title compound (30 mg, 34%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (80 mg) and propargylamine (29 μL).

$^1$H-NMR (CDCl$_3$) δ: 2.21-2.22 (4H, m), 2.29 (3H, s), 3.26 (1H, dd), 3.76-3.79 (4H, m), 3.86-3.91 (1H, m), 4.08-4.13 (1H, m), 4.30 (1H, t), 5.24 (2H, s), 5.43 (2H, d), 6.74-6.76 (1H, br.s), 8.19 (1H, s)

ESI-MS m/z: 424 (M+H)$^+$.

Example 14

4-Amino-2-[(4-methoxy-3,5-dimethylpyridin-2-yl)methyl]-N-(2-phenylethyl)-7,8-dihydro-2H-6-thia-1,2,3,5-tetraazaacenaphthylene-7-carboxamide

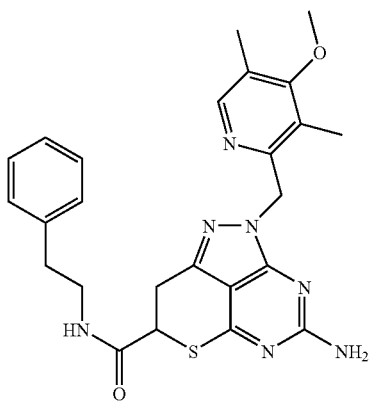

The title compound (10 mg, 16%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 2-phenylethylamine (33 μL).

$^1$H-NMR (CDCl$_3$) δ: 2.20 (3H, s), 2.30 (3H, s), 2.72 (2H, dd), 3.23 (1H, dd), 3.44-3.56 (2H, m), 3.70-3.74 (4H, m), 4.23-4.25 (1H, m), 5.24 (2H, s), 5.45-5.47 (2H, m), 6.49-6.51 (1H, m), 7.03 (2H, d), 7.22-7.28 (3H, m), 8.16 (1H, s).

ESI-MS m/z: 490 (M+H)$^+$.

Example 15

7-[(4-Isopropylpiperazin-1-yl)carbonyl]-2-[(4-methoxy-3,5-dimethylpyridin-2-yl)methyl]-7,8-dihydro-2H-6-thia-1,2,3,5-tetraazaacenaphthylen-4-amine

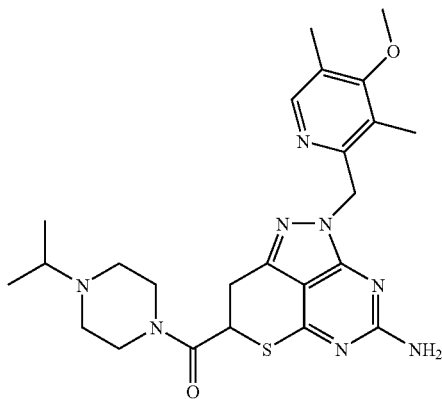

The title compound (6 mg, 12%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg) and 1-isopropylpiperazine (43 μL).

$^1$H-NMR (CDCl$_3$) δ: 1.01 (6H, d), 2.20 (3H, s), 2.27 (3H, s), 2.45-2.54 (4H, m), 2.68-2.72 (1H, m), 3.21 (1H, dd), 3.44-3.51 (3H, m), 3.71-3.73 (4H, m), 3.83 (1H, br.s), 4.68 (1H, dd), 5.16 (2H, s), 5.43 (2H, s), 8.18 (1H, s).

ESI-MS m/z: 497 (M+H)$^+$.

Example 16

4-Amino-N-(2-chloroethyl)-2-[(4-methoxy-3,5-dimethylpyridin-2-yl)methyl]-7,8-dihydro-2H-6-thia-1,2,3,5-tetraazaacenaphthylene-7-carboxamide

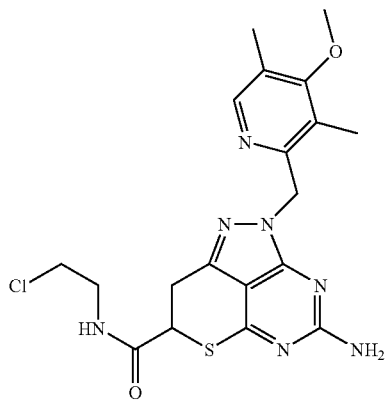

A mixture composed of 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg), 2-chloroethylamine hydrochloride (24 mg), 1-hydroxybenzotriazole monohydrate (24 mg), 1-(3-dimethylaminopropyl)-3-ethylcarbodiimide hydrochloride (40 mg), triethylamine (44 μL) and dehydrated N,N-dimethylformamide (10 mL) was stirred at room temperature for 16 hours. The reaction mixture was concentrated under reduced pressure. The resulting residue was diluted with ethyl acetate and sequentially washed with a saturated sodium bicarbonate solution and brine. The organic layer was dried over anhydrous magnesium sulfate and filtered. Then, the filtrate was concentrated under reduced pressure. The resulting residue was purified by NH silica gel column chromatography (dichloromethane-ethyl acetate) to obtain the title compound (10 mg, 22%) as a solid.

ESI-MS m/z: 448 (M+H)$^+$.

Example 17

4-Amino-N-(3-chloropropyl)-2-[(4-methoxy-3,5-dimethylpyridin-2-yl)methyl]-7,8-dihydro-2H-6-thia-1,2,3,5-tetraazaacenaphthylene-7-carboxamide

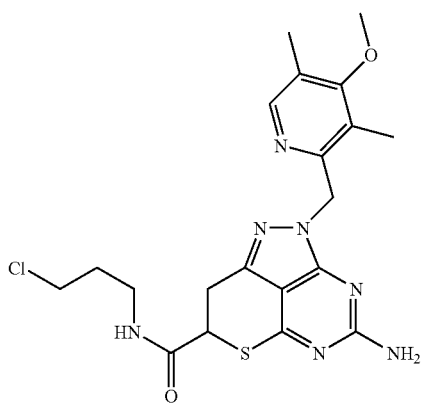

The title compound (60 mg, 50%) was obtained as a solid by the same method as in Example 16 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (100 mg) and 2-chloropropylamine hydrochloride (60 mg).
ESI-MS m/z: 448 (M+H)$^+$.

Example 18

4-Amino-N-[2-(isobutylamino)ethyl]-2-[(4-methoxy-3,5-dimethylpyridin-2-yl)methyl]-7,8-dihydro-2H-6-thia-1,2,3,5-tetraazaacenaphthylene-7-carboxamide

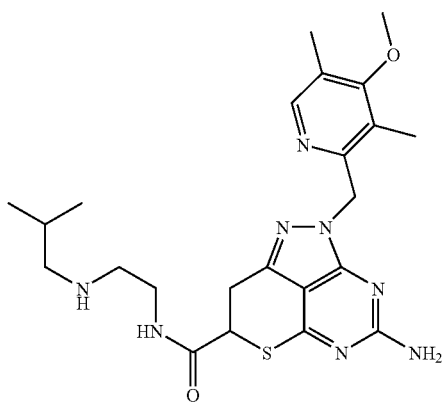

A mixture composed of 4-amino-N-(2-chloroethyl)-2-[(4-methoxy-3,5-dimethylpyridin-2-yl)methyl]-7,8-dihydro-2H-6-thia-1,2,3,5-tetraazaacenaphthylene-7-carboxamide of Example 16 (20 mg), isobutylamine (0.8 mL) and dioxane (3 mL) was heated under reflux for 16 hours, and then the reaction mixture was concentrated under reduced pressure. The resulting residue was purified by reversed phase liquid chromatography to obtain the title compound (6 mg, 28%) as a solid.

$^1$H-NMR (CDCl$_3$) δ: 0.86 (6H, d), 1.64-1.65 (1H, m), 2.19 (3H, s), 2.27 (3H, s), 2.32 (2H, d), 2.65-2.67 (2H, m), 3.23-3.28 (3H, m), 3.62-3.69 (4H, m), 4.30 (1H, dd), 5.24-5.28 (2H, m), 5.41 (2H, d), 7.07 (1H, s), 8.16 (1H, s).
ESI-MS m/z: 485 (M+H)$^+$.

Example 19

4-Amino-N-[3-(isobutylamino)propyl]-2-[(4-methoxy-3,5-dimethylpyridin-2-yl)methyl]-7,8-dihydro-2H-6-thia-1,2,3,5-tetraazaacenaphthylene-7-carboxamide

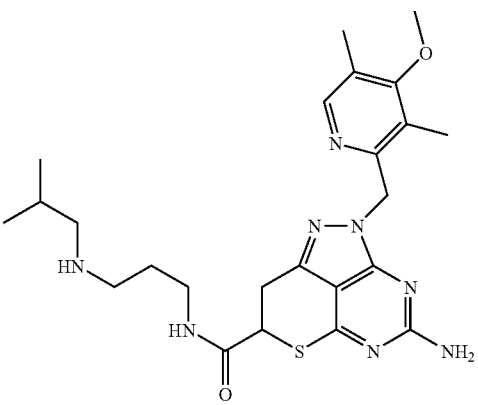

Reaction and post-treatment were performed in the same manner as in Example 18 using 4-amino-N-(3-chloropropyl)-2-[(4-methoxy-3,5-dimethylpyridin-2-yl)methyl]-7,8-dihydro-2H-6-thia-1,2,3,5-tetraazaacenaphthylene-7-carboxamide of Example 17 (30 mg) and isobutylamine (2 mL), followed by purification by NH silica gel column chromatography (dichloromethane-methanol) to obtain the title compound (20 mg, 62%) as a solid.
$^1$H-NMR (CDCl$_3$) δ: 0.87 (6H, d), 1.63-1.70 (3H, m), 2.20 (3H, s), 2.27 (3H, s), 2.35 (2H, dd), 2.60-2.64 (2H, m), 3.23-3.33 (3H, m), 3.58 (1H, dd), 3.72 (3H, s), 4.26 (1H, dd), 5.19 (2H, s), 5.41 (2H, s), 8.05 (1H, br), 8.17 (1H, s).
ESI-MS m/z: 499 (M+H)$^+$.

Example 20

4-Amino-N-{3-[(2,2-dimethylpropyl)amino]propyl}-2-[(4-methoxy-3,5-dimethylpyridin-2-yl)methyl]-7,8-dihydro-2H-6-thia-1,2,3,5-tetraazaacenaphthylene-7-carboxamide

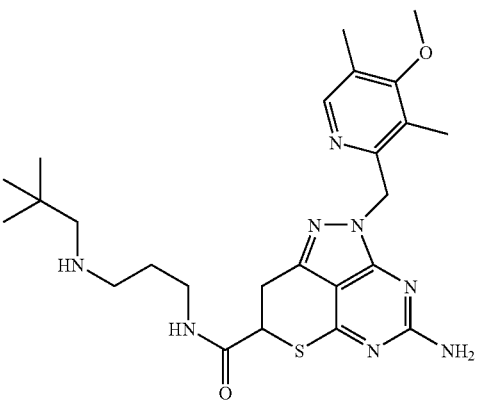

The title compound (10 mg, 29%) was obtained as a solid by the same method as in Example 19 using 4-amino-N-(3-chloropropyl)-2-[(4-methoxy-3,5-dimethylpyridin-2-yl)methyl]-7,8-dihydro-2H-6-thia-1,2,3,5-tetraazaacenaphthylene-7-carboxamide of Example 17 (30 mg) and neopentylamine (2.0 mL).

¹H-NMR (CDCl₃) δ: 0.86 (9H, s), 1.63-1.70 (2H, m), 2.20-2.21 (4H, m), 2.27-2.28 (4H, m), 2.64 (2H, m), 3.25 (1H, dd), 3.32-3.37 (2H, m), 3.57 (1H, dd), 3.72 (3H, s), 4.25 (1H, dd), 5.17 (2H, s), 5.41 (2H, s), 7.88-7.90 (1H, br), 8.17 (1H, s).

ESI-MS m/z: 513 (M+H)⁺.

Example 21

Di-tert-butyl {2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate 1) 1-(2-Amino-4,6-dichloropyrimidin-5-yl)pent-4-en-1-ol

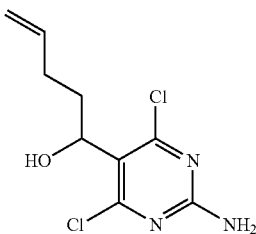

4-Bromo-1-butene (14.54 mL) was added to a mixture composed of a magnesium piece (3.17 g) and dehydrated tetrahydrofuran (150 mL) in a nitrogen atmosphere over one hour. After confirming that the internal temperature was increased, the mixture was stirred at an internal temperature of 25 to 30° C. while cooling in an ice bath for one hour to prepare a Grignard reagent. The Grignard reagent was added to a mixture composed of 2-amino-4,6-dichloro-pyrimidine-5-carbaldehyde (5.00 g) and dehydrated tetrahydrofuran (100 mL) under cooling in a dry ice-acetone bath over three hours, followed by stirring for 1.5 hours. Water (100 mL) was added to the reaction mixture, and the dry ice-acetone bath was removed. A saturated ammonium chloride solution (200 mL) was added to the reaction mixture. Then, ethyl acetate (200 mL) was added and the organic layer was separated off. The aqueous layer was extracted with ethyl acetate, and then the combined organic layers were washed with brine. The organic layers were dried over sodium sulfate and filtered. Then, the filtrate was concentrated under reduced pressure and the solvent was evaporated to obtain a crude product of the title compound (5.06 g, 78%) as a solid. The resulting compound was directly used for the next reaction without purification.

2) 1-(2-Amino-4,6-dichloropyrimidin-5-yl)pent-4-en-1-one

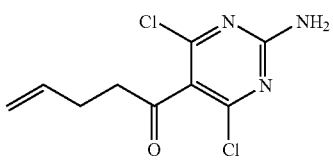

A mixture composed of the above crude 1-(2-amino-4,6-dichloropyrimidin-5-yl)pent-4-en-1-ol (5.06 g), 1,2-dichloroethane (300 mL) and manganese dioxide (20.15 g) was heated under reflux for 15 hours. After confirming that the raw material disappeared, the reaction solution was filtered through Celite, and the filtrate was concentrated under reduced pressure. The resulting residue was purified by silica gel column chromatography (ethyl acetate-chloroform) to obtain the title compound (1.22 g, 24.3%) as a solid.

¹H-NMR (CDCl₃) δ: 2.48 (2H, dd), 2.94 (2H, t), 5.01-5.06 (1H, m), 5.10 (1H, ddd), 5.41 (2H, s), 5.93-5.80 (1H, m).

3) 3-But-3-en-1-yl-4-chloro-1-[(4-methoxy-3,5-dimethylpyridin-2-yl)methyl]-1H-pyrazolo[3,4-d]pyrimidin-6-amine

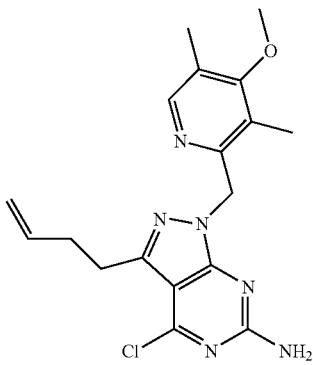

The title compound (4.40 g, 59%) was obtained as a solid by the same method as in Step 5) of Example 1 using 1-(2-amino-4,6-dichloropyrimidin-5-yl)pent-4-en-1-one (4.92 g) and [(4-methoxy-3,5-dimethylpyridin-2-yl)methyl]hydrazine hydrochloride of Step 4) of Example 1 (8.72 g) under cooling in an ice bath.

¹H-NMR (DMSO-d₆) δ: 2.15 (3H, s), 2.19 (3H, s), 2.35-2.42 (2H, m), 2.87-2.93 (2H, m), 3.70 (3H, s), 4.91-4.96 (1H, m), 4.99-5.06 (1H, m), 5.37 (2H, s), 5.89-5.78 (1H, m), 7.17 (2H, S), 8.02 (1H, s)

4) Di-tert-butyl {3-but-3-en-1-yl-4-chloro-1-[(4-methoxy-3,5-dimethylpyridin-2-yl)methyl]-1H-pyrazolo[3,4-d]pyrimidin-6-yl}imidodicarbonate

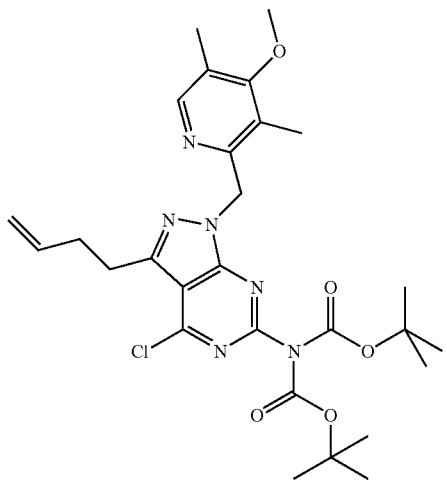

The title compound (6.78 g, 100%) was obtained as a solid by the same method as in Step 6) of Example 1 using the above 3-but-3-en-1-yl-4-chloro-1-[(4-methoxy-3,5-dimethylpyridin-2-yl)methyl]-1H-pyrazolo[3,4-d]pyrimidin-6-amine (4.40 g) and di-tert-butyl dicarbonate (15.46 g).
ESI-MS m/z: 573 (M+H)⁺

5) Di-tert-butyl {4-chloro-3-(3,4-dihydroxybutyl)-1-[(4-methoxy-3,5-dimethylpyridin-2-yl)methyl]-1H-pyrazolo[3,4-d]pyrimidin-6-yl}imidodicarbonate

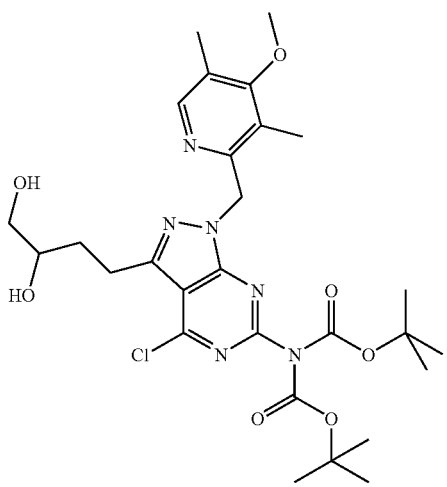

Osmium tetroxide (21 mg) was added to a mixture composed of the above 3-(3-butenyl)-6-di(tert-butoxycarbonyl)amino-4-chloro-1-(4-methoxy-3,5-dimethylpyridin-2-yl)methyl-1H-pyrazolo[3,4-d]pyrimidine (4.78 g), N-methylmorpholine-N-oxide (5.04 g), tetrahydrofuran (60 mL), acetone (60 mL) and water (60 mL), and the mixture was stirred at room temperature for five hours. Ethyl acetate (300 mL) and a 10% sodium thiosulfate solution (500 mL) were added to the reaction mixture, followed by further stirring for 30 minutes. The reaction mixture was separated, and the aqueous layer was extracted with ethyl acetate. Then, the combined organic layers were washed with brine. The organic layers were dried over anhydrous sodium sulfate and then filtered. The filtrate was concentrated under reduced pressure and the solvent was evaporated to obtain a crude product of the title compound (4.60 g, 91%) as a solid. The resulting compound was directly used for the next reaction without purification.

¹H-NMR (CDCl₃) δ: 1.41 (18H, s), 1.98 (2H, dd), 2.20 (3H, s), 2.29 (3H, s), 3.08 (1H, d), 3.27 (2H, t), 3.45-3.51 (1H, m), 3.58-3.64 (1H, m), 3.73-3.76 (4H, m), 5.59-5.69 (2H, m), 8.03 (1H, s).

6) Di-tert-butyl {4-chloro-3-(3-hydroxypropyl)-1-[(4-methoxy-3,5-dimethylpyridin-2-yl)methyl]-1H-pyrazolo[3,4-d]pyrimidin-6-yl}imidodicarbonate

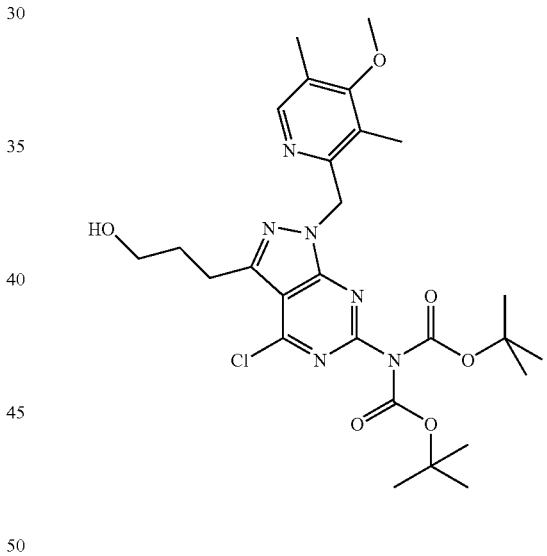

The title compound (128 mg, 60%) was obtained as an oil by the same method as in Step 8) of Example 1 using the above 6-di(tert-butoxycarbonyl)amino-4-chloro-3-(3,4-dihydroxybutyl)-1-(4-methoxy-3,5-dimethylpyridin-2-yl)methyl-1H-pyrazolo[3,4-d]pyrimidine (225 mg) and sodium periodate (396 mg) under cooling in an ice bath.

¹H-NMR (CDCl₃) δ: 1.41 (18H, s), 2.04-2.11 (2H, m), 2.19 (3H, s), 2.28 (3H, s), 3.23 (2H, t), 3.70-3.73 (2H, m), 3.74 (3H, s), 5.65 (2H, s), 8.04 (1H, s).
ESI-MS m/z: 577 (M+H)⁺.

7) Di-tert-butyl {2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

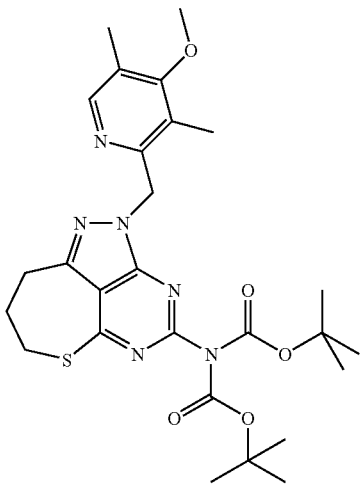

Triethylamine (0.12 mL), p-toluenesulfonyl chloride (152 mg) and 4-dimethylaminopyridine (1 mg) were added to a mixture composed of di-tert-butyl {4-chloro-3-(3-hydroxypropyl)-1-[(4-methoxy-3,5-dimethylpyridin-2-yl)methyl]-1H-pyrazolo[3,4-d]pyrimidin-6-yl}imidodicarbonate (64 mg) and dehydrated dichloromethane (3 mL) under cooling in an ice bath. The ice bath was removed and the mixture was stirred for 17 hours. The reaction mixture was separated with water (30 mL) and ethyl acetate (30 mL), and the organic layer was dried over anhydrous sodium sulfate. After filtration, the filtrate was concentrated under reduced pressure. N,N-Dimethylformamide (1 mL) and potassium thioacetate (25 mg) were added to the resulting residue, and the mixture was heated to 50° C. and stirred for 15 minutes. After confirming that the reaction was completed, the reaction mixture was separated with water and ethyl acetate. The organic layer was washed with brine, and then dried over anhydrous sodium sulfate and filtered. Then, the filtrate was concentrated under reduced pressure. The resulting residue was purified by silica gel column chromatography (ethyl acetate-hexane) to obtain the title compound (34 mg, 55%) as an oil.

$^1$H-NMR (CDCl$_3$) δ: 1.39 (18H, s), 2.21 (3H, s), 2.26 (3H, s), 2.46 (2H, dt), 3.22-3.25 (4H, m), 3.73 (3H, s), 5.62 (2H, s), 8.17 (1H, s).

ESI-MS m/z: 557 (M+H)$^+$.

Example 22

2-[(4-Methoxy-3,5-dimethylpyridin-2-yl)methyl]-2,7,8,9-tetrahydro-6-thia-1,2,3,5-tetraazabenzo[cd]azulen-4-amine

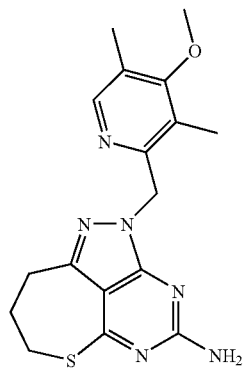

The title compound (28 mg, 62%) was obtained as a solid by the same method as in Example 2 using di-tert-butyl {2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Step 7) of Example 21 (71 mg) under cooling in an ice bath.

$^1$H-NMR (CDCl$_3$) δ: 2.22 (3H, s), 2.26 (3H, s), 2.37-2.43 (2H, m), 3.11 (2H, t), 3.18 (2H, t), 3.74 (3H, s), 5.16 (2H, s), 5.46 (2H, s), 8.20 (1H, s).

ESI-MS m/z: 357 (M+H)$^+$.

Example 23

Di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate 1) Di-tert-butyl {4-chloro-1-[(4-methoxy-3,5-dimethylpyridin-2-yl)methyl]-3-(3-oxopropyl)-1H-pyrazolo[3,4-d]pyrimidin-6-yl}imidodicarbonate

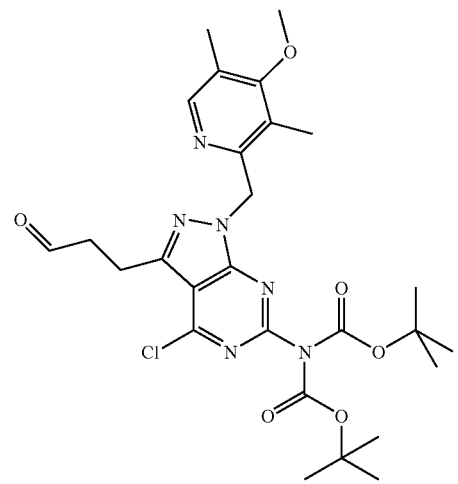

A crude product of the title compound (4.34 g, 100%) was obtained by the same method as in Step 1) of Example 3 using di-tert-butyl {4-chloro-3-(3,4-dihydroxybutyl)-1-[(4-methoxy-3,5-dimethylpyridin-2-yl)methyl]-1H-pyrazolo[3,4-d]pyrimidin-6-yl}imidodicarbonate of Step 5) of Example 21 (4.60 g) and sodium periodate (1.95 g) under cooling in an ice bath. The resulting compound was directly used for the next reaction without purification.

2) Di-tert-butyl {4-chloro-3-(3-cyano-3-hydroxypropyl)-1-[(4-methoxy-3,5-dimethylpyridin-2-yl)methyl]-1H-pyrazolo[3,4-d]pyrimidin-6-yl}imidodicarbonate

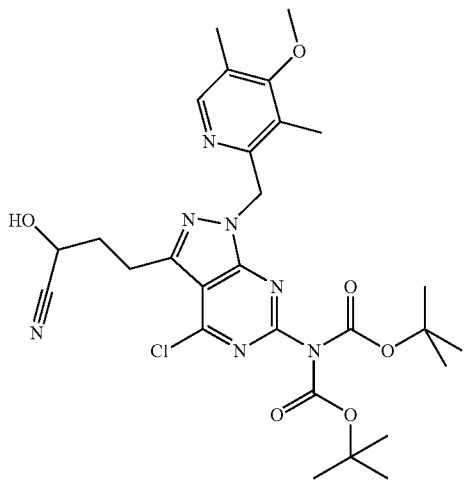

A crude product containing the title compound (1.99 g) was obtained by the same method as in Step 2) of Example 3 using the above di-tert-butyl {4-chloro-1-[(4-methoxy-3,5-dimethylpyridin-2-yl)methyl]-3-(3-oxopropyl)-1H-pyrazolo[3,4-d]pyrimidin-6-yl}imidodicarbonate (1.55 g) and trimethylsilyl cyanide (0.416 mL) under cooling in an ice bath. The resulting compound was directly used for the next reaction without purification.

ESI-MS m/z: 602 (M+H)$^+$.

3) 3-{6-[Bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-cyanopropyl 4-methylbenzenesulfonate

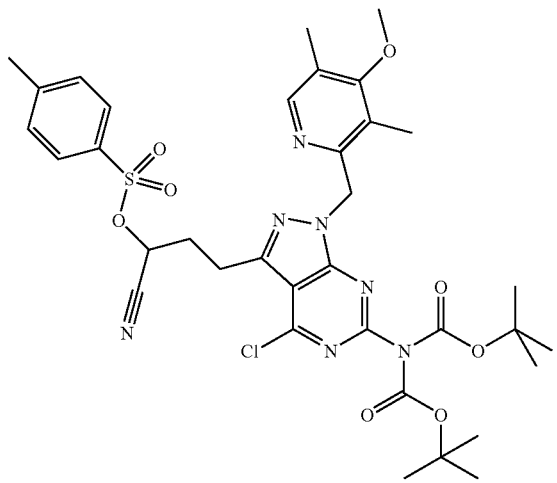

The title compound (2.32 g, 93%) was obtained as a solid by the same method as in Step 3) of Example 3 using the above crude di-tert-butyl {4-chloro-3-(3-cyano-3-hydroxypropyl)-1-[(4-methoxy-3,5-dimethylpyridin-2-yl)methyl]-1H-pyrazolo[3,4-d]pyrimidin-6-yl}imidodicarbonate (1.99 g) and p-toluenesulfonyl chloride (945 mg).

ESI-MS m/z: 756 (M+H)$^+$.

4) Di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

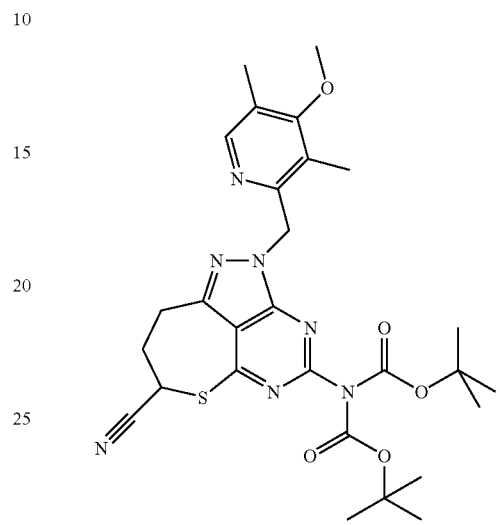

The title compound (1.49 g, 84%) was obtained as an oil by the same method as in Step 4) of Example 3 using the above 3-{6-[bis(tert-butoxycarbonyl)amino]-4-chloro-1-[(4-methoxy-3,5-dimethylpyridin-2-yl)methyl]-1H-pyrazolo[3,4-d]pyrimidin-3-yl}-1-cyanopropyl 4-methylbenzenesulfonate (2.32 g) and sodium bisulfide monohydrate (273 mg) under cooling in an ice bath.

$^1$H-NMR (CDCl$_3$) δ: 1.44 (18H, s), 2.22 (3H, s), 2.28 (3H, s), 2.61-2.68 (1H, m), 2.84-2.92 (1H, m), 3.42-3.59 (2H, m), 3.74 (3H, s), 4.32 (1H, d), 5.65 (2H, s), 8.16 (1H, s).

ESI-MS m/z: 582 (M+H)$^+$.

Example 24

4-Amino-2-[(4-methoxy-3,5-dimethylpyridin-2-yl)methyl]-2,7,8,9-tetrahydro-6-thia-1,2,3,5-tetraazabenzo[cd]azulene-7-carbonitrile

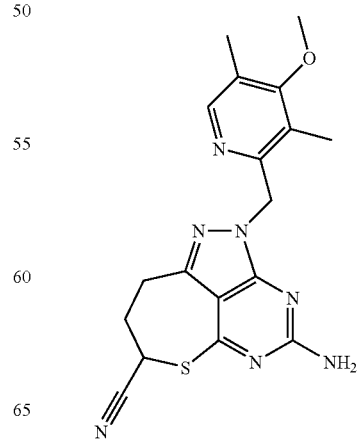

The title compound (21.6 mg, 81%) was obtained as a solid by the same method as in Example 2 using di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Step 4) of Example 23 (53 mg).

$^1$H-NMR (CDCl$_3$) δ: 2.24 (3H, s), 2.29 (3H, s), 2.51-2.61 (1H, m), 2.75-2.85 (1H, m), 3.28-3.45 (2H, m), 3.76 (3H, s), 4.25 (1H, d), 5.34 (2H, br.s), 5.48 (2H, s), 8.22 (1H, s).

ESI-MS m/z: 382 (M+H)$^+$.

Example 25

2-[(4-Methoxy-3,5-dimethylpyridin-2-yl)methyl]-7-(1H-tetrazol-5-yl)-2,7,8,9-tetrahydro-6-thia-1,2,3,5-tetraazabenzo[cd]azulen-4-amine

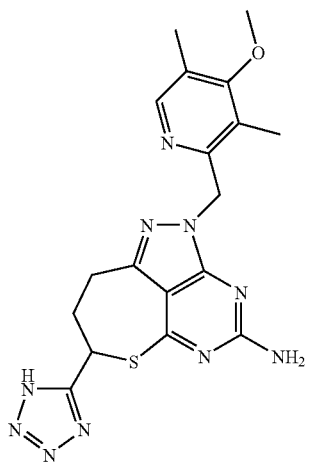

A mixture composed of di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Step 4) of Example 23 (53 mg), N,N-dimethylformamide (1 mL), triethylamine hydrochloride (14.5 m) and sodium azide (6.8 mg) was sealed in a tube and heated with stirring at a bath temperature of 105° C. for 15 hours. After cooling to room temperature, the reaction solution was separated with ethyl acetate and a 0.1 N sodium hydroxide solution. The aqueous layer was made acidic with a 0.1 N hydrochloric acid solution, followed by extraction with ethyl acetate. The organic layer was washed with water and then dried over anhydrous sodium sulfate. After filtration, the filtrate was concentrated under reduced pressure. Dichloromethane (2 mL) and trifluoroacetic acid (0.5 mL) were added to the resulting residue, and the mixture was stirred at room temperature for two hours. The reaction solution was concentrated under reduced pressure, and the resulting residue was purified by silica gel thin-layer chromatography (chloroform-methanol-lower layer of water) to obtain the title compound (5.6 mg, 19%) as a solid.

$^1$H-NMR (CDCl$_3$) δ: 2.09 (3H, s), 2.18 (3H, s), 2.64-3.13 (4H, m), 3.66 (3H, s), 4.57-4.85 (1H, m), 5.29 (2H, s), 8.03 (1H, s).

ESI-MS m/z: 425 (M+H)$^+$.

Example 26

4-Amino-2-[(4-methoxy-3,5-dimethylpyridin-2-yl)methyl]-2,7,8,9-tetrahydro-6-thia-1,2,3,5-tetraazabenzo[cd]azulene-7-carboxamide

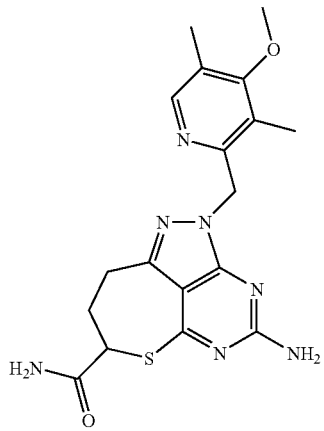

A mixture composed of di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Step 4) of Example 23 (53 mg) and concentrated hydrochloric acid (1 mL) was stirred at room temperature for two hours. The reaction mixture was concentrated under reduced pressure, and the residue was purified by reversed phase liquid chromatography to obtain the title compound (9.7 mg, 35%) as a solid.

$^1$H-NMR (CDCl$_3$) δ: 2.17 (3H, s), 2.21 (3H, s), 2.96-3.00 (2H, m), 3.71 (3H, s), 4.18 (1H, d), 5.32 (1H, d), 5.37 (1H, d), 6.76 (2H, s), 7.32 (1H, s), 7.73 (1H, s), 8.07 (1H, s).

ESI-MS m/z: 400 (M+H)$^+$.

Example 27

4-Amino-2-[(4-methoxy-3,5-dimethylpyridin-2-yl)methyl]-2,7,8,9-tetrahydro-6-thia-1,2,3,5-tetraazabenzo[cd]azulene-7-carboxylic acid

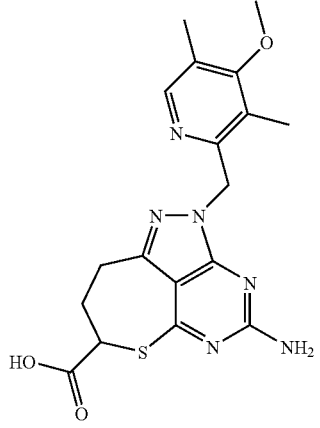

A mixture composed of di-tert-butyl {7-cyano-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Step 4) of Example 23 (745 mg) and concentrated hydrochloric acid (30 mL) was stirred at room temperature for four days. After confirming that the raw material disappeared, the reaction mixture was concentrated under reduced pressure. The residue was diluted with water and then neutralized with a saturated sodium bicarbonate solution. Acetic acid (4 mL) was added to the mixture, followed by cooling in an ice bath for 30 minutes. The precipitate was collected by filtration and then dried to obtain the title compound (420 mg, 82%) as a solid.

ESI-MS m/z: 401 (M+H)$^+$.

Example 28

4-Amino-N-ethyl-2-[(4-methoxy-3,5-dimethylpyridin-2-yl)methyl]-2,7,8,9-tetrahydro-6-thia-1,2,3,5-tetraazabenzo[cd]azulene-7-carboxamide

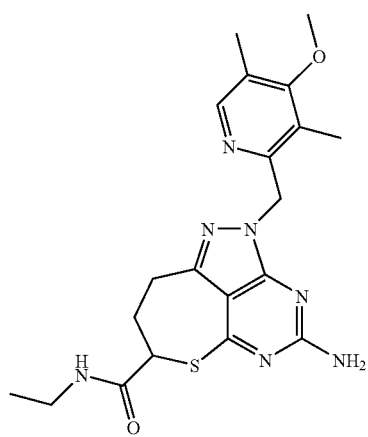

The title compound (22.3 g, 68%) was obtained as a white solid by the same method as in Example 9 using 4-amino-2-[(4-methoxy-3,5-dimethylpyridin-2-yl)methyl]-2,7,8,9-tetrahydro-6-thia-1,2,3,5-tetraazabenzo[cd]azulene-7-carboxylic acid of Example 27 (32 mg) and ethylamine hydrochloride (14 mg).

$^1$H-NMR (CDCl$_3$) δ: 1.12 (3H, t), 2.22 (3H, s), 2.26 (3H, s), 2.64-2.71 (2H, m), 3.02 (1H, dt), 3.17 (1H, dt), 3.24-3.33 (2H, m), 3.75 (3H, s), 4.05 (1H, t), 5.42 (3H, s), 7.11-7.20 (1H, m), 8.12 (1H, s).

ESI-MS m/z: 428 (M+H)$^+$.

Example 29

4-Amino-2-[(4-methoxy-3,5-dimethylpyridin-2-yl)methyl]-N,N-dimethyl-2,7,8,9-tetrahydro-6-thia-1,2,3,5-tetraazabenzo[cd]azulene-7-carboxamide

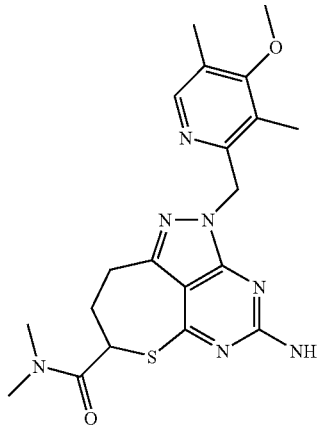

The title compound (22.6 mg, 66%) was obtained as a solid by the same method as in Example 9 using 4-amino-2-[(4-methoxy-3,5-dimethylpyridin-2-yl)methyl]-2,7,8,9-tetrahydro-6-thia-1,2,3,5-tetraazabenzo[cd]azulene-7-carboxylic acid of Example 27 (32 mg) and dimethylamine hydrochloride (14 mg).

$^1$H-NMR (CDCl$_3$) δ: 2.22 (3H, s), 2.28 (3H, s), 2.51-2.63 (1H, m), 2.77-2.85 (1H, m), 2.93-3.01 (1H, m), 3.02 (3H, s), 3.16 (3H, s), 3.23-3.31 (1H, m), 3.74 (3H, s), 4.39 (1H, d), 5.27 (9H, br.s), 5.43 (1H, d), 5.49 (1H, d), 8.19 (1H, s).

ESI-MS m/z: 428 (M+H)$^+$.

Example 30

4-Amino-N-isopropyl-2-[(4-methoxy-3,5-dimethylpyridin-2-yl)methyl]-2,7,8,9-tetrahydro-6-thia-1,2,3,5-tetraazabenzo[cd]azulene-7-carboxamide

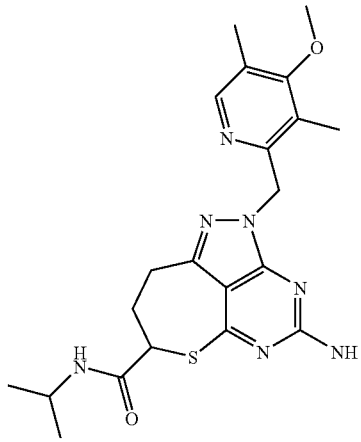

The title compound (27.1 mg, 77%) was obtained as a solid by the same method as in Example 9 using 4-amino-2-[(4-methoxy-3,5-dimethylpyridin-2-yl)methyl]-2,7,8,9-tetrahydro-6-thia-1,2,3,5-tetraazabenzo[cd]azulene-7-carboxylic acid of Example 27 (32 mg) and isopropylamine (0.014 mL).

$^1$H-NMR (CDCl$_3$) δ: 1.12 (3H, d), 1.16 (3H, d), 2.23 (3H, s), 2.25 (3H, s), 2.58-2.78 (2H, m), 2.96-3.08 (1H, m), 3.12-3.23 (1H, m), 3.76 (3H, s), 3.98-4.09 (2H, m), 5.42 (2H, s), 6.95 (1H, d), 8.12 (1H, s).

ESI-MS m/z: 442 (M+H)$^+$.

Example 31

4-Amino-N-[2-(dimethylamino)ethyl]-2-[(4-methoxy-3,5-dimethylpyridin-2-yl)methyl]-2,7,8,9-tetrahydro-6-thia-1,2,3,5-tetraazabenzo[cd]azulene-7-carboxamide

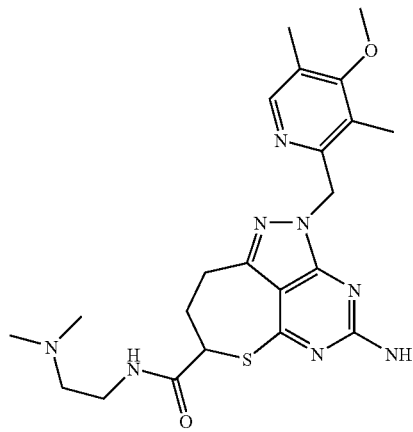

The title compound (20.0 mg, 49%) was obtained as a solid by the same method as in Example 9 using 4-amino-2-[(4-methoxy-3,5-dimethylpyridin-2-yl)methyl]-2,7,8,9-tetrahydro-6-thia-1,2,3,5-tetraazabenzo[cd]azulene-7-carboxylic acid of Example 27 (32 mg) and N,N-diethylethylenediamine (18 µl).

$^1$H-NMR (CD$_3$OD) δ: 2.41 (3H, s), 2.50 (3H, s), 2.70-2.82 (2H, m), 2.94 (6H, s), 3.04-3.40 (6H, m), 3.56-3.75 (2H, m), 4.14 (3H, s), 4.75 (2H, d), 5.72 (2H, s), 8.55 (1H, s).

ESI-MS m/z: 471 (M+H)$^+$.

Example 32

Di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

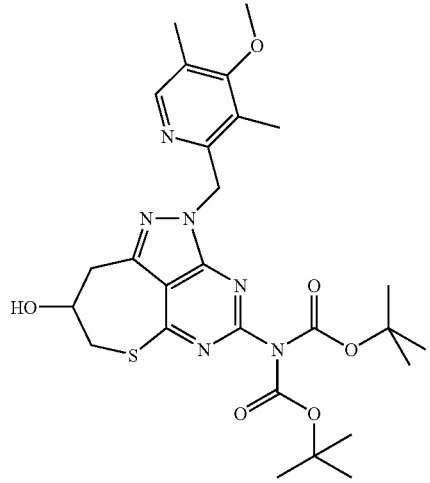

A solution of methanesulfonyl chloride (73 µL) in dehydrated dichloromethane was added dropwise to a mixture composed of di-tert-butyl {4-chloro-3-(2,3-dihydroxypropyl)-1-[(4-methoxy-3,5-dimethylpyridin-2-yl)methyl]-1H-pyrazolo[3,4-d]pyrimidin-6-yl}imidodicarbonate of Step 7) of Example 1 (510 mg), 2,4,6-collidine (1.15 mL) and dehydrated dichloromethane (17 mL) under cooling in an ice bath, and then the mixture was stirred for 15 hours. 0.5 N hydrochloric acid was added to the reaction mixture, followed by extraction with chloroform. The organic layer was washed with water, and then dried over anhydrous sodium sulfate and filtered. Then, the filtrate was concentrated under reduced pressure. The resulting residue was dissolved in N,N-dimethylformamide (10 mL). Sodium bisulfide monohydrate (76 mg) was added under cooling in an ice bath, followed by stirring for 20 minutes. Potassium carbonate (142 mg) was added to the reaction mixture and the ice bath was removed. The mixture was stirred for one hour, and then heated to 50° C. and further heated with stirring for two hours. Water was added to the reaction mixture, followed by extraction with ethyl acetate. The organic layer was sequentially washed with water and brine and then dried over anhydrous sodium sulfate. After filtration, the filtrate was concentrated under reduced pressure. The resulting residue was purified by silica gel column chromatography (ethyl acetate-hexane) to obtain the title compound (453 mg, 92%) as an oil.

$^1$H-NMR (CDCl$_3$) δ: 1.44 (18H, s), 2.22 (3H, s), 2.25 (3H, s), 3.29-3.41 (2H, m), 3.42-3.56 (2H, m), 3.73 (3H, s), 4.55-4.64 (1H, m), 5.60 (1H, d), 5.64 (1H, d), 8.15 (1H, s).

ESI-MS m/z: 573 (M+H)$^+$.

Example 33

4-Amino-2-[(4-methoxy-3,5-dimethylpyridin-2-yl)methyl]-2,7,8,9-tetrahydro-6-thia-1,2,3,5-tetraazabenzo[cd]azulen-8-ol

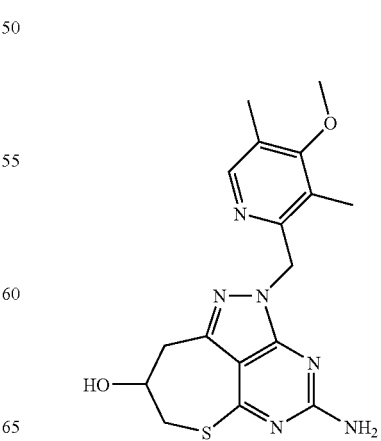

A mixture composed of di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 32 (40 mg), dichloromethane (1 mL), a 4 N solution of hydrochloric acid in dioxane (0.5 mL) and methanol (0.5 mL) was stirred at room temperature for two days. The reaction mixture was concentrated under reduced pressure, and the resulting residue was purified by reversed phase liquid chromatography to obtain the title compound (12.5 mg, 48%) as a solid.

$^1$H-NMR (CDCl$_3$) δ: 2.22 (3H, s), 2.26 (3H, s), 3.19-3.45 (4H, m), 3.74 (3H, s), 4.49-4.50 (1H, m), 5.33 (2H, br.s), 5.44 (2H, s), 8.17 (1H, s).

ESI-MS m/z: 373 (M+H)$^+$.

Example 34

8-Methoxy-2-[(4-methoxy-3,5-dimethylpyridin-2-yl)methyl]-2,7,8,9-tetrahydro-6-thia-1,2,3,5-tetraazabenzo[cd]azulen-4-amine

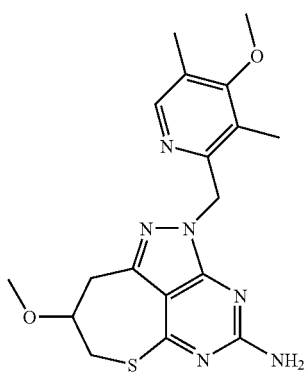

Sodium hydride (6.7 mg) was added to a mixture of di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 32 (40 mg) and dehydrated N,N-dimethylformamide (1 mL), and then the mixture was stirred at room temperature for one hour. Methyl iodide (6.5 µL) was added to the reaction mixture, followed by stirring for 1.5 hours. Then, water (20 mL) was added. The resulting mixture was extracted with ethyl acetate. The organic layer was washed with water and then dried over anhydrous sodium sulfate. After filtration, the filtrate was concentrated under reduced pressure. Dichloromethane (2 mL) and trifluoroacetic acid (0.5 mL) were added to the resulting residue, and the mixture was stirred at room temperature for two hours. The reaction mixture was concentrated under reduced pressure, and the resulting residue was purified by reversed phase liquid chromatography to obtain the title compound (4.8 mg, 18%) as a solid.

$^1$H-NMR (CDCl$_3$) δ: 2.23 (3H, s), 2.28 (3H, s), 2.98 (3H, s), 3.18-3.25 (2H, m), 3.32 (1H, dd), 3.38-3.45 (1H, m), 3.75 (3H, s), 4.48 (1H, dt), 5.44 (1H, d), 5.50 (1H, d), 8.16 (1H, s).

ESI-MS m/z: 387 (M+H)$^+$.

Example 35

4-[Bis(tert-butoxycarbonyl)amino]-2-[(4-methoxy-3,5-dimethylpyridin-2-yl)methyl]-2,7,8,9-tetrahydro-6-thia-1,2,3,5-tetraazabenzo[cd]azulen-8-yl methanesulfonate

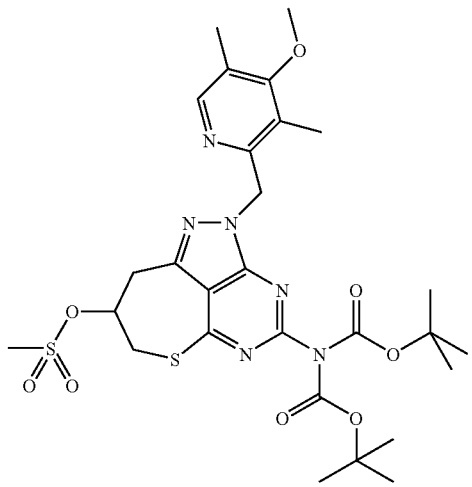

Methanesulfonyl chloride (39 µL) was added dropwise to a mixture composed of di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 32 (240 mg), dehydrated dichloromethane (6 mL) and triethylamine (88 µL) under cooling in an ice bath. The ice bath was removed and the mixture was stirred for two hours. After confirming that the raw material disappeared, the reaction mixture was diluted with chloroform and washed with water. The organic layer was dried over anhydrous sodium sulfate and then filtered, and the filtrate was concentrated under reduced pressure. Dichloromethane and hexane were added to the residue, and the precipitated solid was collected by filtration to obtain the title compound (253 mg, 93%). The resulting compound was directly used for the next reaction without purification.

ESI-MS m/z: 651 (M+H)$^+$.

Example 36

2-[(4-Methoxy-3,5-dimethylpyridin-2-yl)methyl]-2,7-dihydro-6-thia-1,2,3,5-tetraazabenzo[cd]azulen-4-amine

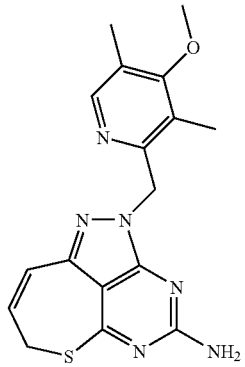

A mixture composed of 4-[bis(tert-butoxycarbonyl) amino]-2-[(4-methoxy-3,5-dimethylpyridin-2-yl)methyl]-2,7,8,9-tetrahydro-6-thia-1,2,3,5-tetraazabenzo[cd]azulen-8-ylmethanesulfonate of Example 35 (65 mg), dehydrated N,N-dimethylformamide (1 mL) and potassium carbonate (14 mg) was heated with stirring at 70° C. for six hours. The reaction mixture was cooled and a saturated sodium bicarbonate solution was added, followed by extraction with ethyl acetate. The organic layer was washed with brine, and then dried over anhydrous sodium sulfate. After filtration, the filtrate was concentrated under reduced pressure. Dichloromethane (2 mL) and trifluoroacetic acid (1 mL) were added to the resulting residue, and the mixture was stirred at room temperature for one hour. After confirming that the raw material disappeared, the reaction mixture was concentrated under reduced pressure. A saturated sodium bicarbonate solution was added to the residue, followed by extraction with ethyl acetate. The organic layer was washed with brine, and then dried over sodium sulfate and filtered. Then, the filtrate was concentrated under reduced pressure. The resulting residue was purified by silica gel thin-layer chromatography (chloroform-methanol) to obtain the title compound (12.9 mg, 36%) as a solid.

$^1$H-NMR (CDCl$_3$) δ: 2.23 (3H, s), 2.29 (3H, s), 3.72 (2H, d), 3.75 (3H, s), 5.51 (2H, s), 6.30 (1H, dt), 6.81 (1H, d), 8.18 (1H, s).

ESI-MS m/z: 355 (M+H)$^+$.

Example 37

4-Amino-2-[(4-methoxy-3,5-dimethylpyridin-2-yl) methyl]-2,7,8,9-tetrahydro-6-thia-1,2,3,5-tetraazabenzo[cd]azulen-8-yl methylcarbamate

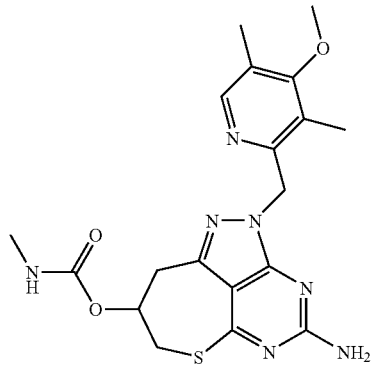

A mixture composed of di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 32 (40 mg), dehydrated dichloromethane (1 mL), pyridine (11 μL) and triphosgene (8.7 mg) was stirred under cooling in an ice bath for three hours. A 2 N solution of methylamine in tetrahydrofuran (0.6 mL) was added to the reaction mixture. Then, the ice bath was removed and the mixture was stirred for 17 hours. After confirming that the raw material disappeared, the reaction mixture was diluted with chloroform and washed with water. The aqueous layer was extracted with chloroform, and then the combined organic layers were dried over anhydrous sodium sulfate. After filtration, the filtrate was concentrated under reduced pressure. Dichloromethane (2 mL) and trifluoroacetic acid (0.5 mL) were added to the resulting residue, and the mixture was stirred at room temperature for 15 hours. The reaction mixture was concentrated under reduced pressure, and the resulting residue was purified by reversed phase liquid chromatography to obtain the title compound (6.6 mg, 22%) as a solid.

$^1$H-NMR (CDCl$_3$) δ: 2.23 (3H, s), 2.27 (3H, s), 2.78 (3H, d), 3.27-3.40 (3H, m), 3.55 (1H, dd), 3.75 (3H, s), 4.97-5.02 (1H, m), 5.19 (2H, br.s), 5.42 (1H, d), 5.47 (1H, d), 8.08 (1H, s), 8.19 (1H, s).

ESI-MS m/z: 430 (M+H)$^+$.

Example 38

4-Amino-2-[(4-methoxy-3,5-dimethylpyridin-2-yl) methyl]-2,7,8,9-tetrahydro-6-thia-1,2,3,5-tetraazabenzo[cd]azulen-8-yl ethylcarbamate

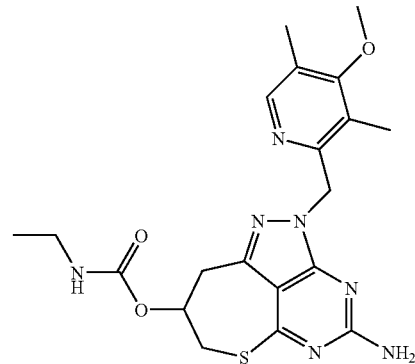

The title compound (18.5 mg, 40%) was obtained as a solid by the same method as in Example 37 using di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd] azulen-4-yl}imidodicarbonate of Example 32 (60 mg), triphosgene (13 mg) and a 2 N solution of ethylamine in tetrahydrofuran (0.25 mL) under cooling in an ice bath.

$^1$H-NMR (CDCl$_3$) δ: 1.12 (3H, t), 2.23 (3H, s), 2.27 (3H, s), 3.16-3.24 (2H, m), 3.28-3.37 (3H, m), 3.54 (1H, dd), 3.75 (3H, s), 5.09-5.15 (1H, m), 5.25-5.52 (4H, m), 8.19 (1H, s).

ESI-MS m/z: 444 (M+H)$^+$.

Example 39

4-[Bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl acetate

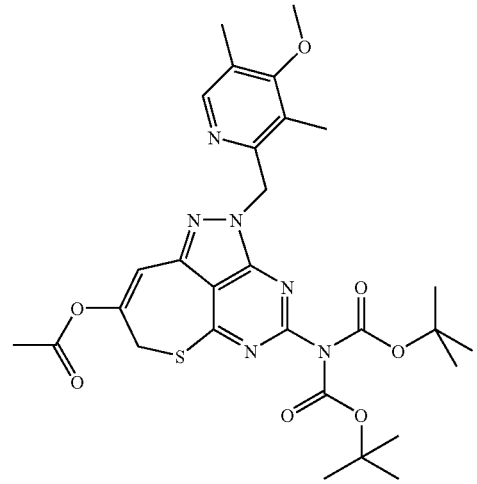

A mixture composed of di-tert-butyl {8-hydroxy-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 32 (778 mg), dimethyl sulfoxide (10 mL) and acetic anhydride (1 mL) was stirred in a nitrogen atmosphere at room temperature for 12 hours. After confirming that the raw material disappeared, the reaction mixture was diluted with ethyl acetate and sequentially washed with water and brine. The organic layer was dried over anhydrous sodium sulfate and filtered. Then, the filtrate was concentrated under reduced pressure. The resulting residue was purified by silica gel column chromatography (ethyl acetate-hexane) to obtain the title compound (507 mg, 61%) as an oil.

$^1$H-NMR (CDCl$_3$) δ: 1.43 (18H, s), 2.21 (3H, s), 2.25 (3H, s), 2.27 (3H, s), 3.74 (3H, s), 3.90 (2H, s), 5.67 (2H, s), 6.70 (1H, s), 8.14 (1H, s).

ESI-MS m/z: 613 (M+H)$^+$.

Example 40

Di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate

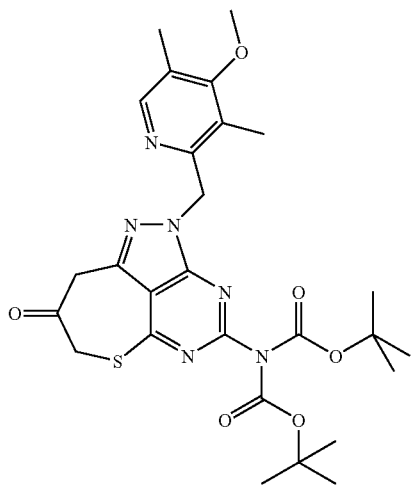

A mixture of 4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl acetate of Example 39 (507 mg), methanol (12 mL) and potassium carbonate (57 mg) was stirred under cooling in an ice bath for 30 minutes. After confirming that the raw material disappeared, a saturated ammonium chloride solution was added to the reaction mixture, followed by extraction with ethyl acetate. The organic layer was washed with brine, and then dried over anhydrous sodium sulfate. After filtration, the filtrate was concentrated under reduced pressure. The resulting residue was purified by silica gel column chromatography (ethyl acetate-hexane) to obtain the title compound (430 mg, 91%) as an oil.

ESI-MS m/z: 571 (M+H)$^+$.

Example 41

4-Amino-2-[(4-methoxy-3,5-dimethylpyridin-2-yl)methyl]-2,9-dihydro-6-thia-1,2,3,5-tetraazabenzo[cd]azulen-8(7H)-one

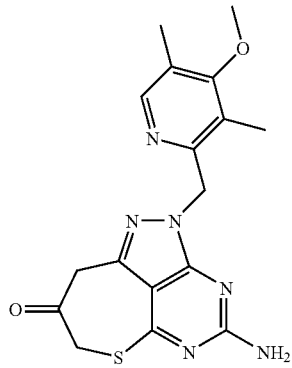

The title compound (21.7 mg, 75%) was obtained as a solid by the same method as in Example 2 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (43 mg).

$^1$H-NMR (CDCl$_3$) δ: 2.23 (3H, s), 2.29 (3H, s), 3.75 (3H, s), 3.80 (2H, s), 4.12-4.13 (1H, m), 4.12 (1H, s), 5.24 (1H, br.s), 5.48 (2H, s), 8.18 (1H, s).

ESI-MS m/z: 371 (M+H)$^+$.

Example 42

Di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

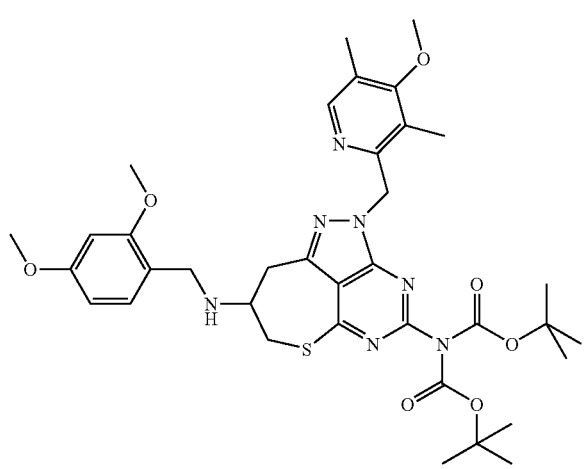

A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4- yl}imidodicarbonate of Example 40 (170 mg), dichloroethane (2 mL), acetic acid (0.034 mL) and 2,4-dimethoxybenzylamine (0.073 mL) was stirred at room temperature for 10 minutes. Then, sodium triacetoxyborohydride (126 mg) was added and the mixture was stirred for two hours. Sodium triacetoxyborohydride (63 mg) was added to the reaction mixture, followed by further stirring for one hour. Methanol (three drops) was added dropwise to the reaction mixture, and then the mixture was separated with chloroform and a 0.5 N sodium hydroxide solution. The aqueous layer was extracted with chloroform, and then the combined organic layers were washed with brine and dried over anhydrous sodium sulfate. After filtration, the filtrate was concentrated under reduced pressure. The resulting residue was purified by silica gel column chromatography (methanol-chloroform) to obtain the title compound (108 mg, 50%) as an oil.

$^1$H-NMR (CDCl$_3$) δ: 1.43 (18H, s), 2.21 (3H, s), 2.25 (3H, s), 3.19-3.36 (4H, m), 3.43-3.48 (1H, m), 3.72 (3H, s), 3.78 (6H, s), 5.60 (2H, s), 6.41-6.44 (2H, m), 7.12 (1H, d), 8.16 (1H, s).

ESI-MS m/z: 722 (M+H)$^+$.

Example 43

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}acetamide

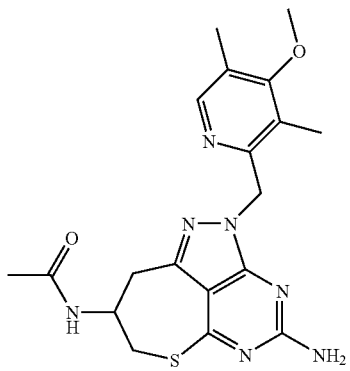

Acetyl chloride (18 μL) was added dropwise to a mixture composed of di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (36 mg), pyridine (40 μL) and dehydrated dichloromethane (0.7 mL) under cooling in an ice bath. The ice bath was removed and the mixture was stirred for three hours. The reaction mixture was diluted with chloroform and then washed with a 0.2 N hydrochloric acid solution. The organic layer was dried over anhydrous sodium sulfate. After filtration, the filtrate was concentrated under reduced pressure, and dichloromethane (1 mL) and 1,3-dimethoxybenzene (12 μL) were added to the resulting residue. Then, trifluoroacetic acid (1 mL) was added and the mixture was stirred at room temperature for 16 hours. The reaction mixture was concentrated under reduced pressure. The resulting residue was dissolved in chloroform and sequentially washed with a saturated sodium bicarbonate solution and brine. The organic layer was dried over anhydrous sodium sulfate and filtered. Then, the filtrate was concentrated under reduced pressure. The resulting residue was purified by silica gel thin-layer chromatography (chloroform-methanol) to obtain the title compound (15.6 mg, 76%) as a solid.

$^1$H-NMR (CDCl$_3$) δ: 1.96 (3H, s), 2.22 (3H, s), 2.30 (3H, s), 3.19 (1H, dd), 3.38 (1H, dd), 3.43-3.51 (2H, m), 3.75 (3H, s), 4.76-4.84 (1H, m), 5.21 (2H, br.s), 5.40 (1H, d), 5.45 (1H, d), 6.37 (1H, d), 8.13 (1H, s).

ESI-MS m/z: 414 (M+H)$^+$.

Example 44

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}acetamide

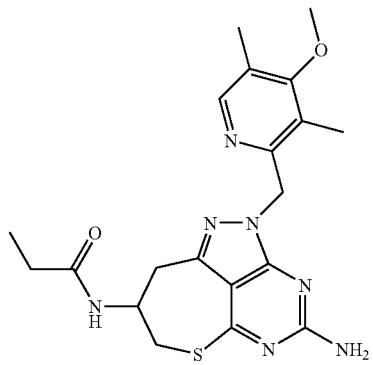

The title compound (14.6 mg, 68%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (36 mg) and propionyl chloride (0.022 mL).

$^1$H-NMR (CDCl$_3$) δ: 1.13 (3H, t), 2.20 (2H, dd), 2.22 (3H, s), 2.31 (3H, s), 3.21 (1H, dd), 3.36 (1H, dd), 3.44 (1H, d), 3.57 (1H, dd), 3.77 (3H, s), 4.75-4.81 (1H, m), 5.18 (1H, d), 5.39 (1H, d), 5.53 (1H, d), 6.89 (1H, d), 8.05 (1H, s).

ESI-MS m/z: 428 (M+H)$^+$.

Example 45

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}cyclopropanecarboxamide

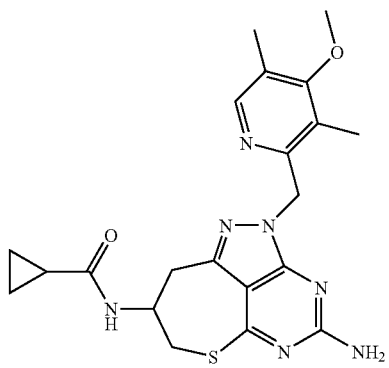

89

The title compound (12 mg, 55%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (36 mg) and cyclopropanecarbonyl chloride (22 μL).

$^1$H-NMR (CDCl$_3$) δ: 0.71-0.76 (2H, m), 0.93-0.97 (2H, m), 1.50-1.58 (1H, m), 2.23 (3H, s), 2.32 (3H, s), 3.30-3.49 (2H, m), 3.60 (1H, dd), 3.79 (3H, s), 4.69-4.76 (1H, m), 5.36 (1H, d), 5.58 (1H, d), 7.84 (1H, d), 7.99 (1H, s).

ESI-MS m/z: 440 (M+H)$^+$.

Example 46

2-[(4-Methoxy-3,5-dimethylpyridin-2-yl)methyl]-N$^8$-methyl-2,7,8,9-tetrahydro-6-thia-1,2,3,5-tetraazabenzo[cd]azulene-4,8-diamine hydrochloride

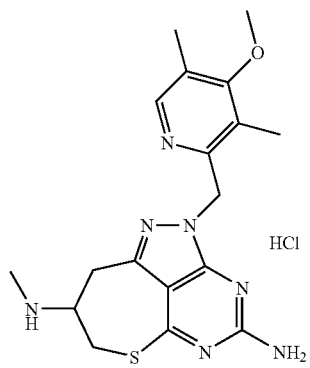

Sodium triacetoxyborohydride (16 mg) was added to a mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (28 mg), dichloroethane (0.5 mL), a 2 N solution of methylamine in tetrahydrofuran (0.1 mL) and acetic acid (6 μL), and the mixture was stirred at room temperature for 17 hours. Methanol (three drops) was added dropwise to the reaction mixture, and then a 0.2 N sodium hydroxide solution was added, followed by extraction with ethyl acetate. The organic layer was dried over anhydrous sodium sulfate and filtered, and then the filtrate was concentrated under reduced pressure. Dichloromethane (2 mL) and trifluoroacetic acid (0.5 mL) were added to the resulting residue, and the mixture was stirred at room temperature for two hours. The reaction mixture was concentrated under reduced pressure, and the resulting residue was purified by reversed phase liquid chromatography. A 4 N solution of hydrochloric acid in dioxane (20 μL) was added to the resulting solid. Methanol and diethyl ether were added and the precipitated solid was collected by filtration to obtain the title compound (5.7 g, 28%) as a solid.

$^1$H-NMR (CD$_3$OD) δ: 2.24 (3H, s), 2.27 (3H, s), 2.68 (3H, s), 3.27 (1H, dd), 3.39 (1H, dd), 3.51-3.54 (2H, m), 3.79 (3H, s), 5.46 (2H, s), 8.04 (1H, s).

ESI-MS m/z: 386 (M+H)$^+$.

90

Example 47

2-[(4-Methoxy-3,5-dimethylpyridin-2-yl)methyl]-N$^8$,N$^8$-dimethyl-2,7,8,9-tetrahydro-6-thia-1,2,3,5-tetraazabenzo[cd]azulene-4,8-diamine hydrochloride

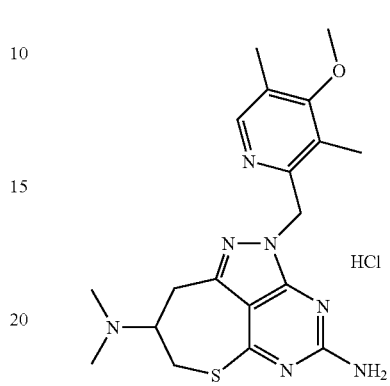

The title compound (11.9 mg, 56%) was obtained as a solid by the same method as in Example 46 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (28 mg) and a 2 N solution of dimethylamine in tetrahydrofuran (0.1 mL).

$^1$H-NMR (CD$_3$OD) δ: 2.24 (3H, s), 2.25 (3H, s), 2.63 (6H, s), 3.42 (1H, d), 3.49 (1H, dd), 3.63-3.69 (1H, m), 3.78 (3H, s), 5.45 (2H, s), 8.06 (1H, s).

ESI-MS m/z: 400 (M+H)$^+$.

Example 48

N$^8$-Ethyl-2-[(4-methoxy-3,5-dimethylpyridin-2-yl)methyl]-2,7,8,9-tetrahydro-6-thia-1,2,3,5-tetraazabenzo[cd]azulene-4,8-diamine hydrochloride

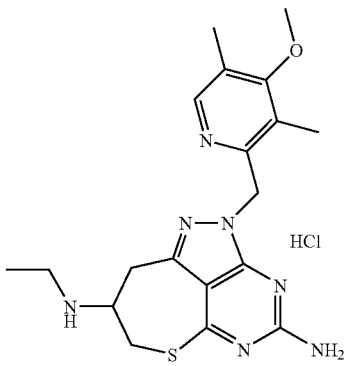

The title compound (2.4 mg, 11%) was obtained as a solid by the same method as in Example 46 using 4-di(tert-butoxycarbonyl)amino-2-(4-methoxy-3,5-dimethyl-pyridin-2-ylmethyl)-8-oxo-2,7,8,9-tetrahydro-6-thia-1,2,3,5-tetraazabenzo[cd]azulene of Example 40 (28 mg) and a 2 N solution of ethylamine in tetrahydrofuran (0.1 mL).

¹H-NMR (CD₃OD) δ: 1.21 (3H, t), 2.24 (3H, s), 2.26 (3H, s), 2.81-3.00 (2H, m), 3.16 (1H, dd), 3.38-3.48 (1H, m), 3.62-3.68 (1H, m), 3.78 (3H, s), 5.45 (2H, s), 8.05 (1H, s).
ESI-MS m/z: 400 (M+H)⁺.

Example 49

2-[(4-Methoxy-3,5-dimethylpyridin-2-yl)methyl]-8-pyrrolidin-1-yl-2,7,8,9-tetrahydro-6-thia-1,2,3,5-tetraazabenzo[cd]azulen-4-amine hydrochloride

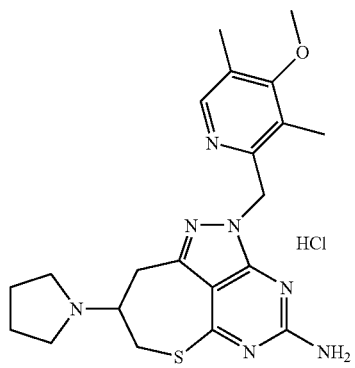

The title compound (12.1 mg, 53%) was obtained as a solid by the same method as in Example 44 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (28 mg) and pyrrolidine (8.2 μL).
¹H-NMR (CD₃OD) δ: 1.91-1.98 (4H, m), 2.24 (3H, s), 2.25 (3H, s), 2.96-3.04 (2H, m), 3.12-3.21 (2H, m), 3.33-3.38 (2H, m), 3.48 (1H, dd), 3.56-3.64 (2H, m), 3.78 (3H, s), 5.43 (1H, d), 5.47 (1H, d), 8.05 (1H, s).
ESI-MS m/z: 426 (M+H)⁺.

Example 50

2-[(4-Methoxy-3,5-dimethylpyridin-2-yl)methyl]-8-morpholin-4-yl-2,7,8,9-tetrahydro-6-thia-1,2,3,5-tetraazabenzo[cd]azulen-4-amine

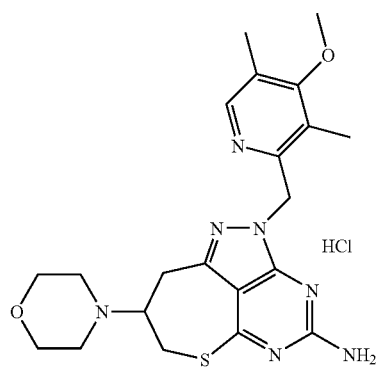

The title compound (11.2 mg, 48%) was obtained as a solid by the same method as in Example 46 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (28 mg) and morpholine (8.6 μL).
¹H-NMR (CD₃OD) δ: 2.21 (3H, s), 2.24 (3H, s), 2.53-2.59 (2H, m), 2.65-2.72 (2H, m), 3.14-3.24 (4H, m), 3.34-3.37 (2H, m), 3.64-3.69 (4H, m), 3.77 (3H, s), 5.43 (2H, s), 8.06 (1H, s).
ESI-MS m/z: 442 (M+H)⁺.

Example 51

N⁸-Cyclopropyl-2-[(4-methoxy-3,5-dimethylpyridin-2-yl)methyl]-2,7,8,9-tetrahydro-6-thia-1,2,3,5-tetraazabenzo[cd]azulene-4,8-diamine hydrochloride

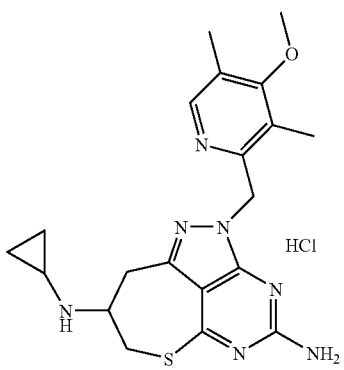

The title compound (5.5 mg, 22%) was obtained as a solid by the same method as in Example 46 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (28 mg) and pyrrolidine (6.8 μL).
¹H-NMR (CD₃OD) δ: 2.21 (3H, s), 2.24 (3H, s), 2.53-2.59 (2H, m), 2.65-2.72 (2H, m), 3.14-3.24 (4H, m), 3.34-3.37 (2H, m), 3.64-3.69 (4H, m), 3.77 (3H, s), 5.43 (2H, s), 8.06 (1H, s).
ESI-MS m/z: 412 (M+H)⁺.

Example 52

2'-[(4-Methoxy-3,5-dimethylpyridin-2-yl)methyl]-2',9'-dihydro spiro[1,3-dioxolane-2,8'-[6]thia[1,2,3,5]tetraazabenzo[cd]azulen]-4'-amine

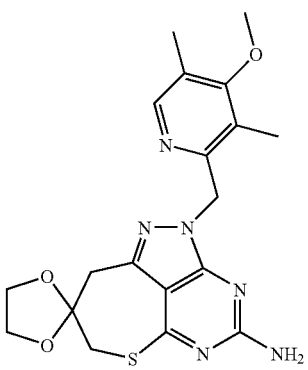

p-Toluenesulfonic acid monohydrate (16 mg) was added to a mixture composed of 4-amino-2-[(4-methoxy-3,5-dimethylpyridin-2-yl)methyl]-2,9-dihydro-6-thia-1,2,3,5-tetraazabenzo[cd]azulen-8(7H)-one of Example 41 (16 mg), ethylene glycol (24 μl) and toluene (0.5 ml), and then the mixture was heated under reflux for 18 hours. After cooling to room temperature, a saturated sodium bicarbonate solution was added to the reaction mixture, followed by extraction with chloroform. The organic layer was washed with brine, and then dried over anhydrous sodium sulfate. After filtration, the filtrate was concentrated, and the resulting residue was purified by silica gel thin-layer chromatography (chloroform-methanol) to obtain the title compound (8.6 mg, 48%) as a solid.

$^1$H-NMR (CDCl$_3$) δ: 2.22 (3H, s), 2.27 (3H, s), 3.38 (2H, s), 3.39 (2H, s), 3.74 (3H, s), 4.06-4.09 (4H, m), 5.11 (2H, s), 5.44 (2H, s), 8.19 (1H, s).

ESI-MS m/z: 415 (M+H)$^+$.

Example 53

2'-[(4-Methoxy-3,5-dimethylpyridin-2-yl)methyl]-2', 9'-dihydrospiro[1,3-dioxane-2,8'-[6]thia[1,2,3,5]tetraazabenzo[cd]azulen]-4'-amine

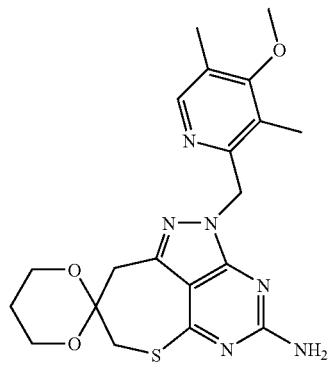

The title compound (5.1 mg, 28%) was obtained as a solid by the same method as in Example 52 using 4-amino-2-[(4-methoxy-3,5-dimethylpyridin-2-yl)methyl]-2,9-dihydro-6-thia-1,2,3,5-tetraazabenzo[cd]azulen-8(7H)-one of Example 41 (16 mg) and 1,3-propanediol (31 μl).

$^1$H-NMR (CDCl$_3$) δ: 1.61-1.70 (1H, m), 1.85-1.96 (1H, m), 2.22 (3H, s), 2.27 (3H, s), 3.44 (2H, s), 3.55 (2H, s), 3.74 (3H, s), 3.96-4.02 (4H, m), 5.06 (2H, s), 5.44 (2H, s), 8.19 (1H, s).

ESI-MS m/z: 429 (M+H)$^+$.

Example 54

2-[(4-Methoxy-3,5-dimethylpyridin-2-yl)methyl]-2,7-dihydro-8-oxa-6-thia-1,2,3,5,9-pentaazabenzo[cd]cyclopenta[h]azulen-4-amine

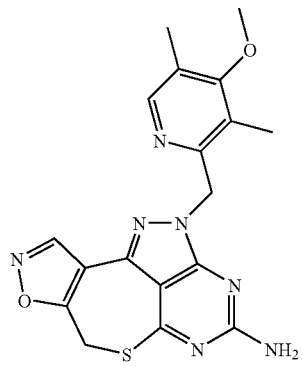

A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg), dimethylformamide-dimethyl acetal (56 μl) and toluene (0.5 ml) was heated with stirring at 80° C. for one hour. After confirming that the raw material disappeared, the reaction solution was concentrated under reduced pressure. Ethanol (0.5 ml) and hydroxylamine hydrochloride (9 mg) were added to the resulting residue, and the mixture was heated with stirring at 80° C. for four hours. The reaction solution was concentrated under reduced pressure. Dichloromethane (2 ml) and trifluoroacetic acid (0.5 ml) were added to the resulting residue, and the mixture was stirred at room temperature for two hours. The reaction solution was concentrated under reduced pressure. Then, the residue was dissolved in chloroform and washed with a saturated sodium bicarbonate solution. The organic layer was dried over anhydrous sodium sulfate and then filtered, and the filtrate was concentrated under reduced pressure. The resulting residue was purified by reversed phase liquid chromatography to obtain the title compound (15.1 mg, 55%) as a solid.

$^1$H-NMR (DMSO-d$_6$) δ: 2.17 (3H, s), 2.27 (3H, s), 3.73 (3H, s), 4.74 (2H, s), 5.48 (2H, s), 7.07 (2H, s), 8.05 (1H, s), 8.97 (1H, s).

ESI-MS m/z: 396 (M+H)$^+$

Example 55

Di-tert-butyl {2-[(4-methoxy-3,5-dimethylpyridin-2-yl)methyl]-9,9-dimethyl-8-oxo-2,7,8,9-tetrahydro-6-thia-1,2,3,5-tetraazabenzo[cd]azulen-4-yl}imidodicarbonate

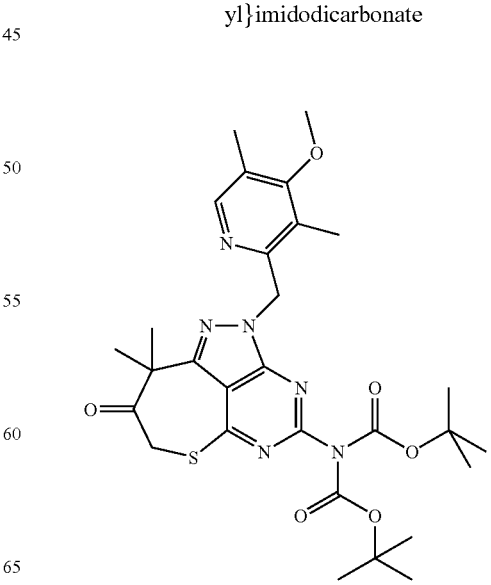

A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (86 mg), methyl iodide (38 μl), potassium carbonate (83 mg) and dehydrated dimethyl sulfoxide (1 ml) was stirred at room temperature for one hour. A saturated ammonium chloride solution was added to the reaction mixture, followed by extraction with ethyl acetate. The organic layer was washed with water. The organic layer was dried over anhydrous sodium sulfate and filtered. Then, the filtrate was concentrated under reduced pressure. The resulting residue was purified by silica gel thin-layer chromatography (ethyl acetate-hexane) to obtain the title compound (28 mg, 31%) as an oil.

$^1$H-NMR (CDCl$_3$) δ: 1.44 (18H, s), 1.63 (6H, s), 2.22 (3H, s), 2.27 (3H, s), 3.74 (3H, s), 3.90 (2H, s), 5.67 (2H, s), 8.11 (1H, s).

ESI-MS m/z: 599 (M+H)$^+$

Example 56

4-Amino-2-[(4-methoxy-3,5-dimethylpyridin-2-yl)methyl]-9,9-dimethyl-2,9-dihydro-6-thia-1,2,3,5-tetraazabenzo[cd]azulen-8(7H)-one

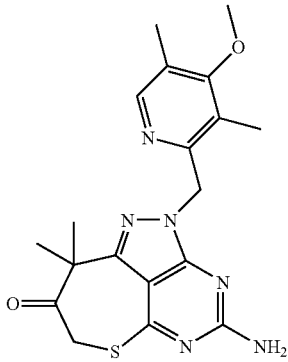

The title compound (12.3 mg, 66%) was obtained as a solid by the same method as in Example 2 using di-tert-butyl {2-[(4-methoxy-3,5-dimethylpyridin-2-yl)methyl]-9,9-dimethyl-8-oxo-2,7,8,9-tetrahydro-6-thia-1,2,3,5-tetraazabenzo[cd]azulen-4-yl}imidodicarbonate of Example 55 (28 mg).

$^1$H-NMR (CDCl$_3$) δ: 1.57 (6H, s), 2.23 (3H, s), 2.30 (3H, s), 3.75 (3H, s), 3.82 (2H, s), 5.25 (2H, br.s), 5.49 (2H, s), 8.17 (1H, s).

ESI-MS m/z: 399 (M+H)$^+$

Example 57

Di-tert-butyl{2'-[(4-methoxy-3,5-dimethylpyridin-2-yl)methyl]-8'-oxo-7',8'-dihydro-2'H-spiro[cyclopropane-1,9'-[6]thia[1,2,3,5]tetraazabenzo[cd]azulen]-4'-yl}imidodicarbonate

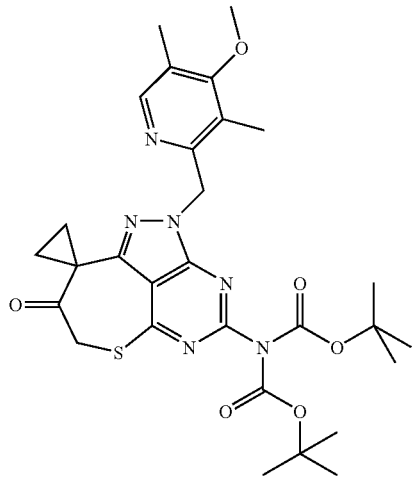

A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg), dibromoethane (9.1 μl), potassium carbonate (28.7 mg) and dimethyl sulfide (0.5 ml) was stirred at room temperature for 38 hours. Water was added to the reaction mixture, followed by extraction with ethyl acetate. The organic layer was washed with brine. The organic layer was dried over anhydrous sodium sulfate and filtered. Then, the filtrate was concentrated under reduced pressure. The resulting residue was purified by silica gel thin-layer chromatography (ethyl acetate-hexane) to obtain the title compound (21 mg, 50%) as an oil.

$^1$H-NMR (CDCl$_3$) δ: 1.45 (18H, s), 1.77-1.81 (2H, m), 1.89-1.93 (2H, m), 2.21 (3H, s), 2.28 (3H, s), 3.74 (3H, s), 3.94 (2H, s), 5.59 (2H, s), 8.10 (1H, s).

ESI-MS m/z: 597 (M+H)$^+$

Example 58

4'-Amino-2'-[(4-methoxy-3,5-dimethylpyridin-2-yl)methyl]-2'H-spiro[cyclopropane-1,9'-[6]thia[1,2,3,5]tetraazabenzo[cd]azulen]-8'(7'H)-one

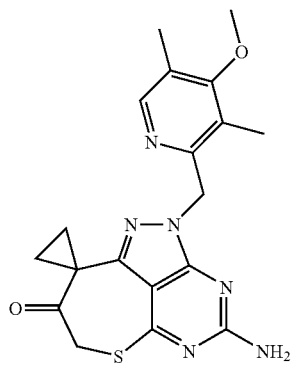

The title compound (12.0 mg, 86%) was obtained as a solid by the same method as in Example 2 using di-tert-butyl {2'-[(4-methoxy-3,5-dimethylpyridin-2-yl)methyl]-8'-oxo-7',8'-dihydro-2'H— spiro[cyclopropane-1,9'-[6]thia[1,2,3]tetraazabenzo[cd]azulen]-4'-yl}imidodicarbonate of Example 57 (21 mg).

$^1$H-NMR (CDCl$_3$) δ: 1.70-1.73 (2H, m), 1.81-1.85 (2H, m), 2.22 (3H, s), 2.31 (3H, s), 3.75 (3H, s), 3.87 (2H, s), 5.26 (2H, br.s), 5.42 (2H, s), 8.16 (1H, s).

ESI-MS m/z: 397 (M+H)$^+$

Example 59

N-{4'-Amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-yl}acetamide 1) Di-tert-butyl {8'-hydroxy-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate

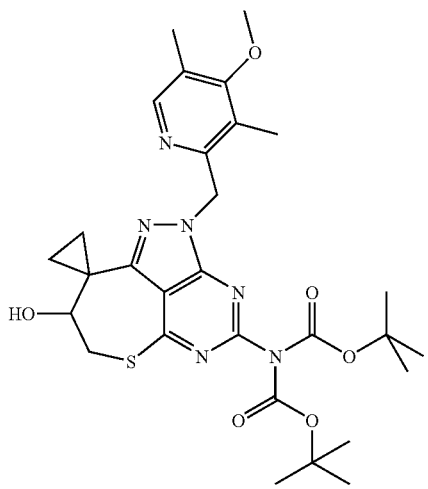

Sodium borohydride (19 mg) was added to a mixture composed of di-tert-butyl {2'-[(4-methoxy-3,5-dimethylpyridin-2-yl)methyl]-8'-oxo-7',8'-dihydro-2'H-spiro[cyclopropane-1,9'-[6]thia[1,2,3,5]tetraazabenzo[cd]azulen]-4'-yl}imidodicarbonate of Example 57 (100 mg) and methanol (4 ml) under cooling in an ice bath, and then the mixture was stirred for 30 minutes. Water was added to the reaction mixture, followed by extraction with ethyl acetate. The organic layer was dried over anhydrous sodium sulfate and filtered. Then, the filtrate was concentrated under reduced pressure to obtain a crude product of the title compound (91 mg, 91%) as an oil.

ESI-MS m/z: 599 (M+H)$^+$ 2) 4'-[Bis(tert-butoxycarbonyl)amino]-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-yl methanesulfonate

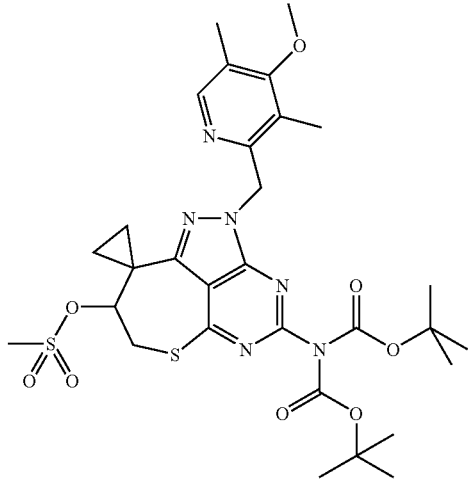

Methanesulfonyl chloride (14 μl) was added to a mixture composed of the above crude di-tert-butyl {8'-hydroxy-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate (91 mg), triethylamine (42 μl) and dichloromethane (4 ml) under cooling in an ice bath. Then, the ice bath was removed and the mixture was stirred for three hours. The reaction solution was cooled in an ice bath again, and methanesulfonyl chloride (6 μl) was added. Then, the ice bath was removed and the mixture was stirred for four hours. The reaction solution was washed with water, and then the organic layer was dried over anhydrous sodium sulfate. After filtration, the filtrate was concentrated under reduced pressure to obtain a crude product of the title compound (115 mg) as an oil. The resulting compound was directly used for the next reaction without purification.

ESI-MS m/z: 677 (M+H)$^+$

3) Di-tert-butyl {8'-azido-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate

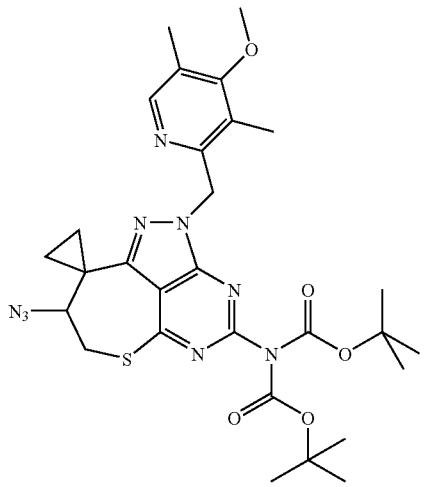

A mixture composed of the above crude 4'-[bis(tert-butoxycarbonyl)amino]-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-yl methanesulfonate (33 mg), sodium azide (37 mg) and N-methylpyrrolidone (0.5 ml) was heated with stirring at 80° C. for three hours. After cooling to room temperature, a 0.2 N sodium hydroxide solution was added to the reaction mixture, followed by extraction with ethyl acetate. The organic layer was washed with brine (30 ml) and then dried over sodium sulfate. After filtration, the filtrate was concentrated under reduced pressure to obtain a crude product of the title compound (35 mg) as an oil. The resulting compound was directly used for the next reaction without purification.

4) N-{4'-Amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-yl}acetamide

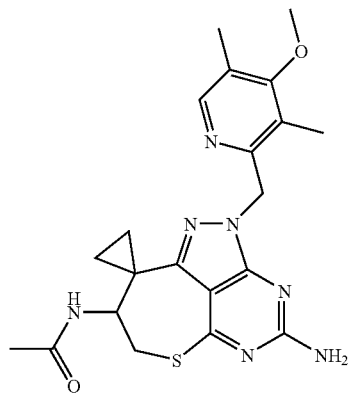

Triphenylphosphine (22 mg) was added to a mixture composed of the above crude di-tert-butyl {8'-azido-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate (35 mg), tetrahydrofuran (0.9 ml) and water (0.1 ml), and then the mixture was heated with stirring at 50° C. for three hours. After cooling to room temperature, water (3 ml) and a 1 N hydrochloric acid solution (0.6 ml) were added to the reaction mixture, followed by washing with ethyl acetate. A 1 N sodium hydroxide solution (1.2 ml) was added to the resulting aqueous layer, followed by extraction with ethyl acetate. The organic layer was concentrated under reduced pressure. Dehydrated dichloromethane (0.5 ml), pyridine 18µ) and acetic anhydride 16 µl) were added to the resulting residue, and the mixture was stirred at room temperature for 18 hours. The reaction mixture was concentrated under reduced pressure. Dichloromethane (2 ml) and trifluoroacetic acid (0.5 ml) were added to the resulting residue, and the mixture was stirred at room temperature for three hours. The reaction mixture was concentrated under reduced pressure. The resulting residue was dissolved in chloroform and sequentially washed with a saturated sodium bicarbonate solution and brine. The organic layer was dried over sodium sulfate and filtered. Then, the filtrate was concentrated under reduced pressure. The resulting residue was purified by silica gel thin-layer chromatography (chloroform-methanol) to obtain the title compound (4.2 mg, 17%) as a solid.

$^1$H-NMR (CDCl$_3$) δ: 0.97-1.05 (2H, m), 1.09-1.15 (1H, m), 1.70-1.76 (1H, m), 1.99 (3H, s), 2.22 (3H, s), 2.32 (3H, s), 3.46 (1H, dd), 3.71 (1H, d), 3.76 (3H, s), 3.85 (1H, t), 5.10 (2H, s), 5.35 (1H, d), 5.43 (1H, d), 6.39 (1H, d), 8.13 (1H, s).

ESI-MS m/z: 440 (M+H)$^+$

Example 60

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}-N-cyclopropylacetamide 1) Di-tert-butyl {8-(cyclopropylamino)-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

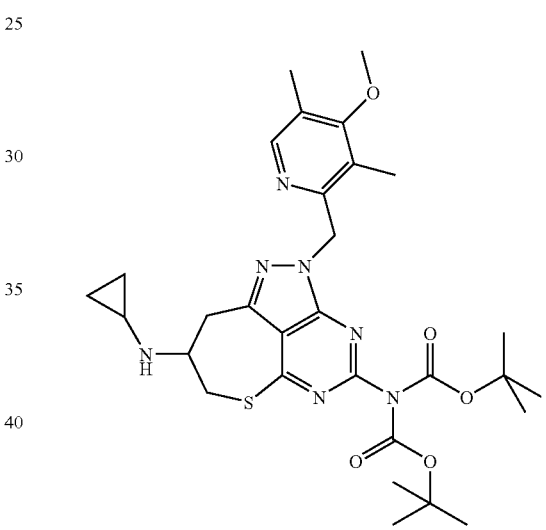

Sodium cyanoborohydride (1.89 g) was added to a mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (5.71 g), methanol (50 mL), tetrahydrofuran (25 mL), cyclopropylamine (1.04 mL) and acetic acid (1.72 mL) under cooling in an ice bath, and the mixture was stirred at room temperature for 14 hours. The reaction mixture was concentrated under reduced pressure and dissolved in ethyl acetate, and the solution was washed with a saturated sodium bicarbonate solution and then with brine. The organic layer was dried over anhydrous sodium sulfate and filtered. Then, the filtrate was concentrated under reduced pressure to obtain the title compound (5.91 g, 97%) as an oil.

$^1$H-NMR (CDCl$_3$) δ: 0.32-0.56 (4H, m), 1.44 (18H, s), 2.17-2.21 (1H, m), 2.21 (3H, s), 2.26 (3H, s), 3.24-3.43 (4H, m), 3.69-3.64 (1H, m), 3.73 (3H, s), 5.62 (2H, s), 8.16 (1H, s).

ESI-MS m/z: 612 (M+H)$^+$.

2) N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}-N-cyclopropylacetamide

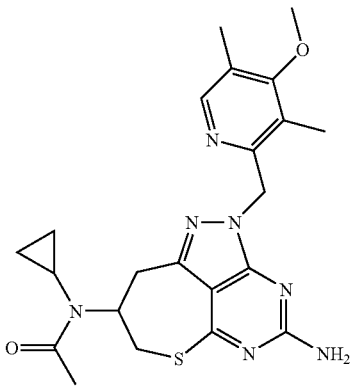

Acetyl chloride (14 µL) was added to a mixture composed of the above di-tert-butyl {8-(cyclopropylamino)-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (100 mg), dichloromethane (2 mL) and triethylamine (42 µL) under cooling in an ice bath, and the mixture was stirred at room temperature for 15 hours. The reaction mixture was diluted with ethyl acetate and washed with a saturated sodium bicarbonate solution. The organic layer was dried over anhydrous sodium sulfate and filtered, and then the filtrate was concentrated under reduced pressure. Dichloromethane (4 mL) and trifluoroacetic acid (1 mL) were added to the resulting residue, and the mixture was stirred at room temperature for one hour. The reaction mixture was concentrated under reduced pressure. A saturated sodium bicarbonate solution was added to the resulting residue under ice-cooling, followed by extraction with chloroform. The organic layer was dried over anhydrous sodium sulfate and filtered, and then the filtrate was concentrated under reduced pressure. The resulting residue was purified by silica gel column chromatography (chloroform-methanol) to obtain the title compound (55 mg, 75%) as an oil.

$^1$H-NMR (CDCl$_3$) δ: 0.76-1.00 (4H, m), 2.21 (3H, s), 2.22 (3H, s), 2.27 (3H, s), 2.71-2.76 (1H, m), 2.97 (1H, d, J=15.9 Hz), 3.14 (1H, d, J=16.6 Hz), 3.74 (3H, s), 3.88-3.99 (2H, m), 4.38-4.33 (1H, m), 5.16 (2H, s), 5.45 (2H, dd, J=26.4, 15.1 Hz), 8.19 (1H, s).

ESI-MS m/z: 454 (M+H)$^+$.

Example 61

N$^8$-Cyclopropyl-2-[(4-methoxy-3,5-dimethylpyridin-2-yl)methyl]-N$^8$-methyl-2,7,8,9-tetrahydro-6-thia-1,2,3,5-tetraazabenzo[cd]azulene-4,8-diamine

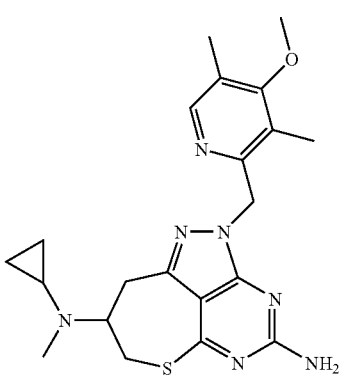

A mixture composed of di-tert-butyl {8-(cyclopropylamino)-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 60 (400 mg), methanol (2 mL), a 35% formalin solution (111 µL), acetic acid (156 µL) and molecular sieves 3A was stirred at room temperature for 40 minutes. Then, sodium cyanoborohydride (163 mg) was added, and the mixture was stirred at room temperature for 14 hours. The molecular sieves were separated off by filtration, and then the solvent was evaporated under reduced pressure. The residue was dissolved in ethyl acetate, and the solution was washed with a saturated sodium bicarbonate solution and then with brine. The organic layer was dried over anhydrous sodium sulfate and filtered, and then the filtrate was concentrated under reduced pressure. Dichloromethane (2 mL) and trifluoroacetic acid (2 mL) were added to the resulting residue, and the mixture was stirred at room temperature for one hour. The reaction mixture was concentrated under reduced pressure. A saturated sodium bicarbonate solution was added to the resulting residue under ice-cooling, followed by extraction with chloroform. The organic layer was dried over anhydrous sodium sulfate and filtered, and then the filtrate was concentrated under reduced pressure. The resulting residue was purified by silica gel column chromatography (chloroform-methanol) to obtain the title compound (233 mg, 84%) as an oil.

$^1$H-NMR (CDCl3) δ: 0.38-0.52 (4H, m), 1.85-1.90 (1H, m), 2.22 (3H, s), 2.27 (3H, s), 2.40 (3H, s), 3.12-3.36 (4H, m), 3.55-3.49 (1H, m), 3.74 (3H, s), 5.19 (2H, s), 5.42 (1H, d, J=15.1 Hz), 5.49 (1H, d, J=15.4 Hz), 8.20 (1H, s).

ESI-MS m/z: 426 (M+H)$^+$.

Example 62

N$^8$-Cyclobutyl-2-[(4-methoxy-3,5-dimethylpyridin-2-yl)methyl]-2,7,8,9-tetrahydro-6-thia-1,2,3,5-tetraazabenzo[cd]azulene-4,8-diamine

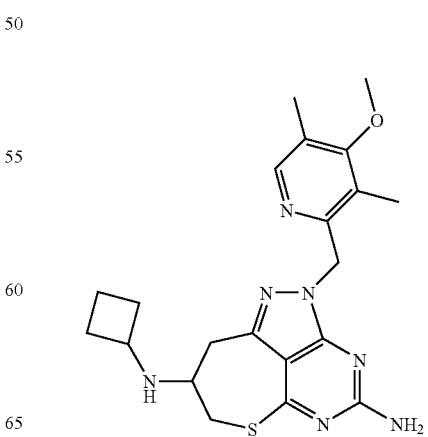

Sodium triacetoxyborohydride (16 mg) was added to a mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg), dichloroethane (0.7 ml), cyclobutylamine (15 μl) and acetic acid (10 μl), and the mixture was stirred at room temperature overnight. Methanol (three drops) was added dropwise to the reaction mixture, and then a 1 N sodium hydroxide solution was added, followed by extraction with ethyl acetate. The organic layer was dried over anhydrous sodium sulfate and filtered, and then the filtrate was concentrated under reduced pressure. Dichloromethane (2 ml) and trifluoroacetic acid (0.5 ml) were added to the resulting residue, and the mixture was stirred at room temperature for two hours. The reaction mixture was concentrated under reduced pressure, and the resulting residue was purified by reversed phase liquid chromatography. The resulting oil was dissolved in dioxane, followed by lyophilization to obtain the title compound (6.3 mg, 25%) as a colorless amorphous.
ESI-MS m/z: 426 (M+H)$^+$ Example 63

N$^8$-(Cyclopropylmethyl)-2-[(4-methoxy-3,5-dimethylpyridin-2-yl)methyl]-2,7,8,9-tetrahydro-6-thia-1,2,3,5-tetraazabenzo[cd]azulene-4,8-diamine

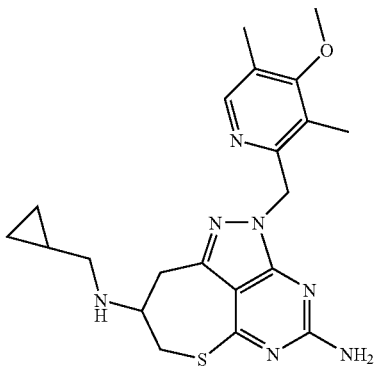

The title compound (6.0 mg, 24%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and cyclopropylmethylamine (17 mg).
ESI-MS m/z: 426 (M+H)$^+$ Example 64

4-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}piperazin-2-one

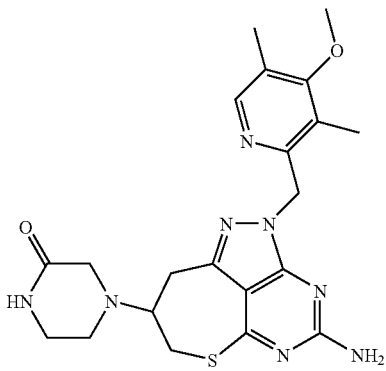

The title compound (5.2 mg, 19%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and 2-piperidinone (18 mg).
ESI-MS m/z: 455 (M+H)$^+$ Example 65

2-[(4-Methoxy-3,5-dimethylpyridin-2-yl)methyl]-8-piperidin-1-yl-2,7,8,9-tetrahydro-6-thia-1,2,3,5-tetraazabenzo[cd]azulen-4-amine

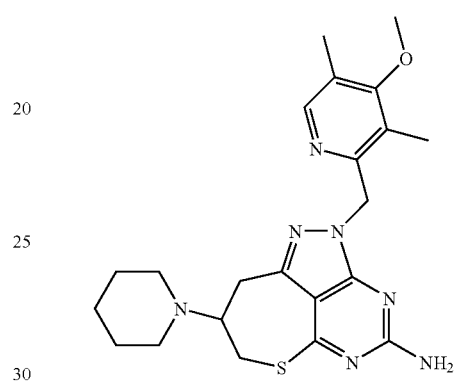

The title compound (13.7 mg, 52%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and piperidine (18 μl).
$^1$H-NMR (CD$_3$OD) δ: 1.57-1.65 (2H, m), 1.68-1.82 (4H, m), 2.93-3.07 (4H, m), 3.38-3.45 (1H, m), 3.51 (1H, dd, J=15.3, 7.2 Hz), 3.64-3.67 (2H, m), 3.78 (3H, s), 5.43-5.47 (2H, m), 8.06 (1H, s).
ESI-MS m/z: 440 (M+H)$^+$ Example 66

8-Azetidin-1-yl-2-[(4-methoxy-3,5-dimethylpyridin-2-yl)methyl]-2,7,8,9-tetrahydro-6-thia-1,2,3,5-tetraazabenzo[cd]azulen-4-amine

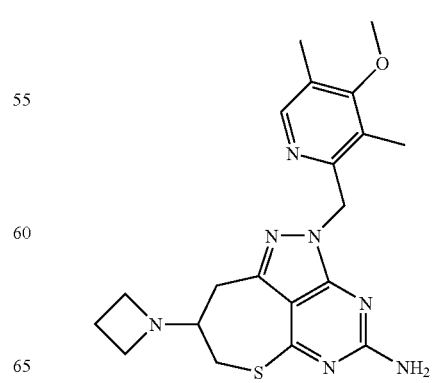

The title compound (18.5 mg, 75%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg), azetidine hydrochloride (17 mg) and triethylamine (17 μl).

$^{1}$H-NMR (CD$_{3}$OD) δ: 2.26 (4H, d, J=9.8 Hz), 2.32-2.43 (2H, m), 3.05-3.13 (1H, m), 3.40-3.48 (1H, m), 3.79 (3H, s), 3.88-3.97 (1H, m), 3.97-4.07 (1H, m), 5.46 (2H, s), 8.06 (1H, s).

ESI-MS m/z: 412 (M+H)$^{+}$

Example 67

1-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}-L-prolinamide

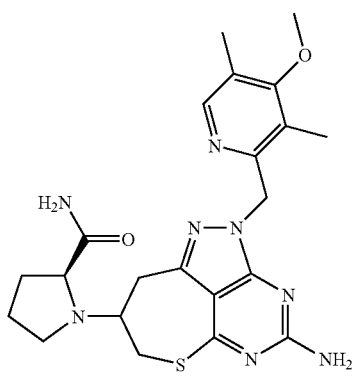

The title compound (12.3 mg, 43%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and (S)-pyrrolidinecarboxylic acid amide (17 mg).

ESI-MS m/z: 469 (M+H)$^{+}$

Example 68

2-[(4-Methoxy-3,5-dimethylpyridin-2-yl)methyl]-8-[(2S)-2-(methoxymethyl)pyrrolidin-1-yl]-2,7,8,9-tetrahydro-6-thia-1,2,3,5-tetraazabenzo[cd]azulen-4-amine

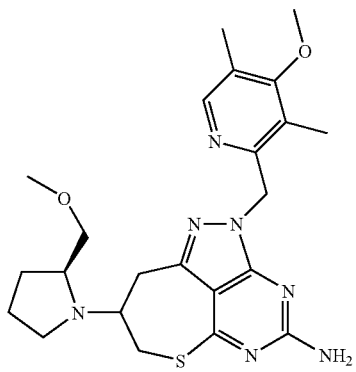

The title compound (11.0 mg, 39%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and (S)-2-methoxymethylpyrrolidine (24 μl).

ESI-MS m/z: 470 (M+H)$^{+}$

Example 69

N-[(3S)-1-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}pyrrolidin-3-yl]acetamide

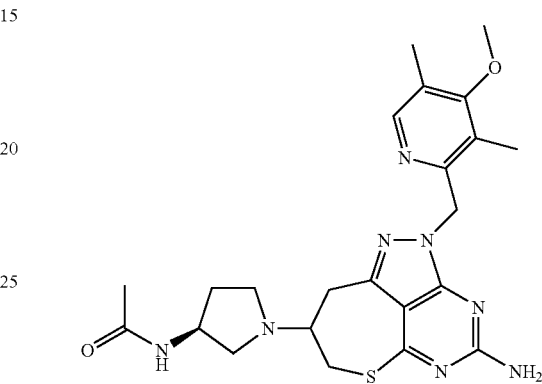

The title compound (22.6 mg, 78%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and (3S)-(−)-3-acetamidopyrrolidine (24 μl).

$^{1}$H-NMR (CD$_{3}$OD) δ: 1.86-1.90 (2H, m), 1.90-1.93 (1H, m), 2.23-2.28 (6H, m), 2.29-2.39 (1H, m), 2.94-3.10 (1H, m), 3.11-3.26 (1H, m), 3.33-3.39 (2H, m), 3.45-3.54 (2H, m), 3.62-3.67 (2H, m), 3.66 (3H, s), 3.80 (3H, s), 4.29-4.38 (1H, m), 5.43-5.50 (2H, m), 8.07 (1H, s).

ESI-MS m/z: 483 (M+H)$^{+}$

Example 70

2-[(4-Methoxy-3,5-dimethylpyridin-2-yl)methyl]-N$^{8}$-[(3R)-tetrahydrofuran-3-yl]-2,7,8,9-tetrahydro-6-thia-1,2,3,5-tetraazabenzo[cd]azulene-4,8-diamine

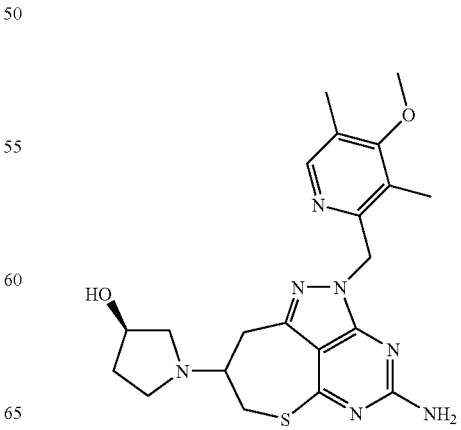

The title compound (17.4 mg, 65%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (34 mg) and (R)-(+)-3-pyrrolidinol (19 µl).

$^1$H-NMR (CD$_3$OD) δ: 1.87-1.96 (1H, m), 2.07-2.21 (1H, m), 3.03-3.18 (2H, m), 3.18-3.27 (1H, m), 3.32-3.40 (4H, m), 3.51-3.61 (3H, m), 3.70-3.76 (1H, m), 3.78 (3H, s), 4.42-4.48 (1H, m), 5.46 (2H, s), 8.06 (1H, s).

ESI-MS m/z: 442 (M+H)$^+$

Example 71

N$^8$-Isopropyl-2-[(4-methoxy-3,5-dimethylpyridin-2-yl)methyl]-2,7,8,9-tetrahydro-6-thia-1,2,3,5-tetraazabenzo[cd]azulene-4,8-diamine

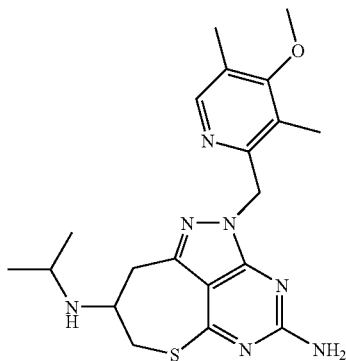

Isopropylamine (5.5 µl) was added to a mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg), methanol (0.4 ml), tetrahydrofuran (0.2 ml) and acetic acid (12 µl), and then the mixture was stirred at room temperature for two hours. A solution of sodium cyanoborohydride (10 mg) in methanol (0.4 ml) was added to the reaction mixture, followed by stirring at room temperature overnight. The reaction mixture was concentrated, and a 0.2 N sodium hydroxide solution was added to the resulting residue, followed by extraction with ethyl acetate. The organic layer was dried over anhydrous sodium sulfate and filtered, and then the filtrate was concentrated under reduced pressure. Dichloromethane (1 ml) and trifluoroacetic acid (0.25 ml) were added to the resulting residue, and the mixture was stirred at room temperature for five hours. The reaction mixture was concentrated under reduced pressure, and the resulting residue was purified by NH silica gel chromatography (chloroform-methanol). The resulting oil was dissolved in dioxane, followed by lyophilization to obtain the title compound (6.3 mg, 29%) as an amorphous.

$^1$H-NMR (CD$_3$OD) δ: 1.08 (3H, d, J=4.2 Hz), 1.10 (3H, d, J=4.2 Hz), 2.24 (6H, s), 2.99-3.07 (2H, m), 3.23 (1H, dd, J=16.8, 3.4 Hz), 3.32-3.38 (1H, m), 3.52-3.57 (1H, m), 3.78 (3H, s), 5.44 (2H, s), 8.05 (1H, s).

ESI-MS m/z: 414 (M+H)$^+$

Example 72

N$^8$-Isobutyl-2-[(4-methoxy-3,5-dimethylpyridin-2-yl)methyl]-2,7,8,9-tetrahydro-6-thia-1,2,3,5-tetraazabenzo[cd]azulene-4,8-diamine

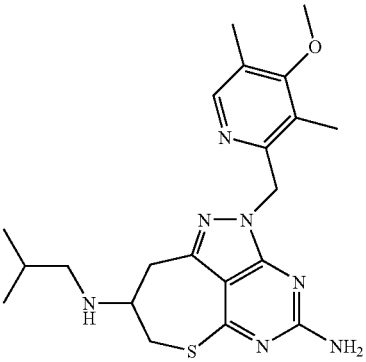

The title compound (19.9 mg, 88%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and isobutylamine (7.9 µl).

$^1$H-NMR (CD$_3$OD) δ: 0.92 (6H, dd, J=6.7, 2.6 Hz), 1.69-1.79 (1H, m), 2.23 (3H, s), 2.23 (3H, s), 2.45 (1H, dd, J=11.3, 6.5 Hz), 2.53 (1H, dd, J=11.3, 7.1 Hz), 3.01-3.10 (1H, m), 3.20-3.39 (4H, m), 3.77 (3H, s), 5.42 (2H, s), 8.05 (1H, s).

ESI-MS m/z: 428 (M+H)$^+$

Example 73

N$^8$-(2,2-Dimethylpropyl)-2-[(4-methoxy-3,5-dimethylpyridin-2-yl)methyl]-2,7,8,9-tetrahydro-6-thia-1,2,3,5-tetraazabenzo[cd]azulene-4,8-diamine

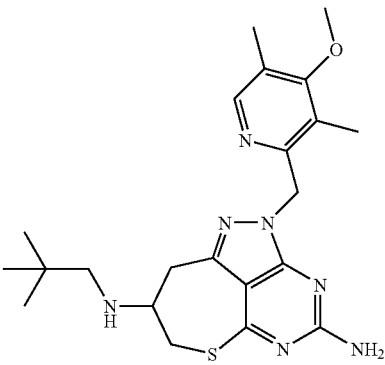

The title compound (20.6 mg, 89%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and neopentylamine (9.2 µl).

¹H-NMR (CD₃OD) δ: 0.90 (9H, s), 2.22 (3H, s), 2.23 (3H, s), 2.38 (1H, d, J=11.3 Hz), 2.50 (1H, d, J=11.0 Hz), 3.04-3.11 (1H, m), 3.19-3.40 (4H, m), 3.77 (3H, s), 5.42 (2H, s), 8.06 (1H, s).
ESI-MS m/z: 442 (M+H)⁺

Example 74

N⁸-(1-Ethylpropyl)-2-[(4-methoxy-3,5-dimethylpyridin-2-yl)methyl]-2,7,8,9-tetrahydro-6-thia-1,2,3,5-tetraazabenzo[cd]azulene-4,8-diamine

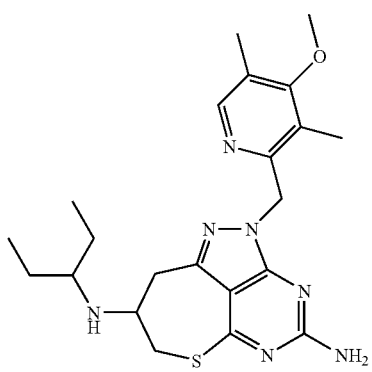

The title compound (11.4 mg, 49%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and 1-ethylpropylamine (9.2 μl).
¹H-NMR (CD₃OD) δ: 0.82 (3H, t, J=7.5 Hz), 0.91 (3H, t, J=7.5 Hz), 1.38-1.53 (4H, m), 2.56 (1H, dt, J=11.8, 5.6 Hz), 3.07 (1H, dd, J=16.8, 8.5 Hz), 3.19 (1H, dd, J=16.8, 3.4 Hz), 3.26-3.38 (2H, m), 3.50-3.56 (1H, m), 3.78 (3H, s), 5.43 (2H, s), 8.06 (1H, s).
ESI-MS m/z: 442 (M+H)⁺

Example 75

N⁸-Cyclohexyl-2-[(4-methoxy-3,5-dimethylpyridin-2-yl)methyl]-2,7,8,9-tetrahydro-6-thia-1,2,3,5-tetraazabenzo[cd]azulene-4,8-diamine

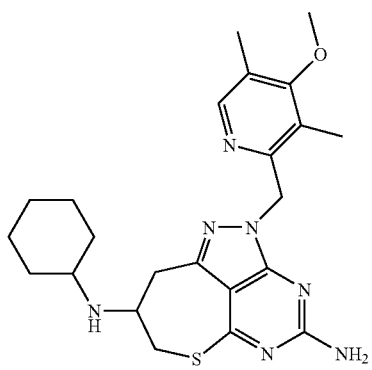

The title compound (15.8 mg, 66%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and cyclohexylamine (9.0 μl).
¹H-NMR (CD₃OD) δ: 1.02-1.31 (4H, m), 1.60-1.77 (4H, m), 1.84-1.97 (2H, m), 2.58-2.66 (1H, m), 3.02 (1H, dd, J=16.9, 8.9 Hz), 3.21 (1H, dd, J=16.9, 3.2 Hz), 3.27-3.37 (2H, m), 3.55-3.62 (1H, m), 3.77 (3H, s), 5.43 (2H, s), 8.05 (1H, s).
ESI-MS m/z: 454 (M+H)⁺

Example 76

N⁸-Cyclopentyl-2-[(4-methoxy-3,5-dimethylpyridin-2-yl)methyl]-2,7,8,9-tetrahydro-6-thia-1,2,3,5-tetraazabenzo[cd]azulene-4,8-diamine

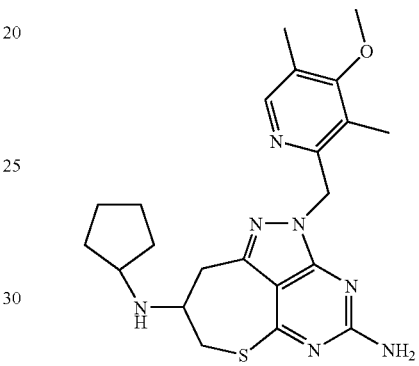

The title compound (16.2 mg, 70%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and cyclopentylamine (7.7 μl).
¹H-NMR (CD₃OD) δ: 1.29-1.39 (2H, m), 1.51-1.60 (2H, m), 1.67-1.75 (2H, m), 1.87-1.95 (2H, m), 2.24 (6H, s), 3.04 (1H, dd, J=16.1, 9.9 Hz), 3.21-3.38 (4H, m), 3.44-3.50 (1H, m), 3.77 (3H, s), 5.43 (2H, s), 8.05 (1H, s).
ESI-MS m/z: 440 (M+H)⁺

Example 77

2-[(4-Methoxy-3,5-dimethylpyridin-2-yl)methyl]-N⁸-propyl-2,7,8,9-tetrahydro-6-thia-1,2,3,5-tetraazabenzo[cd]azulene-4,8-diamine

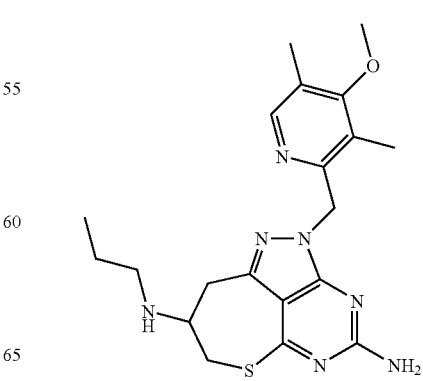

The title compound (15.1 mg, 70%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and n-propylamine (6.5 µl).

$^1$H-NMR (CD$_3$OD) δ: 0.93 (3H, t, J=7.4 Hz), 1.48-1.59 (2H, m), 2.23 (6H, s), 2.55-2.72 (2H, m), 3.05 (1H, dd, J=16.9, 8.8 Hz), 3.21-3.43 (4H, m), 3.77 (3H, s), 5.43 (2H, s), 8.05 (1H, s).

ESI-MS m/z: 414 (M+H)$^+$

Example 78

N$^8$-Butyl-2-[(4-methoxy-3,5-dimethylpyridin-2-yl)methyl]-2,7,8,9-tetrahydro-6-thia-1,2,3,5-tetraazabenzo[cd]azulene-4,8-diamine

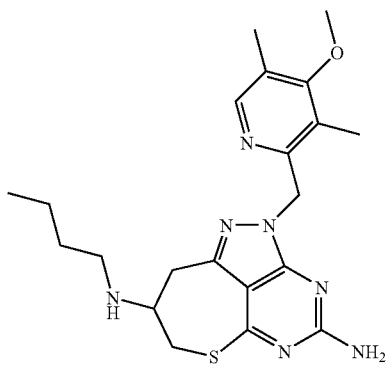

The title compound (16.7 mg, 74%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and n-butylamine (7.8 µl).

$^1$H-NMR (CD$_3$OD) δ: 0.92 (3H, t, J=7.4 Hz), 1.31-1.41 (2H, m), 1.46-1.54 (2H, m), 2.23 (6H, s), 2.58-2.66 (1H, m), 2.68-2.75 (1H, m), 3.05 (1H, dd, J=16.9, 8.8 Hz), 3.21-3.42 (4H, m), 3.77 (3H, s), 5.42 (2H, s), 8.05 (1H, s).

ESI-MS m/z: 428 (M+H)$^+$

Example 79

2-[(4-Methoxy-3,5-dimethylpyridin-2-yl)methyl]-N$^8$-(2-methoxyethyl)-2,7,8,9-tetrahydro-6-thia-1,2,3,5-tetraazabenzo[cd]azulene-4,8-diamine

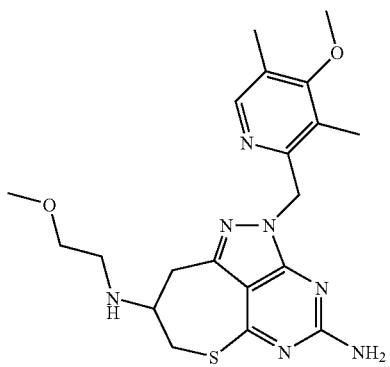

The title compound (17.7 mg, 78%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and 2-methoxyethylamine (6.9 µl).

$^1$H-NMR (CD$_3$OD) δ: 2.23 (3H, s), 2.23 (3H, s), 2.77-2.84 (1H, m), 2.87-2.94 (1H, m), 3.07 (1H, dd, J=16.8, 8.7 Hz), 3.19-3.29 (2H, m), 3.32 (3H, s), 3.34-3.52 (4H, m), 3.77 (3H, s), 5.42 (2H, s), 8.06 (1H, s).

ESI-MS m/z: 430 (M+H)$^+$

Example 80

2-[(4-Methoxy-3,5-dimethylpyridin-2-yl)methyl]-N$^8$-(3-methylbutyl)-2,7,8,9-tetrahydro-6-thia-1,2,3,5-tetraazabenzo[cd]azulene-4,8-diamine

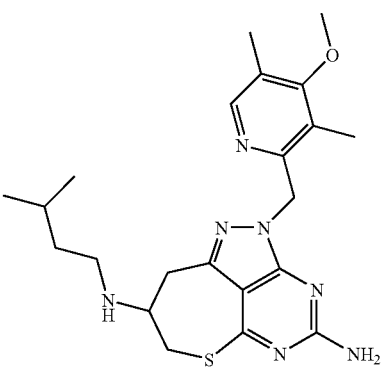

The title compound (16.1 mg, 69%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and isoamylamine (9.1 µl).

$^1$H-NMR (CD$_3$OD) δ: 0.88-0.94 (6H, m), 1.36-1.45 (4H, m), 1.55-1.66 (1H, m), 2.24 (6H, s), 2.59-2.67 (1H, m), 2.70-2.77 (1H, m), 3.06 (1H, dd, J=16.8, 8.7 Hz), 3.21-3.44 (4H, m), 3.77 (3H, s), 5.43 (2H, s), 8.05 (1H, s).

ESI-MS m/z: 442 (M+H)$^+$

Example 81

N$^8$-But-3-en-1-yl-2-[(4-methoxy-3,5-dimethylpyridin-2-yl)methyl]-2,7,8,9-tetrahydro-6-thia-1,2,3,5-tetraazabenzo[cd]azulene-4,8-diamine

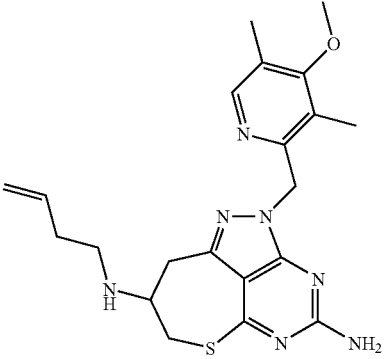

The title compound (7.6 mg, 34%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and 1-amino-3-butene hydrochloride (8.5 mg).

$^1$H-NMR (CD3OD) δ: 2.23 (3H, s), 2.24 (3H, s), 2.25-2.30 (2H, m), 2.65-2.72 (1H, m), 2.75-2.84 (1H, m), 3.07 (1H, dd, J=16.9, 8.6 Hz), 3.19-3.26 (1H, m), 3.33-3.47 (3H, m), 3.78 (3H, s), 4.96-5.01 (1H, m), 5.02-5.10 (1H, m), 5.43 (2H, s), 5.80 (1H, ddt, J=17.4, 10.3, 6.9 Hz), 8.06 (1H, s).
ESI-MS m/z: 426 (M+H)+

Example 82

2-[(4-Methoxy-3,5-dimethylpyridin-2-yl)methyl]-N[8]-(3,3,3-trifluoropropyl)-2,7,8,9-tetrahydro-6-thia-1,2,3,5-tetraazabenzo[cd]azulene-4,8-diamine

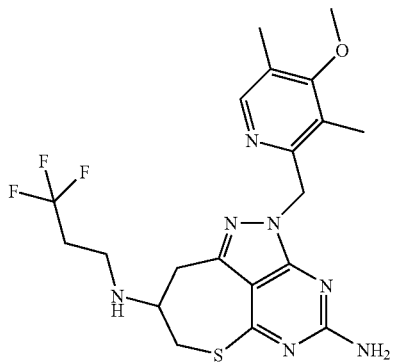

The title compound (10.6 mg, 43%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (30 mg) and 3,3,3-trifluoropropylamine hydrochloride (11.8 mg).

$^1$H-NMR (CD3OD) δ: 2.24 (6H, s), 2.31-2.44 (2H, m), 2.82-2.89 (1H, m), 2.93-3.01 (1H, m), 3.09 (1H, dd, J=16.9, 8.1 Hz), 3.22 (1H, dd, J=16.9, 3.2 Hz), 3.33-3.37 (2H, m), 3.41-3.47 (1H, m), 3.78 (3H, s), 5.43 (2H, s), 8.05 (1H, s).
ESI-MS m/z: 468 (M+H)+

Example 83

(3S)-3-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)piperidin-2-one

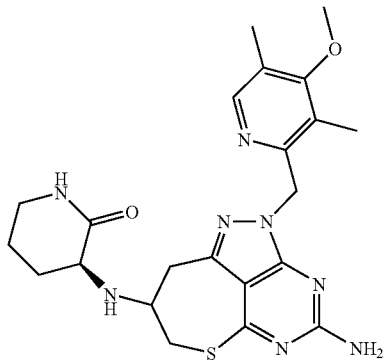

The title compound (18.3 mg, 56%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (S)-3-aminopiperidin-2-one hydrochloride (21 mg).

$^1$H-NMR (CD3OD) δ: 1.55-1.71 (1H, m), 1.77-2.01 (2H, m), 2.18-2.31 (7H, m), 3.12-3.29 (3H, m), 3.40-3.62 (4H, m), 3.68-3.90 (4H, m), 5.44 (2H, s), 8.07 (1H, s), 8.19 (1H, brs).
ESI-MS m/z: 469 (M+H)+

Example 84

(3S)-3-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)pyrrolidin-2-one

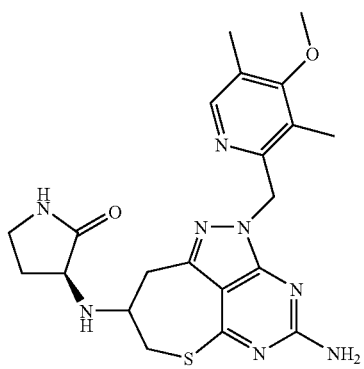

The title compound (18.3 mg, 56%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (S)-3-aminopyrrolidin-2-one hydrochloride (19 mg).

$^1$H-NMR (CD3OD) δ: 1.84-1.99 (1H, m), 2.24-2.26 (6H, m), 2.44-2.53 (1H, m), 3.12-3.22 (1H, m), 3.26-3.39 (3H, m), 3.40-3.47 (2H, m), 3.68-3.77 (2H, m), 3.79 (3H, s), 3.90-3.97 (1H, m), 5.45 (2H, s), 8.07 (1H, s), 8.12 (1H, brs).
ESI-MS m/z: 455 (M+H)+

Example 85

(3R)-3-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)pyrrolidin-2-one

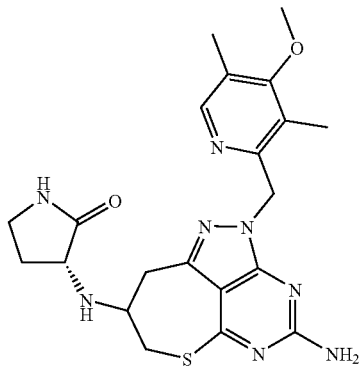

The title compound (12.7 mg, 40%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (R)-3-aminopyrrolidin-2-one hydrochloride (19 mg).

$^1$H-NMR (CD$_3$OD) δ: 1.84-1.99 (1H, m), 2.24-2.26 (6H, m), 2.44-2.53 (1H, m), 3.12-3.22 (1H, m), 3.26-3.39 (3H, m), 3.40-3.47 (2H, m), 3.68-3.77 (2H, m), 3.79 (3H, s), 3.90-3.97 (1H, m), 5.45 (2H, s), 8.07 (1H, s), 8.12 (1H, brs).

ESI-MS m/z: 455 (M+H)$^+$

Example 86

(3S)-3-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)-1-methylpyrrolidin-2-one

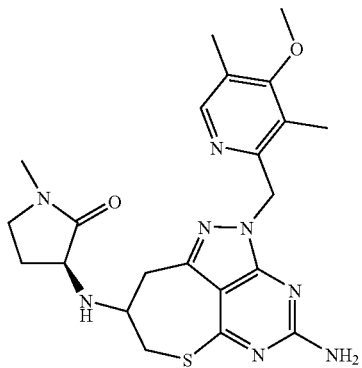

The title compound (21.6 mg, 66%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (S)-3-amino-1-methylpyrrolidin-2-one hydrochloride (17 mg).

$^1$H-NMR (CD$_3$OD) δ: 1.75-1.90 (1H, m), 2.23-2.26 (6H, m), 2.37-2.46 (1H, m), 2.84 (3H, s), 3.08-3.19 (1H, m), 3.23-3.49 (4H, m), 3.65-3.74 (1H, m), 3.79 (3H, s), 3.87-3.94 (1H, m), 5.44 (2H, s), 8.06 (1H, brs), 8.13 (1H, s).

ESI-MS m/z: 469 (M+H)$^+$

Example 87

(3R)-3-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)-1-methylpyrrolidin-2-one

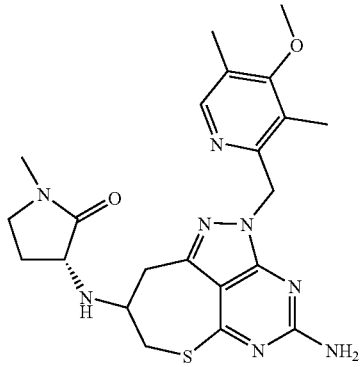

The title compound (21.2 mg, 60%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (R)-3-amino-1-methylpyrrolidin-2-one hydrochloride (16 mg).

$^1$H-NMR (CD$_3$OD) δ: 1.75-1.90 (1H, m), 2.23-2.26 (6H, m), 2.37-2.46 (1H, m), 2.84 (3H, s), 3.08-3.19 (1H, m), 3.23-3.49 (4H, m), 3.65-3.74 (1H, m), 3.79 (3H, s), 3.87-3.94 (1H, m), 5.44 (2H, s), 8.06 (1H, brs), 8.13 (1H, s).

ESI-MS m/z: 469 (M+H)$^+$

Example 88

2-[(4-Methoxy-3,5-dimethylpyridin-2-yl)methyl]-N$^8$-(tetrahydro-2H-pyran-4-yl)-2,7,8,9-tetrahydro-6-thia-1,2,3,5-tetraazabenzo[cd]azulene-4,8-diamine

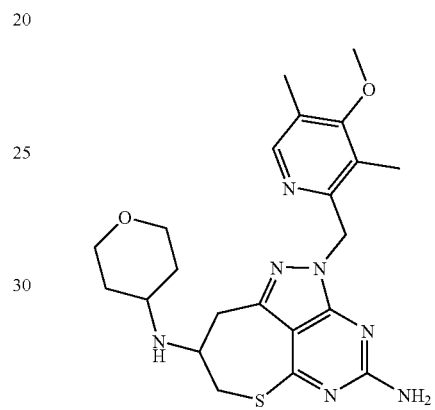

The title compound (6.5 mg, 16%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (50 mg), 4-aminotetrahydropyran hydrochloride (36 mg) and triethylamine (24 μl).

$^1$H-NMR (CDCl$_3$) δ: 1.33-1.49 (2H, m), 1.81 (2H, t, J=12.9 Hz), 2.22 (3H, s), 2.28 (4H, s), 2.79-2.88 (1H, m), 3.11-3.44 (6H, m), 3.62-3.67 (1H, m), 3.74 (3H, s), 3.94-3.99 (2H, m), 5.10 (2H, s), 5.45 (2H, s), 8.18 (1H, s).

ESI-MS m/z: 456 (M+H)

Example 89

2-[(4-Methoxy-3,5-dimethylpyridin-2-yl)methyl]-N$^8$-[(3R)-tetrahydrofuran-3-yl]-2,7,8,9-tetrahydro-6-thia-1,2,3,5-tetraazabenzo[cd]azulene-4,8-diamine

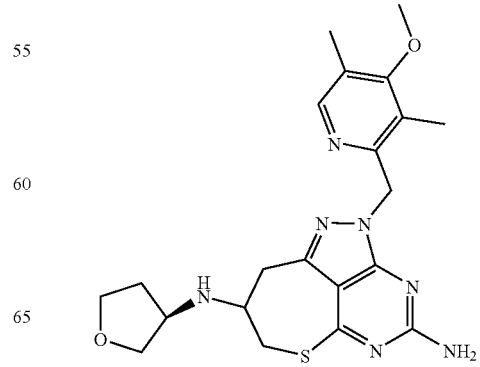

The title compound (7.5 mg, 23%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (50 mg), (R)-3-aminotetrahydrofuran p-toluenesulfonate (68 mg) and triethylamine (24 µl).

$^1$H-NMR (CDCl$_3$) δ: 1.63-1.78 (1H, m), 2.05-2.19 (1H, m), 2.22 (3H, s), 2.28 (3H, s), 3.12-3.37 (4H, m), 3.46-3.58 (3H, m), 3.74 (3H, s), 3.75-3.96 (3H, m), 5.07 (2H, brs), 5.43 (2H, d, J=15.9 Hz), 5.47 (2H, d, J=15.9 Hz), 8.19 (1H, s).

ESI-MS m/z: 442 (M+H)

Example 90

2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)propane-1,3-diol

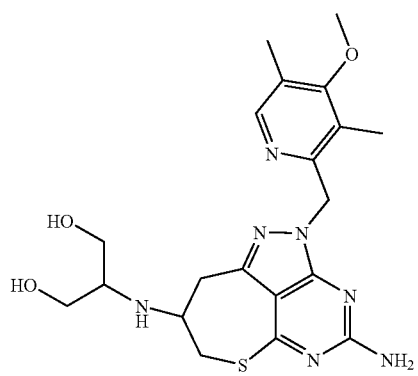

The title compound (13.1 mg, 42%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and 2-aminopropane-1,3-diol (13 mg).

$^1$H-NMR (CD$_3$OD) δ: 2.23 (3H, s), 2.24 (3H, s), 2.85-2.90 (1H, m), 3.10 (1H, dd, J=16.7, 8.7 Hz), 3.23 (1H, dd, J=16.7, 3.3 Hz), 3.34-3.41 (2H, m), 3.47-3.55 (2H, m), 3.57-3.68 (3H, m), 3.78 (2H, s), 5.43 (2H, s), 8.06 (1H, s).

ESI-MS m/z: 446 (M+H)

Example 91 trans-4-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)cyclohexanol

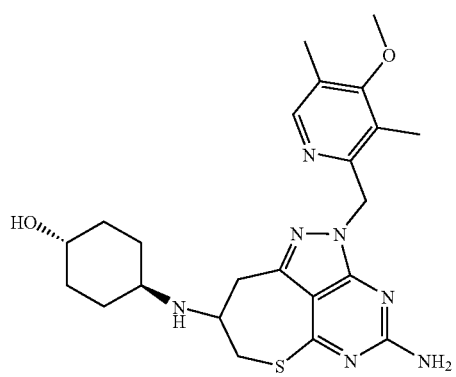

The title compound (7.3 mg, 22%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and trans-4-aminocyclohexanol (16 mg).

$^1$H-NMR (CD$_3$OD+CDCl$_3$) δ: 1.12-1.39 (5H, m), 1.89-2.02 (4H, m), 2.26 (6H, s), 2.60-2.69 (1H, m), 3.10 (1H, dd, J=16.7, 8.4 Hz), 3.20-3.40 (2H, m), 3.50-3.60 (1H, m), 3.60-3.69 (1H, m), 3.79 (3H, s), 5.44 (2H, s), 8.10 (1H, s).

ESI-MS m/z: 470 (M+H)

Example 92

2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)ethanol

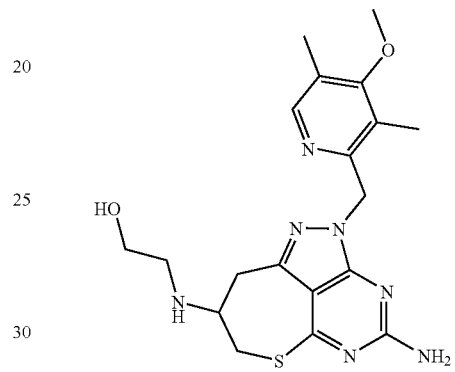

The title compound (3.6 mg, 12%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and 2-aminoethanol hydrochloride (14 mg).

$^1$H-NMR (CD$_3$OD) δ: 2.24 (6H, s), 2.75-2.92 (2H, m), 3.11 (1H, dd, J=16.9, 8.5 Hz), 3.25 (1H, dd, J=16.9, 3.5 Hz), 3.31-3.43 (2H, m), 3.46-3.52 (1H, m), 3.66 (2H, t, J=5.6 Hz), 3.78 (3H, s), 5.44 (2H, s), 8.06 (1H, s).

ESI-MS m/z: 416 (M+H)$^+$.

Example 93

(1R,2R)-2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)cyclohexanol

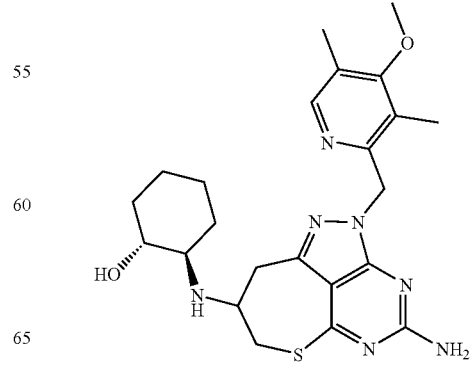

The title compound (5.9 mg, 18%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (1R,2R)-2-aminocyclohexanol (12 mg).

$^1$H-NMR (CDCl$_3$) δ: 1.02-1.10 (1H, m), 1.18-1.32 (3H, m), 1.67-1.82 (3H, m), 1.96-2.11 (2H, m), 2.20-2.29 (6H, m), 2.30-2.39 (1H, m), 3.09-3.23 (3H, m), 3.24-3.38 (2H, m), 3.55-3.71 (1H, m), 3.74 (3H, s), 5.04-5.10 (2H, m), 5.41-5.50 (2H, m), 8.16-8.19 (1H, m).

ESI-MS m/z: 470 (M+H)

Example 94

(1S,2S)-2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)cyclohexanol

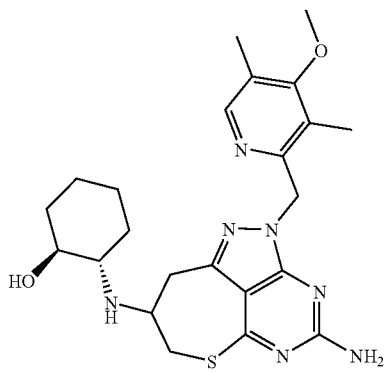

The title compound (6.8 mg, 21%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (1S,2S)-2-aminocyclohexanol (12 mg).

ESI-MS m/z: 470 (M+H)

Example 95

2-[(4-Methoxy-3,5-dimethylpyridin-2-yl)methyl]-N$^8$-[(3S)-tetrahydrofuran-3-yl]-2,7,8,9-tetrahydro-6-thia-1,2,3,5-tetraazabenzo[cd]azulene-4,8-diamine

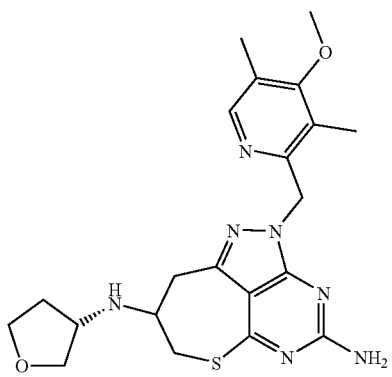

The title compound (17.9 mg, 46%) was obtained as an amorphous by the same method as in Example 62 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (50 mg), (S)-3-aminotetrahydrofuran p-toluenesulfonate (68 mg) and triethylamine (24 µl).

$^1$H-NMR (CDCl$_3$) δ: 1.66-1.77 (1H, m), 2.04-2.18 (1H, m), 2.22 (3H, s), 2.27 (3H, s), 3.11-3.36 (4H, m), 3.46-3.58 (3H, m), 3.74 (6H, s), 3.75-3.96 (3H, m), 5.16 (2H, brs), 5.45 (2H, s), 8.18 (1H, s).

ESI-MS m/z: 442 (M+H)

Example 96

(1R,2R)-2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)cyclopentanol

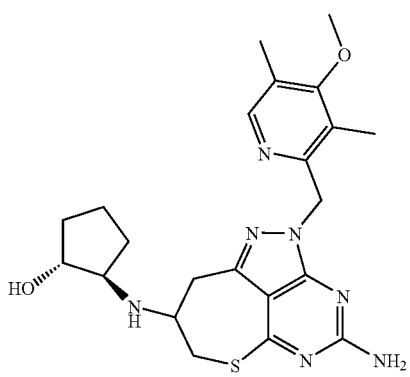

The title compound (2.1 mg, 7%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (1R,2R)-2-aminocyclopentanol (15 mg).

$^1$H-NMR (CDCl$_3$) δ: 0.76-2.07 (6H, m), 2.21 (3H, s), 2.27 (3H, s), 2.94-3.03 (1H, m), 3.17-3.38 (4H, m), 3.53-3.69 (1H, m), 3.74 (2H, s), 3.81-3.90 (1H, m), 5.03-5.10 (2H, m), 5.41-5.46 (2H, m), 8.13-8.19 (1H, m).

ESI-MS m/z: 456 (M+H)

Example 97

(1S,2S)-2-({4-Amino-2-[(4-methoxy-3,5-dimethylpyridin-2-yl)methyl]-2,7,8,9-tetrahydro-6-thia-1,2,3,5-tetraazabenzo[cd]azulen-8-yl}amino)cyclopentanol

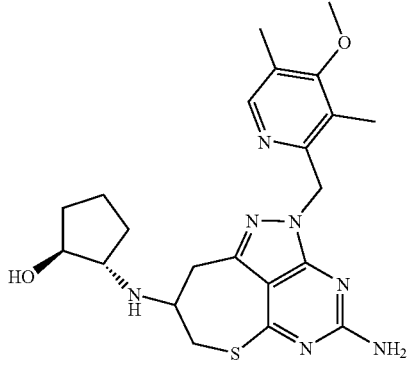

The title compound (3.4 mg, 11%) was obtained as an amorphous by the same method as in Example 71 using di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (40 mg) and (1S,2S)-2-aminocyclopentanol (15 mg).

$^1$H-NMR (CDCl$_3$) δ: 0.77-2.15 (6H, m), 2.21 (3H, s), 2.26-2.28 (3H, m), 2.97-3.07 (1H, m), 3.19-3.41 (4H, m), 3.55-3.72 (1H, m), 3.74 (3H, s), 3.82-3.96 (1H, m), 5.11 (2H, s), 5.40-5.49 (2H, m), 8.12-8.21 (1H, m).

ESI-MS m/z: 456 (M+H)

Example 98

2-[(4-Methoxy-3,5-dimethylpyridin-2-yl)methyl]-2,7,8,9-tetrahydro-6-thia-1,2,3,5-tetraazabenzo[cd]azulene-4,8-diamine

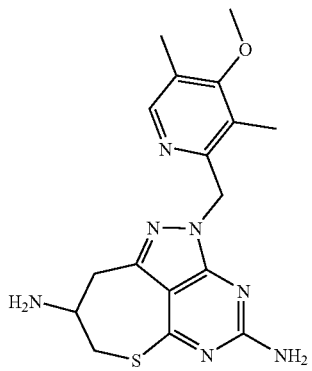

A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (50 mg), ammonium acetate (68 mg), molecular sieves 4A (50 mg) and methanol (1.5 ml) was stirred at room temperature for four hours. Sodium cyanoborohydride (12 mg) was added to the reaction mixture, followed by stirring at room temperature for three days. The insoluble matter in the reaction mixture was removed by filtration through Celite, followed by washing with methanol (4 ml) twice. The filtrate was concentrated under reduced pressure. Dichloromethane (2 ml) and trifluoroacetic acid (0.5 ml) were added to the resulting residue, and the mixture was stirred at room temperature for four hours. The reaction mixture was concentrated under reduced pressure. Diethyl ether (20 ml) was placed into the resulting residue, and the slurry was washed. Then, the solvent was removed by decantation. The resulting residue was purified by reversed phase liquid chromatography to obtain the title compound (14.1 mg, 43%) as a solid.

$^1$H-NMR (CD$_3$OD) δ: 2.24 (3H, s), 2.28 (3H, s), 3.25-3.33 (1H, m), 3.40-3.50 (2H, m), 3.57 (1H, dd, J=15.4, 8.0 Hz), 3.79 (3H, s), 4.12 (1H, dt, J=3.2, 8.0 Hz), 5.44 (1H, d, J=15.9 Hz), 5.49 (1H, d, J=15.9 Hz), 8.04 (1H, s), 8.22 (1H, brs).

ESI-MS m/z: 372 (M+H)$^+$

Example 99

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}-N-methylacetamide

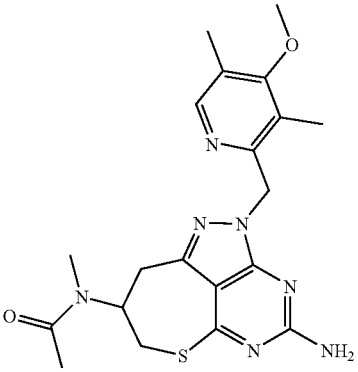

Sodium triacetoxyborohydride (32 mg) was added to a mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (57 mg), dichloroethane (1 ml), a 2 N solution of methylamine in tetrahydrofuran (0.2 ml) and acetic acid (23 μl), and the mixture was stirred at room temperature overnight. Methanol (one drop) was added dropwise to the reaction mixture, and then a 0.2 N sodium hydroxide solution was added, followed by extraction with ethyl acetate. The organic layer was dried over anhydrous sodium sulfate and filtered, and then the filtrate was concentrated under reduced pressure. Dichloromethane (2 ml) was added to the resulting residue, and pyridine (24 μl) and acetyl chloride (14 μl) were added dropwise under ice-cooling. 4-Dimethylaminopyridine (1 mg) was added and the mixture was stirred under ice-cooling for 10 minutes and at room temperature for three hours. Water was added to the reaction mixture, followed by extraction with ethyl acetate. Then, the organic layer was dried over anhydrous sodium sulfate and filtered, and then the filtrate was concentrated under reduced pressure. The resulting residue was purified by silica gel thin-layer chromatography (ethyl acetate), and then the title compound (19 mg, 79%) was obtained as an oil in the same manner as in Example 2.

$^1$H-NMR (CD$_3$OD) δ: 2.11 (3H, s), 2.23 (3H, t, J=11.7 Hz), 2.24 (3H, s), 3.06 (3H, s), 3.11 (2H, d, J=14.6 Hz), 3.45 (1H, dd, J=16.5, 12.1 Hz), 3.72 (1H, dd, J=14.6, 8.1 Hz), 3.78 (3H, s), 3.79 (3H, s), 5.01-5.08 (1H, m), 5.40-5.50 (2H, m), 8.07 (1H, s).

ESI-MS m/z: 428 (M+H)$^+$

Example 100

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}methanesulfonamide

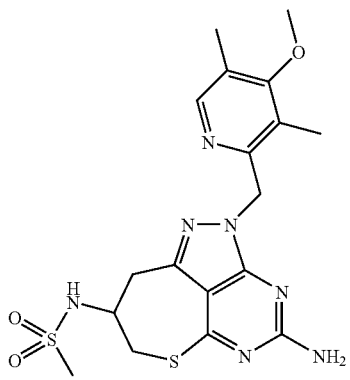

The title compound (7.1 mg, 24%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (47 mg), triethylamine (36 μl) and mesyl chloride (22 μl).

$^1$H-NMR (CD$_3$OD) δ: 2.23 (3H, s), 2.26 (3H, s), 3.01 (3H, s), 3.19-3.26 (1H, m), 3.28-3.34 (1H, m), 3.44-3.47 (2H, m), 3.78 (3H, s), 4.25-4.31 (1H, m), 5.40 (1H, d, J=15.9 Hz), 5.47 (1H, d, J=15.9 Hz), 8.03 (1H, s).

ESI-MS m/z: 450 (M+H)$^+$

Example 101

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}benzenesulfonamide

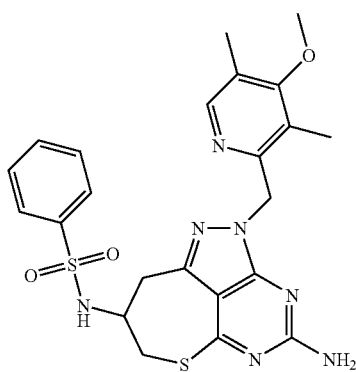

The title compound (22 mg, 65%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (47 mg), triethylamine (36 μl), 4-dimethylaminopyridine (0.8 mg) and benzenesulfonyl chloride (25 μl).

$^1$H-NMR (DMSO-d$_6$) δ: 2.16 (3H, s), 2.18 (3H, s), 2.90-3.01 (2H, m), 3.07-3.16 (1H, m), 3.29-3.44 (2H, m), 3.70 (3H, s), 3.71-3.79 (1H, m), 5.30 (2H, s), 6.78 (2H, s), 7.57-7.69 (3H, m), 7.85 (2H, d, J=7.6 Hz), 8.04 (1H, s), 8.24-8.29 (1H, m).

ESI-MS m/z: 512

Example 102

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}-1-methyl-1H-imidazole-4-sulfonamide

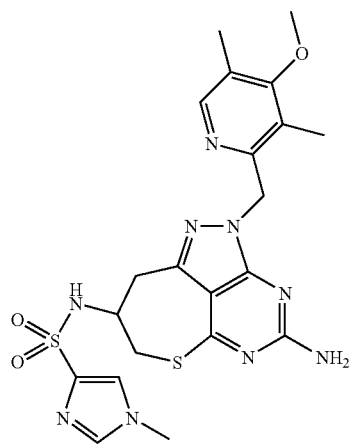

The title compound (18 mg, 60%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (42 mg), triethylamine (41 μl), 4-dimethylaminopyridine (0.7 mg) and 1-methylimidazol-4-ylsulfonyl chloride (32 μl).

$^1$H-NMR (CDCl$_3$) δ: 2.22 (3H, s), 2.27 (3H, s), 3.14-3.28 (2H, m), 3.37 (1H, d, J=14.7 Hz), 3.44 (1H, dd, J=14.5, 7.8 Hz), 3.74 (3H, s), 3.76 (3H, s), 4.19-4.26 (1H, m), 5.39 (1H, d, J=15.7 Hz), 5.46 (1H, d, J=15.7 Hz), 7.49 (1H, s), 7.51 (1H, s), 8.08 (1H, s).

ESI-MS m/z: 516 (M+H)$^+$

Example 103

N-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}pyridine-3-sulfonamide

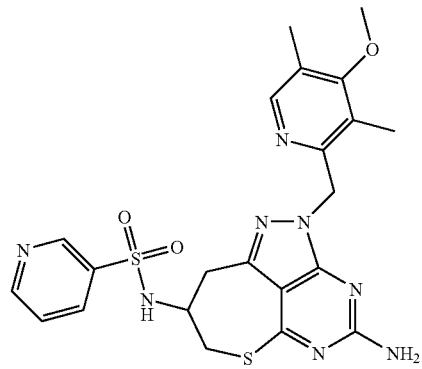

The title compound (15 mg, 50%) was obtained as a solid by the same method as in Example 43 using di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (42 mg), triethylamine (41 μl), 4-dimethylaminopyridine (0.7 mg) and pyridine-3-sulfonyl chloride (31 mg).

$^1$H-NMR (CDCl$_3$) δ: 2.21 (3H, s), 2.25 (3H, s), 3.14 (1H, dd, J=17.1, 3.7 Hz), 3.19-3.30 (2H, m), 3.43 (1H, d, J=14.9 Hz), 3.75 (3H, s), 5.29 (2H, s), 5.35 (2H, s), 6.57-6.63 (1H, brm), 7.36 (1H, dd, J=8.1, 4.9 Hz), 8.11 (1H, s), 8.13 (1H, ddd, J=8.1, 2.4, 1.8 Hz), 8.74 (1H, dd, J=4.9, 1.8 Hz), 9.06 (1H, d, J=2.4 Hz).

ESI-MS m/z: 513 (M+H)$^+$

Example 104

1-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}pyrrolidin-2-one

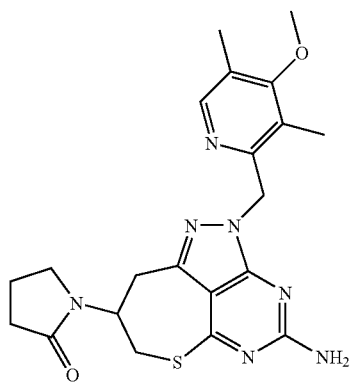

A mixture composed of di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (47 mg), triethylamine (36 μl), dichloromethane (1 ml) and 4-chlorobutyryl chloride (14 μl) was stirred at room temperature for 12 hours. A 0.1 N sodium hydroxide solution was added to the reaction mixture, followed by extraction with ethyl acetate. The organic layer was dried over sodium sulfate and filtered. Then, the filtrate was concentrated under reduced pressure. The resulting residue was dissolved in dehydrated dichloromethane (1.5 ml). 1,3-Dimethoxybenzene (16 μl) and trifluoroacetic acid (1.5 ml) was added and the mixture was stirred at room temperature overnight. The reaction mixture was concentrated under reduced pressure, and a 0.1 N sodium hydroxide solution was added to the resulting residue, followed by extraction with ethyl acetate. The organic layer was dried over sodium sulfate and filtered. Then, the filtrate was concentrated under reduced pressure. Dimethylformamide (1 ml) and potassium tert-butoxide (15 mg) were added to the resulting residue, and the mixture was stirred at room temperature for two hours. The reaction mixture was separated with water and chloroform. Then, the organic layer was dried over sodium sulfate and filtered, and then the filtrate was concentrated under reduced pressure. The resulting residue was purified by silica gel thin-layer chromatography (chloroform-methanol) to obtain the title compound (13 mg, 46%) as a solid.

$^1$H-NMR (CD$_3$OD+CDCl$_3$) δ: 2.06-2.14 (2H, m), 2.25 (3H, s), 2.26 (3H, s), 2.43 (2H, t, J=8.4 Hz), 3.15 (1H, d, J=14.8 Hz), 3.21 (1H, dd, J=17.0, 3.4 Hz), 3.42 (1H, dd, J=17.0, 10.6 Hz), 3.47-3.54 (2H, m), 3.68 (1H, dd, J=14.8, 8.2 Hz), 3.79 (3H, s), 4.73-4.80 (1H, m), 5.45 (2H, s), 8.10 (1H, s).

ESI-MS m/z: 440 (M+H)$^+$

Example 105

1-{4-Amino-2-[(4-methoxy-3,5-dimethylpyridin-2-yl)methyl]-2,7,8,9-tetrahydro-6-thia-1,2,3,5-tetraazabenzo[cd]azulen-8-yl}imidazolidin-2-one

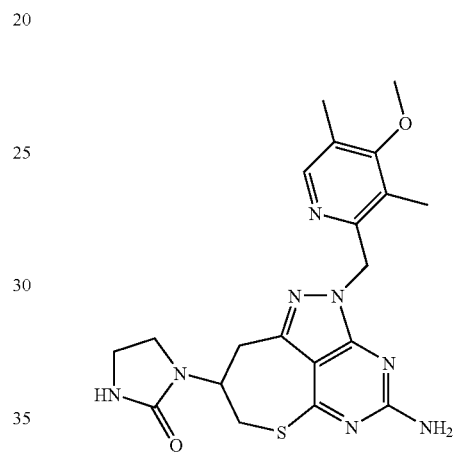

A mixture composed of di-tert-butyl {8-[(2,4-dimethoxybenzyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 42 (47 mg), dichloromethane (1 ml) and 2-chloroethyl isocyanate (8 μl) was stirred at room temperature for 12 hours. A 0.1 N sodium hydroxide solution was added to the reaction mixture, followed by extraction with ethyl acetate. The organic layer was dried over sodium sulfate and filtered. Then, the filtrate was concentrated under reduced pressure. The resulting residue was dissolved in dehydrated dichloromethane (1.5 ml). 1,3-Dimethoxybenzene (16 μl) and trifluoroacetic acid (1.5 ml) was added and the mixture was stirred at room temperature overnight. The reaction mixture was concentrated under reduced pressure, and a 0.1 N sodium hydroxide solution was added to the resulting residue, followed by extraction with ethyl acetate. The organic layer was dried over sodium sulfate and filtered. Then, the filtrate was concentrated under reduced pressure. Dimethylformamide (1 ml) and potassium tert-butoxide (15 mg) were added to the resulting residue, and the mixture was stirred at room temperature for two hours. The reaction mixture was separated with water and chloroform. Then, the organic layer was dried over sodium sulfate and filtered, and then the filtrate was concentrated under reduced pressure. The resulting residue was purified by silica gel thin-layer chromatography (chloroform-methanol) to obtain the title compound (9 mg, 31%) as a solid.

$^1$H-NMR (CD$_3$OD) δ: 2.24 (3H, s), 2.24 (3H, s), 3.13-3.19 (2H, m), 3.35-3.44 (3H, m), 3.48-3.60 (2H, m), 3.64 (1H, dd, J=14.6, 8.3 Hz), 3.78 (3H, s), 4.45-4.52 (1H, m), 5.45 (2H, s), 8.07 (1H, s).

ESI-MS m/z: 441 (M+H)$^+$

Example 106

1) Mixture of di-tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate and tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}carbamate

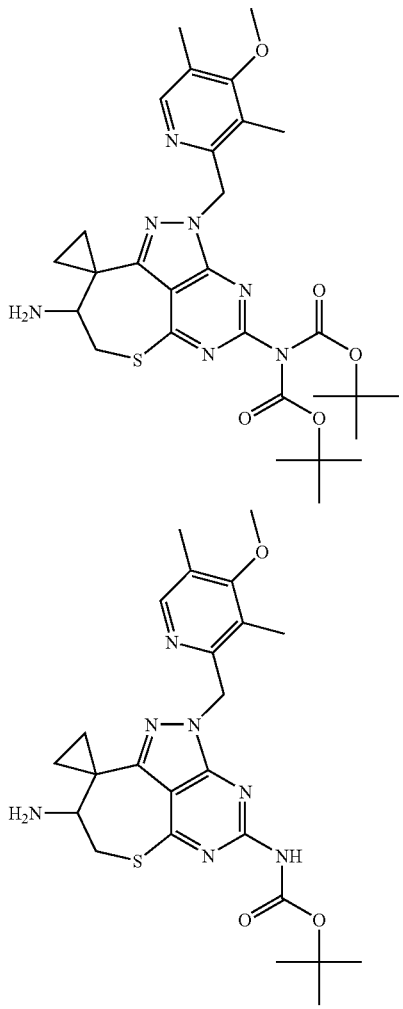

A mixture composed of di-tert-butyl{2'-[(4-methoxy-3,5-dimethylpyridin-2-yl)methyl]-8'-oxo-7',8'-dihydro-2'H-spiro[cyclopropane-1,9'-[6]thia[1,2,3,5]tetraazabenzo[cd]azulen]-4'-yl}imidodicarbonate of Example 57 (203 mg), ammonium acetate (367 mg), molecular sieves 4A (500 mg) and methanol (4 ml) was stirred at room temperature for two days. Sodium cyanoborohydride (68 mg) was added to the reaction mixture, and the mixture was heated with stirring at a bath temperature of 55° C. for 16 hours. The insoluble matter in the reaction mixture was removed by filtration through Celite and washed with methanol (10 ml). The filtrate and the washing liquid were concentrated under reduced pressure, and a 0.2 N sodium hydroxide solution was added to the resulting residue, followed by extraction with ethyl acetate. The organic layer was dried over sodium sulfate and filtered. Then, the filtrate was concentrated under reduced pressure. The title compound as a concentrated residue (177 mg) was obtained as an oil. The product was directly used for the next reaction without further purification.

2) N-{4'-Amino-2'-[(4-methoxy-3,5-dimethylpyridin-2-yl)methyl]-7',8'-dihydro-2'H— spiro[cyclopropane-1,9'-[6]thia[1,2,3,5]tetraazabenzo[cd]azulen]-8'-yl}-N$^2$-methylglycinamide

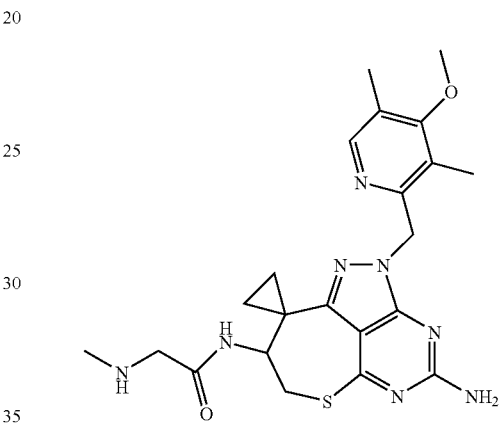

A mixture composed of the above mixture of di-tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate and tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}carbamate (35 mg), dichloromethane (0.8 ml), N-(tert-butoxycarbonyl)-N-methylglycine (20 mg), 1-hydroxybenzotriazole monohydrate (11 mg), 1-(3-dimethylaminopropyl)-3-ethylcarbodiimide hydrochloride (27 mg) and diisopropylethylamine (36 µl) was stirred at room temperature overnight. The reaction mixture was concentrated under reduced pressure, and a 0.2 N sodium hydroxide solution was added to the resulting residue, followed by extraction with ethyl acetate. The organic layer was concentrated under reduced pressure. Dichloromethane (2 ml) and trifluoroacetic acid (0.5 ml) were added to the resulting residue, and the mixture was stirred at room temperature for four hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by silica gel thin-layer chromatography (chloroform-methanol). The resulting oil was dissolved in dioxane, followed by lyophilization to obtain the title compound (4.8 mg, 15%) as an amorphous.

¹H-NMR (CDCl₃) δ: 0.99-1.06 (2H, m), 1.09-1.16 (1H, m), 1.69-1.75 (1H, m), 2.22 (3H, s), 2.29 (3H, s), 2.38 (3H, s), 3.33 (2H, s), 3.45 (1H, dd, J=14.5, 8.2 Hz), 3.72 (1H, d, J=14.5 Hz), 3.74 (3H, s), 3.87 (1H, t, J=7.9 Hz), 5.19 (2H, s), 5.39 (2H, s), 7.92 (1H, d, J=7.8 Hz), 8.13 (1H, s).

ESI-MS m/z: 469 (M+H)⁺

Example 107

N-{4'-Amino-2'-[(4-methoxy-3,5-dimethylpyridin-2-yl)methyl]-7',8'-dihydro-2'H— spiro[cyclopropane-1,9'-[6]thia[1,2,3,5]tetraazabenzo[cd]azulen-8'-yl}-N²,N²-dimethylglycinamide

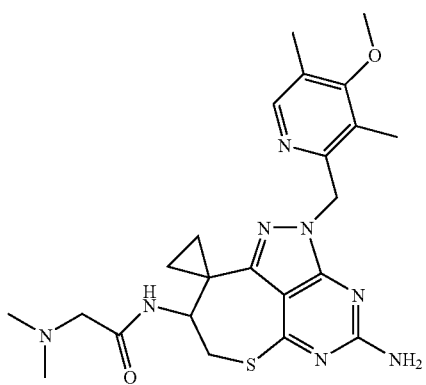

The title compound (12 mg, 85%) was obtained as an amorphous by the same method as in Example 106-2) using the mixture of di-tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate and tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}carbamate of Example 106-1) (35 mg) and N,N-dimethylglycine (11 mg).

¹H-NMR (CD₃OD) δ: 0.96-1.15 (3H, m), 1.61-1.71 (1H, m), 2.24-2.28 (12H, m), 3.05 (2H, s), 3.53 (1H, dd, J=14.6, 8.3 Hz), 3.74-3.83 (4H, m), 5.37 (1H, d, J=15.6 Hz), 5.45 (1H, d, J=15.6 Hz), 8.04 (1H, s).

ESI-MS m/z: 483 (M+H)⁺

Example 108

N-{4'-Amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-yl}azetidine-3-carboxamide

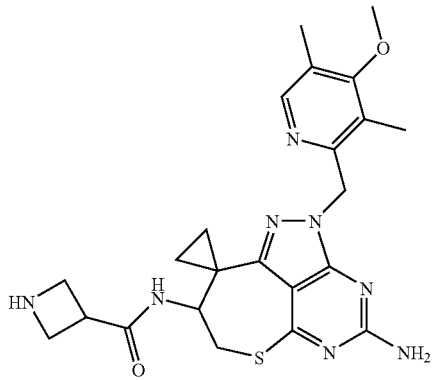

The title compound (1.9 mg, 6%) was obtained as an amorphous by the same method as in Example 106-2) using the mixture of di-tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}imidodicarbonate and tert-butyl {8'-amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4'-yl}carbamate of Example 106-1) (35 mg) and tert-butoxycarbonylazetidine-3-carboxylic acid (21 mg).

¹H-NMR (CDCl₃) δ: 0.96-1.14 (4H, m), 1.69-1.77 (1H, m), 2.22 (3H, s), 2.31 (3H, s), 3.35-3.45 (1H, m), 3.51 (1H, dd, J=14.6, 8.3 Hz), 3.61-3.78 (6H, m), 3.78-3.97 (3H, m), 5.08 (2H, brs), 5.34 (1H, d, J=15.4 Hz), 5.43 (1H, d, J=15.4 Hz), 6.74 (1H, d, J=5.9 Hz), 8.11 (1H, s).

ESI-MS m/z: 481 (M+H)⁺

Example 109

2'-[(4-Methoxy-3,5-dimethylpyridin-2-yl)methyl]-7',8'-dihydro-2'H-spiro[cyclopropane-1,9'-[6]thia[1,2,3,5]tetraazabenzo[cd]azulen]-4',8'-diamine

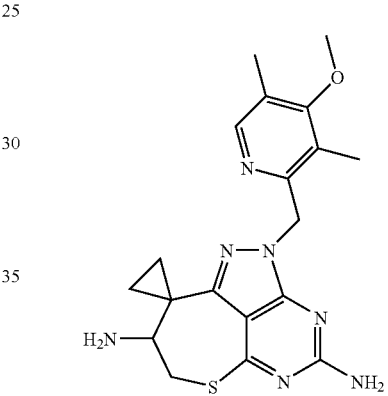

A mixture composed of di-tert-butyl{2'-[(4-methoxy-3,5-dimethylpyridin-2-yl)methyl]-8'-oxo-7',8'-dihydro-2'H-spiro[cyclopropane-1,9'-[6]thia[1,2,3,5]tetraazabenzo[cd]azulen]-4'-yl}imidodicarbonate of Example 57 (29 mg), ammonium acetate (45 mg) and methanol (0.5 ml) was stirred at room temperature for 12 hours. Sodium cyanoborohydride (6.4 mg) was added to the reaction mixture, followed by stirring at room temperature for four hours. Sodium cyanoborohydride (6.4 mg) was further added and the mixture was heated with stirring at 45° C. for three hours and at 55° C. for five hours. The reaction mixture was concentrated under reduced pressure, and a 0.5 N sodium hydroxide solution was added to the resulting residue, followed by extraction with ethyl acetate. The organic layer was dried over sodium sulfate and filtered. Then, the filtrate was concentrated under reduced pressure. Dichloromethane (2 ml) and trifluoroacetic acid (0.5 ml) were added to the resulting residue, and the mixture was stirred at room temperature for four hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by NH silica gel chromatography (chloroform-methanol). The resulting oil was dissolved in dioxane, followed by lyophilization to obtain the title compound (8.7 mg, 45%) as an amorphous.

¹H-NMR (CD₃OD) δ: 0.86-0.97 (2H, m), 1.00-1.06 (1H, m), 1.61-1.67 (1H, m), 2.23 (3H, s), 2.24 (3H, s), 2.79 (1H, d, J=7.8 Hz), 3.24 (1H, dd, J=14.8, 7.8 Hz), 3.77 (1H, s), 3.79 (1H, d, J=14.8 Hz), 5.35 (1H, d, J=15.5 Hz), 5.41 (1H, d, J=15.5 Hz), 8.03 (1H, s).

ESI-MS m/z: 398 (M+H)⁺

Example 110

4'-Amino-2'-[(4-methoxy-3,5-dimethylpyridin-2-yl)methyl]-7',8'-dihydro-2'H-spiro[cyclopropane-1,9'-[6]thia[1,2,3,5]tetraazabenzo[cd]azulen]-8'-ol

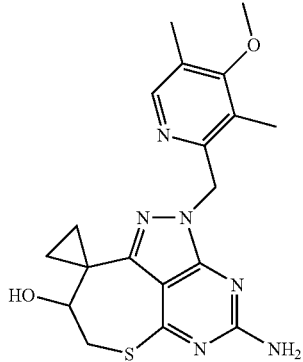

Sodium borohydride (6 mg) was added to a mixture composed of 4-di-tert-butyl {2'-[(4-methoxy-3,5-dimethylpyridin-2-yl)methyl]-8'-oxo-7',8'-dihydro-2'H-spiro[cyclopropane-1,9'-[6]thia[1,2,3,5]tetraazabenzo[cd]azulen]-4'-yl}imidodicarbonate of Example 57 (29 mg) and methanol (2 ml) under ice-cooling, and then the mixture was stirred at 0° C. for 30 minutes. Water was added to the reaction mixture, followed by extraction with ethyl acetate. The organic layer was dried over sodium sulfate and filtered. Then, the filtrate was concentrated under reduced pressure. Dichloromethane (2 ml) and trifluoroacetic acid (0.5 ml) were added to the resulting residue, and the mixture was stirred at room temperature for two days. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by silica gel thin-layer chromatography (chloroform-methanol) to obtain the title compound (16 mg, 81%) as a solid.

¹H-NMR (CDCl₃+CD₃OD) δ: 0.91-0.99 (1H, m), 1.02-1.17 (2H, m), 1.56-1.63 (1H, m), 2.23 (3H, s), 2.27 (3H, s), 3.34 (2H, dd, J=14.6, 8.3 Hz), 3.65 (1H, d, J=14.6 Hz), 3.68 (1H, d, J=8.3 Hz), 3.76 (3H, s), 5.33 (1H, d, J=15.6 Hz), 5.41 (1H, d, J=15.4 Hz), 8.06 (1H, s).

ESI-MS m/z: 399 (M+H)⁺

Example 111

Methyl {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetate

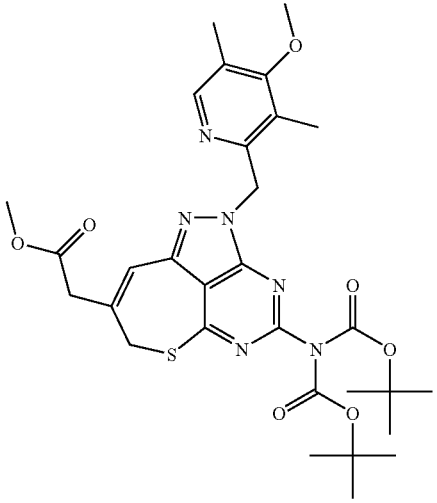

1) A mixture composed of di-tert-butyl {2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate of Example 40 (752 mg), methyl triphenylphosphanylideneacetate (617 mg) and toluene (14 ml) was heated with stirring at 60° C. for 10 hours. Ethyl acetate was added to the reaction mixture, followed by washing with water. Then, the organic layer was dried over sodium sulfate and filtered, and then the filtrate was concentrated under reduced pressure. The concentrated residue was purified by silica gel column chromatography (ethyl acetate-chloroform) to obtain the title compound (275 mg, 33%) as an oil.

¹H-NMR (CDCl₃) δ: 1.43 (18H, s), 2.21 (3H, s), 2.27 (3H, s), 3.39 (2H, s), 3.73 (3H, s), 3.74 (3H, s), 3.86 (2H, s), 5.67 (2H, s), 6.80 (1H, s), 8.14 (1H, s).

ESI-MS m/z: 627 (M+H)⁺

2) {4-[Bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid

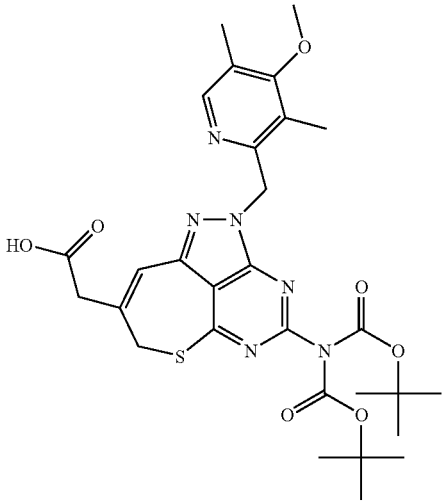

A mixture composed of the above methyl {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetate (69 mg), methanol (2 ml) and a 1 N sodium hydroxide solution (0.22 ml) was stirred at room temperature for 16 hours. A 1 N sodium hydroxide solution (0.5 ml) was added, followed by stirring for three hours. Then, a 1 N sodium hydroxide solution (0.3 ml) was further added, followed by stirring for three hours. A 1 N hydrochloric acid solution (1.5 ml) was added dropwise to the reaction mixture. Then, water was added, followed by extraction with ethyl acetate. The organic layer was dried over sodium sulfate and filtered. Then, the filtrate was concentrated under reduced pressure. An oil (60 mg, 89%) was obtained as a residue. Although the product contained a by-product, it was directly used for the next reaction without further purification.

ESI-MS m/z: 613 (M+H)$^+$

3) Di-tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate

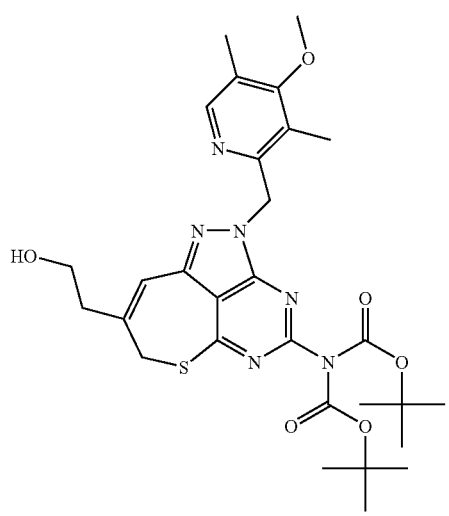

N-Methylmorpholine (22 μl) was added to a mixture composed of the above {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid (60 mg) and tetrahydrofuran (2 ml). Then, isobutyl chloroformate (39 μl) was added and the mixture was stirred at 0° C. for one hour. N-Methylmorpholine (44 μl) and isobutyl chloroformate (39 μl) were added to the reaction mixture, and the mixture was further stirred at 0° C. for 30 minutes. Water was added to the reaction mixture, followed by extraction with ethyl acetate. The organic layer was dried over sodium sulfate and filtered. Then, the filtrate was concentrated under reduced pressure. Tetrahydrofuran (2 ml) and water (0.4 ml) were added to the resulting residue. Then, sodium borohydride (15 mg) was added under ice-cooling, and the mixture was stirred at 0° C. for one hour. Methanol (2 ml) was added dropwise to the reaction mixture. Then, the mixture was returned to room temperature and stirred for 16 hours. Water was added to the reaction mixture, followed by extraction with ethyl acetate. The organic layer was washed with brine, and then dried over sodium sulfate and filtered. Then, the filtrate was concentrated under reduced pressure. The resulting residue was purified by silica gel thin-layer chromatography (hexane-ethyl acetate) to obtain the title compound (16 mg, 27%) as an oil.

$^1$H-NMR (CDCl$_3$) δ: 1.43 (18H, s), 2.21 (3H, s), 2.27 (3H, s), 2.62 (2H, t, J=6.0 Hz), 3.73 (3H, s), 3.79 (2H, s), 3.89 (2H, t, J=6.0 Hz), 5.66 (2H, s), 6.76 (1H, s), 8.15 (1H, s).

ESI-MS m/z: 599 (M+H)$^+$ 4) 2-{4-Amino-2-[(4-methoxy-3,5-dimethylpyridin-2-yl)methyl]-2,7-dihydro-6-thia-1,2,3,5-tetraazabenzo[cd]azulen-8-yl}ethanol

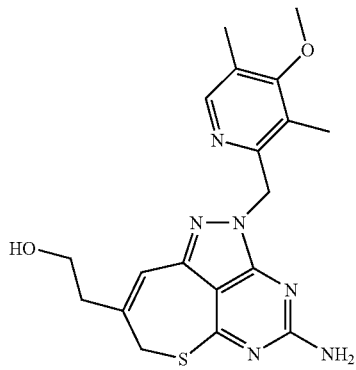

A mixture composed of the above di-tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate (16 mg), dichloromethane (2 ml) and trifluoroacetic acid (0.5 ml) was stirred at room temperature for four hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by NH silica gel chromatography (chloroform-methanol). The resulting oil was dissolved in dioxane, followed by lyophilization to obtain the title compound (8.3 mg, 78%) as an amorphous.

$^1$H-NMR (CDCl$_3$) δ: 2.22 (3H, s), 2.28 (3H, s), 2.59 (2H, t, J=6.0 Hz), 3.72 (2H, s), 3.74 (3H, s), 3.87 (2H, t, J=6.0 Hz), 5.18 (2H, brs), 5.50 (2H, s), 6.64 (1H, s), 8.19 (1H, s).

ESI-MS m/z: 399 (M+H)$^+$

Example 112

Di-tert-butyl {8-(aminomethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate

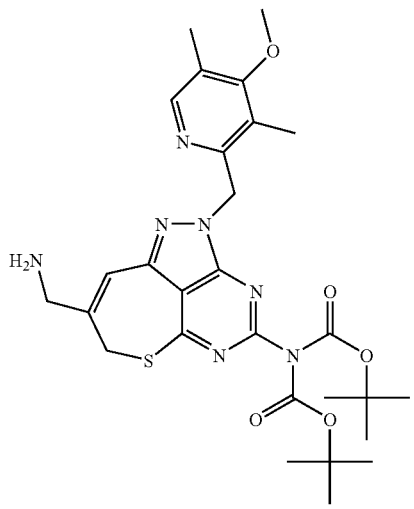

1) A mixture composed of methyl {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetate of Example 111 (121 mg), diphenylphosphoryl azide (64 μl), triethylamine (69 μl) and benzene (2 ml) was heated with stirring at a bath temperature of 55° C. for two hours. The reaction mixture was concentrated under reduced pressure. Tetrahydrofuran (8 ml) and a 1 N sodium hydroxide solution (4 ml) were added to the resulting residue, and the mixture was heated with stirring at a bath temperature of 55° C. for one hour. A 0.2 N sodium hydroxide solution was added, followed by extraction with ethyl acetate. The organic layer was dried over sodium sulfate and filtered. Then, the filtrate was concentrated under reduced pressure. The concentrated residue was purified by silica gel column chromatography (chloroform-methanol) to obtain the title compound (41 mg) as a brown oil. Although the product contained impurities, it was directly used for the next reaction without further purification.

ESI-MS m/z: 584 (M+H)$^+$.

2) 8-(Aminomethyl)-2-[(4-methoxy-3,5-dimethylpyridin-2-yl)methyl]-2,7-dihydro-6-thia-1,2,3,5-tetraazabenzo[cd]azulen-4-amine

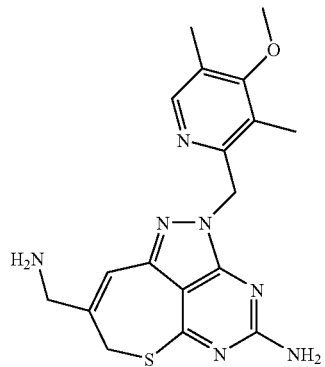

The title compound (2.6 mg) was obtained as an amorphous by synthesis by the same method as in Example 111 using the above di-tert-butyl {8-(aminomethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate (8.6 mg).

$^1$H-NMR (CDCl$_3$) δ: 2.22 (3H, s), 2.29 (3H, s), 3.55 (2H, s), 3.73 (2H, s), 3.74 (3H, s), 5.14 (2H, s), 5.51 (2H, s), 6.73 (1H, s), 8.19 (1H, s).

ESI-MS m/z: 384 (M+H)$^+$

Example 113

2-[(4-Methoxy-3,5-dimethylpyridin-2-yl)methyl]-8-(morpholin-4-ylmethyl)-2,7-dihydro-6-thia-1,2,3,5-tetraazabenzo[cd]azulen-4-amine

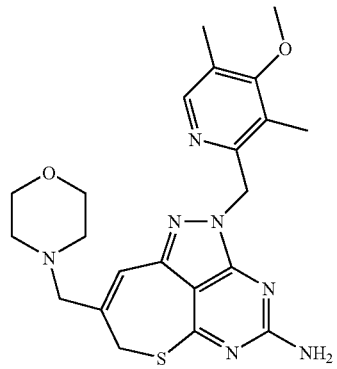

A mixture composed of di-tert-butyl {8-(aminomethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate of Example 112 (20 mg), 90% bis(2-bromoethyl)ether (10 μl), potassium carbonate (9.5 mg) and acetonitrile (0.3 ml) was heated with stirring at 55° C. for 24 hours. Water was added to the reaction mixture, followed by extraction with chloroform. The organic layer was dried over sodium sulfate and filtered. Then, the filtrate was concentrated under reduced pressure. Dichloromethane (2 ml) and trifluoroacetic acid (0.5 ml) were added to the resulting residue, and the mixture was stirred at room temperature for four hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by NH silica gel chromatography (chloroform-methanol). The resulting oil was dissolved in dioxane, followed by lyophilization to obtain the title compound (5.6 mg) as an amorphous.

$^1$H-NMR (CDCl$_3$) δ: 2.22 (3H, s), 2.30 (3H, s), 2.45-2.48 (4H, m), 3.14 (2H, s), 3.70 (4H, t, J=4.5 Hz), 3.74 (3H, s), 5.14 (2H, s), 5.50 (2H, s), 6.70 (1H, s), 8.20 (1H, s).

ESI-MS m/z: 454 (M+H)$^+$

Example 114

N-({4-Amino-2-[(4-methoxy-3,5-dimethylpyridin-2-yl)methyl]-2,7-dihydro-6-thia-1,2,3,5-tetraazabenzo[cd]azulen-8-yl}methyl)acetamide

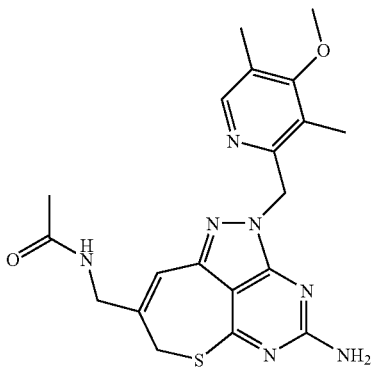

A mixture composed of di-tert-butyl {8-(aminomethyl)-2-[(4-methoxy-3,5-dimethylpyridin-2-yl)methyl]-2,7-dihydro-6-thia-1,2,3,5-tetraazabenzo[cd]azulen-4-yl}imidodicarbonate of Example 112 (20 mg), pyridine (8.3 µl), acetic anhydride (5 µl) and dichloromethane (0.5 ml) was stirred at room temperature for 20 hours. The reaction mixture was concentrated under reduced pressure. Dichloromethane (2 ml) and trifluoroacetic acid (0.5 ml) were added to the resulting residue, and the mixture was stirred at room temperature for 20 hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by silica gel thin-layer chromatography (chloroform-methanol) to obtain the title compound (3.7 mg) as a solid.

$^1$H-NMR (CDCl$_3$+CD$_3$OD) δ: 2.04 (3H, s), 2.24 (3H, s), 2.27 (3H, s), 3.68 (2H, s), 3.76 (3H, s), 4.09 (2H, d, J=4.8 Hz), 5.48 (2H, s), 6.62 (1H, s), 6.92 (1H, t, J=4.8 Hz), 8.14 (1H, s).

ESI-MS m/z: 426 (M+H)$^+$

Example 115

2-{4-Amino-2-[(4-methoxy-3,5-dimethylpyridin-2-yl)methyl]-2,7-dihydro-6-thia-1,2,3,5-tetraazabenzo[cd]azulen-8-yl}acetamide

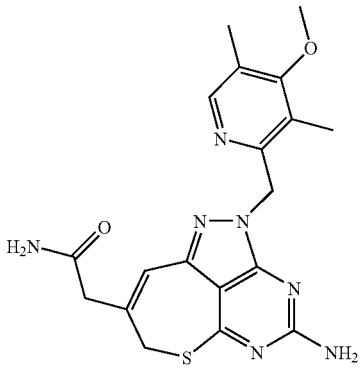

A mixture composed of {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 111 (24 mg), dimethylformamide (0.7 ml), ammonium chloride (13 mg), 1-hydroxybenzotriazole monohydrate (6 mg), 1-(3-dimethylaminopropyl)-3-ethylcarbodiimide hydrochloride (15 mg) and diisopropylethylamine (34 µl) was stirred at room temperature for three days. The solvent in the reaction mixture was evaporated by spraying, and a 0.2 N sodium hydroxide solution was added to the resulting residue, followed by extraction with ethyl acetate. The organic layer was concentrated under reduced pressure. Dichloromethane (2 ml) and trifluoroacetic acid (0.5 ml) were added to the resulting residue, and the mixture was stirred at room temperature for 20 hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by silica gel thin-layer chromatography (chloroform-methanol) to obtain the title compound (16.1 mg, 70%) as a solid.

$^1$H-NMR (CDCl$_3$+CD$_3$OD) δ: 2.24 (3H, s), 2.27 (3H, s), 3.27 (2H, s), 3.77 (3H, s), 3.82 (2H, s), 5.48 (2H, s), 6.67 (1H, s), 8.13 (1H, s).

ESI-MS m/z: 412 (M+H)$^+$

Example 116

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-methylacetamide

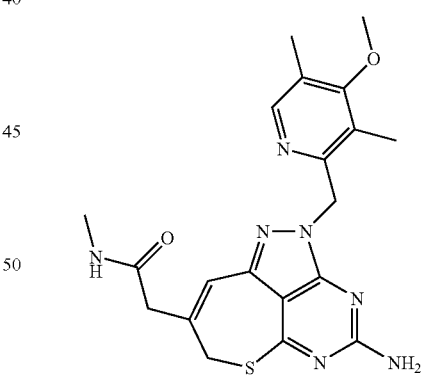

The title compound (12.5 mg, 75%) was obtained as a solid by synthesis by the same method as in Example 115 using {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 111 (24 mg) and methylamine hydrochloride (17 mg).

$^1$H-NMR (CDCl$_3$+CD$_3$OD) δ: 2.24 (3H, s), 2.28 (3H, s), 2.79 (3H, d, J=4.7 Hz), 3.24 (2H, s), 3.76 (3H, s), 3.80 (2H, s), 5.49 (2H, s), 6.59-6.64 (1H, m), 6.66 (1H, s), 8.14 (1H, s).

ESI-MS m/z: 426 (M+H)$^+$

Example 117

2-{4-Amino-2-[(4-methoxy-3,5-dimethylpyridin-2-yl)methyl]-2,7-dihydro-6-thia-1,2,3,5-tetraazabenzo[cd]azulen-8-yl}-N,N-dimethylacetamide

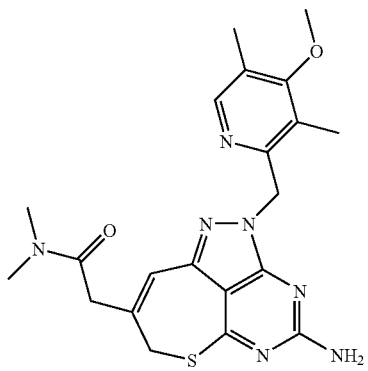

The title compound (8.7 mg, 50%) was obtained as a solid by synthesis by the same method as in Example 115 using {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 111 (24 mg) and dimethylamine hydrochloride (20 mg).

$^1$H-NMR (CDCl$_3$) δ: 2.22 (3H, s), 2.28 (3H, s), 2.97 (3H, s), 3.05 (3H, s), 3.41 (2H, s), 3.74 (3H, s), 3.81 (2H, s), 5.13 (2H, brs), 5.50 (2H, s), 6.61 (1H, s), 8.19 (1H, s).

ESI-MS m/z: 440 (M+H)$^+$

Example 118

{4-[(tert-Butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid

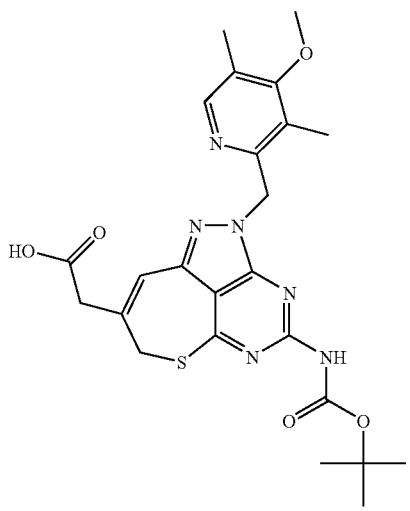

1) A mixture composed of methyl {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetate of Example 111 (218 mg), methanol (8 ml) and a 1 N sodium hydroxide solution (0.22 ml) was stirred at room temperature for eight hours. A 1 N hydrochloric acid solution (2.5 ml) was added dropwise to the reaction mixture under ice-cooling, and methanol in the reaction mixture was evaporated under reduced pressure. A 0.5 N hydrochloric acid solution was added to the resulting residue, followed by extraction with chloroform. The organic layer was concentrated to dryness under reduced pressure to obtain the title compound (173 mg, 97%) as an amorphous.

ESI-MS m/z: 513 (M+H)$^+$ 2) 2-{4-Amino-2-[(4-methoxy-3,5-dimethylpyridin-2-yl)methyl]-2,7-dihydro-6-thia-1,2,3,5-tetraazabenzo[cd]azulen-8-yl}-N-ethylacetamide

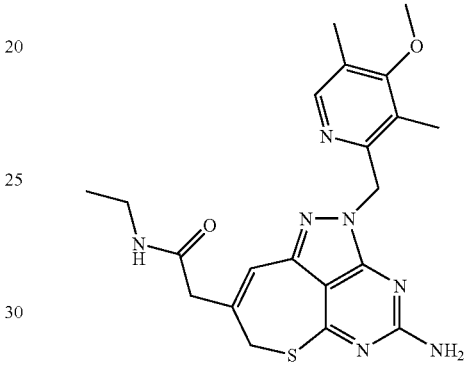

The title compound (8.3 mg, 46%) was obtained as a solid by synthesis by the same method as in Example 115 using the above {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid (21 mg) and ethylamine hydrochloride (11 mg).

$^1$H-NMR (CDCl$_3$+CD$_3$OD) δ: 1.13 (3H, t, J=7.4 Hz), 2.23 (3H, s), 2.29 (3H, s), 3.25 (2H, s), 3.29 (2H, dt, J=13.0, 7.4 Hz), 3.75 (3H, s), 3.78 (2H, s), 5.32-5.35 (2H, m), 5.50 (2H, s), 6.06-6.12 (1H, m), 6.68 (1H, s), 8.16 (1H, s).

ESI-MS m/z: 440 (M+H)$^+$

Example 119

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-[(3R)-tetrahydrofuran-3-yl]acetamide

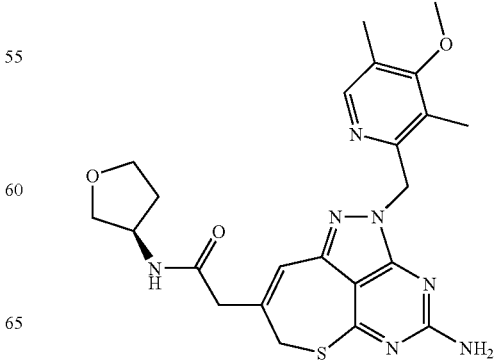

The title compound (9.7 mg, 49%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (21 mg) and (R)-3-aminotetrahydrofuran p-toluenesulfonate (32 mg).

$^1$H-NMR (CDCl$_3$+CD$_3$OD) δ: 1.78-1.86 (1H, m), 2.20-2.28 (1H, m), 2.23 (3H, s), 2.28 (3H, s), 3.23 (2H, s), 3.66 (1H, dd, J=9.4, 2.6 Hz), 3.73-3.84 (3H, m), 3.76 (3H, s), 3.80 (2H, s), 3.91 (1H, q, J=7.8 Hz), 4.45-4.53 (1H, m), 5.40 (2H, brs), 5.49 (2H, s), 6.66 (1H, s), 6.80 (1H, d, J=7.1 Hz), 8.15 (1H, s).
ESI-MS m/z: 482 (M+H)$^+$ Example 120

2-[(4-Methoxy-3,5-dimethylpyridin-2-yl)methyl]-8-(2-morpholin-4-yl-2-oxoethyl)-2,7-dihydro-6-thia-1,2,3,5-tetraazabenzo[cd]azulen-4-amine

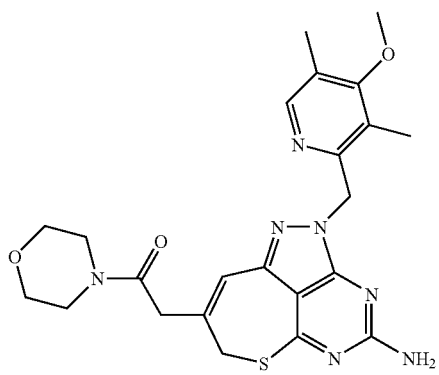

The title compound (7.2 mg, 36%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (21 mg) and morpholine (11 µl).

$^1$H-NMR (CDCl$_3$) δ: 2.23 (3H, s), 2.29 (3H, s), 3.42 (2H, d, J=1.2 Hz), 3.48-3.52 (2H, m), 3.62-3.70 (6H, m), 3.75 (3H, s), 3.81 (2H, s), 5.24 (2H, s), 5.50 (2H, s), 6.62 (1H, t, J=1.2 Hz), 8.19 (1H, s).
ESI-MS m/z: 482 (M+H)$^+$

Example 121

2-[(4-Methoxy-3,5-dimethylpyridin-2-yl)methyl]-8-(2-oxo-2-piperazin-1-ylethyl)-2,7-dihydro-6-thia-1,2,3,5-tetraazabenzo[cd]azulen-4-amine

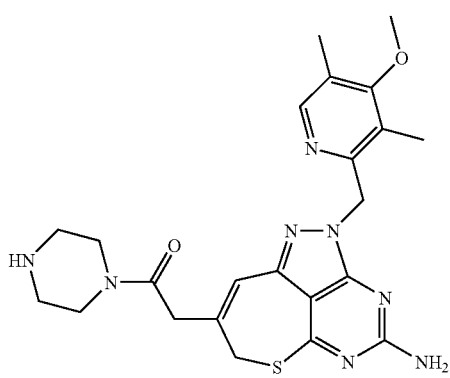

The title compound (15.3 mg, 78%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (21 mg) and N-(tert-butoxycarbonyl)-piperazine (23 mg).

$^1$H-NMR (CDCl$_3$) δ: 2.22 (3H, s), 2.29 (3H, s), 2.84 (4H, dd, J=10.1, 5.0 Hz), 3.42 (2H, s), 3.46 (2H, t, J=5.0 Hz), 3.60 (2H, t, J=5.0 Hz), 3.74 (3H, s), 3.81 (2H, s), 5.24 (2H, brs), 5.50 (2H, s), 6.62 (1H, s), 8.19 (1H, s).
ESI-MS m/z: 481 (M+H)$^+$ Example 122

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-(trans-4-hydroxycyclohexyl)acetamide

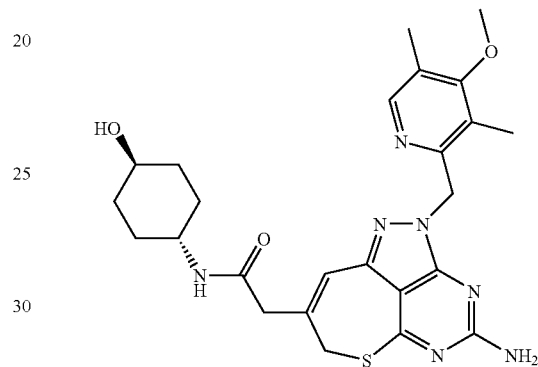

The title compound (7.1 mg, 34%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (21 mg) and trans-4-aminocyclohexanol (14 mg).

$^1$H-NMR (CDCl$_3$) δ: 1.14-1.25 (2H, m), 1.33-1.43 (2H, m), 1.92-2.00 (4H, m), 2.23 (3H, s), 2.29 (3H, s), 3.23 (2H, s), 3.50-3.58 (1H, m), 3.68-3.75 (1H, m), 3.76 (3H, s), 3.78 (2H, s), 5.49 (2H, s), 6.21 (1H, d, J=8.1 Hz), 6.66 (1H, s), 8.15 (1H, s).
ESI-MS m/z: 510 (M+H)$^+$

Example 123

8-(2-Azetidin-1-yl-2-oxoethyl)-2-[(4-methoxy-3,5-dimethylpyridin-2-yl)methyl]-2,7-dihydro-6-thia-1,2,3,5-tetraazabenzo[cd]azulen-4-amine

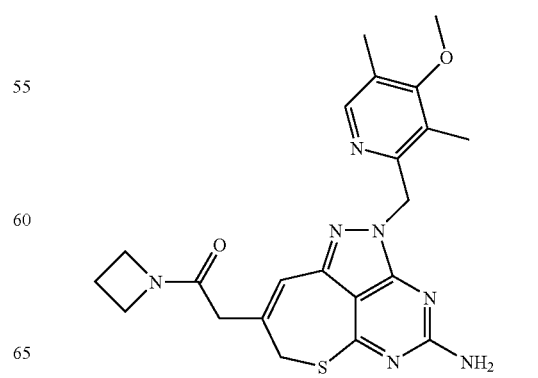

The title compound (9.2 mg, 42%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and azetidine hydrochloride (14 mg).

$^1$H-NMR (CDCl$_3$) δ: 2.23 (3H, s), 2.28 (3H, s), 2.28 (1H, q, J=7.7 Hz), 3.15 (2H, s), 3.72 (1H, q, J=7.7 Hz), 3.75 (3H, s), 3.83 (2H, s), 4.05 (2H, t, J=7.7 Hz), 4.20 (2H, t, J=7.7 Hz), 5.34 (2H, brs), 5.51 (2H, s), 6.61 (1H, s), 8.21 (1H, s).

ESI-MS m/z: 452 (M+H)$^+$

Example 124

[(2S)-1-({4-Amino-2-[(4-methoxy-3,5-dimethylpyridin-2-yl)methyl]-2,7-dihydro-6-thia-1,2,3,5-tetraazabenzo[cd]azulen-8-yl}acetyl)azetidin-2-yl]methanol

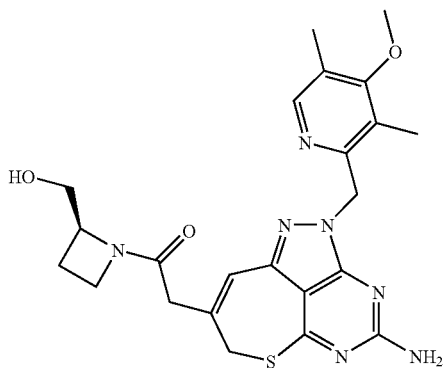

The title compound (11.2 mg, 48%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and (2S)-azetidin-2-ylmethanol oxalate (26 mg).

$^1$H-NMR (CDCl$_3$) δ: 2.23 (3H, s), 2.25-2.34 (1H, m), 2.29 (3H, s), 3.17 (2H, s), 3.68-3.80 (3H, m), 3.75 (3H, s), 3.82 (2H, s), 4.04-4.19 (2H, m), 4.60-4.68 (1H, m), 5.29 (1H, s), 5.50 (2H, s), 6.63 (1H, s), 8.20 (1H, s).

ESI-MS m/z: 482 (M+H)$^+$

Example 125

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-[(3S)-tetrahydrofuran-3-yl]acetamide

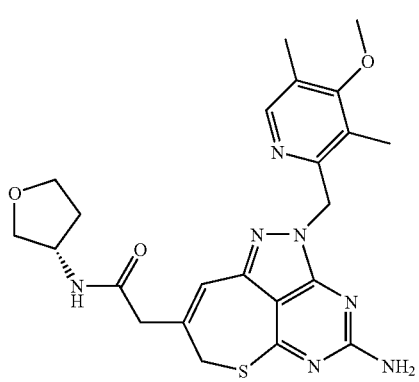

The title compound (12.6 mg, 54%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and (R)-3-aminotetrahydrofuran p-toluenesulfonate (38 mg).

$^1$H-NMR (CDCl$_3$+CD$_3$OD) δ: 1.77-1.86 (1H, m), 2.19-2.27 (1H, m), 2.23 (3H, s), 2.29 (3H, s), 3.23 (2H, s), 3.66 (1H, dd, J=9.6, 2.6 Hz), 3.73-3.84 (3H, m), 3.76 (3H, s), 3.79 (2H, s), 3.91 (1H, q, J=7.8 Hz), 4.46-4.53 (1H, m), 5.39 (2H, brs), 5.50 (2H, s), 6.66 (1H, s), 8.16 (1H, s).

ESI-MS m/z: 482 (M+H)$^+$

Example 126

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-[(1R,2R)-2-hydroxycyclopentyl]acetamide

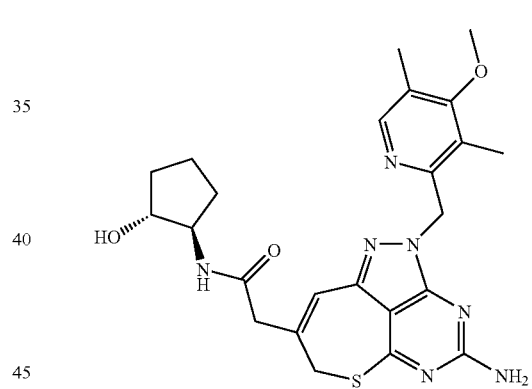

The title compound (9.1 mg, 38%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and (1R,2R)-2-aminocyclopentanol hydrochloride (14 mg).

$^1$H-NMR (CDCl$_3$+CD$_3$OD) δ: 1.37-1.47 (1H, m), 1.58-1.71 (2H, m), 1.73-1.84 (1H, m), 1.91-2.01 (1H, m), 2.07-2.17 (1H, m), 2.23 (3H, s), 2.29 (3H, s), 3.26 (2H, s), 3.76 (3H, s), 3.79 (2H, s), 3.80-3.88 (1H, m), 3.95 (1H, dd, J=12.7, 5.9 Hz), 5.40 (2H, s), 5.49 (2H, s), 6.62 (1H, d, J=4.9 Hz), 6.67 (1H, s), 8.15 (1H, s).

ESI-MS m/z: 496 (M+H)$^+$

Example 127

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-[(1R,2R)-2-hydroxycyclopentyl]acetamide

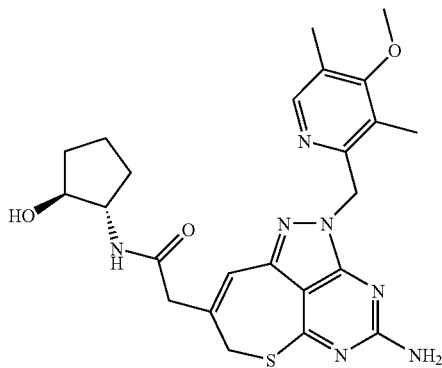

The title compound (7.4 mg, 31%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and (1S,2S)-2-aminocyclopentanol hydrochloride (14 mg).

$^1$H-NMR (CDCl$_3$+CD$_3$OD) δ: 1.37-1.47 (1H, m), 1.59-1.71 (2H, m), 1.74-1.84 (1H, m), 1.92-2.02 (1H, m), 2.07-2.17 (1H, m), 2.23 (3H, s), 2.29 (3H, s), 3.26 (2H, s), 3.76 (3H, s), 3.80 (2H, s), 3.82-3.87 (1H, m), 3.95 (1H, dd, J=12.7, 5.9 Hz), 5.49 (2H, s), 6.61 (1H, d, J=4.9 Hz), 6.67 (1H, s), 8.15 (1H, s).
ESI-MS m/z: 496 (M+H)$^+$

Example 128

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-cyclopropylacetamide

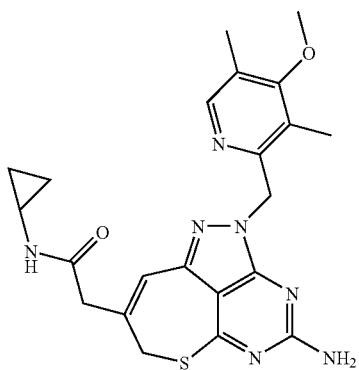

The title compound (11.8 mg, 53%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and cyclopropylamine (10 µl).

$^1$H-NMR (CDCl$_3$+CD$_3$OD) δ: 0.47-0.53 (2H, m), 0.72-0.78 (2H, m), 2.23 (3H, s), 2.28 (3H, s), 2.65-2.73 (1H, m), 3.21 (2H, s), 3.76 (3H, s), 3.79 (2H, s), 5.49 (2H, s), 6.63 (1H, s), 8.15 (1H, s).
ESI-MS m/z: 452 (M+H)$^+$

Example 129

1-({4-Amino-2-[(4-methoxy-3,5-dimethylpyridin-2-yl)methyl]-2,7-dihydro-6-thia-1,2,3,5-tetraazabenzo[cd]azulen-8-yl}acetyl)piperidin-4-ol

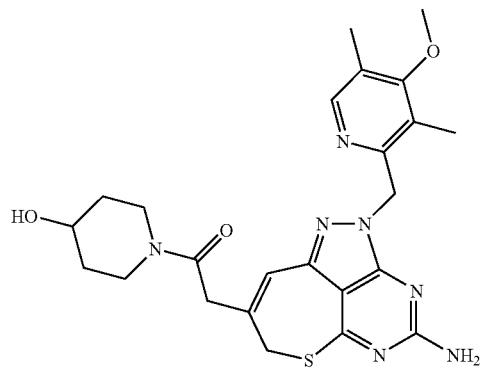

The title compound (10.2 mg, 42%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (25 mg) and piperidin-4-ol (15 mg).

$^1$H-NMR (CDCl$_3$+CD$_3$OD) δ: 1.45-1.57 (2H, m), 1.79-1.92 (2H, m), 2.23 (3H, s), 2.28 (3H, s), 3.19-3.30 (2H, m), 3.44 (2H, s), 3.76 (3H, s), 3.80 (2H, s), 3.86-3.93 (2H, m), 4.02-4.10 (1H, m), 5.50 (2H, s), 6.61 (1H, s), 8.18 (1H, s).
ESI-MS m/z: 496 (M+H)$^+$

Example 130

2-{4-Amino-2-[(4-methoxy-3,5-dimethylpyridin-2-yl)methyl]-2,7-dihydro-6-thia-1,2,3,5-tetraazabenzo[cd]azulen-8-yl}-N,N-diethylacetamide

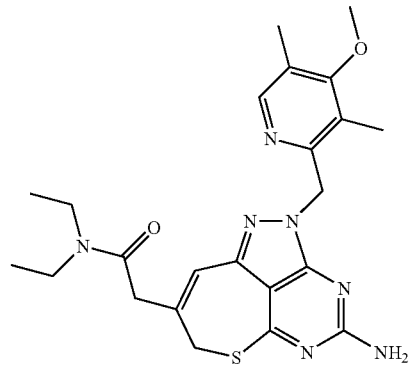

The title compound (8.2 mg, 32%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (28 mg) and diethylamine (17 μl).

$^1$H-NMR (CDCl$_3$) δ: 1.13 (3H, t, J=7.1 Hz), 1.20 (3H, t, J=7.1 Hz), 2.22 (3H, s), 2.28 (3H, s), 3.31-3.41 (4H, m), 3.39 (2H, s), 3.74 (3H, s), 3.84 (2H, s), 5.20 (2H, brs), 5.50 (2H, s), 6.62 (1H, s), 8.20 (1H, s).

ESI-MS m/z: 468 (M+H)$^+$

Example 131

2-[(4-Methoxy-3,5-dimethylpyridin-2-yl)methyl]-8-(2-oxo-2-pyrrolidin-1-ylethyl)-2,7-dihydro-6-thia-1,2,3,5-tetraazabenzo[cd]azulen-4-amine

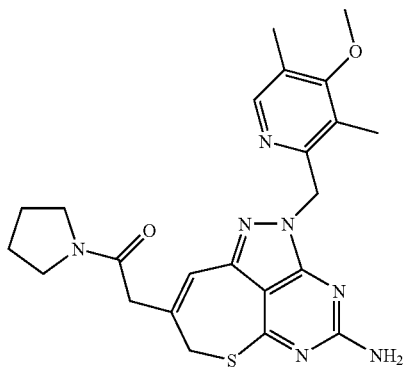

The title compound (7.0 mg, 27%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (28 mg) and pyrrolidine (14 μl).

$^1$H-NMR (CDCl$_3$) δ: 1.82-1.89 (2H, m), 1.92-1.98 (2H, m), 2.22 (3H, s), 2.28 (3H, s), 3.35 (2H, s), 3.48 (4H, td, J=6.7, 4.1 Hz), 3.74 (4H, s), 3.85 (2H, s), 5.19 (2H, brs), 5.50 (2H, s), 6.62 (1H, s), 8.19 (1H, s).

ESI-MS m/z: 466 (M+H)$^+$

Example 132

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-(2-methoxyethyl)-N-methylacetamide

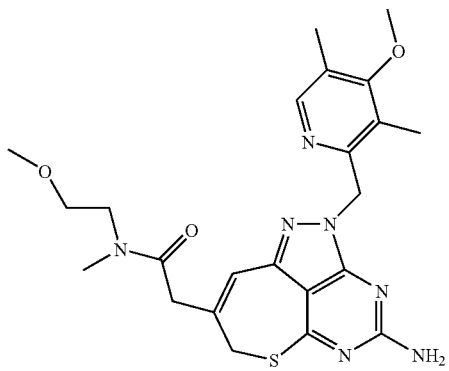

The title compound (11.8 mg, 48%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (28 mg) and 2-methoxy-N-methylethanamine (15 μl).

$^1$H-NMR (CDCl$_3$) δ: 8.19 (1H, s), 6.66-6.60 (1H, m), 5.50 (2H, s), 5.19 (2H, s), 3.81-3.80 (2H, m), 3.74 (3H, s), 3.59-2.97 (12H, m), 2.29-2.22 (6H, m).

ESI-MS m/z: 484 (M+H)$^+$

Example 133

2-{4-Amino-2-[(4-methoxy-3,5-dimethylpyridin-2-yl)methyl]-2,7-dihydro-6-thia-1,2,3,5-tetraazabenzo[cd]azulen-8-yl}-N-isopropylacetamide

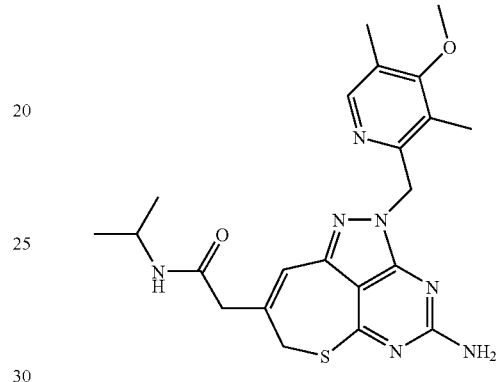

The title compound (8.9 mg, 36%) was obtained as a solid by synthesis by the same method as in Example 115 using {4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetic acid of Example 118 (28 mg) and isopropylamine (14 μl).

$^1$H-NMR (CDCl$_3$) δ: 1.14 (3H, s), 1.15 (3H, s), 2.22 (3H, s), 2.31 (3H, s), 3.24 (2H, s), 3.75 (3H, s), 3.77 (2H, s), 4.04-4.14 (1H, m), 5.23 (2H, brs), 5.51 (2H, s), 5.60 (1H, d, J=7.8 Hz), 6.70 (1H, s), 8.20 (1H, s).

ESI-MS m/z: 454 (M+H)$^+$

Example 134

1) tert-Butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate

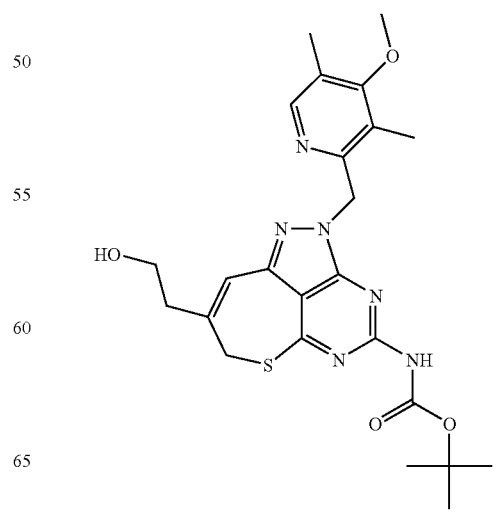

Lithium borohydride (67 mg) was added to a mixture composed of methyl {4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl}acetate of Example 111 (957 mg) and dehydrated tetrahydrofuran (18 ml) under ice-cooling. The mixture was stirred at 0° C. for two hours, and then returned to room temperature and stirred overnight. The mixture was ice-cooled again and lithium borohydride (33 mg) was added, followed by stirring at 0° C. for two hours. Methanol (6 ml) and a 1 N sodium hydroxide solution (6 ml) were added to the reaction mixture. Then, the mixture was returned to room temperature and stirred for four hours. The organic solvent in the reaction mixture was evaporated under reduced pressure. Then, a 0.2 N hydrochloric acid solution was added, followed by extraction with chloroform. The organic layer was washed with brine, and then dried over magnesium sulfate and filtered. Then, the filtrate was concentrated under reduced pressure. The concentrated residue was purified by silica gel column chromatography (chloroform-methanol) to obtain the title compound (301 mg, 40%) as an oil.

$^1$H-NMR (CDCl$_3$) δ: 1.53 (10H, s), 2.21 (3H, s), 2.31 (3H, s), 2.60 (2H, t, J=6.1 Hz), 3.74 (3H, s), 3.75 (2H, s), 3.88 (2H, s), 5.63 (2H, s), 6.70 (1H, s), 7.42 (1H, s), 8.18 (1H, s).

ESI-MS m/z: 499 (M+H)$^+$ 2) tert-Butyl {8-(2-azidoethyl)-2-[(4-methoxy-3,5-dimethylpyridin-2-yl)methyl]-2,7-dihydro-6-thia-1,2,3,5-tetraazabenzo[cd]azulen-4-yl}carbamate

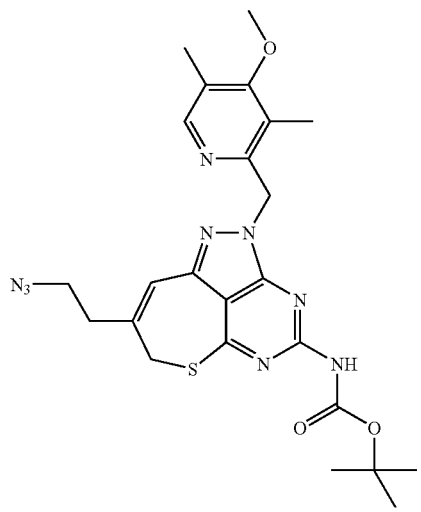

Mesyl chloride (5 µl) was added dropwise to a mixture composed of the above tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate (25 mg), triethylamine (15 µl) and dehydrated dichloromethane (0.5 ml) under ice-cooling, and the mixture was stirred at 0° C. for 20 minutes. Water was added to the reaction mixture, followed by extraction with ethyl acetate. The organic layers were combined and dried over sodium sulfate and filtered, and then the solvent in the filtrate was evaporated under reduced pressure. Sodium azide (5.3 mg) and dehydrated dimethylformamide (0.5 ml) were added to the resulting residue, and the mixture was stirred at a bath temperature of 55° C. for 16 hours. The solvent was evaporated and then a 0.2 N sodium hydroxide solution (4 ml) was added, followed by extraction with ethyl acetate. The organic layer was dried over sodium sulfate and concentrated. The title compound (31 mg) was obtained as an oil. The product was directly used for the next reaction.

ESI-MS; m/z: 524 (M+H)$^+$.

3) tert-Butyl {8-(2-aminoethyl)-2-[(4-methoxy-3,5-dimethylpyridin-2-yl)methyl]-2,7-dihydro-6-thia-1,2,3,5-tetraazabenzo[cd]azulen-4-yl}carbamate

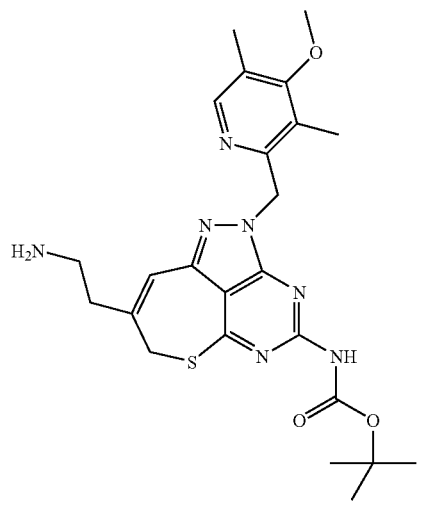

A mixture composed of the above tert-butyl {8-(2-azidoethyl)-2-[(4-methoxy-3,5-dimethylpyridin-2-yl)methyl]-2,7-dihydro-6-thia-1,2,3,5-tetraazabenzo[cd]azulen-4-yl}carbamate (31 mg), triphenylphosphine (23 mg), tetrahydrofuran (0.9 ml) and water (0.1 ml) was stirred at room temperature for five hours. A 0.2 N sodium hydroxide solution (2.5 ml) was added to the reaction mixture, followed by extraction with ethyl acetate. The organic layer was dried over sodium sulfate and filtered, and then the solvent in the filtrate was evaporated under reduced pressure. The resulting residue was purified by silica gel column chromatography (NH silica used, ethyl acetate-chloroform) to obtain the title compound (17 mg) as an oil.

$^1$H-NMR (CDCl3) δ: 1.53 (9H, s), 2.21 (3H, s), 2.31 (3H, s), 2.49 (2H, t, J=6.5 Hz), 2.96 (2H, t, J=6.5 Hz), 3.71 (2H, s), 3.74 (3H, s), 5.63 (2H, s), 6.66 (1H, s), 7.52 (1H, brs), 8.18 (1H, s).

ESI-MS; m/z: 498 (M+H)$^+$.

4) 8-(2-Aminoethyl)-2-[(4-methoxy-3,5-dimethylpyridin-2-yl)methyl]-2,7-dihydro-6-thia-1,2,3,5-tetraazabenzo[cd]azulen-4-amine

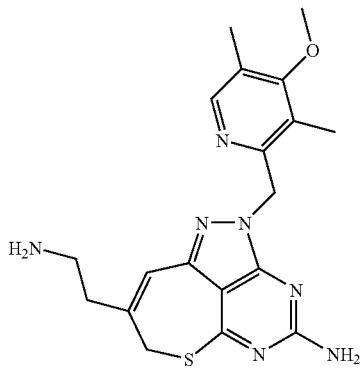

Trifluoroacetic acid (0.5 ml) was added to a mixture composed of the above tert-butyl {8-(2-aminoethyl)-2-[(4-methoxy-3,5-dimethylpyridin-2-yl)methyl]-2,7-dihydro-6-thia-1,2,3,5-tetraazabenzo[cd]azulen-4-yl}carbamate (17 mg) and dichloromethane (2 ml), and then the mixture was stirred at room temperature for six hours. The solvent in the reaction mixture was evaporated, and a 0.2 N sodium hydroxide solution was added to the resulting residue, followed by extraction with chloroform. The organic layer was dried over sodium sulfate and filtered, and then the solvent in the filtrate was evaporated under reduced pressure. The resulting residue was purified by NH silica gel column chromatography (chloroform-methanol) to obtain an oil. The oil was dissolved in dioxane (0.5 ml), followed by lyophilization to obtain the title compound (9.4 mg) as an amorphous.

$^1$H-NMR (CDCl$_3$) δ: 2.22 (3H, s), 2.29 (3H, s), 2.47 (2H, t, J=6.4 Hz), 2.96 (2H, t, J=6.4 Hz), 3.68 (2H, s), 3.74 (3H, s), 5.19 (2H, brs), 5.50 (2H, s), 6.61 (1H, s), 8.19 (1H, s).

ESI-MS; m/z: 398 (M+H)$^+$.

Example 135

1) tert-Butyl {2-[(4-methoxy-3,5-dimethylpyridin-2-yl)methyl]-8-(2-morpholin-4-ylethyl)-2,7-dihydro-6-thia-1,2,3,5-tetraazabenzo[cd]azulen-4-yl}carbamate

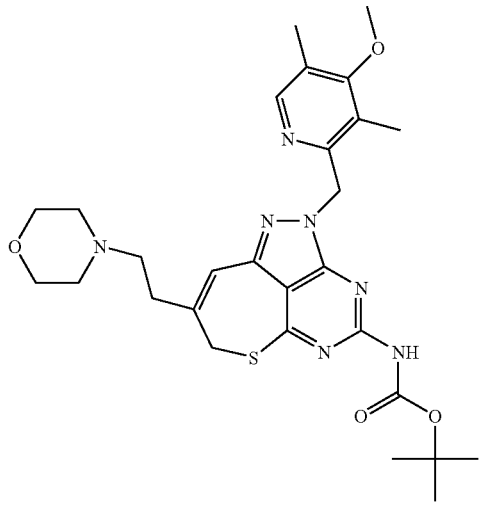

Mesyl chloride (5 μl) was added dropwise to a mixture composed of tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (25 mg), dehydrated dichloromethane (0.5 ml) and triethylamine (15 μl) under ice-cooling, and the mixture was stirred at 0° C. for 10 minutes. After confirming that the raw material disappeared, the solvent in the reaction mixture was evaporated by spraying. Dioxane (0.2 ml) and morpholine (44 μl) as an amine were added to the residue, and the mixture was stirred at 60° C. for six hours. The reaction mixture was concentrated under reduced pressure, and a 0.5 N sodium hydroxide solution was added to the resulting residue, followed by extraction with ethyl acetate. The organic layer was concentrated, and the resulting residue was purified by NH silica gel column chromatography (hexane-ethyl acetate) to obtain the title compound (17 mg, 60%) as an oil.

$^1$H-NMR (CDCl$_3$) δ: 1.53 (9H, s), 2.22 (3H, s), 2.31 (3H, s), 2.47-2.62 (8H, m), 3.70-3.73 (6H, m), 3.74 (3H, s), 5.62 (2H, s), 6.65 (1H, s), 7.46 (1H, s), 8.18 (1H, s).

ESI-MS m/z: 568 (M+H)$^+$

2) 2-[(4-Methoxy-3,5-dimethylpyridin-2-yl)methyl]-8-(2-morpholin-4-ylethyl)-2,7-dihydro-6-thia-1,2,3,5-tetraazabenzo[cd]azulen-4-amine

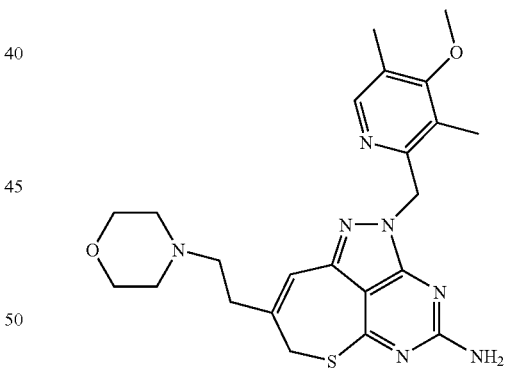

The title compound (11.6 mg, 68%) was obtained as an amorphous by synthesis by the same method as in Example 111 using the above tert-butyl {2-[(4-methoxy-3,5-dimethylpyridin-2-yl)methyl]-8-(2-morpholin-4-ylethyl)-2,7-dihydro-6-thia-1,2,3,5-tetraazabenzo[cd]azulen-4-yl}carbamate (17 mg).

$^1$H-NMR (CDCl$_3$) δ: 2.22 (3H, s), 2.29 (3H, s), 2.47-2.61 (8H, m), 3.70-3.73 (6H, m), 3.74 (3H, s), 5.16 (2H, s), 5.50 (2H, s), 6.60 (1H, s), 8.19 (1H, s).

ESI-MS m/z: 468 (M+H)$^+$

Example 136

1) tert-Butyl {8-[2-(dimethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate

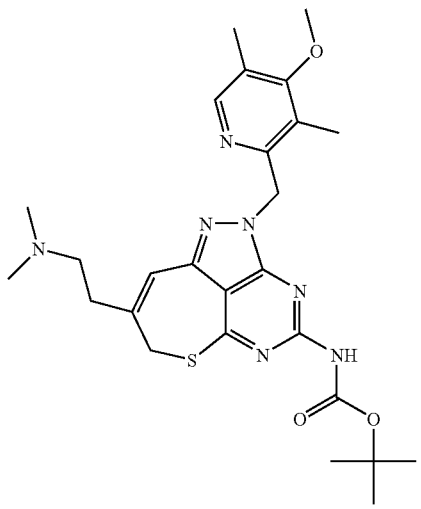

The title compound (17 mg, 60%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (27 mg) and a 2 N solution of dimethylamine in tetrahydrofuran (0.2 ml) as an amine.

$^1$H-NMR (CDCl$_3$) δ: 1.53 (9H, s), 2.21 (3H, s), 2.26 (6H, s), 2.30 (3H, s), 2.51 (2H, s), 3.72-3.75 (5H, m), 5.62 (2H, s), 6.65 (1H, s), 7.46 (1H, s), 8.18 (1H, s).
ESI-MS m/z: 526 (M+H)$^+$ 2) 8-[2-(Dimethylamino)ethyl]-2-[(4-methoxy-3,5-dimethylpyridin-2-yl)methyl]-2,7-dihydro-6-thia-1,2,3,5-tetraazabenzo[cd]azulen-4-amine

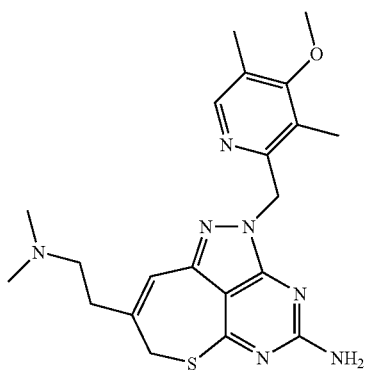

The title compound (7.9 mg, 57%) was obtained as an amorphous by synthesis by the same method as in Example 111 using the above tert-butyl {8-[2-(dimethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (17 mg).

$^1$H-NMR (CDCl$_3$) δ: 2.22 (3H, s), 2.26 (6H, s), 2.28 (3H, s), 2.47-2.51 (4H, m), 3.70 (2H, s), 3.74 (3H, s), 5.14 (2H, brs), 5.49 (2H, s), 6.60 (1H, s), 8.19 (1H, s).
ESI-MS m/z: 426 (M+H)$^+$

Example 137

1) tert-Butyl {8-[2-(1H-imidazol-1-yl)ethyl]-2-[(4-methoxy-3,5-dimethylpyridin-2-yl)methyl]-2,7-dihydro-6-thia-1,2,3,5-tetraazabenzo[cd]azulen-4-yl}carbamate

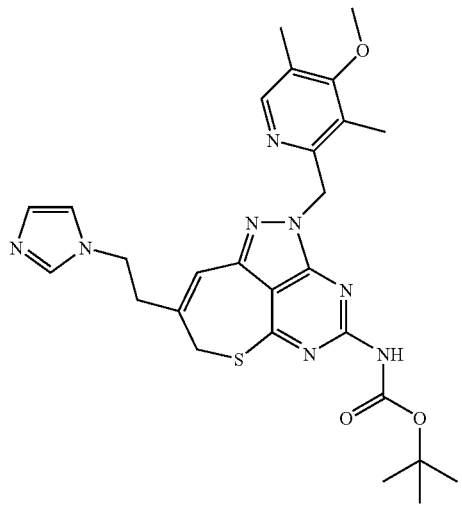

The title compound (11 mg, 37%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (27 mg) and imidazole (37 mg) as an amine.

$^1$H-NMR (CDCl$_3$) δ: 1.53 (9H, s), 2.22 (3H, s), 2.31 (3H, s), 2.80 (2H, t, J=7.1 Hz), 3.67 (2H, s), 3.75 (3H, s), 4.19 (2H, t, J=7.1 Hz), 5.61 (2H, s), 6.58-6.58 (1H, m), 6.95 (1H, t, J=1.2 Hz), 7.04 (1H, t, J=1.2 Hz), 7.45 (1H, s), 7.49-7.52 (1H, m), 8.17 (1H, s).
ESI-MS m/z: 549 (M+H)$^+$ 2) 8-[2-(1H-Imidazol-1-yl)ethyl]-2-[(4-methoxy-3,5-dimethylpyridin-2-yl)methyl]-2,7-dihydro-6-thia-1,2,3,5-tetraazabenzo[cd]azulen-4-amine

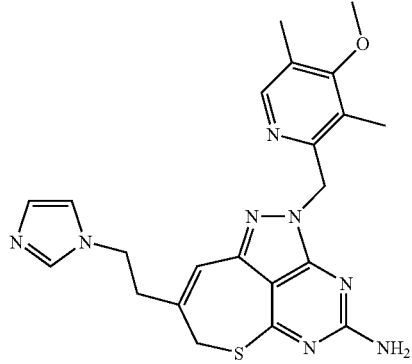

The title compound (6.1 mg, 68%) was obtained as an amorphous by synthesis by the same method as in Example 111 using the above tert-butyl {8-[2-(1H-imidazol-1-yl)ethyl]-2-[(4-methoxy-3,5-dimethylpyridin-2-yl)methyl]-2,7-dihydro-6-thia-1,2,3,5-tetraazabenzo[cd]azulen-4-yl}carbamate (11 mg).

$^1$H-NMR (CDCl$_3$) δ: 2.22 (3H, s), 2.29 (3H, s), 2.78 (2H, t, J=7.0 Hz), 3.65 (2H, s), 3.74 (3H, s), 4.18 (2H, t, J=7.0 Hz), 5.16 (2H, brs), 5.49 (2H, s), 6.52 (1H, s), 6.95-6.96 (1H, m), 7.04-7.04 (1H, m), 7.51 (1H, s), 8.19 (1H, s).

ESI-MS m/z: 449 (M+H)$^+$

The title compound (7.4 mg, 100%) was obtained as an amorphous by synthesis by the same method as in Example 111 using the above tert-butyl {2-[(4-methoxy-3,5-dimethylpyridin-2-yl)methyl]-8-[2-(methylamino)ethyl]-2,7-dihydro-6-thia-1,2,3,5-tetraazabenzo[cd]azulen-4-yl}carbamate (9 mg).

$^1$H-NMR (CDCl$_3$) δ: 2.22 (3H, s), 2.29 (3H, s), 2.45 (3H, s), 2.53 (2H, t, J=6.5 Hz), 2.82 (2H, t, J=6.5 Hz), 3.69 (2H, s), 3.74 (3H, s), 5.16 (2H, brs), 5.50 (2H, s), 6.61 (1H, s), 8.19 (1H, s).

ESI-MS m/z: 412 (M+H)$^+$

Example 138

1) tert-Butyl {2-[(4-methoxy-3,5-dimethylpyridin-2-yl)methyl]-8-[2-(methylamino)ethyl]-2,7-dihydro-6-thia-1,2,3,5-tetraazabenzo[cd]azulen-4-yl}carbamate

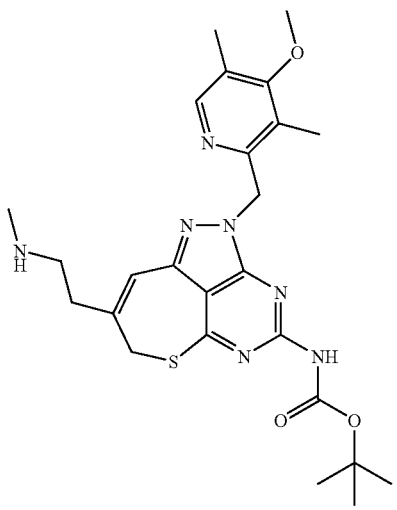

The title compound (9 mg, 33%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (27 mg) and a 2 N solution of methylamine in tetrahydrofuran (0.2 ml) as an amine.

$^1$H-NMR (CDCl$_3$) δ: 1.53 (9H, s), 2.22 (3H, s), 2.31 (3H, s), 2.45 (3H, s), 2.54 (2H, t, J=6.7 Hz), 2.83 (2H, t, J=6.7 Hz), 3.72 (2H, s), 3.74 (3H, s), 5.62 (2H, s), 6.66 (1H, s), 7.50 (1H, brs), 8.18 (1H, s).

ESI-MS m/z: 512 (M+H)$^+$ 2) 2-[(4-Methoxy-3,5-dimethylpyridin-2-yl)methyl]-8-[2-(methylamino)ethyl]-2,7-dihydro-6-thia-1,2,3,5-tetraazabenzo[cd]azulen-4-amine

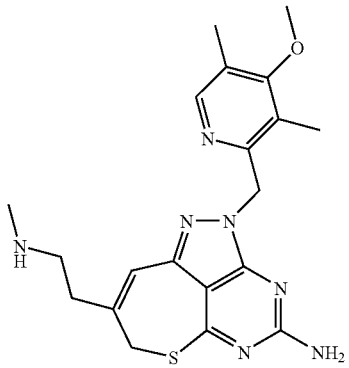

Example 139

1) tert-Butyl {8-[2-(ethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate

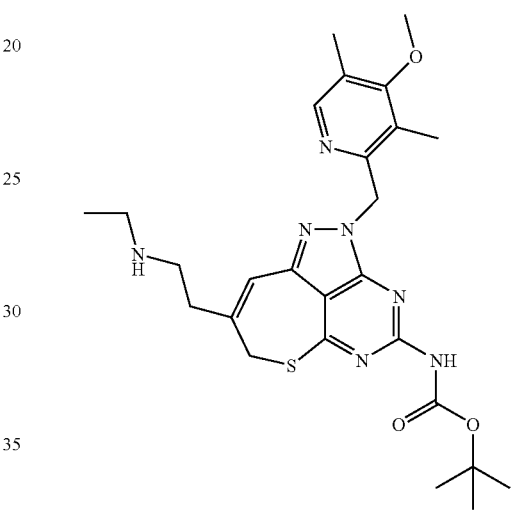

The title compound (17 mg, 56%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg) and a 2 N solution of ethylamine in tetrahydrofuran (0.5 ml) as an amine.

ESI-MS m/z: 526 (M+H)$^+$ 2) 8-[2-(Ethylamino)ethyl]-2-[(4-methoxy-3,5-dimethylpyridin-2-yl)methyl]-2,7-dihydro-6-thia-1,2,3,5-tetraazabenzo[cd]azulen-4-amine

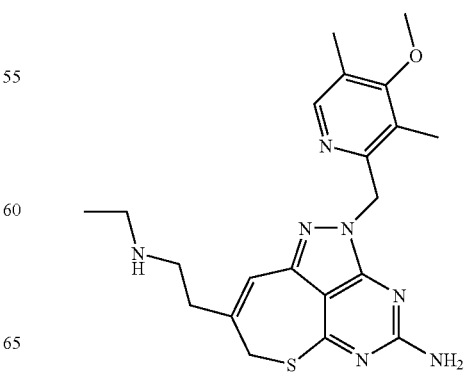

Synthesis was performed by the same method as in Example 111 using the above tert-butyl {8-[2-(ethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (17 mg), followed by trituration with diethyl ether to obtain the title compound (4.4 mg, 31%) as a solid.

$^1$H-NMR (CDCl$_3$) δ: 1.31 (3H, t, J=7.2 Hz), 2.21 (3H, s), 2.28 (3H, s), 2.75 (2H, t, J=7.6 Hz), 2.97 (2H, q, J=7.2 Hz), 3.07 (2H, t, J=7.6 Hz), 3.69 (2H, s), 3.74 (3H, s), 5.26 (2H, brs), 5.48 (2H, s), 6.61 (1H, s), 8.18 (1H, s), 8.46 (1H, brs).

ESI-MS m/z: 426 (M+H)$^+$

Example 140

1) tert-Butyl {8-[2-(cyclopropylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate

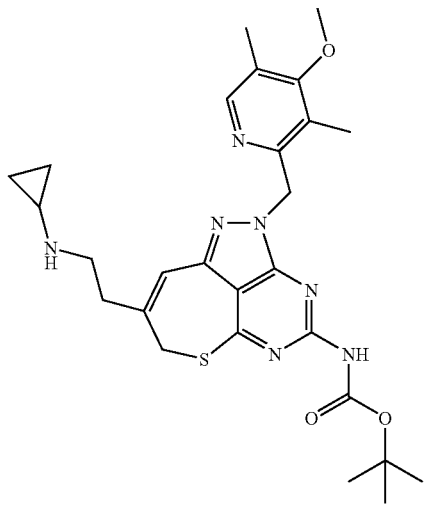

The title compound (16 mg, 51%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), cyclopropylamine (20 μl) as an amine and tetrahydrofuran (0.5 ml) as an amination reaction solvent.

ESI-MS m/z: 538 (M+H)$^+$ 2) 8-[2-(Cyclopropylamino)ethyl]-2-[(4-methoxy-3,5-dimethylpyridin-2-yl)methyl]-2,7-dihydro-6-thia-1,2,3,5-tetraazabenzo[cd]azulen-4-amine

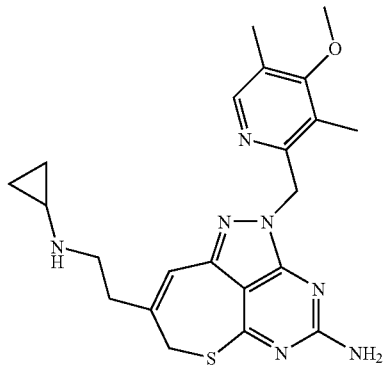

The title compound (6.3 mg, 48%) was obtained as an amorphous by synthesis by the same method as in Example 111 using the above tert-butyl {8-[2-(cyclopropylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (16 mg).

$^1$H-NMR (CDCl$_3$) δ: 0.60-0.66 (2H, m), 0.69-0.74 (2H, m), 2.22 (3H, s), 2.29 (3H, s), 2.32-2.38 (1H, m), 2.66 (2H, t, J=7.5 Hz), 3.09 (2H, t, J=7.5 Hz), 3.70 (2H, s), 3.75 (3H, s), 5.33 (2H, brs), 5.49 (2H, s), 6.62 (1H, s), 8.19 (1H, s), 8.26 (1H, brs).

ESI-MS m/z: 438 (M+H)$^+$

Example 141

1) tert-Butyl {2-[(4-methoxy-3,5-dimethylpyridin-2-yl)methyl]-8-(2-pyrrolidin-1-ylethyl)-2,7-dihydro-6-thia-1,2,3,5-tetraazabenzo[cd]azulen-4-yl}carbamate

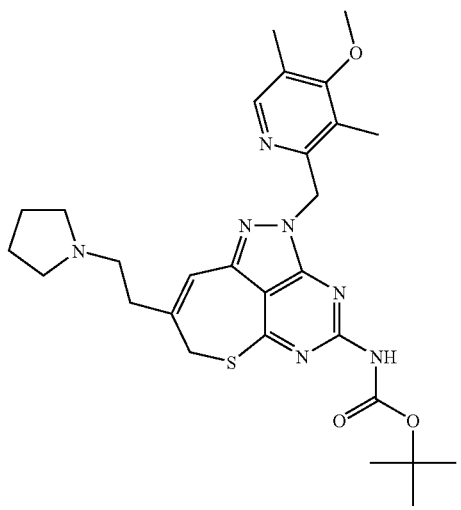

The title compound (11 mg, 34%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), pyrrolidine (24 μl) as an amine and tetrahydrofuran (0.5 ml) as an amination reaction solvent.

ESI-MS m/z: 552 (M+H)$^+$ 2) 2-[(4-Methoxy-3,5-dimethylpyridin-2-yl)methyl]-8-(2-pyrrolidin-1-ylethyl)-2,7-dihydro-6-thia-1,2,3,5-tetraazabenzo[cd]azulen-4-amine

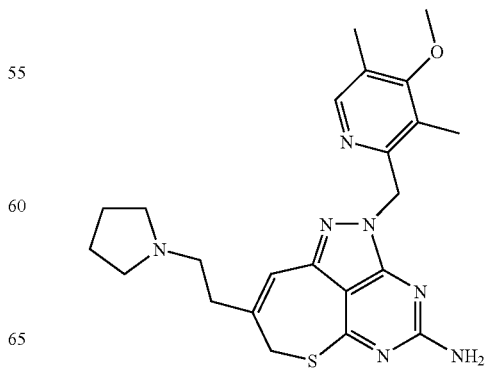

The title compound (4.8 mg, 53%) was obtained as an amorphous by synthesis by the same method as in Example 111 using the above tert-butyl {2-[(4-methoxy-3,5-dimethylpyridin-2-yl)methyl]-8-(2-pyrrolidin-1-ylethyl)-2,7-dihydro-6-thia-1,2,3,5-tetraazabenzo[cd]azulen-4-yl}carbamate (11 mg).

$^1$H-NMR (CDCl$_3$) δ: 1.99-2.03 (4H, m), 2.22 (4H, s), 2.29 (3H, s), 2.73-2.79 (2H, m), 3.06-3.12 (6H, m), 3.73 (2H, s), 3.74 (3H, s), 5.19 (2H, brs), 5.49 (2H, s), 6.59 (1H, s), 8.19 (1H, s), 8.47 (1H, brs).

ESI-MS m/z: 452 (M+H)$^+$

The title compound (4.4 mg, 36%) was obtained as an amorphous by synthesis by the same method as in Example 111 using the above tert-butyl {8-[2-(isopropylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (16 mg).

$^1$H-NMR (CDCl$_3$) δ: 1.07 (6H, d, J=6.1 Hz), 2.22 (3H, s), 2.30 (3H, s), 2.54 (2H, t, J=6.5 Hz), 2.80-2.88 (3H, m), 3.70 (2H, s), 3.74 (3H, s), 5.12 (2H, brs), 5.50 (2H, s), 6.62 (1H, s), 8.19 (1H, s).

ESI-MS m/z: 440 (M+H)$^+$

Example 142

1) tert-Butyl {8-[2-(isopropylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate Example 143

1) tert-Butyl {8-[2-(cyclobutylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate

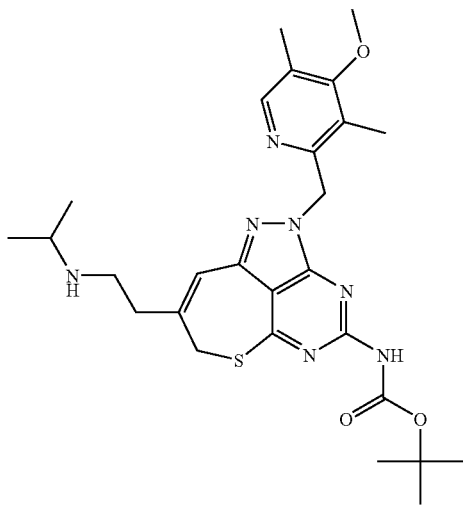

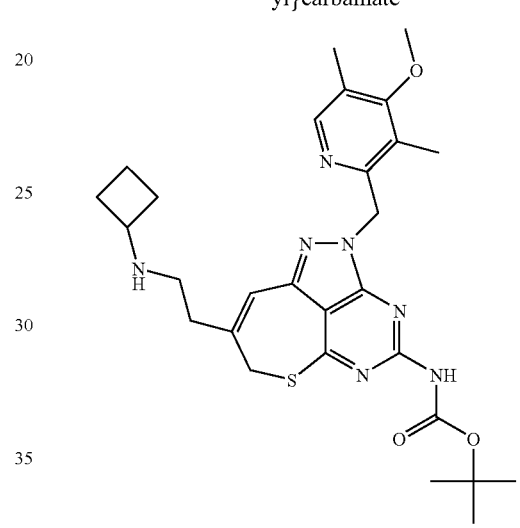

The title compound (16 mg, 51%) was obtained as an oil by synthesis by the same method as in Example 134 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), isopropylamine (25 μl) as an amine and tetrahydrofuran (0.5 ml) as an amination reaction solvent.

ESI-MS m/z: 540 (M+H)$^+$ 2) 8-[2-(Isopropylamino)ethyl]-2-[(4-methoxy-3,5-dimethylpyridin-2-yl)methyl]-2,7-dihydro-6-thia-1,2,3,5-tetraazabenzo[cd]azulen-4-amine The title compound (20 mg, 62%) was obtained as an oil by synthesis by the same method as in Example 134 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), cyclobutylamine (25 μl) and tetrahydrofuran (0.5 ml) as a reaction solvent.

ESI-MS m/z: 552 (M+H)$^+$ 2) 8-[2-(Cyclobutylamino)ethyl]-2-[(4-methoxy-3,5-dimethylpyridin-2-yl)methyl]-2,7-dihydro-6-thia-1,2,3,5-tetraazabenzo[cd]azulen-4-amine

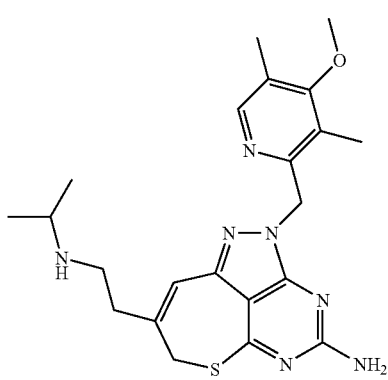

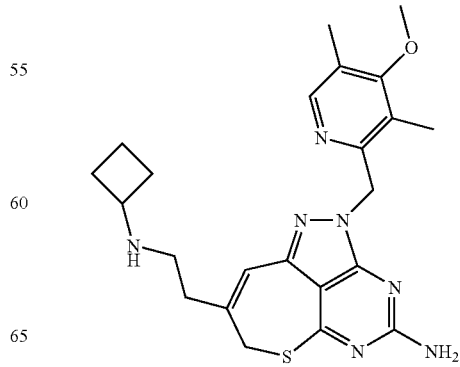

The title compound (8.0 mg, 49%) was obtained as an amorphous by synthesis by the same method as in Example 111 using the above tert-butyl {8-[2-(cyclobutylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (20 mg).

$^1$H-NMR (CDCl$_3$) δ: 1.74-1.59 (4H, m), 2.19-2.23 (2H, m), 2.22 (3H, s), 2.30 (3H, s), 2.50 (2H, t, J=6.8 Hz), 2.77 (2H, t, J=6.8 Hz), 3.24-3.32 (1H, m), 3.69 (2H, s), 3.74 (3H, s), 5.15 (2H, brs), 5.50 (2H, s), 6.61 (1H, s), 8.19 (1H, s).

ESI-MS m/z: 452 (M+H)$^+$

Example 144

1) tert-Butyl (2-[(4-methoxy-3,5-dimethylpyridin-2-yl)methyl]-8-{2-[(3R)-tetrahydrofuran-3-ylamino]ethyl}-2,7-dihydro-6-thia-1,2,3,5-tetraazabenzo[cd]azulen-4-yl)carbamate

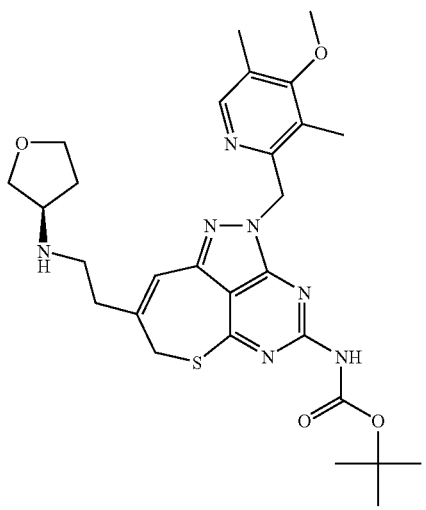

The title compound (10 mg, 30%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), (R)-3-aminotetrahydrofuran p-toluenesulfonate (91 mg) and diisopropylethylamine (50 µl) as amines and dehydrated dimethylformamide (0.5 ml) as an amination reaction solvent.

ESI-MS m/z: 568 (M+H)$^+$ 2) 2-[(4-Methoxy-3,5-dimethylpyridin-2-yl)methyl]-8-{2-[(3R)-tetrahydrofuran-3-ylamino]ethyl}-2,7-dihydro-6-thia-1,2,3,5-tetraazabenzo[cd]azulen-4-amine

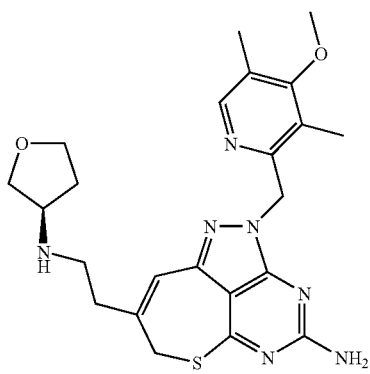

The title compound (6.0 mg, 73%) was obtained as an amorphous by synthesis by the same method as in Example 111 using the above tert-butyl (2-[(4-methoxy-3,5-dimethylpyridin-2-yl)methyl]-8-{2-[(3R)-tetrahydrofuran-3-ylamino]ethyl}-2,7-dihydro-6-thia-1,2,3,5-tetraazabenzo[cd]azulen-4-yl)carbamate (10 mg).

$^1$H-NMR (CDCl$_3$) δ: 1.68-1.76 (1H, m), 2.04-2.14 (1H, m), 2.22 (3H, s), 2.30 (3H, s), 2.53 (2H, t, J=6.5 Hz), 2.80-2.88 (2H, m), 3.37-3.43 (1H, m), 3.57 (1H, dd, J=8.9, 4.0 Hz), 3.70 (2H, d, J=3.7 Hz), 3.74 (3H, s), 3.75-3.84 (2H, m), 3.87-3.93 (1H, m), 5.14 (2H, brs), 5.50 (2H, s), 6.62 (1H, s), 8.19 (1H, s).

ESI-MS m/z: 468 (M+H)$^+$

Example 145

1) tert-Butyl {2-[(4-methoxy-3,5-dimethylpyridin-2-yl)methyl]-8-(2-piperidin-1-ylethyl)-2,7-dihydro-6-thia-1,2,3,5-tetraazabenzo[cd]azulen-4-yl}carbamate

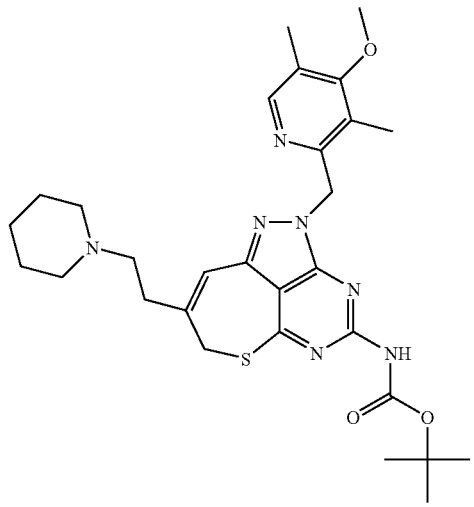

The title compound (25 mg, 75%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), piperidine (29 µl) and tetrahydrofuran (0.5 ml) as a reaction solvent.

ESI-MS m/z: 566 (M+H)$^+$ 2) 2-[(4-Methoxy-3,5-dimethylpyridin-2-yl)methyl]-8-(2-piperidin-1-ylethyl)-2,7-dihydro-6-thia-1,2,3,5-tetraazabenzo[cd]azulen-4-amine

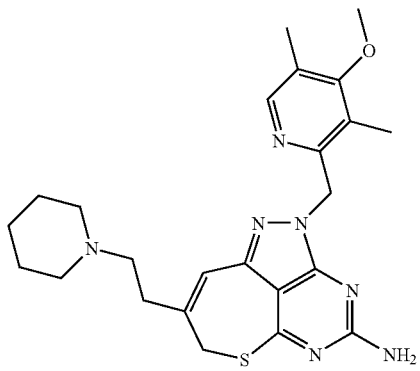

The title compound (16.8 mg, 83%) was obtained as an amorphous by synthesis by the same method as in Example 111 using the above tert-butyl {2-[(4-methoxy-3,5-dimethylpyridin-2-yl)methyl]-8-(2-piperidin-1-ylethyl)-2,7-dihydro-6-thia-1,2,3,5-tetraazabenzo[cd]azulen-4-yl}carbamate (25 mg).

$^1$H-NMR (CDCl$_3$) δ: 1.40-1.47 (2H, m), 1.56-1.62 (4H, m), 2.21 (3H, s), 2.28 (3H, s), 2.39-2.46 (4H, m), 2.48-2.56 (4H, m), 3.70 (2H, s), 3.74 (3H, s), 5.23 (2H, brs), 5.49 (2H, s), 6.58 (1H, s), 8.19 (1H, s).

ESI-MS m/z: 466 (M+H)$^+$

Example 146

1) tert-Butyl {8-[2-(3-fluoroazetidin-1-yl)ethyl]-2-[(4-methoxy-3,5-dimethylpyridin-2-yl)methyl]-2,7-dihydro-6-thia-1,2,3,5-tetraazabenzo[cd]azulen-4-yl}carbamate

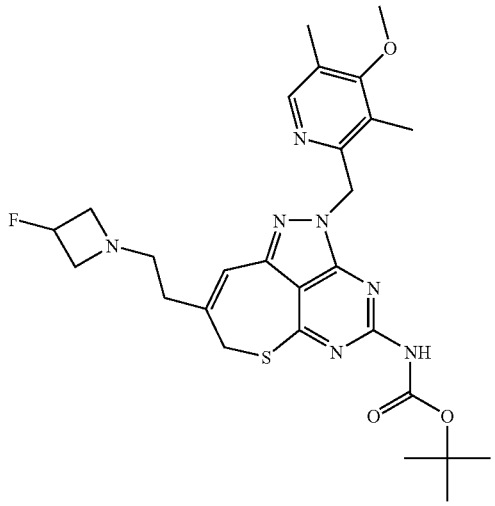

The title compound (9 mg, 27%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), 3-fluoroazetidine hydrochloride (23 mg) and 1,8-diazabicyclo[5.4.0]-7-undecene (26 μl) as amines and dehydrated dimethyl sulfoxide (0.5 ml) as an amination reaction solvent.

ESI-MS m/z: 556 (M+H)$^+$ 2) 8-[2-(3-Fluoroazetidin-1-yl)ethyl]-2-[(4-methoxy-3,5-dimethylpyridin-2-yl)methyl]-2,7-dihydro-6-thia-1,2,3,5-tetraazabenzo[cd]azulen-4-amine

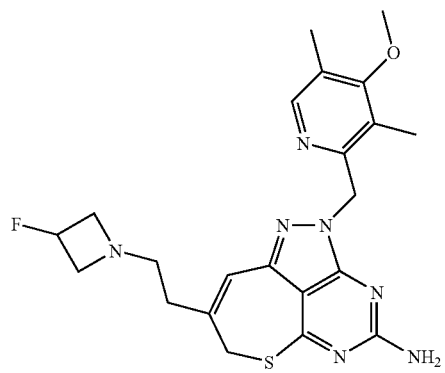

The title compound (4.6 mg, 65%) was obtained as an amorphous by synthesis by the same method as in Example 111 using the above tert-butyl {8-[2-(3-fluoroazetidin-1-yl)ethyl]-2-[(4-methoxy-3,5-dimethylpyridin-2-yl)methyl]-2,7-dihydro-6-thia-1,2,3,5-tetraazabenzo[cd]azulen-4-yl}carbamate (9 mg).

$^1$H-NMR (CDCl$_3$) δ: 2.22 (3H, s), 2.29 (3H, s), 2.37 (2H, t, J=7.3 Hz), 2.72 (2H, t, J=7.3 Hz), 3.09-3.19 (2H, m), 3.65-3.75 (2H, m), 3.68 (2H, s), 3.74 (3H, s), 5.00-5.20 (1H, m), 5.11 (2H, s), 5.50 (2H, s), 6.58 (1H, s), 8.19 (1H, s).

ESI-MS m/z: 456 (M+H)$^+$

Example 147

1) tert-Butyl {8-[2-(diethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate

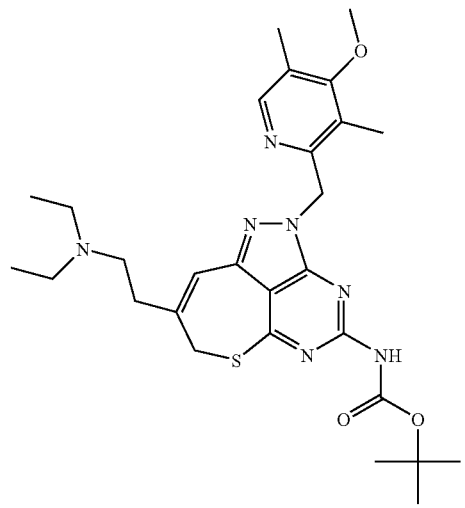

The title compound (14 mg, 44%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), diethylamine (90 μl) and tetrahydrofuran (0.5 ml) as a reaction solvent.

ESI-MS m/z: 554 (M+H)+

2) 8-[2-(Diethylamino)ethyl]-2-[(4-methoxy-3,5-dimethylpyridin-2-yl)methyl]-2,7-dihydro-6-thia-1,2,3,5-tetraazabenzo[cd]azulen-4-amine

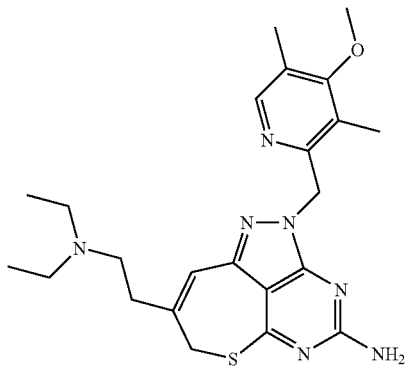

The title compound (8.9 mg, 77%) was obtained as an amorphous by synthesis by the same method as in Example 111 using the above tert-butyl {8-[2-(diethylamino)ethyl]-2-[(4-methoxy-3,5-dimethylpyridin-2-yl)methyl]-2,7-dihydro-6-thia-1,2,3,5-tetraazabenzo[cd]azulen-4-yl}carbamate (14 mg).

$^1$H-NMR (CDCl$_3$) δ: 1.03 (6H, t, J=7.2 Hz), 2.22 (3H, s), 2.28 (3H, s), 2.47 (2H, dd, J=9.2, 6.2 Hz), 2.56 (4H, q, J=7.2 Hz), 2.68 (2H, dd, J=9.2, 6.2 Hz), 3.70 (2H, s), 3.74 (3H, s), 5.15 (2H, s), 5.49 (2H, s), 6.58 (1H, s), 8.20 (1H, s).

ESI-MS m/z: 454 (M+H)+

Example 148

1) tert-Butyl {8-(2-azetidin-1-ylethyl)-2-[(4-methoxy-3,5-dimethylpyridin-2-yl)methyl]-2,7-dihydro-6-thia-1,2,3,5-tetraazabenzo[cd]azulen-4-yl}carbamate

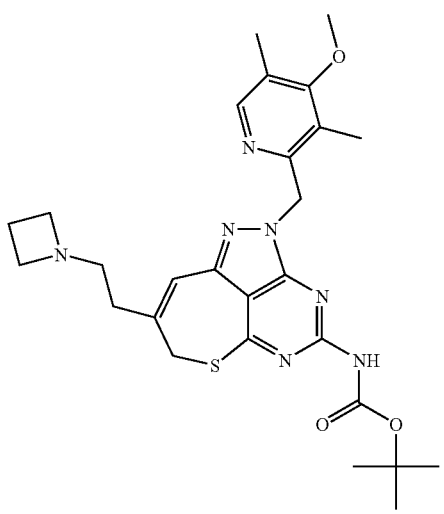

The title compound (10 mg, 31%) was obtained as an oil by synthesis by the same method as in Example 135 using tert-butyl {8-(2-hydroxyethyl)-2-[(4-methoxy-3,5-dimethylpyridin-2-yl)methyl]-2,7-dihydro-6-thia-1,2,3,5-tetraazabenzo[cd]azulen-4-yl}carbamate of Example 134 (29 mg), azetidine hydrochloride (27 mg) and 1,8-diazabicyclo[5.4.0]-7-undecene (39 μl) as amines and dehydrated dimethyl sulfoxide (0.5 ml) as an amination reaction solvent.

ESI-MS m/z: 538 (M+H)+

2) 8-(2-Azetidin-1-ylethyl)-2-[(4-methoxy-3,5-dimethylpyridin-2-yl)methyl]-2,7-dihydro-6-thia-1,2,3,5-tetraazabenzo[cd]azulen-4-amine

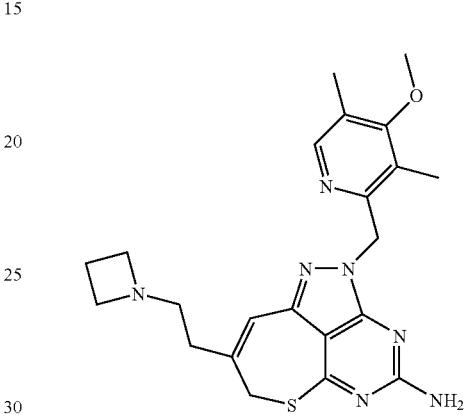

The title compound (7.7 mg, 75%) was obtained as an amorphous by synthesis by the same method as in Example 111 using the above tert-butyl {8-(2-azetidin-1-ylethyl)-2-[(4-methoxy-3,5-dimethylpyridin-2-yl)methyl]-2,7-dihydro-6-thia-1,2,3,5-tetraazabenzo[cd]azulen-4-yl}carbamate (10 mg).

$^1$H-NMR (CDCl$_3$) δ: 2.03-2.10 (2H, m), 2.22 (3H, s), 2.28 (3H, s), 2.33 (2H, t, J=7.6 Hz), 2.60 (2H, t, J=7.4 Hz), 3.20 (4H, t, J=7.0 Hz), 3.68 (2H, s), 3.74 (3H, s), 5.11 (2H, s), 5.49 (2H, s), 6.57 (1H, s), 8.19 (1H, s).

ESI-MS m/z: 438 (M+H)+

Example 149

2-[(4-Methoxy-3,5-dimethylpyridin-2-yl)methyl]-7,9,10,11-tetrahydro-2H-8-oxa-6-thia-1,2,3,5-tetraazadibenzo[cd,h]azulen-4-amine

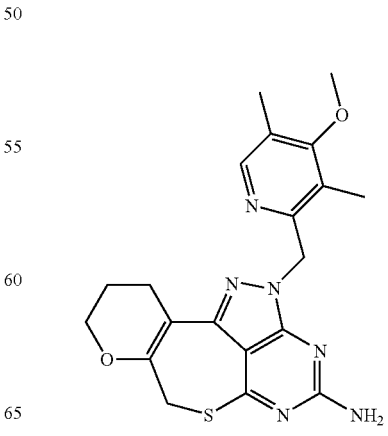

A mixture composed of 4-di-(tert-butoxycarbonyl)amino-2-(4-methoxy-3,5-dimethyl-pyridin-2-ylmethyl)-8-oxo-2,7,8,9-tetrahydro-6-thia-1,2,3,5-tetraazabenzo[cd]azulene of Example 40 (40 mg), 1,3-dibromopropane (11 µl), potassium carbonate (19 mg) and dimethyl sulfoxide (0.5 ml) was stirred at room temperature for 20 hours. Water was added to the reaction mixture, followed by extraction with ethyl acetate. The organic layer was washed with brine. The organic layer was dried over anhydrous sodium sulfate and filtered. Then, the filtrate was concentrated under reduced pressure. Dichloromethane (2 ml) and trifluoroacetic acid (0.5 ml) were added to the resulting residue, and the mixture was stirred at room temperature for three hours. The reaction mixture was concentrated under reduced pressure. A saturated sodium bicarbonate solution was placed into the resulting residue, followed by extraction with chloroform. The organic layer was dried over sodium sulfate and filtered. Then, the filtrate was concentrated under reduced pressure. The resulting residue was purified by silica gel thin-layer chromatography (chloroform-methanol) to obtain the title compound (13.3 mg, 46%) as a solid.

$^1$H-NMR (CDCl$_3$) δ: 1.94 (2H, tt, J=6.4, 5.0 Hz), 2.23 (3H, s), 2.33 (3H, s), 2.50 (2H, t, J=6.4 Hz), 3.69 (2H, s), 3.76 (3H, s), 4.10 (2H, t, J=5.0 Hz), 5.41 (2H, brs), 5.48 (2H, s), 8.19 (1H, s).

ESI-MS m/z: 411 (M+H)$^+$

Example 150

1) Di-tert-butyl {9,9-difluoro-2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate

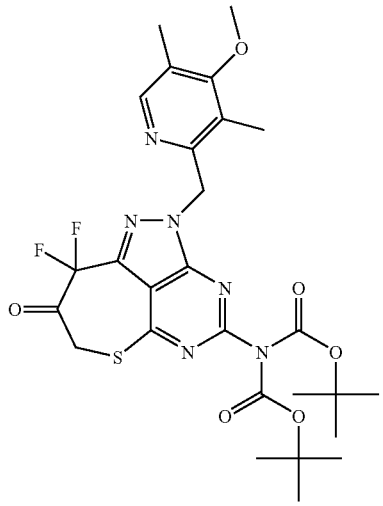

60% sodium hydride (8 mg) was added to a mixture composed of 4-di-(tert-butoxycarbonyl)amino-2-(4-methoxy-3,5-dimethyl-pyridin-2-ylmethyl)-8-oxo-2,7,8,9-tetrahydro-6-thia-1,2,3,5-tetraazabenzo[cd]azulene of Example 40 (57 mg) and dehydrated dimethyl formamide (1.5 ml) under ice-cooling, and the mixture was stirred at 0° C. for 15 minutes. Then, a solution of N-fluorobenzenesulfonimide (63 mg) in dehydrated dimethylformamide (0.5 ml) was added dropwise, and the mixture was stirred at 0° C. for 20 minutes. Water was added to the reaction mixture, followed by extraction with ethyl acetate. Then, the organic layer was washed with water. The organic layer was dried over sodium sulfate and filtered. Then, the filtrate was concentrated under reduced pressure. The title compound as a residue (83 mg) was obtained as an oil. Although the product contained impurities, it was directly used for the next reaction.

2) 4-Amino-9,9-difluoro-2-[(4-methoxy-3,5-dimethylpyridin-2-yl)methyl]-2,7,8,9-tetrahydro-6-thia-1,2,3,5-tetraazabenzo[cd]azulen-8-ol

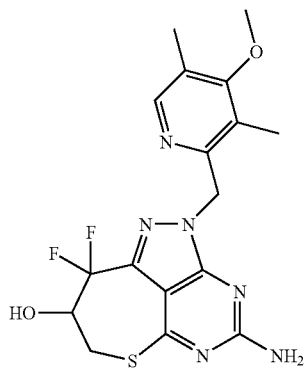

Sodium borohydride (6 mg) was added to a mixture composed of the above di-tert-butyl {9,9-difluoro-2-[(4-methoxy-3,5-dimethylpyridin-2-yl)methyl]-8-oxo-2,7,8,9-tetrahydro-6-thia-1,2,3,5-tetraazabenzo[cd]azulen-4-yl}imidodicarbonate (41 mg) and methanol (2 ml) under ice-cooling, and the mixture was stirred at 0° C. for 30 minutes. Water was added to the reaction mixture, followed by extraction with ethyl acetate. The organic layer was washed with water. The organic layer was dried over sodium sulfate and filtered. Then, the filtrate was concentrated under reduced pressure. Dichloromethane (2 ml) and trifluoroacetic acid (0.5 ml) were added to the resulting residue, and the mixture was stirred at room temperature for four hours. The reaction mixture was concentrated under reduced pressure, and the resulting residue was purified by reversed phase liquid chromatography to obtain the title compound (8.7 mg, 42% in total from Example 110) as a solid.

$^1$H-NMR (CDCl$_3$) δ: 2.22 (3H, s), 2.31 (3H, s), 3.47 (2H, dd, J=15.9, 7.6 Hz), 3.53 (1H, d, J=15.9 Hz), 3.75 (3H, s), 4.59-4.66 (1H, m), 5.34 (2H, brs), 5.57 (2H, s), 8.14 (1H, s).

ESI-MS m/z: 409 (M+H)$^+$

Example 151

1) 1-(2-Amino-4,6-dichloropyrimidin-5-yl)prop-2-en-1-ol

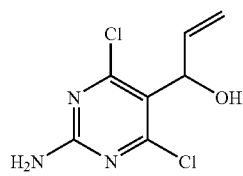

2-Amino-4,6-dichloropyrimidine-5-carbaldehyde (100 g) was suspended in tetrahydrofuran (4000 ml), and a 1 N solution of vinylmagnesium bromide in tetrahydrofuran (2200 g) was added dropwise under ice-cooling. After completion of the dropwise addition, the mixture was stirred under ice-cooling for two hours. Water (2000 ml) was added to the reaction solution, and the solution was made acidic with a 1 N hydrochloric acid solution (2500 ml), followed by extraction with ethyl acetate. The organic layer was dried over sodium sulfate and filtered, followed by concentration. Methanol was added to the resulting residue, followed by stirring for one hour. The insoluble matter was filtered off, and the filtrate was concentrated under reduced pressure. The resulting residue was purified by silica gel column chromatography (ethyl acetate-chloroform) to obtain the title compound (50 g, 49%) as a solid.

ESI-MS m/z: 220 (M+H)$^+$.

2) 2-[(4-Methoxy-3,5-dimethylpyridin-2-yl)methyl]-2H-6-thia-1,2,3,5-tetraazaacenaphthylen-4-amine

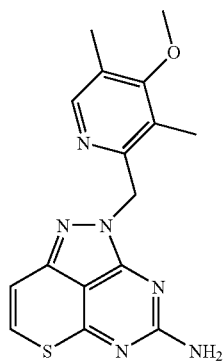

The title compound was synthesized using the same method as in Example 1-7), Example 32, Example 35 and Example 36 for the above 1-(2-amino-4,6-dichloropyrimidin-5-yl)prop-2-en-1-ol.

ESI-MS m/z: 341 (M+H)$^+$.

$^1$H-NMR (CDCl$_3$) δ: 8.22 (1H, s), 7.06 (1H, d, J=9.8 Hz), 6.72 (1H, d, J=9.8 Hz), 5.45 (2H, s), 5.15 (2H, brs), 3.74 (3H, s), 2.29 (3H, s), 2.23 (3H, s).

Example 152

1) 4-Chloro-3-[(2,2-dimethyl-1,3-dioxolan-4-yl)methyl]-1-(4-methoxybenzyl)-1H-pyrazolo[3,4-d]pyrimidin-6-amine

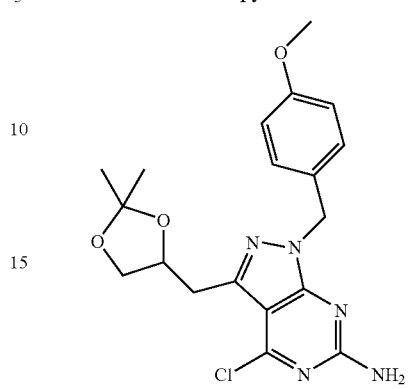

A solution of triethylamine (29.1 ml) in dichloromethane (100 ml) was added to a mixture composed of 1-(2-amino-4,6-dichloropyrimidin-5-yl)-2-(2,2-dimethyl-[1,3]dioxolan-4-yl)ethan-1-one (16 g), (4-methoxybenzyl)-hydrazine hydrochloride (14.1 g) and dichloromethane (400 ml) under cooling in an ice bath over 15 minutes. After stirring under cooling in an ice bath for 1.5 hours, a 0.2 N hydrochloric acid solution (1000 ml) was added to the reaction mixture, followed by extraction with dichloromethane (400 ml). The organic layer was washed with brine (500 ml) and dried over anhydrous magnesium sulfate. After filtration, the filtrate was concentrated under reduced pressure. The resulting residue was purified by silica gel column chromatography (ethyl acetate-chloroform) to obtain the title compound (16.5 g, 78%) as a solid.

$^1$H-NMR (CDCl$_3$) δ: 1.36 (4H, s), 1.43 (3H, s), 3.10 (1H, dd, J=14.6, 8.2 Hz), 3.43 (1H, dd, J=14.6, 5.4 Hz), 3.75 (1H, dd, J=8.3, 6.6 Hz), 3.77 (3H, s), 4.07 (1H, dd, J=8.3, 5.9 Hz), 4.54-4.61 (1H, m), 5.22 (2H, s), 5.30 (2H, s), 6.82 (2H, d, J=8.5 Hz), 7.24 (2H, d, J=8.5 Hz).

ESI-MS m/z: 404 (M+H)$^+$.

2) Di-tert-butyl {4-chloro-3-[(2,2-dimethyl-1,3-dioxolan-4-yl)methyl]-1-(4-methoxybenzyl)-1H-pyrazolo[3,4-d]pyrimidin-6-yl}imidodicarbonate

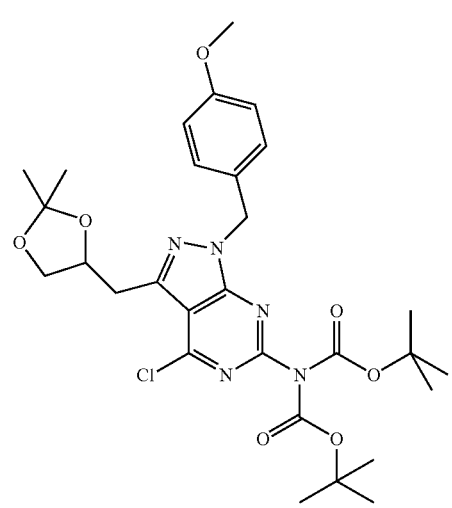

4-Dimethylaminopyridine (500 mg) and di-tert-butyl dicarbonate (53.5 g) were added to a mixture composed of the above 4-chloro-3-[(2,2-dimethyl-1,3-dioxolan-4-yl)methyl]-1-(4-methoxybenzyl)-1H-pyrazolo[3,4-d]pyrimidin-6-amine (16.5 g) and tetrahydrofuran (400 mL), and then the mixture was stirred at room temperature for 12 hours. The reaction mixture was filtered and then the filtrate was concentrated under reduced pressure. The resulting residue was purified by silica gel column chromatography (ethyl acetate-hexane) to obtain the title compound (22 g, 89%) as an oil.

$^1$H-NMR (CDCl$_3$) δ: 1.37 (3H, s), 1.40 (3H, s), 1.45 (18H, s), 3.25 (1H, dd, J=15.1, 7.1 Hz), 3.52 (1H, dd, J=15.1, 5.0 Hz), 3.73-3.81 (1H, m), 3.77 (3H, s), 4.12 (1H, t, J=7.1 Hz), 4.58-4.66 (1H, m), 5.46 (1H, d, J=15.1 Hz), 5.51 (1H, d, J=15.1 Hz), 6.81 (2H, d, J=7.8 Hz), 7.28 (2H, d, J=7.8 Hz).

ESI-MS m/z: 604 (M+H)$^+$.

3) Di-tert-butyl {4-chloro-3-(2,3-dihydroxypropyl)-1-(4-methoxybenzyl)-1H-pyrazolo[3,4-d]pyrimidin-6-yl}imidodicarbonate

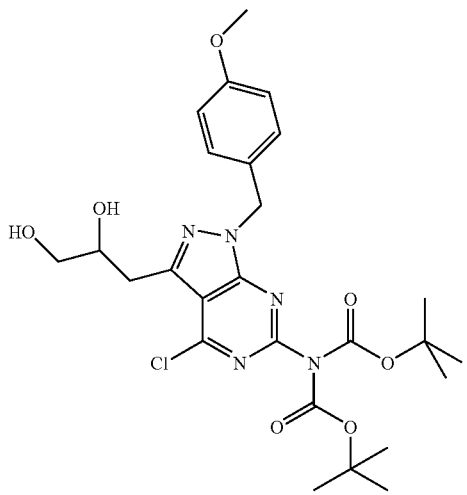

The above di-tert-butyl {4-chloro-3-[(2,2-dimethyl-1,3-dioxolan-4-yl)methyl]-1-(4-methoxybenzyl)-1H-pyrazolo[3,4-d]pyrimidin-6-yl}imidodicarbonate (22 g) was dissolved in methanol (400 ml). Pyridinium p-toluenesulfonate (10 g) was added and the mixture was stirred at room temperature for 16 hours. The reaction solution was concentrated, and water (100 ml) was added to the resulting residue, followed by extraction with ethyl acetate (500 ml). The organic layer was washed with brine, and then dried over anhydrous sodium sulfate. After filtration, the filtrate was concentrated under reduced pressure to obtain the title compound (19.5 g, 95%) as an amorphous.

ESI-MS m/z: 564 (M+H)$^+$.

4) Di-tert-butyl {4-chloro-3-(2-hydroxyethyl)-1-(4-methoxybenzyl)-1H-pyrazolo[3,4-d]pyrimidin-6-yl}imidodicarbonate

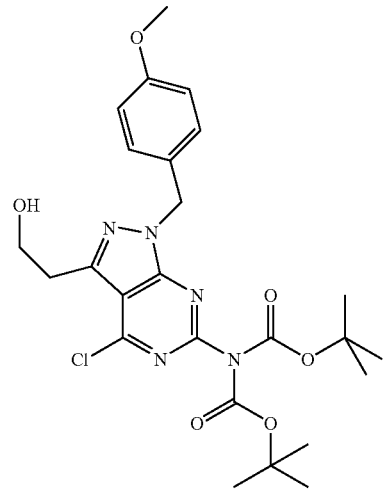

Sodium periodate (19 g) was added to a mixture composed of the above di-tert-butyl {4-chloro-3-(2,3-dihydroxypropyl)-1-(4-methoxybenzyl)-1H-pyrazolo[3,4-d]pyrimidin-6-yl}imidodicarbonate (10 g), tetrahydrofuran (100 ml), methanol (100 ml) and water (100 ml) under cooling in an ice bath, and the mixture was stirred at room temperature for one hour. The reaction mixture was separated with water (600 mL) and ethyl acetate (400 mL). The organic layer was washed with brine, and then dried over anhydrous sodium sulfate and filtered. Then, the filtrate was concentrated under reduced pressure. Methanol (200 mL) was added to the resulting residue. Sodium borohydride (1000 mg) was added under cooling in an ice bath, and the mixture was stirred for one hour. Water (400 ml) was added to the reaction mixture, followed by extraction with ethyl acetate (300 ml) twice. Then, the organic layers were washed with brine. The organic layers were dried over anhydrous sodium sulfate and filtered. Then, the filtrate was concentrated under reduced pressure and the solvent was evaporated to obtain the title compound (8.5 g, 90%) as an oil.

ESI-MS m/z: 534 (M+H)$^+$.

5) Di-tert-butyl {2-(4-methoxybenzyl)-7,8-dihydro-2H-6-thia-1,2,3,5-tetraazaacenaphthylen-4-yl}imidodicarbonate

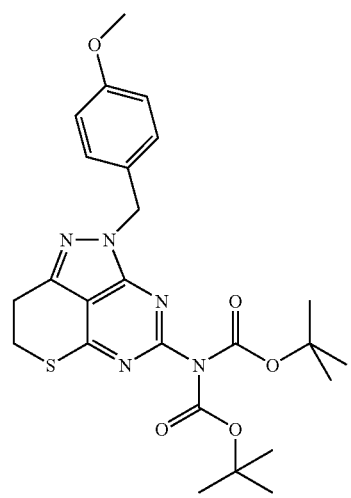

The above di-tert-butyl {4-chloro-3-(2-hydroxyethyl)-1-(4-methoxybenzyl)-1H-pyrazolo[3,4-d]pyrimidin-6-yl}imidodicarbonate (8.5 g) was dissolved in dichloromethane (100 ml), triethylamine (4.5 ml) was added. Methanesulfonyl chloride (1.9 ml) was added under cooling in an ice bath, and the mixture was stirred at room temperature for two hours. The reaction solution was diluted with dichloromethane and ethyl acetate and washed with water. Then, the organic layer was dried over anhydrous sodium sulfate and filtered, and then the filtrate was concentrated under reduced pressure. The resulting residue was dissolved in N,N-dimethylformamide (100 mL), and sodium bisulfide monohydrate (1.5 g) was added under cooling in an ice bath. Then, the ice bath was removed and the mixture was stirred for one hour. Potassium carbonate (3.3 g) was added to the reaction mixture, followed by further stirring for 16 hours. Water (1000 ml) was added to the reaction mixture, followed by extraction with dichloromethane (500 ml) twice. The organic layer was washed with brine, and then dried over anhydrous sodium sulfate. After filtration, the filtrate was concentrated under reduced pressure. The resulting residue was purified by silica gel column chromatography (ethyl acetate-hexane) to obtain the title compound (6.0 g, 74%) as an oil.

$^1$H-NMR (CDCl$_3$) δ: 1.46 (18H, s), 3.23 (2H, t, J=6.1 Hz), 3.50 (2H, t, J=6.1 Hz), 3.77 (3H, s), 5.44 (2H, s), 6.82-6.84 (2H, m), 7.28-7.31 (2H, m).

ESI-MS m/z: 514 (M+H)$^+$.

6) 7,8-Dihydro-2H-6-thia-1,2,3,5-tetraazaacenaphthylen-4-amine

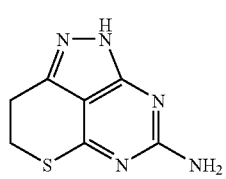

Anisole (2.5 ml) and trifluoroacetic acid (30 ml) were added to the above di-tert-butyl {2-(4-methoxybenzyl)-7,8-dihydro-2H-6-thia-1,2,3,5-tetraazaacenaphthylen-4-yl}imidodicarbonate (6.0 g). The mixture was stirred at room temperature for 16 hours and then stirred at 55° C. for six hours. The reaction solution was concentrated under reduced pressure. Ethyl acetate was added to the resulting residue, followed by stirring. The precipitated solid was filtered off and washed with ethyl acetate to obtain the title compound (1.75 g, 78%) as a solid.

$^1$H-NMR (DMSO-D$_6$) δ: 3.06 (2H, s), 3.52 (2H, s).
ESI-MS m/z: 194 (M+H)$^+$.

7) 2-(Quinolin-2-ylmethyl)-7,8-dihydro-2H-6-thia-1,2,3,5-tetraazaacenaphthylen-4-amine

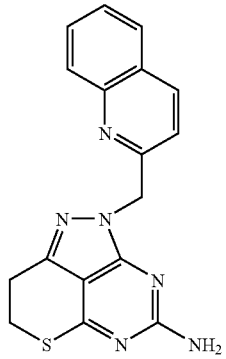

A mixture composed of the above 7,8-dihydro-2H-6-thia-1,2,3,5-tetraazaacenaphthylen-4-amine (30 mg), 2-(chloromethyl)quinoline hydrochloride (51 mg), potassium carbonate (98 mg) and dimethylformamide (1 mL) was stirred at 60° C. overnight. The insoluble matter was separated off by filtration, and then the solvent was evaporated in a nitrogen stream. The residue was purified by reversed phase liquid chromatography (acetonitrile-formic acid) to obtain the title compound (19 mg, 35%) as an amorphous.

$^1$H-NMR (CDCl$_3$) δ: 3.15 (2H, t, J=6.1 Hz), 3.46 (2H, t, J=6.1 Hz), 5.44 (2H, s), 5.68 (2H, s), 7.17 (1H, d, J=8.5 Hz), 7.52 (1H, dd, J=7.6, 7.6 Hz), 7.69-7.78 (2H, m), 8.11-8.07 (2H, m).

ESI-MS m/z: 335 (M+H)$^+$.

Example 153

2-(Isoquinolin-2-ylmethyl)-7,8-dihydro-2H-6-thia-1,2,3,5-tetraazaacenaphthylen-4-amine

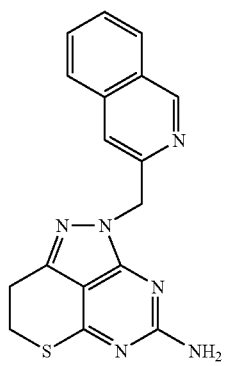

The title compound (19 mg, 35%) was obtained as an amorphous by the same method as in Example 152-7) using 7,8-dihydro-2H-6-thia-1,2,3,5-tetraazaacenaphthylen-4-amine of Example 152-6) (30 mg) and 2-(chloromethyl)isoquinoline hydrochloride (49 mg).

$^1$H-NMR (CDCl$_3$) δ: 3.16 (2H, t, J=6.1 Hz), 3.47 (2H, t, J=6.1 Hz), 5.42 (2H, s), 5.65 (2H, s), 7.45 (1H, s), 7.57 (1H, dd, J=8.0, 8.0 Hz), 7.66 (1H, dd, J=8.0, 8.0 Hz), 7.75 (1H, d, J=8.0 Hz), 7.95 (1H, d, J=8.0 Hz), 9.23 (1H, s).
ESI-MS m/z: 335 (M+H)$^+$.

Example 154

2-[(3-Bromo-6-ethoxypyridin-2-yl)methyl]-7,8-dihydro-2H-6-thia-1,2,3,5-tetraazaacenaphthylen-4-amine

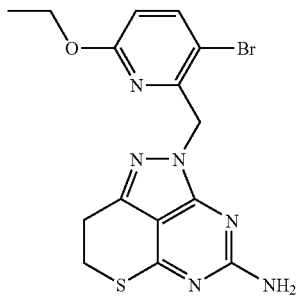

The title compound (2 mg, 4%) was obtained as an amorphous by the same method as in Example 152-7) using 7,8-dihydro-2H-6-thia-1,2,3,5-tetraazaacenaphthylen-4-amine of Example 152-6) (25 mg) and 3-bromo-2-bromomethyl-6-ethoxypyridine hydrobromide (59 mg).
$^1$H-NMR (CDCl$_3$) δ: 1.41 (3H, t, J=7.0 Hz), 3.19-3.13 (1H, m), 3.48-3.45 (1H, m), 3.79 (1H, q, J=7.0 Hz), 4.00 (1H, brs), 4.38 (2H, q, J=7.0 Hz), 4.67 (2H, s), 6.58 (1H, d, J=8.6 Hz), 7.68 (1H, d, J=8.6 Hz).
ESI-MS m/z: 407 (M+H)$^+$.

Example 155

2-[(5-Methylpyridin-2-yl)methyl]-7,8-dihydro-2H-6-thia-1,2,3,5-tetraazaacenaphthylen-4-amine

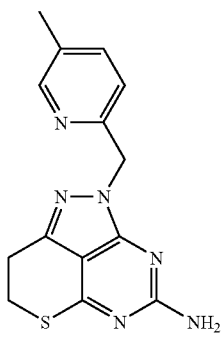

The title compound (5 mg, 14%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-5-methylpyridine hydrochloride (38 mg).
$^1$H-NMR (CDCl$_3$) δ: 2.38 (3H, s), 3.14 (2H, t, J=6.1 Hz), 3.45 (2H, t, J=6.1 Hz), 5.47 (2H, s), 7.00 (1H, d, J=7.8 Hz), 7.44 (1H, d, J=7.8 Hz), 8.24 (1H, s), 8.41 (1H, s).
ESI-MS m/z: 299 (M+H)$^+$.

Example 156

2-[(5-Bromopyridin-2-yl)methyl]-7,8-dihydro-2H-6-thia-1,2,3,5-tetraazaacenaphthylen-4-amine

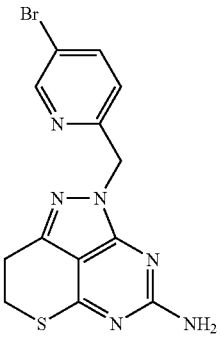

The title compound (8 mg, 16%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-5-bromopyridine hydrochloride (38 mg).
$^1$H-NMR (CDCl$_3$) δ: 3.15 (2H, t, J=6.0 Hz), 3.46 (2H, t, J=6.0 Hz), 5.20 (2H, s), 5.45 (2H, s), 7.01 (1H, d, J=8.3 Hz), 7.75 (1H, dd, J=8.3, 2.2 Hz), 8.63 (1H, d, J=2.2 Hz).
ESI-MS m/z: 363 (M+H)$^+$.

Example 157

2-[(5-Bromo-3-methylpyridin-2-yl)methyl]-7,8-dihydro-2H-6-thia-1,2,3,5-tetraazaacenaphthylen-4-amine

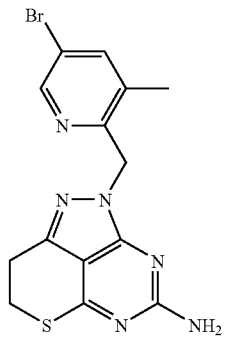

The title compound (4 mg, 8%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-3-methyl-5-bromopyridine (40 mg).
$^1$H-NMR (CDCl$_3$) δ: 2.38 (3H, s), 3.12 (2H, t, J=6.1 Hz), 3.44 (2H, t, J=6.1 Hz), 5.23 (2H, s), 5.43 (2H, s), 7.63 (1H, s), 8.45 (1H, s).
ESI-MS m/z: 377 (M+H)$^+$.

Example 158

2-[(3,4-Dimethoxypyridin-2-yl)methyl]-7,8-dihydro-2H-6-thia-1,2,3,5-tetraazaacenaphthylen-4-amine

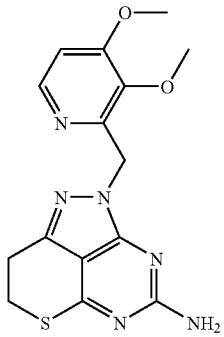

The title compound (4 mg, 9%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-3,4-dimethoxypyridine hydrochloride (35 mg).

$^1$H-NMR (CDCl$_3$) δ: 3.12 (2H, t, J=6.1 Hz), 3.43 (2H, t, J=6.1 Hz), 3.84 (3H, s), 3.91 (3H, s), 5.51 (2H, s), 6.79 (1H, d, J=5.4 Hz), 8.03 (1H, s), 8.18 (1H, d, J=5.4 Hz).

ESI-MS m/z: 345 (M+H)$^+$.

Example 159

2-(1,3-Benzothiazol-2-ylmethyl)-7,8-dihydro-2H-6-thia-1,2,3,5-tetraazaacenaphthylen-4-amine

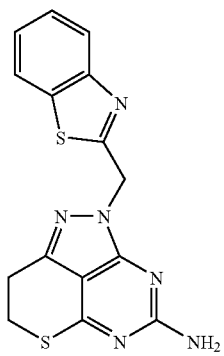

The title compound (15 mg, 34%) was obtained as an amorphous by the same method as in Example 152-7) using 7,8-dihydro-2H-6-thia-1,2,3,5-tetraazaacenaphthylen-4-amine of Example 152-6) (25 mg) and 2-bromomethylbenzothiazole (59 mg).

$^1$H-NMR (CDCl$_3$) δ: 3.18 (2H, t, J=6.1 Hz), 3.47 (2H, t, J=6.1 Hz), 5.26 (2H, s), 5.78 (2H, s), 7.38-7.37 (1H, m), 7.47-7.45 (1H, m), 7.81 (1H, d, J=8.0 Hz), 8.03 (1H, d, J=8.3 Hz).

ESI-MS m/z: 341 (M+H)$^+$.

Example 160

2-[(3,5-Dimethylpyridin-2-yl)methyl]-7,8-dihydro-2H-6-thia-1,2,3,5-tetraazaacenaphthylen-4-amine

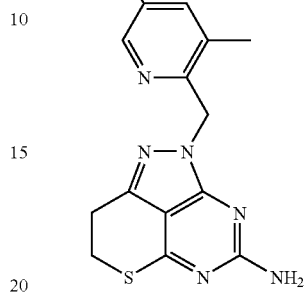

The title compound (5 mg, 12%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-3,5-dimethyl-pyridine hydrochloride (50 mg).

$^1$H-NMR (CDCl$_3$) δ: 2.26 (3H, s), 2.34 (3H, s), 3.12 (2H, t, J=6.1 Hz), 3.42 (2H, t, J=6.1 Hz), 5.15-5.10 (2H, m), 5.45 (2H, s), 7.18 (1H, s), 8.24 (1H, s).

ESI-MS m/z: 313 (M+H)$^+$.

Example 161

2-[4-Chloro-3-(trifluoromethyl)benzyl]-7,8-dihydro-2H-6-thia-1,2,3,5-tetraazaacenaphthylen-4-amine

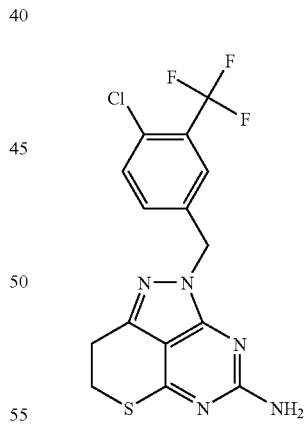

The title compound (5 mg, 10%) was obtained as an amorphous by the same method as in Example 152-7) using 7,8-dihydro-2H-6-thia-1,2,3,5-tetraazaacenaphthylen-4-amine of Example 152-6) (25 mg) and 1-chloro-4-chloromethyl-2-trifluoromethylbenzene (60 mg).

$^1$H-NMR (CDCl$_3$) δ: 3.13 (2H, t, J=6.1 Hz), 3.45 (2H, t, J=6.1 Hz), 5.18 (2H, s), 5.35 (2H, s), 7.46-7.43 (2H, m), 7.68-7.68 (1H, m).

ESI-MS m/z: 386 (M+H)$^+$.

Example 162

2-[2-Methyl-5-(trifluoromethyl)benzyl]-7,8-dihydro-2H-6-thia-1,2,3,5-tetraazaacenaphthylen-4-amine

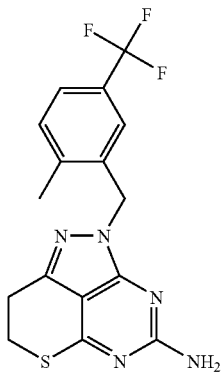

The title compound (5 mg, 10%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-1-methyl-4-trifluoromethylbenzene (56 mg).

$^1$H-NMR (CDCl$_3$) δ: 3.14 (2H, t, J=6.1 Hz), 3.46 (2H, t, J=6.1 Hz), 5.17 (2H, s), 5.36 (2H, s), 7.29 (1H, d, J=8.0 Hz), 7.38 (1H, s), 7.44 (1H, d, J=8.0 Hz).

ESI-MS m/z: 366 (M+H)$^+$.

Example 163

2-(3,4-Dichlorobenzyl)-7,8-dihydro-2H-6-thia-1,2,3,5-tetraazaacenaphthylen-4-amine

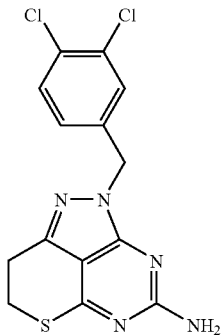

The title compound (5 mg, 10%) was obtained as an amorphous by the same method as in Example 152-7) using 7,8-dihydro-2H-6-thia-1,2,3,5-tetraazaacenaphthylen-4-amine of Example 152-6) (25 mg) and 1,2-dichloro-4-chloromethyl-benzene (51 mg).

$^1$H-NMR (CDCl$_3$) δ: 3.14 (2H, t, J=6.1 Hz), 3.45 (2H, t, J=6.1 Hz), 5.17 (2H, s), 5.29 (2H, s), 7.15 (1H, dd, J=8.2, 2.1 Hz), 7.40-7.38 (2H, m).

ESI-MS m/z: 352 (M+H)$^+$.

Example 164

2-[(4-Methoxy-3-methylpyridin-2-yl)methyl]-7,8-dihydro-2H-6-thia-1,2,3,5-tetraazaacenaphthylen-4-amine

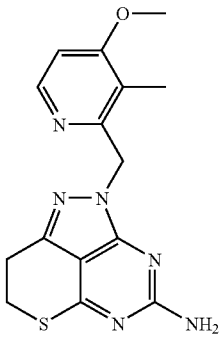

The title compound (5 mg, 12%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-4-methoxy-3-methyl-pyridine hydrochloride (45 mg).

$^1$H-NMR (CDCl$_3$) δ: 2.23 (3H, s), 3.12 (2H, t, J=6.1 Hz), 3.43 (2H, t, J=6.1 Hz), 3.86 (3H, s), 5.46 (2H, s), 6.71 (1H, d, J=5.6 Hz), 8.30 (1H, d, J=5.6 Hz).

ESI-MS m/z: 329 (M+H)$^+$.

Example 165

3-[(4-Amino-7,8-dihydro-2H-6-thia-1,2,3,5-tetraazaacenaphthylen-2-yl)methyl]-1-methylquinolin-2(1H)-one

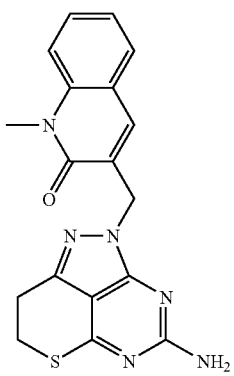

The title compound (5 mg, 18%) was obtained as an amorphous by the same method as in Example 152-7) using 7,8-dihydro-2H-6-thia-1,2,3,5-tetraazaacenaphthylen-4-amine of Example 152-6) (15 mg) and 3-chloromethyl-1-methyl-1H-quinolin-2-one (33 mg).

$^1$H-NMR (CDCl$_3$) δ: 3.18 (2H, t, J=6.2 Hz), 3.48 (2H, t, J=6.2 Hz), 3.75 (3H, s), 5.30 (2H, s), 5.40 (2H, s), 7.20 (1H, dd, J=7.8, 7.8 Hz), 7.32 (1H, s), 7.35 (1H, d, J=8.7 Hz), 7.48 (1H, dd, J=7.8, 1.4 Hz), 7.57-7.52 (1H, m).

ESI-MS m/z: 365 (M+H)$^+$.

Example 166

2-(2,3-Dihydro-1,4-benzodioxin-6-ylmethyl)-7,8-dihydro-2H-6-thia-1,2,3,5-tetraazaacenaphthylen-4-amine

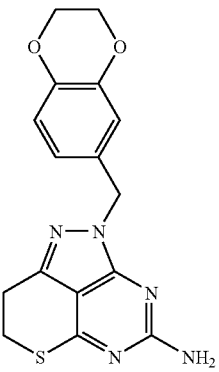

The title compound (5 mg, 19%) was obtained as an amorphous by the same method as in Example 152-7) using 7,8-dihydro-2H-6-thia-1,2,3,5-tetraazaacenaphthylen-4-amine of Example 152-6) (15 mg) and 6-chloromethyl-2,3-dihydrobenzo[1,4]dioxin (29 mg).

$^1$H-NMR (CDCl$_3$) δ: 3.13 (2H, t, J=6.0 Hz), 3.43 (2H, t, J=6.0 Hz), 4.24-4.22 (4H, m), 5.22 (2H, s), 6.82-6.81 (3H, m).

ESI-MS m/z: 342 (M+H)$^+$.

Example 167

2-(1,3-Benzodioxol-5-ylmethyl)-7,8-dihydro-2H-6-thia-1,2,3,5-tetraazaacenaphthylen-4-amine

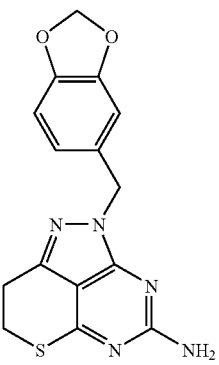

The title compound (5 mg, 20%) was obtained as an amorphous by the same method as in Example 152-7) using 7,8-dihydro-2H-6-thia-1,2,3,5-tetraazaacenaphthylen-4-amine of Example 152-6) (15 mg) and 5-chloromethylbenzo[1,3]dioxole (27 mg).

$^1$H-NMR (CDCl$_3$) δ: 3.13 (2H, t, J=6.2 Hz), 3.44 (2H, t, J=6.2 Hz), 5.19 (2H, s), 5.25 (2H, s), 5.92 (2H, s), 6.75 (1H, d, J=7.8 Hz), 6.84-6.82 (2H, m).

ESI-MS m/z: 328 (M+H)$^+$.

Example 168

6-[(4-Amino-7,8-dihydro-2H-6-thia-1,2,3,5-tetraazaacenaphthylen-2-yl)methyl]-3-methyl-1,3-benzoxazol-2(3H)-one

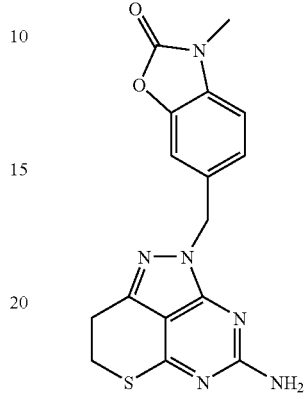

The title compound (5 mg, 14%) was obtained as an amorphous by the same method as in Example 152-7) using 7,8-dihydro-2H-6-thia-1,2,3,5-tetraazaacenaphthylen-4-amine of Example 152-6) (20 mg) and 6-chloromethyl-3-methyl-3H-benzoxazol-2-one (39 mg).

$^1$H-NMR (CDCl$_3$) δ: 3.13 (2H, t, J=6.1 Hz), 3.39 (3H, s), 3.46 (2H, t, J=6.1 Hz), 5.36 (2H, s), 6.94 (1H, d, J=8.1 Hz), 7.23-7.21 (2H, m).

ESI-MS m/z: 355 (M+H)$^+$.

Example 169

2-(1,3-Benzothiazol-6-ylmethyl)-7,8-dihydro-2H-6-thia-1,2,3,5-tetraazaacenaphthylen-4-amine

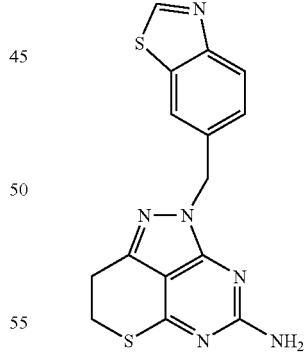

The title compound (5 mg, 14%) was obtained as an amorphous by the same method as in Example 152-7) using 7,8-dihydro-2H-6-thia-1,2,3,5-tetraazaacenaphthylen-4-amine of Example 152-6) (20 mg) and 6-chloromethylbenzothiazole (39 mg).

$^1$H-NMR (CDCl$_3$) δ: 3.14 (2H, t, J=6.1 Hz), 3.47 (2H, t, J=6.1 Hz), 5.50 (2H, s), 7.52 (1H, d, J=8.3 Hz), 7.91 (1H, s), 8.07 (1H, d, J=8.3 Hz), 9.01 (1H, s).

ESI-MS m/z: 341 (M+H)$^+$.

Example 170

2-(3-Fluoro-2,4-dimethylbe,3.12 (2H, t, J=6.1 Hz)nzyl)-7,8-dihydro-2H-6-thia-1,2,3,5-tetraazaacenaphthylen-4-amine

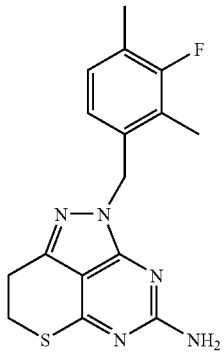

The title compound (10 mg, 29%) was obtained as an amorphous by the same method as in Example 152-7) using 7,8-dihydro-2H-6-thia-1,2,3,5-tetraazaacenaphthylen-4-amine of Example 152-6) (20 mg) and 1-chloromethyl-3-fluoro-2,4-dimethylbenzene (36 mg).

$^1$H-NMR (CDCl$_3$) δ: 2.22 (3H, s), 2.29 (3H, s), 3.44 (2H, t, J=6.1 Hz), 5.17 (2H, s), 5.30 (2H, s), 6.81 (1H, d, J=7.8 Hz), 6.95 (1H, m).

ESI-MS m/z: 330 (M+H)$^+$.

Example 171

2-[(7-Bromo-2,3-dihydro-1,4-benzodioxin-6-yl)methyl]-7,8-dihydro-2H-6-thia-1,2,3,5-tetraazaacenaphthylen-4-amine

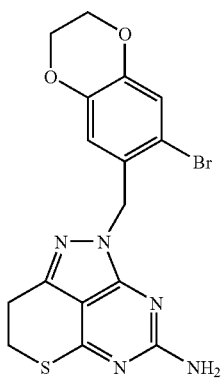

The title compound (5 mg, 12%) was obtained as an amorphous by the same method as in Example 152-7) using 7,8-dihydro-2H-6-thia-1,2,3,5-tetraazaacenaphthylen-4-amine of Example 152-6) (20 mg) and 6-bromo-7-chloromethyl-2,3-dihydrobenzo[1,4]dioxin (55 mg).

$^1$H-NMR (CDCl$_3$) δ: 3.16 (2H, t, J=6.1 Hz), 3.46 (2H, t, J=6.1 Hz), 4.20-4.18 (4H, m), 5.16 (2H, s), 5.35 (2H, s), 6.40 (1H, s), 7.09 (1H, s).

ESI-MS m/z: 420 (M+H)$^+$.

Example 172

2-(2,3-Dihydro[1,4]dioxino[2,3-c]pyridin-7-ylmethyl)-7,8-dihydro-2H-6-thia-1,2,3,5-tetraazaacenaphthylen-4-amine

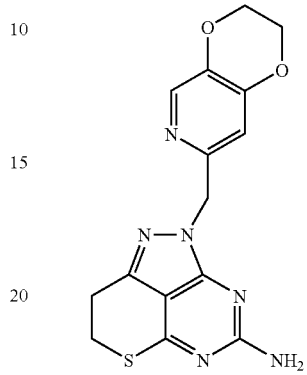

The title compound (2 mg, 5.7%) was obtained as an amorphous by the same method as in Example 152-7) using 7,8-dihydro-2H-6-thia-1,2,3,5-tetraazaacenaphthylen-4-amine of Example 152-6) (20 mg) and 6-chloromethyl-2,3-dihydrobenzo[1,4]dioxin (39 mg).

$^1$H-NMR (CDCl$_3$) δ: 3.15 (2H, t, J=6.1 Hz), 3.45 (2H, t, J=6.1 Hz), 4.29-4.25 (4H, m), 5.32 (2H, s), 5.37 (2H, s), 6.61 (1H, s), 8.13 (1H, s).

ESI-MS m/z: 343 (M+H)$^+$.

Example 173

2-{[5-(1,3-Benzodioxol-5-yl)-1,3-thiazol-2-yl]methyl}-7,8-dihydro-2H-6-thia-1,2,3,5-tetraazaacenaphthylen-4-amine

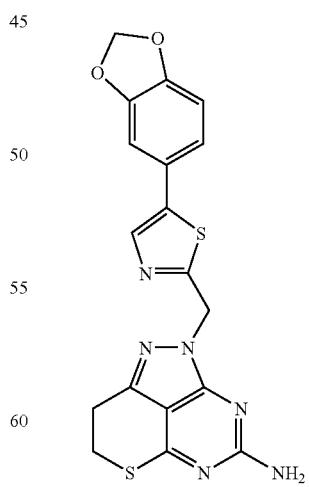

The title compound (5 mg, 12%) was obtained as an amorphous by the same method as in Example 152-7) using 7,8-dihydro-2H-6-thia-1,2,3,5-tetraazaacenaphthylen-4-amine of Example 152-6) (20 mg) and 5-benzo[1,3]dioxol-5-yl-2-chloromethylthiazole (53 mg).

$^1$H-NMR (CDCl$_3$) δ: 3.18 (2H, t, J=6.1 Hz), 3.48 (2H, t, J=6.1 Hz), 5.70 (2H, s), 5.99 (2H, s), 6.85 (1H, d, J=8.3 Hz), 7.27 (1H, s), 7.35 (1H, d, J=1.7 Hz), 7.39 (1H, dd, J=8.3, 1.7 Hz).

ESI-MS m/z: 411 (M+H)$^+$.

Example 174

2-[(7-Chloro-1,3-benzothiazol-2-yl)methyl]-7,8-dihydro-2H-6-thia-1,2,3,5-tetraazaacenaphthylen-4-amine

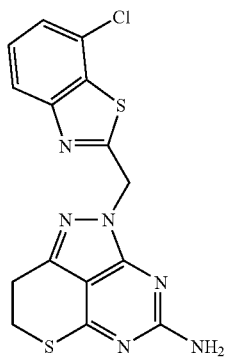

The title compound (2 mg, 10%) was obtained as an amorphous by the same method as in Example 152-7) using 7,8-dihydro-2H-6-thia-1,2,3,5-tetraazaacenaphthylen-4-amine of Example 152-6) (10 mg) and 2-bromomethyl-7-chlorobenzothiazole (20 mg).

$^1$H-NMR (CDCl$_3$) δ: 3.19 (2H, t, J=6.1 Hz), 3.49 (2H, t, J=6.1 Hz), 5.24 (2H, s), 5.77 (2H, s), 7.37 (1H, d, J=7.8 Hz), 7.42 (1H, dd, J=7.8, 7.8 Hz), 7.93 (1H, d, J=7.8 Hz).

ESI-MS m/z: 375 (M+H)$^+$.

Example 175

2-[(4-Chloro-3,5-dimethylpyridin-2-yl)methyl]-7,8-dihydro-2H-6-thia-1,2,3,5-tetraazaacenaphthylen-4-amine

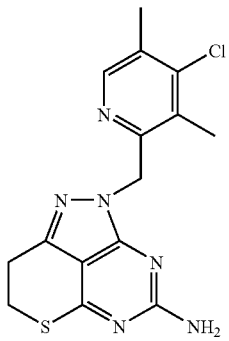

The title compound (5.1 mg, 11%) was obtained as an amorphous by the same method as in Example 152-7) using 7,8-dihydro-2H-6-thia-1,2,3,5-tetraazaacenaphthylen-4-amine of Example 152-6) (25 mg) and 4-chloro-2-chloromethyl-3,5-dimethylpyridine (44 mg).

$^1$H-NMR (CDCl$_3$) δ: 2.32 (3H, s), 2.43 (3H, s), 3.12 (2H, t, J=6.1 Hz), 3.43 (2H, t, J=6.1 Hz), 5.20 (2H, brs), 5.49 (2H, s), 8.25 (1H, s).

ESI-MS m/z: 347 (M+H)$^+$.

Example 176

2-[(4-Ethyl-3,5-dimethylpyridin-2-yl)methyl]-7,8-dihydro-2H-6-thia-1,2,3,5-tetraazaacenaphthylen-4-amine

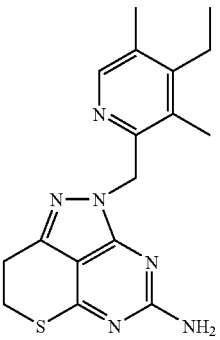

The title compound (9.1 mg, 21%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-4-ethyl-3,5-dimethylpyridine hydrochloride obtained in Reference Example 1 (51 mg).

$^1$H-NMR (CDCl$_3$) δ: 1.09 (3H, t, J=7.6 Hz), 2.25 (3H, s), 2.31 (3H, s), 2.65 (2H, q, J=7.6 Hz), 3.12 (2H, t, J=6.1 Hz), 3.43 (2H, t, J=6.1 Hz), 5.34 (2H, s), 5.47 (2H, s), 8.17 (1H, s).

ESI-MS m/z: 341 (M+H)$^+$.

Example 177

2-[(3,4-Dichloro-5-methylpyridin-2-yl)methyl]-7,8-dihydro-2H-6-thia-1,2,3,5-tetraazaacenaphthylen-4-amine

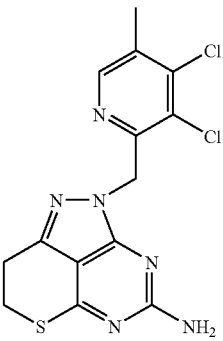

The title compound (8.0 mg, 17%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-3,4-dichloro-5-methylpyridine hydrochloride obtained in Reference Example 2 (57 mg).

¹H-NMR (CDCl₃) δ: 2.36 (3H, s), 3.14 (2H, t, J=6.1 Hz), 3.45 (2H, t, J=6.1 Hz), 5.22 (2H, s), 5.61 (2H, s), 8.25 (1H, s).
ESI-MS m/z: 367 (M+H)⁺.

Example 178

2-[(3-Chloro-4-methoxy-5-methylpyridin-2-yl)methyl]-7,8-dihydro-2H-6-thia-1,2,3,5-tetraazaacenaphthylen-4-amine

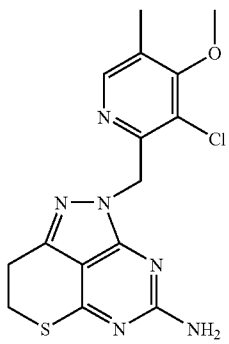

The title compound (16 mg, 34%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-3-chloro-4-methoxy-5-methylpyridine hydrochloride obtained in Reference Example 3 (56 mg).

¹H-NMR (CDCl₃) δ: 2.24 (3H, s), 3.14 (2H, t, J=6.1 Hz), 3.45 (2H, t, J=6.1 Hz), 3.90 (3H, s), 5.26 (2H, s), 5.58 (2H, s), 8.20 (1H, s).
ESI-MS m/z: 363 (M+H)⁺.

Example 179

2-[(5-Chloro-4-methoxy-3-methylpyridin-2-yl)methyl]-7,8-dihydro-2H-6-thia-1,2,3,5-tetraazaacenaphthylen-4-amine

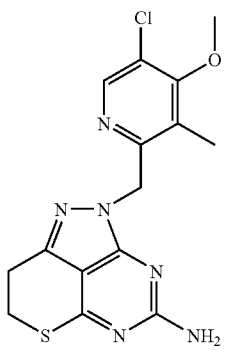

The title compound (16 mg, 34%) was obtained as an amorphous by the same method as in Example 152-7) using 7,8-dihydro-2H-6-thia-1,2,3,5-tetraazaacenaphthylen-4-amine of Example 152-6) (25 mg) and 2-chloromethyl-5-chloro-4-methoxy-3-methylpyridine hydrochloride obtained in Reference Example 4 (56 mg).

¹H-NMR (CDCl₃) δ: 2.33 (3H, s), 3.13 (2H, t, J=6.1 Hz), 3.44 (2H, t, J=6.1 Hz), 3.89 (3H, s), 5.19 (2H, s), 5.44 (2H, s), 8.35 (1H, s).
ESI-MS m/z: 363 (M+H)⁺.

Example 180

4-Amino-2-[(4-methoxy-3,5-dimethylpyridin-2-yl)methyl]-7-prop-2-yn-1-yl-7,8-dihydro-2H-6-thia-1,2,3,5-tetraazaacenaphthylene-7-carbonitrile

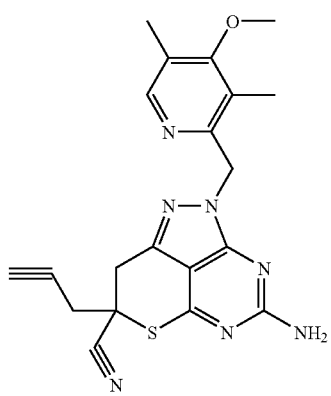

4-Amino-2-[(4-methoxy-3,5-dimethylpyridin-2-yl)methyl]-7,8-dihydro-2H-6-thia-1,2,3,5-tetraazaacenaphthylene-7-carbonitrile of Example 4 (50 mg) was dissolved in tetrahydrofuran (5 ml). A 2 N solution of lithium diisopropylamide in tetrahydrofuran (0.050 ml) was added at −78° C., and the mixture was stirred at the same temperature for 15 minutes. Then, propargyl bromide (0.015 ml) was added and the mixture was stirred at the same temperature for three hours. Water was added to the reaction solution, and then the mixture was heated to room temperature, followed by extraction with ethyl acetate. The organic layer was dried over magnesium sulfate and filtered, and the filtrate was concentrated. The resulting residue was purified by reversed phase liquid chromatography. The resulting solid was dissolved in a 50% solution of trifluoroacetic acid in dichloromethane (1 ml), followed by stirring for one hour. The reaction solution was concentrated under reduced pressure and azeotropically distilled with ethanol. The resulting solid was washed with ether to obtain the title compound (2 mg, 99%) as a solid.

¹H-NMR (CDCl₃) δ: 2.22 (3H, s), 2.28 (3H, s), 3.34 (1H, dd, J=16.6, 8.5 Hz), 3.44 (1H, dd, J=16.6, 4.6 Hz), 3.74 (3H, s), 3.78 (2H, s), 4.49 (1H, dd, J=8.5, 4.6 Hz), 5.20 (2H, s), 5.45 (2H, d, J=3.2 Hz), 8.20 (1H, s).
ESI-MS; m/z: 406 (M+H)⁺

Example 181

1) Di-tert-butyl {8-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

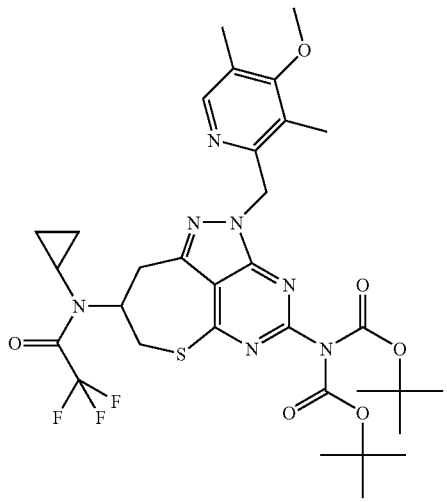

A solution containing trifluoroacetic anhydride (1.55 g) in dichloromethane (30 ml) was added to a mixture composed of di-tert-butyl {8-(cyclopropylamino)-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate of Example 60 (3.0 g) and dichloromethane (60 ml) under ice-cooling, and the mixture was stirred under ice-cooling for two hours. The reaction mixture was poured into ice water, followed by extraction with ethyl acetate. The organic layer was dried over magnesium sulfate and filtered, and the filtrate was concentrated. The resulting residue was purified by silica gel column chromatography (ethyl acetate:n-hexane; 1:1, v/v) to obtain the title compound (2.9 g, 84%) as a colorless solid.

ESI-MS; m/z: 708 (M+H)$^+$

2) Di-tert-butyl {8-(S)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate
Di-tert-butyl {8-(R)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate

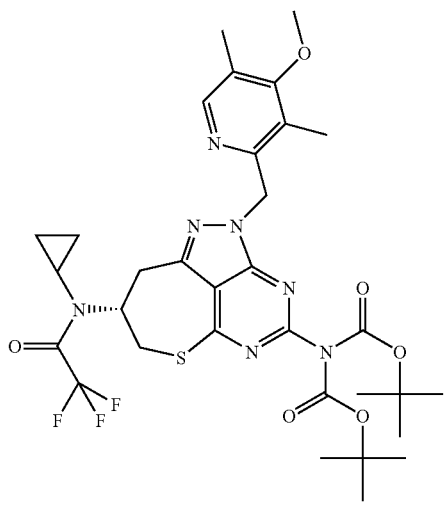

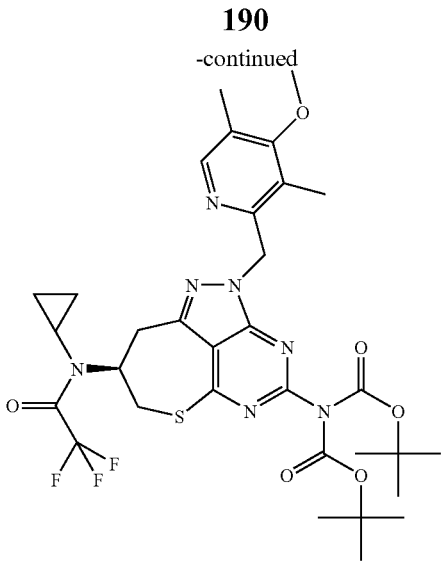

Di-tert-butyl {8-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (1.0 g) was dissolved in ethanol (20 ml) and optically resolved by AD column 50×500 mm (15% ethanol/n-hexane 50.0 ml/min). This operation was repeated three times to obtain di-tert-butyl {8-(S)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (RT=70 min) (1.3 g, 43%) and di-tert-butyl {8-(R)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (RT=130 min) (1.0 g, 33%).

3) N$^8$-(S)-Cyclopropyl-2-[(4-methoxy-3,5-dimethylpyridin-2-yl)methyl]-2,7,8,9-tetrahydro-6-thia-1,2,3,5-tetraazabenzo[cd]azulene-4,8-diamine

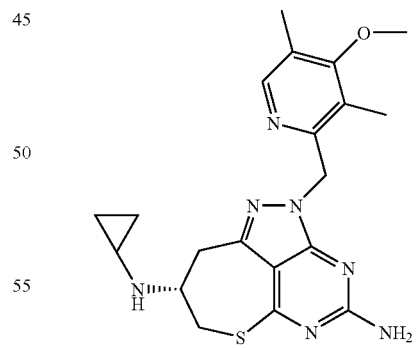

Di-tert-butyl {8-(S)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (400 mg) was dissolved in hydrochloric acid-methanol (50 ml). The internal atmosphere was replaced with nitrogen, followed by sealing. The reaction solution was stirred at 65° C. for two days. The reaction solution was concentrated, diluted with ethyl acetate (300 ml) and separated with 30 ml of a 0.5 N sodium hydroxide solution under ice-cooling. Then, the aqueous layer was extracted with ethyl acetate (50 ml). The organic layers were combined, dried over magnesium sulfate and filtered, and then the filtrate was concentrated under reduced pressure. The resulting residue was purified by NH silica gel chromatography (chloroform) to obtain the title compound (150 mg, 65%) as an amorphous.

$^1$H-NMR (CDCl$_3$) δ: 0.37-0.48 (4H, m), 2.22 (4H, s), 2.26 (3H, s), 3.16-3.32 (4H, m), 3.58-3.60 (1H, brm), 3.73 (3H, s), 5.02 (2H, s), 5.45 (2H, s), 8.19 (1H, s).

Example 182

N$^8$-(R)-Cyclopropyl-2-[(4-methoxy-3,5-dimethylpyridin-2-yl)methyl]-2,7,8,9-tetrahydro-6-thia-1,2,3,5-tetraazabenzo[cd]azulene-4,8-diamine

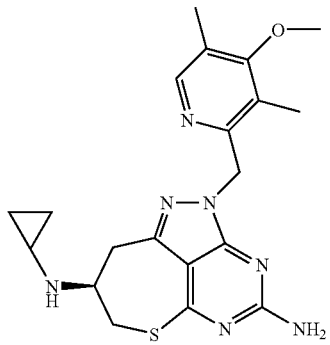

The title compound (150 mg, 57%) was obtained as an amorphous by synthesis by the same method as in Example 181 from di-tert-butyl {8-(R)-[cyclopropyl(trifluoroacetyl)amino]-2-[(4-methoxy-3,5-dimethylpyridin-2-yl)methyl]-2,7,8,9-tetrahydro-6-thia-1,2,3,5-tetraazabenzo[cd]azulen-4-yl}imidodicarbonate (450 mg).

$^1$H-NMR (CDCl$_3$) δ: 0.35-0.51 (4H, m), 2.19 (4H, s), 2.27 (3H, s), 3.15-3.32 (4H, m), 3.58-3.62 (1H, m), 3.74 (3H, s), 5.01 (2H, s), 5.45 (2H, s), 8.19 (1H, s).

Example 183

4-Amino-N-cyclohexyl-2-[(4-methoxy-3,5-dimethylpyridin-2-yl)methyl]-7,8-dihydro-2H-6-thia-1,2,3,5-tetraazaacenaphthylene-7-carboxamide

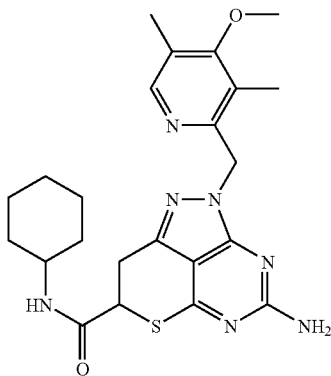

The title compound (6 mg, 10%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg) and cyclohexylamine (0.030 ml).

$^1$H-NMR (CDCl$_3$) δ: 1.11-1.17 (2H, m), 1.30-1.37 (2H, m), 1.55-1.69 (6H, m), 2.26 (3H, s), 2.29 (3H, s), 3.27 (1H, dd, J=16.7, 4.3 Hz), 3.60 (1H, dd, J=16.7, 7.7 Hz), 3.69-3.70 (1H, m), 3.80 (3H, s), 4.34 (1H, dd, J=7.7, 4.3 Hz), 5.47 (2H, d, J=3.5 Hz), 6.62 (1H, brs), 8.22 (1H, s).

ESI-MS m/z: 468 (M+H)$^+$.

Example 184

4-Amino-N-cyclohexyl-2-[(4-methoxy-3,5-dimethylpyridin-2-yl)methyl]-N-methyl-7,8-dihydro-2H-6-thia-1,2,3,5-tetraazaacenaphthylene-7-carboxamide

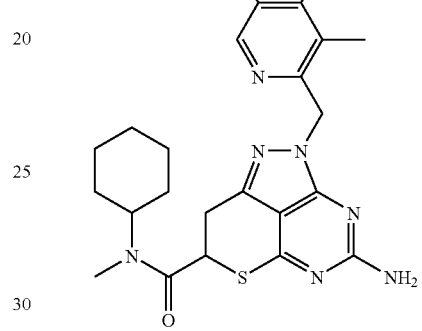

The title compound (6 mg, 10%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg) and N-methylcyclohexylamine (0.030 ml).

$^1$H-NMR (CDCl$_3$) δ: 1.07-1.81 (10H, m), 2.19-2.22 (6H, m), 2.27-2.28 (3H, m), 2.59-2.60 (3H, m), 3.15-3.20 (1H, m), 3.45-3.51 (1H, m), 3.67-3.69 (1H, m), 3.73 (3H, s), 4.65-4.72 (1H, m), 5.32 (2H, s), 5.42-5.44 (2H, brm), 8.19 (1H, s).

ESI-MS m/z: 482 (M+H)$^+$.

Example 185

N-Allyl-4-amino-N-cyclohexyl-2-[(4-methoxy-3,5-dimethylpyridin-2-yl)methyl]-7,8-dihydro-2H-6-thia-1,2,3,5-tetraazaacenaphthylene-7-carboxamide

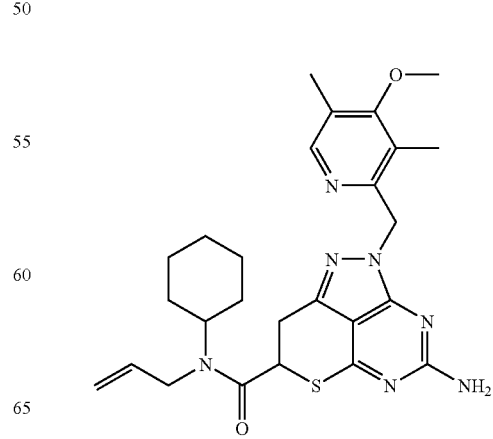

The title compound (3 mg, 5%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg) and N-allylcyclohexylamine (0.038 ml).

$^1$H-NMR (CDCl$_3$) δ: 1.07-2.06 (10H, m), 2.24 (3H, s), 2.27 (3H, d, J=6.8 Hz), 3.11-3.19 (1H, m), 3.44-3.51 (1H, m), 3.77-3.77 (3H, bsm), 3.90-4.04 (2H, m), 4.41 (1H, brs), 4.53 (1H, dd, J=10.7, 3.9 Hz), 4.74-4.75 (1H, m), 5.08-5.18 (2H, m), 5.28 (2H, s), 5.48-5.49 (2H, m), 5.80 (1H, brs), 8.25 (1H, s).

ESI-MS m/z: 508 (M+H)$^+$.

Example 186

4-Amino-2-[(4-methoxy-3,5-dimethylpyridin-2-yl)methyl]-N-[2-(2-thienyl)ethyl]-7,8-dihydro-2H-6-thia-1,2,3,5-tetraazaacenaphthylene-7-carboxamide

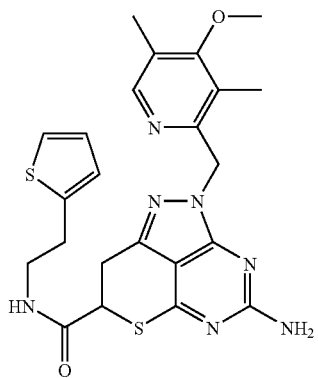

The title compound (10 mg, 20%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (40 mg) and 2-(2-thienyl)ethanamine (0.024 ml).

$^1$H-NMR (CDCl$_3$) δ: 2.22 (3H, s), 2.27 (3H, s), 2.91-2.94 (2H, m), 3.22 (1H, dd, J=16.7, 4.8 Hz), 3.40 (1H, dd, J=13.3, 6.2 Hz), 3.52 (1H, dd, J=13.3, 6.2 Hz), 3.70 (1H, dd, J=16.7, 6.2 Hz), 3.75 (3H, s), 4.26-4.28 (1H, m), 5.31 (1H, brs), 5.46 (2H, d, J=3.4 Hz), 6.62 (1H, dd, J=2.4 Hz), 6.71 (1H, brs), 6.86 (1H, dd, J=5.1, 3.4 Hz), 7.09 (1H, dd, J=5.1, 1.2 Hz), 8.20 (1H, s).

ESI-MS m/z: 496 (M+H)$^+$.

Example 187

4-Amino-N-(1,3-benzodioxol-5-ylmethyl)-2-[(4-methoxy-3,5-dimethylpyridin-2-yl)methyl]-7,8-dihydro-2H-6-thia-1,2,3,5-tetraazaacenaphthylene-7-carboxamide

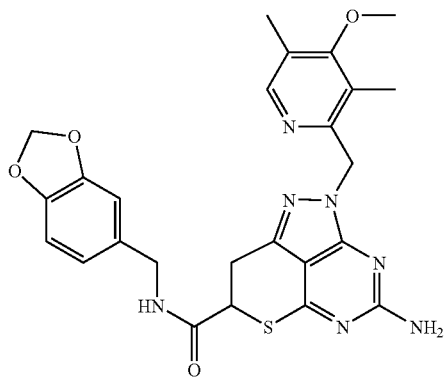

The title compound (20 mg, 30%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1-(1,3-benzodioxol-5-yl)methanamine (0.038 ml).

$^1$H-NMR (DMSO-d$_6$) δ: 2.16 (3H, s), 2.20 (3H, s), 3.10-3.25 (2H, m), 3.70 (3H, s), 4.18-4.20 (2H, m), 4.59 (1H, dd, J=8.8, 4.4 Hz), 5.31 (2H, s), 5.97 (2H, s), 6.69-6.71 (1H, m), 6.79 (1H, d, J=1.7 Hz), 6.82 (1H, d, J=7.8 Hz), 6.93 (2H, s), 8.07 (1H, s), 8.75 (1H, t, J=5.8 Hz).

ESI-MS m/z: 520 (M+H)$^+$.

Example 188

4-Amino-N-(5-methylfuran-2-ylmethyl)-2-[(4-methoxy-3,5-dimethylpyridin-2-yl)methyl]-7,8-dihydro-2H-6-thia-1,2,3,5-tetraazaacenaphthylene-7-carboxamide

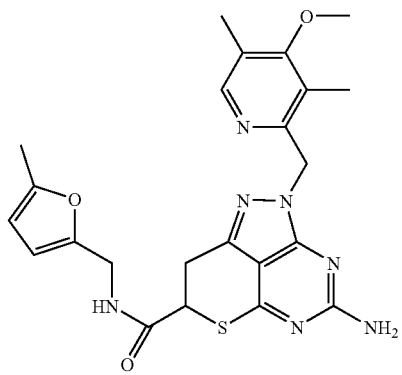

The title compound (20 mg, 32%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1-(5-methyl-2-furyl)methanamine (29 mg).

$^1$H-NMR (DMSO-d$_6$) δ: 2.16 (3H, s), 2.20 (3H, s), 2.21 (3H, s), 3.14-3.22 (2H, m), 3.70 (3H, s), 4.20-4.23 (2H, m), 4.56 (1H, dd, J=9.1, 4.4 Hz), 5.30 (2H, s), 5.97-5.97 (1H, m), 6.09 (1H, d, J=2.9 Hz), 6.93 (2H, s), 8.07 (1H, s), 8.74 (1H, t, J=5.5 Hz)

ESI-MS m/z: 480 (M+H)$^+$.

Example 189

4-Amino-N-(2-furylmethyl)-2-[(4-methoxy-3,5-dimethylpyridin-2-yl)methyl]-7,8-dihydro-2H-6-thia-1,2,3,5-tetraazaacenaphthylene-7-carboxamide

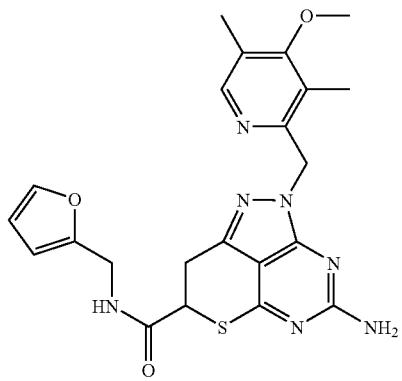

The title compound (20 mg, 33%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1-(2-furyl)methanamine (25 mg).

$^1$H-NMR (DMSO-d$_6$) δ: 2.16 (3H, s), 2.20 (3H, s), 3.10-3.18 (2H, m), 3.70 (3H, s), 4.27-4.29 (2H, m), 4.57 (1H, dd, J=9.1, 4.4 Hz), 5.30 (2H, s), 6.23 (1H, dd, J=3.2, 0.7 Hz), 6.38 (1H, dd, J=3.2, 2.0 Hz), 6.94 (2H, s), 7.57-7.57 (1H, m), 8.07 (1H, s), 8.79 (1H, t, J=5.5 Hz)

ESI-MS m/z: 466 (M+H)$^+$.

Example 190

4-Amino-2-[(4-methoxy-3,5-dimethylpyridin-2-yl)methyl]-N-(2-thienylmethyl)-7,8-dihydro-2H-6-thia-1,2,3,5-tetraazaacenaphthylene-7-carboxamide

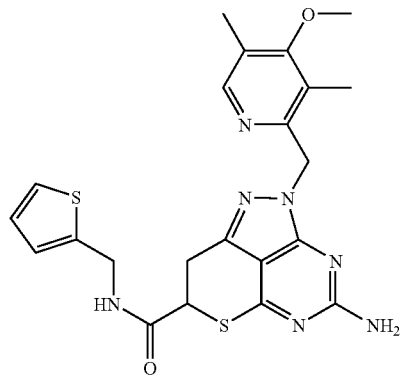

The title compound (20 mg, 32%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1-(2-thienyl)methanamine (29 mg).

$^1$H-NMR (DMSO-d$_6$) δ: 2.16 (3H, s), 2.20 (3H, s), 3.11-3.18 (2H, m), 3.70 (3H, s), 4.44-4.46 (2H, m), 4.57 (1H, dd, J=8.9, 4.5 Hz), 5.31 (2H, s), 6.94-6.95 (4H, m), 7.38 (1H, dd, J=4.7, 1.7 Hz), 8.07 (1H, s), 8.94 (1H, t, J=5.5 Hz)

ESI-MS m/z: 482 (M+H)$^+$.

Example 191

4-Amino-2-[(4-methoxy-3,5-dimethylpyridin-2-yl)methyl]-N-(1,3-thiazol-2-yl)-7,8-dihydro-2H-6-thia-1,2,3,5-tetraazaacenaphthylene-7-carboxamide

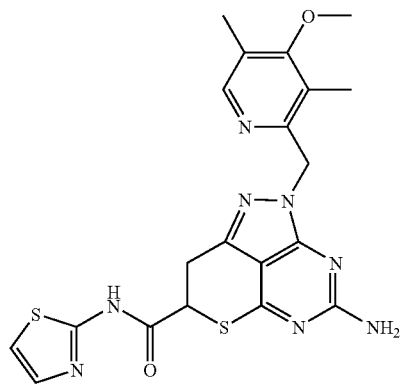

The title compound (20 mg, 33%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1,3-thiazol-2-amine (26 mg).

$^1$H-NMR (DMSO-d$_6$) δ: 2.19 (3H, s), 2.22 (3H, s), 3.28-3.36 (2H, m), 3.72 (3H, s), 4.79 (1H, t, J=5.6 Hz), 5.34 (2H, s), 6.97 (2H, s), 7.23 (1H, d, J=3.4 Hz), 7.48 (1H, d, J=3.4 Hz), 8.10 (1H, s)

ESI-MS m/z: 469 (M+H)$^+$.

Example 192

4-Amino-N-(4,5-dihydro-1,3-thiazol-2-yl)-2-[(4-methoxy-3,5-dimethylpyridin-2-yl)methyl]-7,8-dihydro-2H-6-thia-1,2,3,5-tetraazaacenaphthylene-7-carboxamide

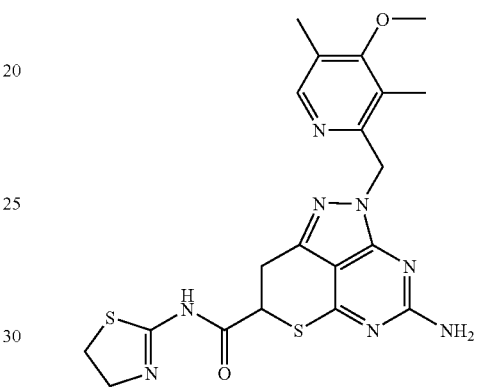

The title compound (16 mg, 26%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 4,5-dihydro-1,3-thiazol-2-amine (36 mg).

$^1$H-NMR (DMSO-d$_6$) δ: 2.18 (3H, s), 2.22 (3H, s), 3.08 (1H, dd, J=16.8, 9.4 Hz), 3.22-3.27 (3H, m), 3.62 (2H, t, J=8.1 Hz), 3.71 (3H, s), 4.68 (1H, dd, J=9.4, 4.4 Hz), 5.31 (2H, s), 6.90 (2H, s), 8.09 (1H, s)

ESI-MS m/z: 471 (M+H)$^+$.

Example 193

4-Amino-2-[(4-methoxy-3,5-dimethylpyridin-2-yl)methyl]-N-1,3,4-thiadiazol-2-yl-7,8-dihydro-2H-6-thia-1,2,3,5-tetraazaacenaphthylene-7-carboxamide

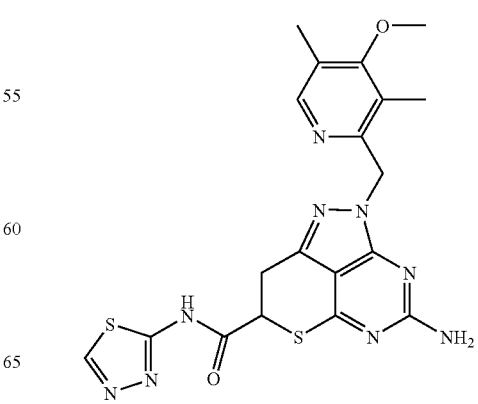

The title compound (25 mg, 41%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1,3,4-thiadiazol-2-amine (26 mg).

$^1$H-NMR (DMSO-d$_6$) δ: 2.18 (3H, s), 2.22 (3H, s), 3.28-3.31 (2H, m), 3.72 (3H, s), 4.81 (1H, t, J=5.6 Hz), 5.34 (2H, s), 6.99 (2H, s), 8.10 (1H, s), 9.16 (1H, s)

ESI-MS m/z: 470 (M+H)$^+$.

Example 194

4-Amino-2-[(4-methoxy-3,5-dimethylpyridin-2-yl)methyl]-N-(5-methyl-1,3-thiazol-2-yl)-7,8-dihydro-2H-6-thia-1,2,3,5-tetraazaacenaphthylene-7-carboxamide

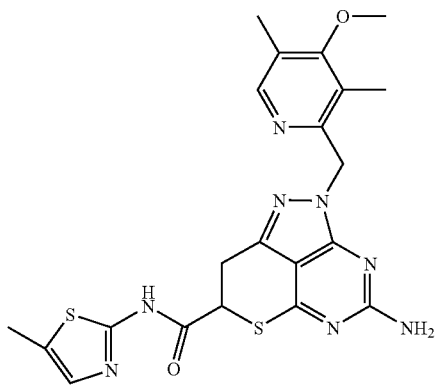

The title compound (20 mg, 32%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-methyl-1,3-thiazol-2-amine (30 mg).

$^1$H-NMR (DMSO-d$_6$) δ: 2.18 (3H, s), 2.22 (3H, s), 2.33 (3H, s), 3.24 (2H, dd, J=16.8, 7.0 Hz), 3.72 (3H, s), 4.76 (1H, dd, J=7.0, 4.7 Hz), 5.33 (2H, s), 6.99 (2H, s), 7.15 (1H, s), 8.10 (1H, s)

ESI-MS m/z: 483 (M+H)$^+$.

Example 195

4-Amino-N-1,3-benzothiazol-2-yl-2-[(4-methoxy-3,5-dimethylpyridin-2-yl)methyl]-7,8-dihydro-2H-6-thia-1,2,3,5-tetraazaacenaphthylene-7-carboxamide

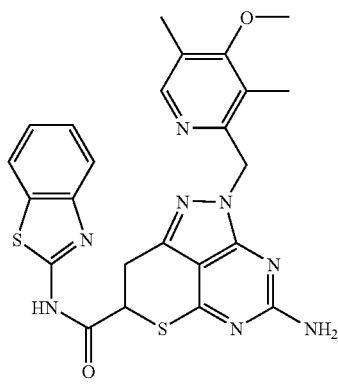

The title compound (20 mg, 33%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and benzothiazol-2-amine (24 mg).

$^1$H-NMR (DMSO-d$_6$) δ: 2.19 (3H, s), 2.23 (3H, s), 3.35-3.38 (2H, m), 3.72 (3H, s), 4.84 (1H, t, J=5.5 Hz), 5.35 (2H, s), 6.96 (2H, s), 7.30 (1H, t, J=7.6 Hz), 7.43 (1H, t, J=7.6 Hz), 7.75 (1H, d, J=7.6 Hz), 7.94 (1H, d, J=7.6 Hz), 8.10 (1H, s), 8.28 (1H, s).

ESI-MS m/z: 519 (M+H)$^+$.

Example 196

4-Amino-2-[(4-methoxy-3,5-dimethylpyridin-2-yl)methyl]-N-pyridin-2-yl-7,8-dihydro-2H-6-thia-1,2,3,5-tetraazaacenaphthylene-7-carboxamide

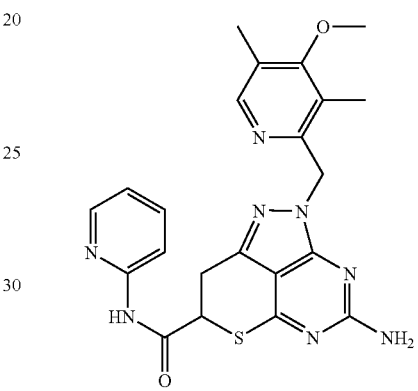

The title compound (15 mg, 25%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 3-aminopyridine (24 mg).

$^1$H-NMR (CDCl$_3$) δ: 2.21 (3H, s), 2.27 (3H, s), 3.35 (1H, dd, J=16.7, 4.4 Hz), 3.69-3.73 (4H, m), 4.45-4.48 (1H, m), 5.45 (4H, s), 7.05 (1H, dd, J=7.4, 4.9 Hz), 7.68 (1H, t, J=8.0 Hz), 8.11 (1H, d, J=8.0 Hz), 8.16 (1H, s), 8.28 (1H, d, J=3.9 Hz), 9.23 (1H, s).

ESI-MS m/z: 463 (M+H)$^+$.

Example 197

4-Amino-2-[(4-methoxy-3,5-dimethylpyridin-2-yl)methyl]-N-phenyl-7,8-dihydro-2H-6-thia-1,2,3,5-tetraazaacenaphthylene-7-carboxamide

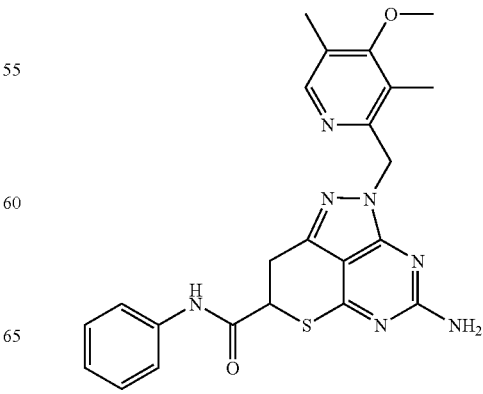

The title compound (15 mg, 25%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and aniline (0.025 ml).

$^1$H-NMR (CDCl$_3$) δ: 2.23 (3H, s), 2.28 (3H, s), 3.35 (1H, dd, J=16.7, 4.2 Hz), 3.62 (1H, dd, J=16.7, 8.8 Hz), 3.76 (3H, s), 4.58 (1H, dd, J=8.8, 4.2 Hz), 5.43 (2H, d, J=4.2 Hz), 7.12 (1H, t, J=7.4 Hz), 7.32 (1H, t, J=7.4 Hz), 7.53-7.55 (2H, m), 8.12 (1H, s)

ESI-MS m/z: 462 (M+H)$^+$.

Example 198

4-Amino-N-isoxazol-3-yl-2-[(4-methoxy-3,5-dimethylpyridin-2-yl)methyl]-7,8-dihydro-2H-6-thia-1,2,3,5-tetraazaacenaphthylene-7-carboxamide

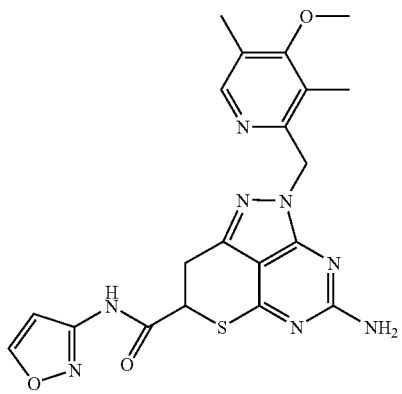

The title compound (10 mg, 17%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1,2-oxazol-3-amine (0.019 ml).

$^1$H-NMR (CDCl$_3$) δ: 2.21 (3H, s), 2.28 (3H, s), 3.34 (1H, dd, J=16.2, 4.6 Hz), 3.74-3.78 (4H, m), 4.47 (1H, t, J=5.4 Hz), 5.27 (2H, s), 5.45 (2H, d, J=4.6 Hz), 6.99 (1H, s), 8.17 (1H, s), 8.27 (1H, d, J=1.7 Hz), 9.60 (1H, s)

ESI-MS m/z: 453 (M+H)$^+$.

Example 199

4-Amino-2-[(4-methoxy-3,5-dimethylpyridin-2-yl)methyl]-N-pyridin-3-yl-7,8-dihydro-2H-6-thia-1,2,3,5-tetraazaacenaphthylene-7-carboxamide

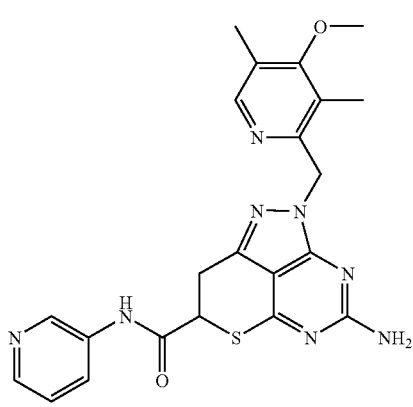

The title compound (10 mg, 17%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 3-aminopyridine (24 mg).

$^1$H-NMR (CDCl$_3$) δ: 2.24 (3H, s), 2.28 (3H, s), 3.37-3.38 (1H, m), 3.53 (1H, dd, J=16.5, 8.9 Hz), 3.77 (3H, s), 4.62 (1H, dd, J=8.9, 4.2 Hz), 5.44 (2H, s), 7.29-7.32 (1H, m), 8.12 (1H, s), 8.24 (1H, d, J=8.3 Hz), 8.29 (1H, d, J=4.9 Hz), 8.56 (1H, s).

ESI-MS m/z: 463 (M+H)$^+$.

Example 200

4-Amino-2-[(4-methoxy-3,5-dimethylpyridin-2-yl)methyl]-N-pyridin-4-yl-7,8-dihydro-2H-6-thia-1,2,3,5-tetraazaacenaphthylene-7-carboxamide

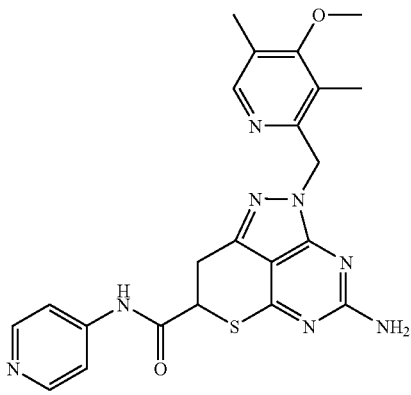

The title compound (15 mg, 25%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 4-aminopyridine (24 mg).

$^1$H-NMR (CDCl$_3$) δ: 2.24 (3H, s), 2.29 (3H, d, J=5.6 Hz), 3.34 (1H, dd, J=16.7, 4.2 Hz), 3.53 (1H, dd, J=16.7, 8.8 Hz), 3.77 (3H, s), 4.59 (1H, dd, J=8.8, 4.2 Hz), 5.44 (2H, d, J=4.2 Hz), 7.56 (2H, dd, J=4.9, 1.5 Hz), 8.12 (1H, s), 8.43 (2H, dd, J=4.9, 1.5 Hz).

ESI-MS m/z: 463 (M+H)$^+$.

Example 201

4-Amino-2-[(4-methoxy-3,5-dimethylpyridin-2-yl)methyl]-N-(5-methylisoxazol-3-yl)-7,8-dihydro-2H-6-thia-1,2,3,5-tetraazaacenaphthylene-7-carboxamide

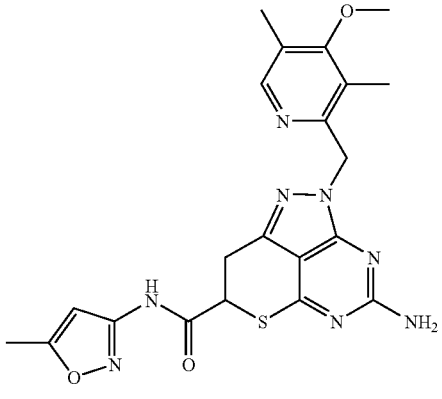

The title compound (8 mg, 13%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-methyl-1,2-oxazol-3-amine (25 mg).

$^1$H-NMR (CDCl$_3$) δ: 2.38-2.41 (9H, m), 3.13 (2H, q, J=7.1 Hz), 4.01 (3H, s), 4.70 (1H, s), 5.63 (2H, s), 6.61 (1H, s), 8.48 (1H, s).

ESI-MS m/z: 467 (M+H)$^+$.

Example 202

Ethyl 2-[({4-amino-2-[(4-methoxy-3,5-dimethylpyridin-2-yl)methyl]-7,8-dihydro-2H-6-thia-1,2,3,5-tetraazaacenaphthylen-7-yl}carbonyl)amino]-4-methyl-1,3-thiazole-5-carboxylate

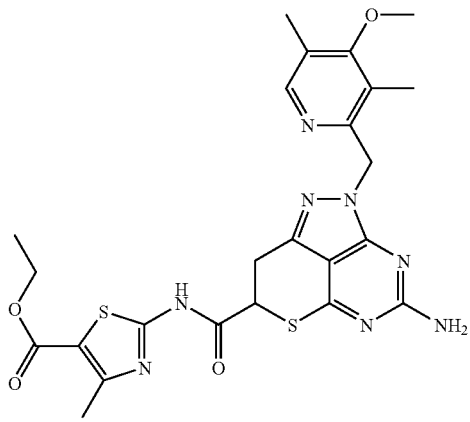

The title compound (20 mg, 32%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 2-amino-4-methylthiazole-5-carboxylic acid ethyl ester (48 mg).

$^1$H-NMR (CDCl$_3$) δ: 1.33 (3H, t, J=7.1 Hz), 2.28 (3H, s), 2.29 (3H, s), 2.62 (3H, s), 3.38 (1H, dd, J=16.7, 4.4 Hz), 3.59 (1H, dd, J=16.7, 7.4 Hz), 3.82 (3H, s), 4.29 (2H, q, J=7.1 Hz), 4.65 (1H, dd, J=7.4, 4.4 Hz), 5.50 (2H, d, J=8.1 Hz), 8.25 (1H, s).

ESI-MS m/z: 555 (M+H)$^+$.

Example 203

Ethyl 2-[({4-amino-2-[(4-methoxy-3,5-dimethylpyridin-2-yl)methyl]-7,8-dihydro-2H-6-thia-1,2,3,5-tetraazaacenaphthylen-7-yl}carbonyl)amino]-1,3-thiazole-5-carboxylate

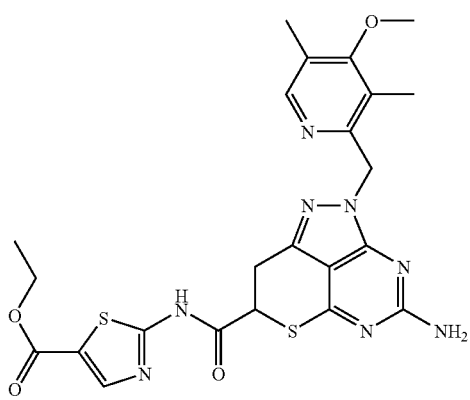

The title compound (20 mg, 29%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 2-aminothiazole-5-carboxylic acid ethyl ester (45 mg).

$^1$H-NMR (CDCl$_3$) δ: 1.39 (3H, t, J=7.1 Hz), 2.25 (3H, s), 2.27 (3H, s), 3.36-3.41 (1H, m), 3.55 (1H, dd, J=16.8, 7.5 Hz), 3.77 (3H, s), 4.39 (2H, q, J=7.5 Hz), 4.63 (1H, dd, J=7.5, 4.4 Hz), 5.45 (2H, s), 7.82 (1H, s), 8.16 (1H, s).

ESI-MS m/z: 541 (M+H)$^+$.

Example 204

N-(5-Acetyl-4-methyl-1,3-thiazol-2-yl)-4-amino-2-[(4-methoxy-3,5-dimethylpyridin-2-yl)methyl]-7,8-dihydro-2H-6-thia-1,2,3,5-tetraazaacenaphthylene-7-carboxamide

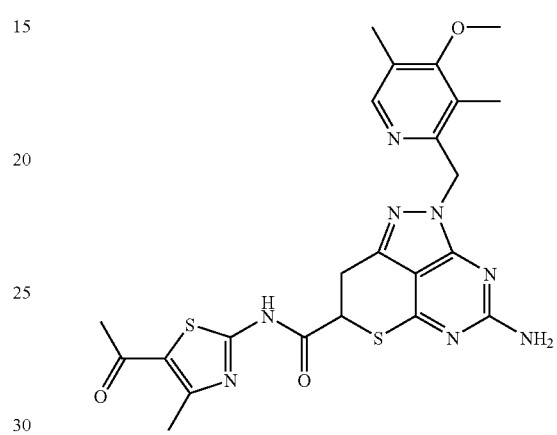

The title compound (20 mg, 30%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 1-(2-amino-4-methylthiazol-5-yl)ethanone (40 mg).

$^1$H-NMR (CDCl$_3$) δ: 2.30 (6H, s), 2.49 (3H, s), 2.64 (3H, s), 3.37-3.40 (1H, m), 3.53 (1H, dd, J=16.7, 7.4 Hz), 3.85 (3H, s), 4.68 (1H, dd, J=7.4, 4.4 Hz), 5.51 (2H, d, J=8.6 Hz), 8.26 (1H, s).

ESI-MS m/z: 525 (M+H)$^+$.

Example 205

Ethyl {2-[({4-amino-2-[(4-methoxy-3,5-dimethylpyridin-2-yl)methyl]-7,8-dihydro-2H-6-thia-1,2,3,5-tetraazaacenaphthylen-7-yl}carbonyl)amino]-1,3-thiazol-4-yl}acetate

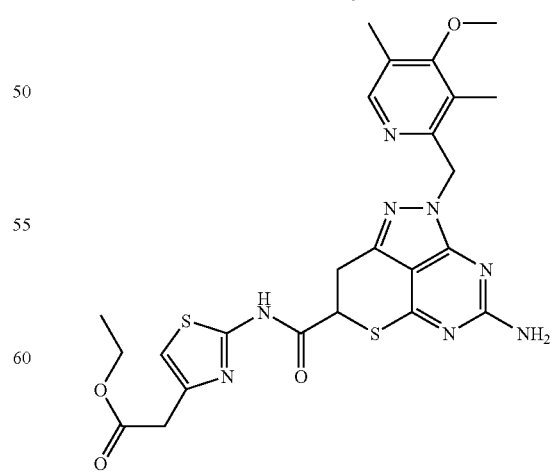

The title compound (20 mg, 28%) was obtained as a solid by the same method as in Example 12 using 4-amino-2-[(4-methoxy-3,5-dimethylpyridin-2-yl)methyl]-7,8-dihydro- 2H-6-thia-1,2,3,5-tetraazaacenaphthylene-7-carboxylic acid of Example 8 (50 mg) and (2-aminothiazol-4-yl)acetic acid ethyl ester (48 mg).

$^1$H-NMR (CDCl$_3$) δ: 1.27 (3H, t, J=7.1 Hz), 2.30 (3H, s), 2.32 (3H, s), 3.37 (1H, dd, J=16.7, 4.5 Hz), 3.55 (1H, dd, J=16.7, 7.7 Hz), 3.69 (2H, s), 3.88 (3H, s), 4.18 (2H, q, J=7.2 Hz), 4.67 (1H, dd, J=7.7, 4.5 Hz), 5.54 (2H, d, J=6.6 Hz), 6.82 (1H, s), 8.32 (1H, s).

ESI-MS m/z: 555 (M+H)$^+$.

Example 206

4-Amino-2-[(4-methoxy-3,5-dimethylpyridin-2-yl)methyl]-N-(5-nitro-1,3-thiazol-2-yl)-7,8-dihydro-2H-6-thia-1,2,3,5-tetraazaacenaphthylene-7-carboxamide

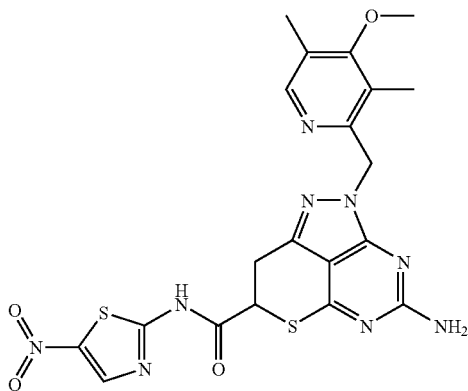

The title compound (20 mg, 30%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-nitrothiazol-2-amine (38 mg).

$^1$H-NMR (CDCl$_3$) δ: 2.27 (3H, s), 2.28 (3H, s), 3.37 (1H, dd, J=16.7, 4.5 Hz), 3.52 (1H, dd, J=16.7, 7.1 Hz), 3.81 (3H, s), 4.68 (1H, dd, J=7.1, 4.5 Hz), 5.47 (2H, s), 8.17 (1H, s), 8.32 (1H, s).

ESI-MS m/z: 514 (M+H)$^+$.

Example 207

4-Amino-2-[(4-methoxy-3,5-dimethylpyridin-2-yl)methyl]-N-[4-(2-morpholin-4-yl-2-oxoethyl)-1,3-thiazol-2-yl]-7,8-dihydro-2H-6-thia-1,2,3,5-tetraazaacenaphthylene-7-carboxamide

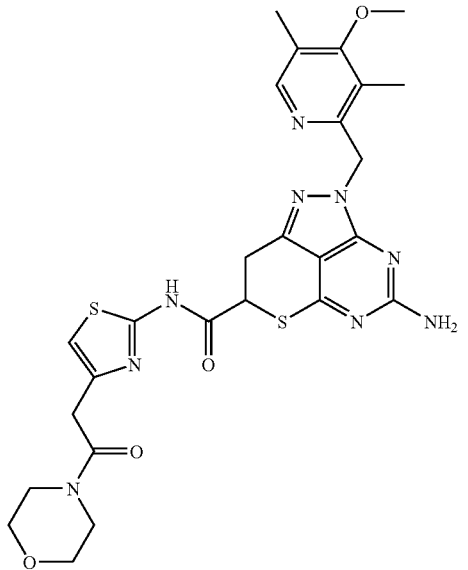

The title compound (30 mg, 39%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 2-(2-amino-thiazol-4-yl)-1-morpholin-4-yl-ethanone (59 mg).

$^1$H-NMR (CDCl$_3$) δ: 2.24 (3H, s), 2.27 (3H, s), 3.38-3.39 (1H, m), 3.56-3.62 (9H, m), 3.77 (3H, s), 4.65 (1H, dd, J=7.8, 4.4 Hz), 5.43 (2H, d, J=2.0 Hz), 6.77 (1H, s), 8.13 (1H, s).

ESI-MS m/z: 596 (M+H)$^+$.

Example 208

4-Amino-2-[(4-methoxy-3,5-dimethylpyridin-2-yl)methyl]-N-[5-(morpholin-4-ylmethyl)-1,3-thiazol-2-yl]-7,8-dihydro-2H-6-thia-1,2,3,5-tetraazaacenaphthylene-7-carboxamide

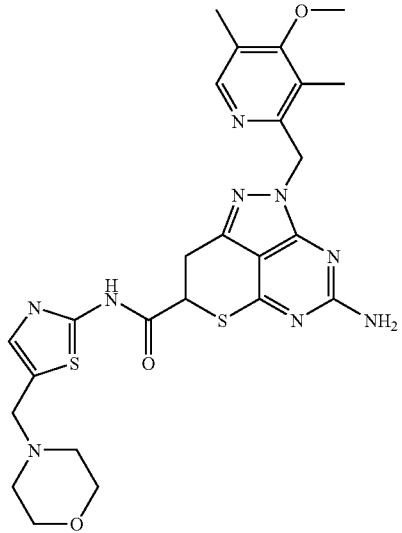

The title compound (20 mg, 27%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-(morpholin-4-yl)-1,3-thiazol-2-amine (52 mg).

$^1$H-NMR (CDCl$_3$) δ: 2.24 (3H, s), 2.28 (3H, s), 2.48 (4H, s), 3.38 (1H, d, J=3.9 Hz), 3.53 (1H, dd, J=16.5, 7.7 Hz), 3.70 (4H, t, J=4.5 Hz), 3.77 (3H, s), 4.65 (1H, dd, J=7.7, 4.5 Hz), 5.44 (2H, d, J=2.7 Hz), 7.22 (1H, s), 8.14 (1H, s).

ESI-MS m/z: 568 (M+H)$^+$.

Example 209

4-Amino-N-(3-carbamoyl-4-methyl-2-thienyl)-2-[(4-methoxy-3,5-dimethylpyridin-2-yl)methyl]-7,8-dihydro-2H-6-thia-1,2,3,5-tetraazaacenaphthylene-7-carboxamide

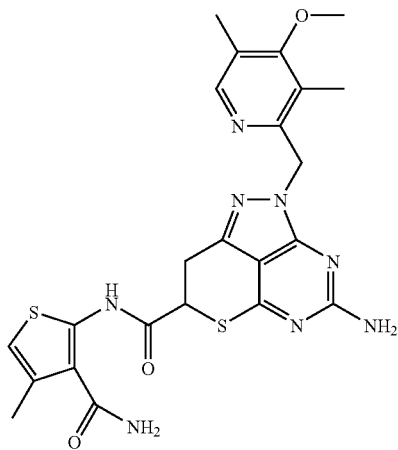

The title compound (10 mg, 15%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 2-amino-4-methyl-thiophene-3-carboxamide (40 mg).

$^1$H-NMR (CDCl$_3$) δ: 2.23 (3H, s), 2.25 (3H, s), 2.44 (3H, s), 3.35-3.40 (1H, m), 3.67 (1H, dd, J=16.6, 6.3 Hz), 3.77 (3H, s), 4.67 (1H, dd, J=6.3, 4.6 Hz), 5.42 (2H, d, J=3.4 Hz), 6.53 (1H, d, J=1.2 Hz), 7.49 (2H, s), 8.14 (1H, brs).
ESI-MS m/z: 525 (M+H)$^+$.

Example 210

4-Amino-2-[(4-methoxy-3,5-dimethylpyridin-2-yl)methyl]-N-1H-pyrazol-5-yl-7,8-dihydro-2H-6-thia-1,2,3,5-tetraazaacenaphthylene-7-carboxamide

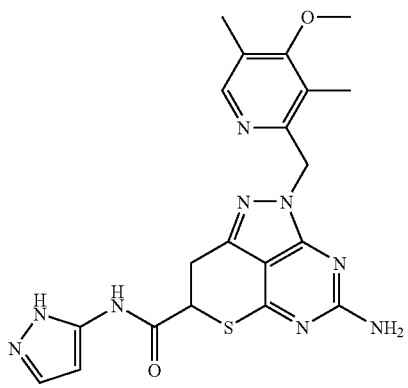

The title compound (8 mg, 14%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-aminopyrazole (22 mg).

$^1$H-NMR (CDCl$_3$) δ: 2.24 (3H, s), 2.25 (3H, s), 3.40-3.45 (2H, m), 3.76 (3H, s), 5.44 (2H, s), 5.55 (1H, t, J=5.4 Hz), 5.98 (1H, d, J=3.2 Hz), 7.93 (1H, d, J=2.9 Hz), 8.16 (1H, s).
ESI-MS m/z: 452 (M+H)$^+$.

Example 211

4-Amino-2-[(4-methoxy-3,5-dimethylpyridin-2-yl)methyl]-N-{5-[(4-methylpiperazin-1-yl)methyl]-1,3-thiazol-2-yl}-7,8-dihydro-2H-6-thia-1,2,3,5-tetraazaacenaphthylene-7-carboxamide

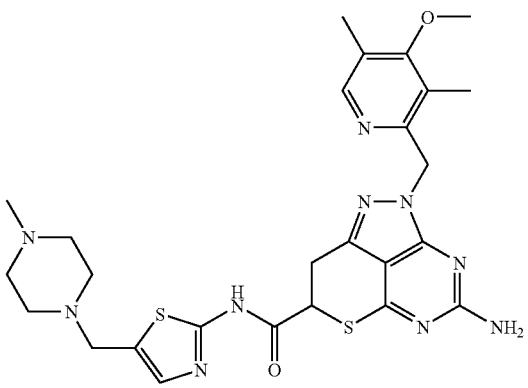

The title compound (20 mg, 28%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and 5-((4-methyl-piperazin-1-yl)methyl)-1,3-thiazol-2-amine (55 mg).

$^1$H-NMR (CDCl$_3$) δ: 2.25 (4H, brs), 2.28 (6H, s), 2.48 (8H, brs), 3.37 (1H, dd, J=16.8, 4.4 Hz), 3.54 (1H, dd, J=16.8, 8.1 Hz), 3.66 (2H, s), 3.77 (3H, s), 4.65 (1H, dd, J=8.1, 4.4 Hz), 5.44 (2H, d, J=2.9 Hz), 7.22 (1H, s), 8.15 (1H, s).
ESI-MS m/z: 581 (M+H)$^+$.

Example 212

4-Amino-N-[5-(hydroxymethyl)-1,3-thiazol-2-yl]-2-[(4-methoxy-3,5-dimethylpyridin-2-yl)methyl]-7,8-dihydro-2H-6-thia-1,2,3,5-tetraazaacenaphthylene-7-carboxamide

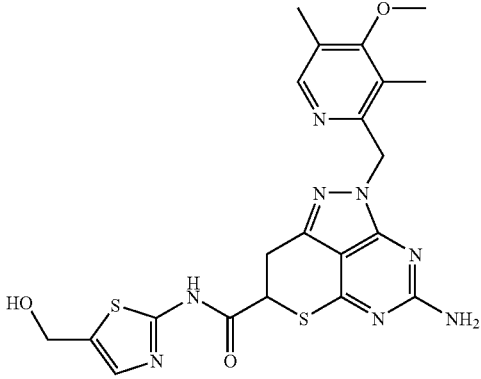

The title compound (15 mg, 23%) was obtained as a solid by the same method as in Example 12 using 4-amino-2-[(4-methoxy-3,5-dimethylpyridin-2-yl)methyl]-7,8-dihydro-2H-6-thia-1,2,3,5-tetraazaacenaphthylene-7-carboxylic acid of Example 8 (50 mg) and (2-amino-1,3-thiazol-5-yl)-methanol (34 mg).

$^{1}$H-NMR (DMSO-$d_6$) δ: 2.18 (3H, s), 2.21 (3H, s), 3.27-3.29 (2H, m), 3.72 (3H, s), 4.57 (2H, d, J=5.1 Hz), 4.78-4.79 (1H, m), 5.34 (2H, s), 5.38 (1H, t, J=5.6 Hz), 6.98 (2H, s), 7.31 (1H, s), 8.10 (1H, s).

ESI-MS m/z: 499 (M+H)$^+$.

Example 213
1) 4-[Bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl trifluoromethanesulfonate

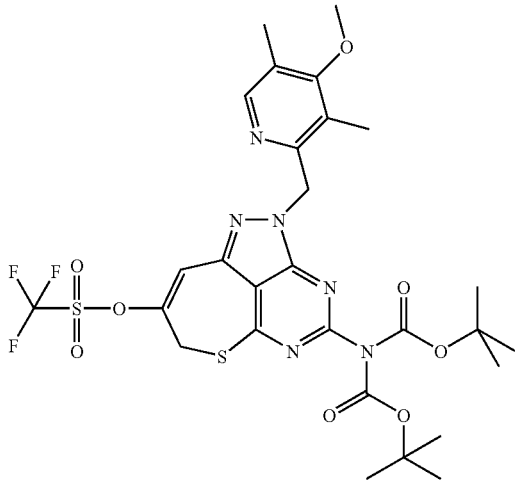

4-[Bis(tert-butoxycarbonyl)amino]-2-[(4-methoxy-3,5-dimethylpyridin-2-yl)methyl]-2,9-dihydro-6-thia-1,2,3,5-tetraazabenzo[cd]azulen-8-one (300 mg) was dissolved in dehydrated dichloromethane (5 ml) under cooling in an ice bath, followed by addition of triethylamine (146 μl). Then, trifluoromethanesulfonic anhydride (106 μl) was added and the mixture was stirred at 0° C. for three hours. A saturated ammonium chloride solution was added to the reaction solution, followed by extraction with ethyl acetate. The organic layer was sequentially washed with water and brine and dried over sodium sulfate. The solvent was evaporated, and the resulting residue was purified by silica gel column chromatography (hexane-ethyl acetate) to obtain the title compound as a solid (255 mg, 69%).

ESI-MS m/z: 703 (M+H)$^+$.

2) Ethyl 4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulene-8-carboxylate

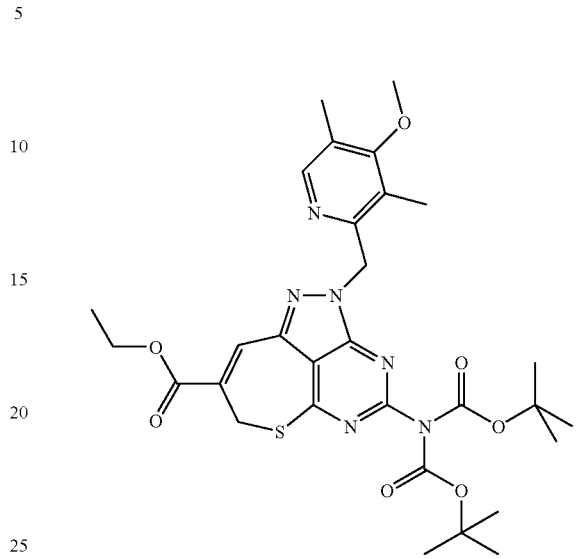

4-[Bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl trifluoromethanesulfonate (25 mg) was dissolved in ethanol (2 ml). Triethylamine (6 μl) and bis(triphenylphosphine)palladium (II) dichloride (2.5 mg) were added at room temperature, and the mixture was stirred in a carbon monoxide atmosphere at 40° C. for three hours. The reaction solution was concentrated, and the resulting residue was purified by silica gel column chromatography (hexane-ethyl acetate) to obtain the title compound as an oil (14 mg, 62%).

$^{1}$H-NMR (CDCl$_3$) δ: 1.35 (3H, t, J=7.19 Hz), 1.44 (18H, s), 2.22 (3H, s), 2.30 (3H, s), 3.75 (3H, s), 4.18 (2H, s), 4.31 (2H, q, J=7.15 Hz), 5.73 (2H, s), 8.02 (1H, s), 8.15 (1H, s).

ESI-MS m/z: 627 (M+H)$^+$.

3) 4-[(tert-Butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid

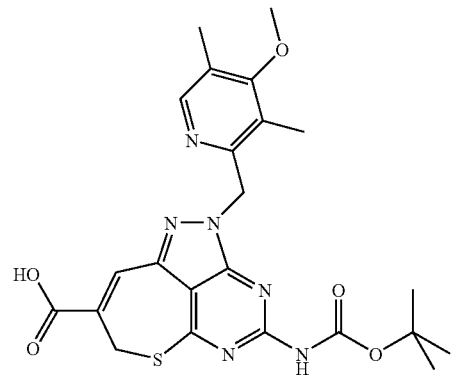

Ethyl 4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulene-8-carboxylate (0.92 g) was dissolved in methanol (10 ml) under cooling in an ice bath. A 1 N sodium hydroxide solution (10 ml) was added, and the mixture was stirred for 16 hours while gradually returning to room temperature. The reaction solution was neutralized with a 0.5 N hydrochloric acid solution, and then the solvent was concentrated. The resulting residue was diluted with chloroform and washed with a 10% citric acid solution, and the organic layer was dried over sodium sulfate. The solvent was evaporated, and the resulting residue was recrystallized from hexane and ethyl acetate to obtain the title compound as a solid (0.68 g, 91%).

$^1$H-NMR (CD$_3$OD) δ: 1.54 (9H, s), 2.25 (3H, s), 2.32 (3H, s), 3.81 (3H, s), 4.18 (2H, s), 5.78 (2H, s), 7.81 (1H, s), 8.07 (1H, s).

ESI-MS m/z: 499 (M+H)$^+$.

4) 4-Amino-2-[(4-methoxy-3,5-dimethylpyridin-2-yl)methyl]-2,7-dihydro-6-thia-1,2,3,5-tetraazabenzo[cd]azulen-8-carboxylic acid

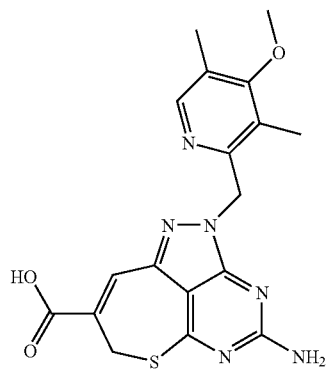

The title compound was obtained as a solid (15 mg, 63%) by synthesis by the same method as in Example 2 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (30 mg).

$^1$H-NMR (DMSO-D$_6$) δ: 2.17 (3H, s), 2.26 (3H, s), 3.73 (3H, s), 4.09 (2H, s), 5.50 (2H, s), 7.05 (2H, brs), 7.61 (1H, s), 8.05 (1H, s).

ESI-MS m/z: 399 (M+H)$^+$.

Example 214

1) tert-Butyl {8-(hydroxymethyl)-2-[(4-methoxy-3,5-dimethylpyridin-2-yl)methyl]-2,7-dihydro-6-thia-1,2,3,5-tetraazabenzo[cd]azulen-4-yl}carbamate

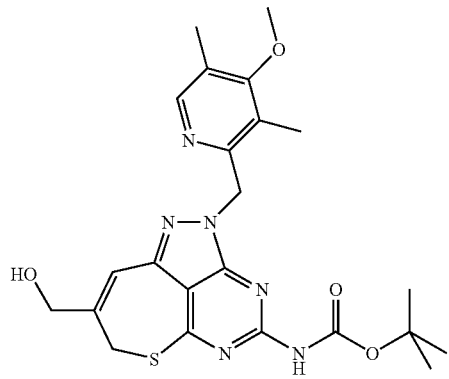

4-[(tert-Butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) was dissolved in tetrahydrofuran (1 ml) under cooling in an ice bath. N-Methylmorpholine (13 μl) and ethyl chloroformate (12 μl) were added, followed by stirring for two hours. Subsequently, sodium borohydride (12 mg) and methanol (1 ml) were added to the reaction solution, and the mixture was stirred for three hours while gradually returning to room temperature. A 10% citric acid solution was added to the reaction solution, followed by extraction with ethyl acetate. The resulting organic layer was sequentially washed with a saturated sodium bicarbonate solution and brine and dried over anhydrous sodium sulfate. The solvent was evaporated, and the resulting residue was purified by silica gel column chromatography (chloroform-methanol) to obtain the title compound as an oil (35 mg, 72%).

$^1$H-NMR (CDCl$_3$) δ: 1.53 (9H, s), 2.22 (3H, s), 2.31 (3H, s), 3.74 (3H, s), 3.75 (2H, s), 4.32-4.35 (2H, m), 5.64 (2H, s), 6.85 (1H, t, J=1.38 Hz), 7.43 (1H, s), 8.17 (1H, s).

ESI-MS m/z: 485 (M+H)$^+$.

2) {4-Amino-2-[(4-methoxy-3,5-dimethylpyridin-2-yl)methyl]-2,7-dihydro-6-thia-1,2,3,5-tetraazabenzo[cd]azulen-8-yl}methanol

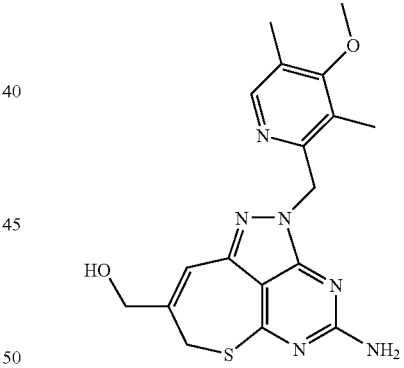

The title compound was obtained as a solid (15 mg, 54%) by synthesis by the same method as in Example 2 using tert-butyl {8-(hydroxymethyl)-2-[(4-methoxy-3,5-dimethylpyridin-2-yl)methyl]-2,7-dihydro-6-thia-1,2,3,5-tetraazabenzo[cd]azulen-4-yl}carbamate (35 mg).

$^1$H-NMR (CDCl$_3$) δ: 2.22 (3H, s), 2.27 (3H, s), 3.71 (2H, s), 3.74 (3H, s), 4.31 (2H, d, J=1.38 Hz), 5.19 (2H, brs), 5.51 (2H, s), 6.78-6.79 (1H, m), 8.19 (1H, s).

ESI-MS m/z: 385 (M+H)$^+$.

Example 215

1) tert-Butyl {8-[butyl(methyl)carbamoyl]-2-[(4-methoxy-3,5-dimethylpyridin-2-yl)methyl]-2,7-dihydro-6-thia-1,2,3,5-tetraazabenzo[cd]azulen-4-yl}carbamate

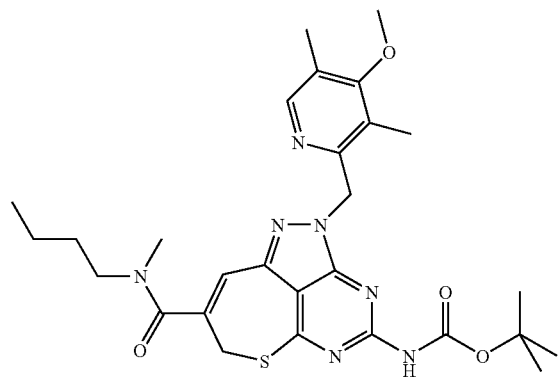

The title compound was obtained as a solid (54 mg, 95%) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and n-methyl-n-butylamine (23 µl).

ESI-MS m/z: 568 (M+H)$^+$.

2) 4-Amino-N-butyl-2-[(4-methoxy-3,5-dimethylpyridin-2-yl)methyl]-N-methyl-2,7-dihydro-6-thia-1,2,3,5-tetraazabenzo[cd]azulene-8-carboxamide

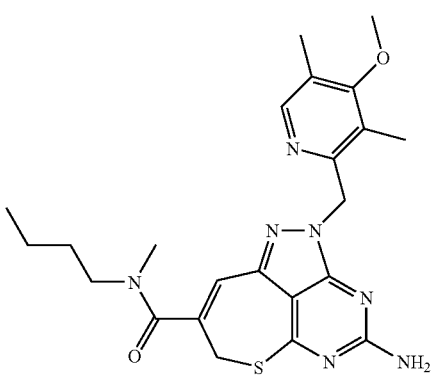

The title compound was obtained as a solid (22 mg, 50%) by synthesis by the same method as in Example 2 using tert-butyl {8-[butyl(methyl)carbamoyl]-2-[(4-methoxy-3,5-dimethylpyridin-2-yl)methyl]-2,7-dihydro-6-thia-1,2,3,5-tetraazabenzo[cd]azulen-4-yl}carbamate (54 mg).

$^1$H-NMR (CDCl$_3$) δ: 0.89-0.96 (3H, m), 1.26-1.36 (2H, m), 1.54-1.61 (2H, m), 2.23 (3H, s), 2.30 (3H, s), 3.06 (3H, brs), 3.47 (2H, t, J=7.57 Hz), 3.75 (3H, s), 3.94 (2H, s), 5.19 (2H, s), 5.54 (2H, s), 6.89 (1H, s), 8.19 (1H, s).

ESI-MS m/z: 468 (M+H)$^+$.

Example 216

1) tert-Butyl {2-[(4-methoxy-3,5-dimethylpyridin-2-yl)methyl]-8-[methyl(phenyl)carbamoyl]-2,7-dihydro-6-thia-1,2,3,5-tetraazabenzo[cd]azulen-4-yl}carbamate

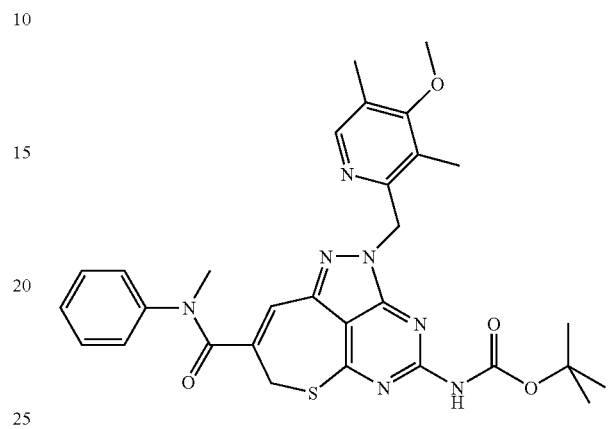

The title compound was obtained as a solid (63 mg, 59%) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and N-methylaniline (21 µl).

$^1$H-NMR (CDCl$_3$) δ: 1.51 (9H, s), 2.21 (3H, s), 2.28 (3H, s), 3.41 (3H, s), 3.74 (3H, s), 3.79 (2H, s), 5.59 (2H, s), 7.03 (1H, s), 7.16-7.24 (3H, m), 7.32-7.39 (3H, m), 8.15 (1H, s).

ESI-MS m/z: 588 (M+H)$^+$.

2) 4-Amino-2-[(4-methoxy-3,5-dimethylpyridin-2-yl)methyl]-N-methyl-N-phenyl-2,7-dihydro-6-thia-1,2,3,5-tetraazabenzo[cd]azulene-8-carboxamide

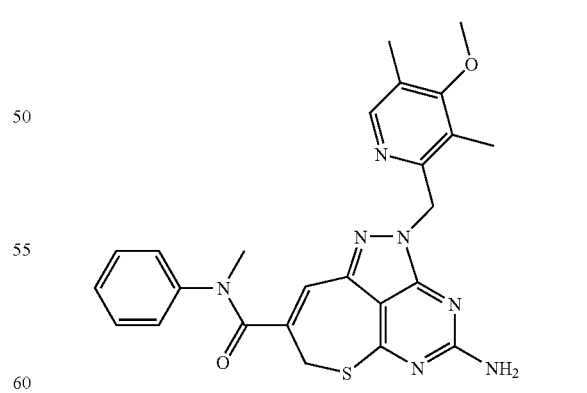

The title compound was obtained as a solid (23 mg, 44%) by synthesis by the same method as in Example 2 using tert-butyl {2-[(4-methoxy-3,5-dimethylpyridin-2-yl)methyl]-8-[methyl(phenyl)carbamoyl]-2,7-dihydro-6-thia-1,2,3,5-tetraazabenzo[cd]azulen-4-yl}carbamate (63 mg).

¹H-NMR (CDCl₃) δ: 2.23 (3H, s), 2.25 (3H, s), 3.41 (3H, s), 3.75 (3H, s), 3.77 (2H, s), 5.15 (2H, brs), 5.48 (2H, s), 6.97 (1H, s), 7.16-7.24 (3H, m), 7.34 (2H, t, J=7.79 Hz), 8.19 (1H, s).
ESI-MS m/z: 488 (M+H)⁺.

Example 217

1) tert-Butyl {8-(dimethylcarbamoyl)-2-[(4-methoxy-3,5-dimethylpyridin-2-yl)methyl]-2,7-dihydro-6-thia-1,2,3,5-tetraazabenzo[cd]azulen-4-yl}carbamate

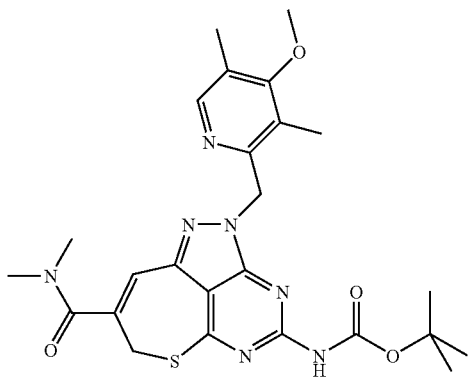

The title compound was obtained as a solid (53 mg, quant.) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and dimethylamine hydrochloride (16 mg).
¹H-NMR (CDCl₃) δ: 1.53 (9H, s), 2.22 (3H, s), 2.34 (3H, s), 3.10 (6H, brs), 3.75 (3H, s), 3.97 (2H, s), 5.67 (2H, s), 6.97 (1H, s), 7.46 (1H, s), 8.17 (1H, s).
ESI-MS m/z: 526 (M+H)⁺.

2) 4-Amino-2-[(4-methoxy-3,5-dimethylpyridin-2-yl)methyl]-N,N-dimethyl-2,7-dihydro-6-thia-1,2,3,5-tetraazabenzo[cd]azulene-8-carboxamide

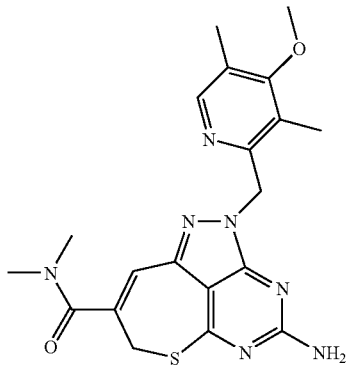

The title compound was obtained as a solid (17 mg, 40%) by synthesis by the same method as in Example 2 using tert-butyl {8-(dimethylcarbamoyl)-2-[(4-methoxy-3,5-dimethylpyridin-2-yl)methyl]-2,7-dihydro-6-thia-1,2,3,5-tetraazabenzo[cd]azulen-4-yl}carbamate (53 mg).
¹H-NMR (CDCl₃) δ: 2.23 (3H, s), 2.31 (3H, s), 3.10 (6H, brs), 3.75 (3H, s), 3.95 (2H, s), 5.19 (2H, s), 5.54 (2H, s), 6.92 (1H, s), 8.19 (1H, s).
ESI-MS m/z: 426 (M+H)⁺.

Example 218

1) tert-Butyl {8-[(3,3-difluoropyrrolidin-1-yl)carbonyl]-2-[(4-methoxy-3,5-dimethylpyridin-2-yl)methyl]-2,7-dihydro-6-thia-1,2,3,5-tetraazabenzo[cd]azulen-4-yl}carbamate

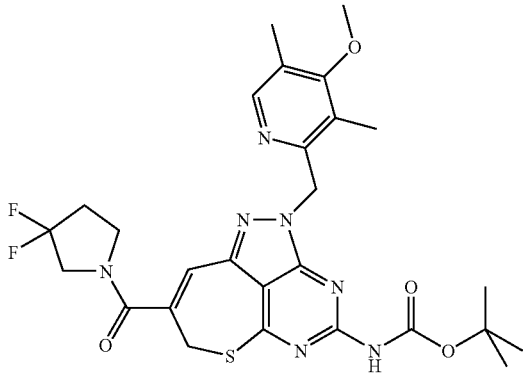

The title compound was obtained as a solid (60 mg, quant.) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and 3,3-difluoropyrrolidine hydrochloride (29 mg).
¹H-NMR (CDCl₃) δ: 1.54-1.57 (9H, m), 2.23 (3H, s), 2.35 (3H, s), 2.37-2.44 (2H, m), 3.76 (3H, s), 3.87 (2H, t, J=6.88 Hz), 3.94 (2H, t, J=12.61 Hz), 4.02 (2H, s), 5.67 (2H, s), 7.10 (1H, s), 7.46 (1H, s), 8.18 (1H, s).
ESI-MS m/z: 588 (M+H)⁺.

2) 8-[(3,3-Difluoropyrrolidin-1-yl)carbonyl]-2-[(4-methoxy-3,5-dimethylpyridin-2-yl)methyl]-2,7-dihydro-6-thia-1,2,3,5-tetraazabenzo[cd]azulen-4-amine

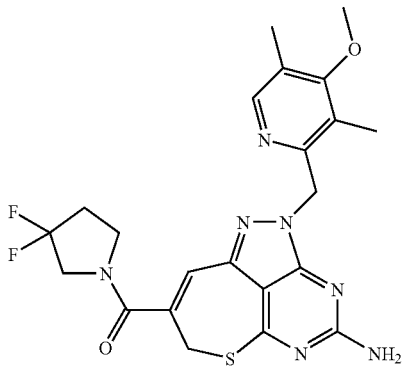

The title compound was obtained as a solid (23 mg, 46%) by synthesis by the same method as in Example 2 using tert-butyl {8-[(3,3-difluoropyrrolidin-1-yl)carbonyl]-2-[(4-methoxy-3,5-dimethylpyridin-2-yl)methyl]-2,7-dihydro-6-thia-1,2,3,5-tetraazabenzo[cd]azulen-4-yl}carbamate (60 mg).

¹H-NMR (DMSO-D₆) δ: 2.17 (3H, s), 2.25 (3H, s), 2.38-2.47 (2H, m), 3.31-3.34 (2H, m), 3.72 (4H, s), 3.78-3.88 (2H, m), 3.81 (2H, s), 5.47 (2H, s), 7.01 (1H, s), 7.03 (2H, brs), 8.06 (1H, s).

ESI-MS m/z: 488 (M+H)⁺.

Example 219

1) tert-Butyl {8-(butylcarbamoyl)-2-[(4-methoxy-3,5-dimethylpyridin-2-yl)methyl]-2,7-dihydro-6-thia-1,2,3,5-tetraazabenzo[cd]azulen-4-yl}carbamate

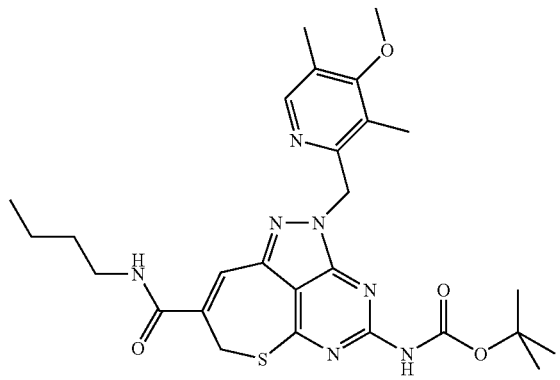

The title compound was obtained as a solid (53 mg, 95%) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and n-butylamine (20 μl).

¹H-NMR (CDCl₃) δ: 0.95 (3H, t, J=7.34 Hz), 1.35-1.44 (3H, m), 1.50-1.56 (17H, m), 2.22 (3H, s), 2.33 (3H, s), 3.37 (3H, dd, J=12.61, 7.11 Hz), 3.75 (3H, s), 4.14 (2H, s), 5.67 (2H, s), 5.96 (2H, brs), 7.29 (1H, s), 7.45 (1H, s), 8.18 (1H, s).

ESI-MS m/z: 554 (M+H)⁺.

2) 4-Amino-N-butyl-2-[(4-methoxy-3,5-dimethylpyridin-2-yl)methyl]-2,7-dihydro-6-thia-1,2,3,5-tetraazabenzo[cd]azulene-8-carboxamide

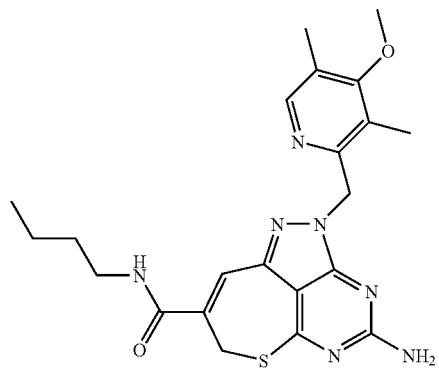

The title compound was obtained as a solid (27 mg, 62%) by synthesis by the same method as in Example 2 using tert-butyl {8-(butylcarbamoyl)-2-[(4-methoxy-3,5-dimethylpyridin-2-yl)methyl]-2,7-dihydro-6-thia-1,2,3,5-tetraazabenzo[cd]azulen-4-yl}carbamate (53 mg).

¹H-NMR (DMSO-D₆) δ: 0.88 (3H, t, J=7.34 Hz), 1.25-1.34 (2H, m), 1.42-1.49 (2H, m), 2.17 (3H, s), 2.24 (3H, s), 3.17 (2H, q, J=6.42 Hz), 3.72 (3H, s), 4.06 (2H, s), 5.47 (2H, s), 7.02 (2H, brs), 7.39 (1H, s), 8.07 (1H, s), 8.40 (1H, t, J=5.50 Hz).

ESI-MS m/z: 454 (M+H)⁺.

Example 220

1) tert-Butyl {8-(anilinocarbonyl)-2-[(4-methoxy-3,5-dimethylpyridin-2-yl)methyl]-2,7-dihydro-6-thia-1,2,3,5-tetraazabenzo[cd]azulen-4-yl}carbamate

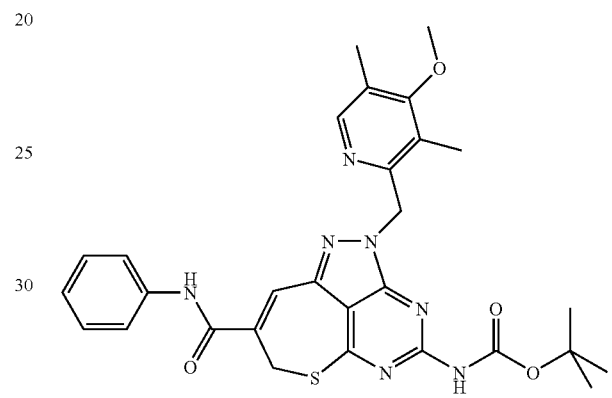

The title compound was obtained as a solid (56 mg, 97%) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and aniline (18 μl).

¹H-NMR (CDCl₃) δ: 1.57 (9H, s), 2.23 (3H, s), 2.34 (3H, s), 3.76 (3H, s), 4.19 (2H, s), 5.69 (2H, s), 7.16 (1H, t, J=7.34 Hz), 7.36 (2H, t, J=7.79 Hz), 7.49 (1H, s), 7.56 (2H, d, J=7.79 Hz), 7.78 (1H, s), 8.18 (1H, s).

ESI-MS m/z: 574 (M+H)⁺.

2) 4-Amino-2-[(4-methoxy-3,5-dimethylpyridin-2-yl)methyl]-N-phenyl-2,7-dihydro-6-thia-1,2,3,5-tetraazabenzo[cd]azulene-8-carboxamide

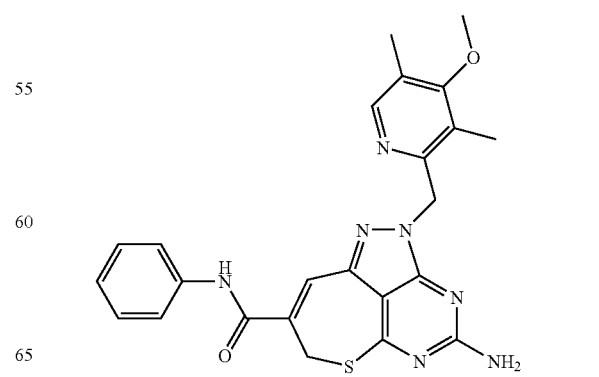

The title compound was obtained as a solid (25 mg, 54%) by synthesis by the same method as in Example 2 using tert-butyl {8-(anilinocarbonyl)-2-[(4-methoxy-3,5-dimethylpyridin-2-yl)methyl]-2,7-dihydro-6-thia-1,2,3,5-tetraazabenzo[cd]azulen-4-yl}carbamate (56 mg).

$^1$H-NMR (DMSO-D$_6$) δ: 2.18 (3H, s), 2.26 (3H, s), 3.73 (3H, s), 4.15 (2H, s), 5.51 (2H, s), 7.06-7.11 (3H, m), 7.33 (2H, t, J=7.79 Hz), 7.61 (1H, s), 7.71 (2H, d, J=7.79 Hz), 8.08 (1H, s), 10.24 (1H, s).

ESI-MS m/z: 474 (M+H)$^+$.

Example 221

1) tert-Butyl (8-{[2-(dimethylamino)-2-oxoethyl]carbamoyl}-2-[(4-methoxy-3,5-dimethylpyridin-2-yl)methyl]-2,7-dihydro-6-thia-1,2,3,5-tetraazabenzo[cd]azulen-4-yl)carbamate

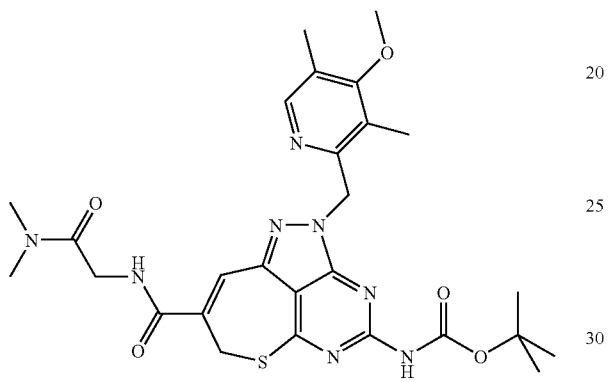

The title compound was obtained as a solid (22 mg, 38%) by synthesis by the same method as in Example 9 using 4-[(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-carboxylic acid (50 mg) and glycinedimethylamide acetate (81 mg).

$^1$H-NMR (CDCl$_3$) δ: 1.53 (9H, s), 2.23 (3H, s), 2.33 (3H, s), 3.01 (6H, s), 3.76 (3H, s), 4.12-4.14 (4H, m), 5.68 (2H, s), 7.19 (1H, s), 7.49 (1H, s), 8.19 (1H, s).

ESI-MS m/z: 583 (M+H)$^+$.

2) 4-Amino-N-[2-(dimethylamino)-2-oxoethyl]-2-[(4-methoxy-3,5-dimethylpyridin-2-yl)methyl]-2,7-dihydro-6-thia-1,2,3,5-tetraazabenzo[cd]azulene-8-carboxamide

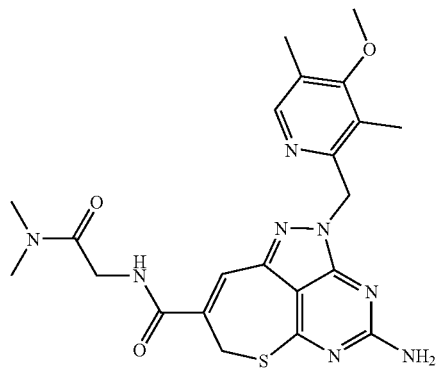

The title compound was obtained as a solid (10 mg, 60%) by synthesis by the same method as in Example 2 using tert-butyl (8-{[2-(dimethylamino)-2-oxoethyl]carbamoyl}-2-[(4-methoxy-3,5-dimethylpyridin-2-yl)methyl]-2,7-dihydro-6-thia-1,2,3,5-tetraazabenzo[cd]azulen-4-yl)carbamate (20 mg).

$^1$H-NMR (DMSO-D$_6$) δ: 2.17 (3H, s), 2.25 (3H, s), 2.83 (3H, s), 2.99 (3H, s), 3.29 (2H, s), 4.01 (2H, d, J=5.96 Hz), 4.08 (2H, s), 5.49 (3H, s), 7.01 (2H, brs), 7.48 (1H, s), 8.07 (1H, s), 8.55 (1H, t, J=5.96 Hz).

ESI-MS m/z: 483 (M+H)$^+$.

Example 222

1) Di-tert-butyl {2-[(4-methoxy-3,5-dimethylpyridin-2-yl)methyl]-8-pyrimidin-5-yl-2,7-dihydro-6-thia-1,2,3,5-tetraazabenzo[cd]azulen-4-yl}imidodicarbonate

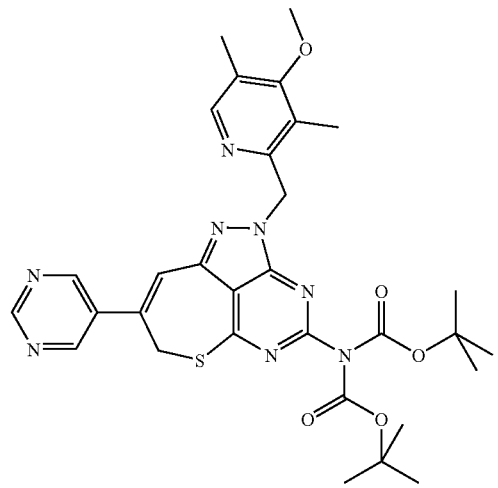

4-[Bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl trifluoromethanesulfonate (50 mg) was dissolved in 1,4-dioxane (4 ml). Pyrimidine-5-boronic acid (13 mg), a 2 N sodium carbonate solution (2 ml) and bis(triphenylphosphine)palladium (II) dichloride (5 mg) were added and the mixture was stirred at 40° C. for two hours. Water was placed into the reaction solution, followed by extraction with ethyl acetate. The resulting organic layer was sequentially washed with water and brine and dried over anhydrous sodium sulfate. The solvent was evaporated, and the resulting residue was purified by silica gel column chromatography (chloroform-methanol) to obtain the title compound as an oil (45 mg).

$^1$H-NMR (CDCl$_3$) δ: 1.45 (9H, s), 1.56 (9H, s), 2.22 (3H, s), 2.32 (3H, s), 3.75 (3H, s), 4.21 (2H, s), 5.73 (2H, s), 7.26 (1H, s), 8.15 (1H, s), 8.90 (2H, s), 9.21 (1H, s).

ESI-MS m/z: 633 (M+H)$^+$.

2) 2-[(4-Methoxy-3,5-dimethylpyridin-2-yl)methyl]-
8-pyrimidin-5-yl-2,7-dihydro-6-thia-1,2,3,5-tetraaza-
benzo[cd]azulen-4-amine

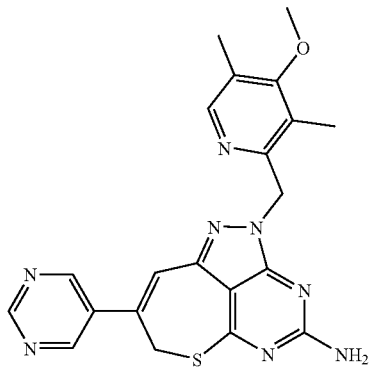

The title compound was obtained as a solid (8 mg, 26%) by synthesis by the same method as in Example 2 using di-tert-butyl {2-[(4-methoxy-3,5-dimethylpyridin-2-yl)methyl]-8-pyrimidin-5-yl-2,7-dihydro-6-thia-1,2,3,5-tetraazabenzo[cd]azulen-4-yl}imidodicarbonate (45 mg).

¹H-NMR (DMSO-D₆) δ: 2.18 (3H, s), 2.25 (3H, s), 3.73 (3H, s), 4.32 (2H, s), 5.48 (2H, s), 7.01 (2H, brs), 7.28 (1H, s), 8.08 (1H, s), 9.11 (2H, s), 9.14 (1H, s).
ESI-MS m/z: 433 (M+H)⁺.

Example 223

1) Di-tert-butyl {2-[(4-methoxy-3,5-dimethylpyridin-2-yl)methyl]-8-pyridin-3-yl-2,7-dihydro-6-thia-1,2,3,5-tetraazabenzo[cd]azulen-4-yl}imidodicarbonate

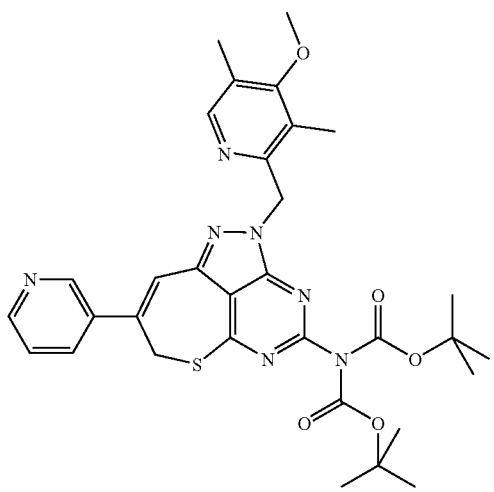

The title compound was obtained as a solid (48 mg, quant.) by synthesis by the same method as in Example 222 using 4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl trifluoromethanesulfonate (50 mg) and pyridine-3-boronic acid neopentyl glycol ester (21 mg).

¹H-NMR (CDCl₃) δ: 1.45 (18H, s), 2.22 (3H, s), 2.31 (3H, s), 3.75 (3H, s), 4.21 (2H, s), 5.72 (2H, s), 7.21 (1H, s), 7.65-7.81 (2H, m), 8.16 (1H, s), 8.60 (1H, dd, J=4.58, 1.38 Hz), 8.79 (1H, d, J=1.83 Hz).

2) 2-[(4-Methoxy-3,5-dimethylpyridin-2-yl)methyl]-
8-pyridin-3-yl-2,7-dihydro-6-thia-1,2,3,5-tetraaza-
benzo[cd]azulen-4-amine

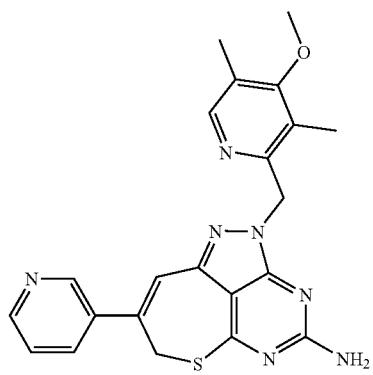

The title compound was obtained as a solid (12 mg, 36%) by synthesis by the same method as in Example 2 using di-tert-butyl {2-[(4-methoxy-3,5-dimethylpyridin-2-yl)methyl]-8-pyridin-3-yl-2,7-dihydro-6-thia-1,2,3,5-tetraazabenzo[cd]azulen-4-yl}imidodicarbonate (49 mg).

¹H-NMR (DMSO-D₆) δ: 2.18 (3H, s), 2.25 (3H, s), 3.73 (3H, s), 4.29 (2H, s), 5.47 (2H, s), 6.98 (2H, brs), 7.13 (1H, s), 7.43 (1H, dd, J=8.02, 4.81 Hz), 8.04-8.08 (2H, m), 8.54 (1H, dd, J=4.81, 1.60 Hz), 8.86 (1H, d, J=2.29 Hz).
ESI-MS m/z: 432 (M+H)⁺.

Example 224

1) Di-tert-butyl {2-[(4-methoxy-3,5-dimethylpyridin-2-yl)methyl]-8-phenyl-2,7-dihydro-6-thia-1,2,3,5-tetraazabenzo[cd]azulen-4-yl}imidodicarbonate

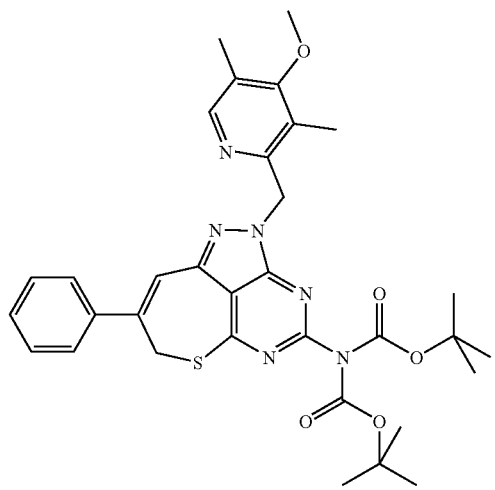

The title compound was obtained as a solid (32 mg, 71%) by synthesis by the same method as in Example 222 using 4-[bis(tert-butoxycarbonyl)amino]-2-[(4-methoxy-3,5-dimethylpyridin-2-yl)methyl]-2,7-dihydro-6-thia-1,2,3,5-tetraazabenzo[cd]azulen-8-yl trifluoromethanesulfonate (50 mg) and phenylboronic acid (13 mg).

$^1$H-NMR (CDCl$_3$) δ: 1.45 (18H, s), 2.22 (3H, s), 2.30 (3H, s), 3.74 (3H, s), 4.22 (2H, s), 5.71 (2H, s), 7.17 (1H, s), 7.35-7.52 (5H, m), 8.17 (1H, s).

ESI-MS m/z: 631 (M+H)$^+$.

2) 2-[(4-Methoxy-3,5-dimethylpyridin-2-yl)methyl]-8-phenyl-2,7-dihydro-6-thia-1,2,3,5-tetraazabenzo[cd]azulen-4-amine

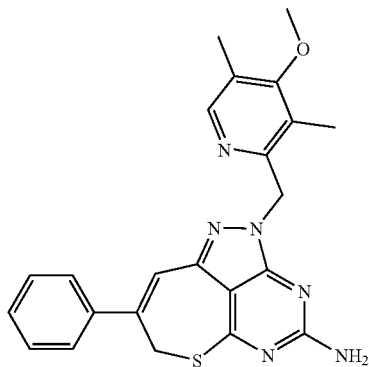

The title compound was obtained as a solid (12 mg, 55%) by synthesis by the same method as in Example 2 using di-tert-butyl {2-[(4-methoxy-3,5-dimethylpyridin-2-yl)methyl]-8-phenyl-2,7-dihydro-6-thia-1,2,3,5-tetraazabenzo[cd]azulen-4-yl}imidodicarbonate (32 mg).

$^1$H-NMR (DMSO-D$_6$) δ: 2.18 (3H, s), 2.25 (3H, s), 3.73 (3H, s), 4.26 (2H, s), 5.46 (2H, s), 6.96 (2H, brs), 7.00 (1H, s), 7.34-7.37 (1H, m), 7.40-7.44 (2H, m), 7.62-7.65 (2H, m), 8.08 (1H, s).

ESI-MS m/z: 431 (M+H)$^+$.

Reference Example 1

1) 4-Ethyl-2,3,5-trimethylpyridine 1-oxide

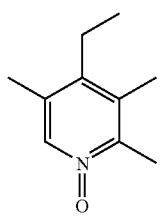

A mixture composed of 4-bromo-2,3,5-trimethylpyridine 1-oxide (5.76 g), tetrahydrofuran (60 mL), a 15% solution of triethylaluminum in toluene (40 mL) and tetrakis(triphenylphosphine)palladium (0) (1.54 g) was heated under reflux for six hours. After leaving to cool to room temperature, toluene (60 mL), methanol (12 mL) and subsequently a saturated ammonium chloride solution (18 mL) were added, and the mixture was heated under reflux for one hour. After leaving to cool to room temperature, the insoluble matter was separated off by filtration, and the filtrate was dried over anhydrous magnesium sulfate. The solvent was evaporated under reduced pressure, and the resulting residue was purified by silica gel column chromatography (chloroform-methanol) to obtain the title compound (3.84 g, 87%) as an oil.

$^1$H-NMR (CDCl$_3$) δ: 1.10 (3H, t, J=7.6 Hz), 2.22 (3H, s), 2.27 (3H, s), 2.52 (3H, s), 2.62 (2H, q, J=7.6 Hz), 8.01 (1H, s).

ESI-MS m/z: 166 (M+H)$^+$.

2) (4-Ethyl-3,5-dimethylpyridin-2-yl)methyl acetate

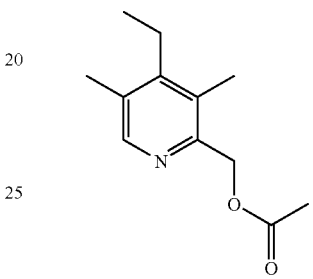

A mixture composed of the above 4-ethyl-2,3,5-trimethylpyridine 1-oxide (3.84 g) and acetic anhydride (50 mL) was heated under reflux for 30 minutes. After leaving to cool to room temperature, the reaction solution was concentrated under reduced pressure. The residue was dissolved in chloroform and then washed with a saturated sodium bicarbonate solution. The organic layer was dried over anhydrous magnesium sulfate, and then the solvent was evaporated under reduced pressure. The resulting residue was purified by silica gel column chromatography (ethyl acetate-hexane) to obtain the title compound (3.64 g, 76%) as an oil.

$^1$H-NMR (CDCl$_3$) δ: 1.12 (3H, t, J=7.6 Hz), 2.12 (3H, s), 2.29 (3H, s), 2.29 (3H, s), 2.68 (2H, q, J=7.6 Hz), 5.22 (2H, s), 8.21 (1H, s).

ESI-MS m/z: 208 (M+H)$^+$.

3) 2-Chloromethyl-4-ethyl-3,5-dimethylpyridine hydrochloride

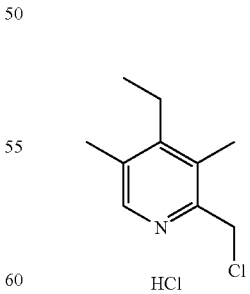

A mixture composed of the above (4-ethyl-3,5-dimethylpyridin-2-yl)methyl acetate (415 mg), methanol (5 mL) and potassium carbonate (553 mg) was stirred at 50° C. for 30 minutes. After leaving to cool to room temperature, the reaction solution was concentrated under reduced pressure. The residue was dissolved in chloroform and then washed with water. The organic layer was dried over anhydrous magnesium sulfate, and then the solvent was evaporated under reduced pressure. The resulting residue was dissolved in chloroform. Thionyl chloride (1 mL) was added under ice-cooling, and the mixture was stirred at room temperature for two hours. The solvent was evaporated under reduced pressure, and the residue was washed with toluene by decantation to obtain the title compound (299 mg, 68%) as a solid.

$^1$H-NMR (CDCl$_3$) δ: 1.23 (3H, t, J=7.7 Hz), 2.50 (3H, s), 2.55 (3H, s), 2.90 (2H, q, J=7.7 Hz), 5.16 (2H, s), 8.34 (1H, s).

ESI-MS m/z: 184 (M+H)$^+$.

Reference Example 2

1) 3-Chloro-2,5-dimethylpyridine 1-oxide

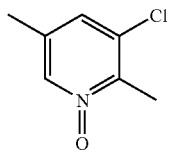

3-Chloro-2,5-dimethylpyridine (1.10 g) was dissolved in dichloromethane (30 mL). m-Chloroperbenzoic acid (1.61 g) was added with stirring under ice-cooling, and the mixture was stirred at room temperature overnight. The reaction solution was washed with 1 N sodium hydroxide, and the organic layer dried over anhydrous magnesium sulfate. The solvent was evaporated under reduced pressure to obtain the title compound (1.21 g, 99%) as a solid.

$^1$H-NMR (CDCl$_3$) δ: 2.27 (3H, s), 2.59 (3H, s), 7.13 (1H, s), 8.07 (1H, s).

ESI-MS m/z: 158 (M+H)$^+$.

2) 3-Chloro-2,5-dimethyl-4-nitropyridine 1-oxide

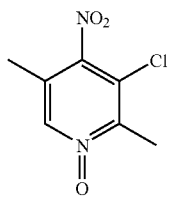

The above 3-chloro-2,5-dimethylpyridine 1-oxide (1.20 g) was dissolved in concentrated sulfuric acid (6 mL), and a mixture of fuming nitric acid (9.5 mL) and fuming sulfuric acid (5.5 mL) was added dropwise over 25 minutes. After stirring in that state for 30 minutes, the mixture was stirred at 90° C. for two hours. The reaction solution was left to cool, and then introduced into ice water and neutralized with ammonium carbonate with stirring at room temperature. The insoluble matter was separated off by filtration, followed by extraction with chloroform. The organic layer was dried over anhydrous magnesium sulfate. The solvent was evaporated under reduced pressure, and the residue was purified by silica gel column chromatography (chloroform-methanol) to obtain the title compound (1.11 g, 72%) as a solid.

$^1$H-NMR (CDCl$_3$) δ: 2.29 (3H, s), 2.63 (3H, s), 8.13 (1H, s).

ESI-MS m/z: 203 (M+H)$^+$.

3) 3,4-Dichloro-2,5-dimethylpyridine 1-oxide

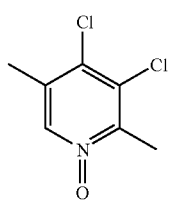

The above 3-chloro-2,5-dimethyl-4-nitropyridine 1-oxide (405 mg) was dissolved in dichloromethane (5 mL), and phosphorus oxychloride (915 μL) was added with stirring under ice-cooling. After stirring at room temperature overnight, the reaction solution was introduced into ice water and neutralized with 5 N sodium hydroxide and a saturated sodium bicarbonate solution with stirring under ice-cooling. The mixture was extracted with chloroform, and the organic layer was dried over anhydrous magnesium sulfate. The solvent was evaporated under reduced pressure to obtain the title compound (387 mg, quant.) as a solid.

$^1$H-NMR (CDCl$_3$) δ: 2.34 (3H, s), 2.66 (3H, s), 8.12 (1H, s).

ESI-MS m/z: 192 (M+H)$^+$.

4) (3,4-Dichloro-5-methylpyridin-2-yl)methyl acetate

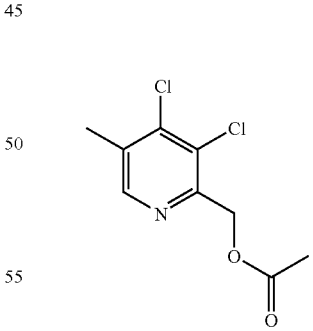

The title compound (156 mg, 33%) was obtained as an oil by the same method as in Reference Example 1-2) using the above 3,4-dichloro-2,5-dimethylpyridine 1-oxide (384 mg).

$^1$H-NMR (CDCl$_3$) δ: 2.16 (3H, s), 2.40 (3H, s), 5.32 (2H, s), 8.33 (1H, s).

ESI-MS m/z: 234 (M+H)$^+$.

5) 2-Chloromethyl-3,4-dichloro-5-methylpyridine hydrochloride

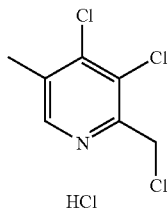

The title compound (141 mg, 89%) was obtained as a solid by the same method as in Reference Example 1-3) using the above (3,4-dichloro-5-methylpyridin-2-yl)methyl acetate (150 mg).
$^1$H-NMR (CDCl$_3$) δ: 2.60 (3H, s), 5.13 (2H, s), 8.56 (1H, s).
ESI-MS m/z: 210 (M+H)$^+$.

Reference Example 3

1) 3-Chloro-4-methoxy-2,5-dimethylpyridine 1-oxide

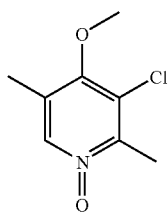

3-Chloro-2,5-dimethyl-4-nitropyridine 1-oxide obtained in Reference Example 2-2) (700 mg) was added to a 0.59 M solution of sodium methoxide in methanol, and the mixture was stirred in an argon atmosphere at room temperature for 18 hours. The reaction solution was concentrated and a saturated ammonium chloride solution was added, followed by extraction with chloroform. The organic layer was dried over anhydrous magnesium sulfate, and then the solvent was evaporated under reduced pressure to obtain the title compound (625 mg, 96%) as a solid.
$^1$H-NMR (CDCl$_3$) δ: 2.24 (3H, s), 2.62 (3H, s), 3.87 (3H, s), 8.07 (1H, s).
ESI-MS m/z: 188 (M+H)$^+$.

2) (3-Chloro-4-methoxy-5-methylpyridin-2-yl)methyl acetate

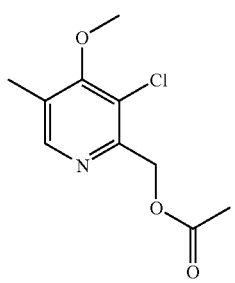

The title compound (460 mg, 61%) was obtained as an oil by the same method as in Reference Example 1-2) using the above 3-chloro-4-methoxy-2,5-dimethylpyridine 1-oxide (620 mg).
$^1$H-NMR (CDCl$_3$) δ: 2.16 (3H, s), 2.29 (3H, s), 3.92 (3H, s), 5.30 (2H, s), 8.29 (1H, s).
ESI-MS m/z: 230 (M+H)$^+$.

3) 2-Chloromethyl-3-chloro-4-methoxy-5-methylpyridine hydrochloride

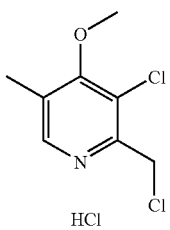

The title compound (118 mg, 79%) was obtained as a solid by the same method as in Reference Example 1-3) using the above (3-chloro-4-methoxy-5-methylpyridin-2-yl)methyl acetate (450 mg).
$^1$H-NMR (CDCl$_3$) δ: 2.45 (3H, s), 4.29 (3H, s), 5.15 (2H, s), 8.43 (1H, s).
ESI-MS m/z: 206 (M+H)$^+$.

Reference Example 4

1) 5-Chloro-2,3-dimethylpyridine 1-oxide

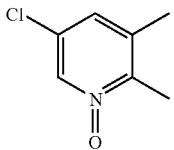

The title compound (1.92 g, quant.) was obtained as a solid by the same method as in Reference Example 2-1) using 5-chloro-2,3-dimethylpyridine (1.72 g).
$^1$H-NMR (CDCl$_3$) δ: 2.34 (3H, s), 2.46 (3H, s), 7.08 (1H, s), 8.20 (1H, s).
ESI-MS m/z: 158 (M+H)$^+$.

2) 5-Chloro-2,3-dimethyl-4-nitropyridine 1-oxide

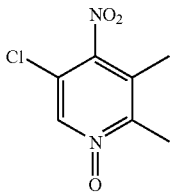

The title compound (1.94 g, 79%) was obtained as a solid by the same method as in Reference Example 2-2) using the above 5-chloro-2,3-dimethylpyridine 1-oxide (1.90 g).

$^1$H-NMR (CDCl$_3$) δ: 2.33 (3H, s), 2.51 (3H, s), 8.29 (1H, s).

ESI-MS m/z: 203 (M+H)$^+$.

3) 5-Chloro-4-methoxy-2,3-dimethylpyridine 1-oxide

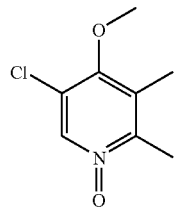

The title compound (405 mg, 96%) was obtained as a solid by the same method as in Reference Example 3-1) using the above 5-chloro-2,3-dimethyl-4-nitropyridine 1-oxide (455 mg).

$^1$H-NMR (CDCl$_3$) δ: 2.28 (3H, s), 2.48 (3H, s), 3.86 (3H, s), 8.24 (1H, s).

ESI-MS m/z: 188 (M+H)$^+$.

4)
(5-Chloro-4-methoxy-3-methylpyridin-2-yl)methyl acetate

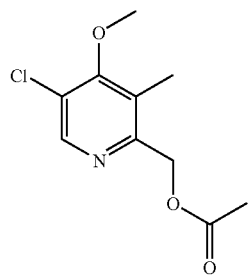

The title compound (346 mg, 71%) was obtained as an oil by the same method as in Reference Example 1-2) using the above 5-chloro-4-methoxy-2,3-dimethylpyridine 1-oxide (400 mg).

$^1$H-NMR (CDCl$_3$) δ: 2.13 (3H, s), 2.29 (3H, s), 3.92 (3H, s), 5.19 (2H, s), 8.39 (1H, s).

ESI-MS m/z: 230 (M+H)$^+$.

5)
2-Chloromethyl-5-chloro-4-methoxy-3-methylpyridine hydrochloride

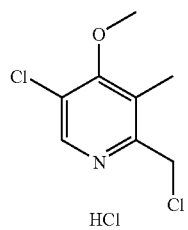

The title compound (326 mg, 91%) was obtained as a solid by the same method as in Reference Example 1-3) using the above (5-chloro-4-methoxy-3-methylpyridin-2-yl)methyl acetate (340 mg).

$^1$H-NMR (CDCl$_3$) δ: 2.47 (3H, s), 4.32 (3H, s), 5.09 (2H, s), 8.54 (1H, s).

ESI-MS m/z: 206 (M+H)$^+$.

Test Example 1

Cell Growth Inhibition Assay

A cell growth inhibition assay was performed using two types of cells (human breast cancer cell line SK-BR-3 and human lung cancer cell line NCI-H460).

Cells of each type were suspended in a medium and seeded into a 96-well multi-well plate at 500 cells/150 μl/well. The test compound was dissolved in DMSO, and this was diluted with medium to prepare a sample solution (DMSO concentration: 0.5% or less). On the day following the seeding, 50 μL of DMSO-containing medium to which the test compound was not added (hereinafter called DMSO diluted solution; DMSO concentration: 0.5% or less) or the sample solution was added to the cells. An MTT assay was performed immediately after and 72 hours after adding the sample solution or the DMSO diluted solution to the cells. The MTT assay was performed as follows.

5 mg/mL of an MTT (3-(4,5-dimethylthiazol-2-yl)-2,5-diphenyltetrazolium bromide) solution was added at 20 μL per well. Thereafter, the plate was incubated at 37° C. in 5% CO$_2$ for four hours. The plate was centrifuged at 1200 rpm for five minutes, and then the culture supernatant was removed by suction using a dispenser. DMSO was added at 150 μL per well, and the generated formazan was dissolved. The plate was stirred using a plate mixer to uniformly color the respective wells. The absorbance of each well was measured using a plate reader at an OD of 540 nm with a reference of 660 nm.

T/C (%) for each concentration was determined by the following calculation formula and a dose-response curve was drawn to calculate the 50% growth inhibitory concentration (GI$_{50}$ value), based on the assumption that the OD value measured immediately after adding the sample solution was S, the OD value measured 72 hours after adding the sample solution was T, and the OD value measured 72 hours after adding the DMSO diluted solution was C.

$$T/C(\%) = (T-S)/(C-S) \times 100$$

The results are shown below.

TABLE 1

| | GI$_{50}$ value (nM) | |
|---|---|---|
| | SK-BR-3 | NCI-H460 |
| Compound of Example 2 | 148 | 224 |
| Compound of Example 4 | 44 | 69 |
| Compound of Example 9 | 137 | 159 |
| Compound of Example 12 | 150 | 460 |
| Compound of Example 36 | 52 | 86 |
| Compound of Example 37 | 307 | 411 |
| Compound of Example 43 | 91 | 253 |
| Compound of Example 51 | 58 | 150 |
| Compound of Example 67 | 130 | 300 |
| Compound of Example 99 | 320 | 650 |
| Compound of Example 111 | 49 | 94 |
| Compound of Example 115 | 77 | 194 |
| Compound of Example 116 | 37 | 89 |
| Compound of Example 118 | 33 | 510 |
| Compound of Example 123 | 38 | 71 |
| Compound of Example 137 | 67 | 200 |
| Compound of Example 141 | 41 | 260 |
| Compound of Example 145 | 19 | 45 |
| Compound of Example 151 | 48 | 110 |
| Compound of Example 153 | 2600 | 5900 |
| Compound of Example 164 | 410 | 760 |
| Compound of Example 165 | 6800 | 16000 |
| Compound of Example 167 | 3300 | 7300 |
| Compound of Example 172 | Not determined | Not determined |
| Compound of Example 174 | Not determined | Not determined |
| Compound of Example 175 | Not determined | Not determined |
| Compound of Example 176 | Not determined | Not determined |
| Compound of Example 181 | 45 | 76 |
| Compound of Example 191 | 20 | 57 |
| Compound of Example 194 | 17 | 37 |
| Compound of Example 218 | 75 | 160 |
| Compound of Example 223 | 140 | 250 |

Test Example 2

Hsp90 ATPase Assay

An Hsp90 ATPase assay was performed using a recombinant yeast Hsp90 protein (hereinafter called rHsp90). Yeast Hsp90 DNA was cloned from a yeast genomic DNA library according to a conventional method. The cloned yeast Hsp90 DNA was incorporated into a plasmid for expression in *Escherichia coli*, and the plasmid was expressed in *Escherichia coli* to obtain rHsp90.

The test compound was dissolved in DMSO to 10 mM. The dissolved solution was diluted with DMSO to eight concentrations ranging in three-fold dilutions from 4 mM. Each diluted solution was further 10-fold diluted with an assay buffer (100 mM Tris, pH 7.4, 20 mM KCl, 6 mM MgCl$_2$) (concentration of each test compound solution: 400 µM, 133 µM, 44.4 µM, 14.8 µM, 4.94 µM, 1.65 µM, 0.549 µM, 0.183 µM; DMSO concentration: 10%).

rHsp90 was dissolved in a TE buffer (20 mM Tris, pH 7.4, 1 mM EDTA) to a concentration of 2.531 mg/mL. The dissolved solution was diluted with assay buffer to 125 µg/mL and dispensed to a 96-well assay plate at 40 µL per well (final concentration: 100 µg/mL).

The test compound solution was dispensed at 5 µL per well, and then the solutions in the respective wells were mixed using a plate mixer. 100 mM ATP (Sigma, Catalog No. A-7699) was diluted with assay buffer to 1 mM and dispensed at 5 µL per well (final concentration: 100 µM). The solutions in the respective wells were mixed using a plate mixer, and then the assay plate was allowed to stand in an incubator set at 37° C. for two hours.

BIOMOL GREEN Reagent (BIOMOL, Catalog No. AK-111) was dispensed at 100 µL per well, and the reaction was terminated. The solutions in the respective wells were mixed by pipetting (three times), and then 34% sodium citrate was dispensed at 10 µL per well. The solutions in the respective wells were mixed by pipetting (three times), and then the assay plate was left to stand at room temperature for 10 minutes. The absorbance at 630 nm of each well was measured with a microplate reader.

The ratio of the absorbance of the test compound-added group to the absorbance of the test compound-free group (T/C value) was determined by the following calculation formula, based on the assumption that the absorbance of the well to which the test compound and rHsp90 were added was A, the absorbance of the well to which only rHsp90 was added was B, and the absorbance of the well to which neither the test compound nor rHsp90 was added was C.

$$T/C = (A-C)/(B-C)$$

Further, the concentration for 50% inhibition of ATP activity (IC$_{50}$ value) was calculated using GraphPad Prism 4 (GraphPad Software, Inc.). The results are shown below.

TABLE 2

| | IC$_{50}$ value (µM) |
|---|---|
| Compound of Example 2 | 1.0 |
| Compound of Example 4 | 0.87 |
| Compound of Example 9 | 1.2 |
| Compound of Example 12 | 2.2 |
| Compound of Example 36 | 0.97 |
| Compound of Example 37 | 3.3 |
| Compound of Example 43 | 1.4 |
| Compound of Example 51 | 2.4 |
| Compound of Example 67 | 1.2 |
| Compound of Example 99 | 0.82 |
| Compound of Example 111 | 0.81 |
| Compound of Example 115 | 0.74 |
| Compound of Example 116 | 1.1 |
| Compound of Example 118 | 0.61 |
| Compound of Example 123 | 0.63 |
| Compound of Example 137 | 0.95 |
| Compound of Example 141 | 1.0 |
| Compound of Example 145 | 0.89 |
| Compound of Example 151 | 0.89 |
| Compound of Example 153 | 1.9 |
| Compound of Example 164 | 0.97 |
| Compound of Example 165 | 2.0 |
| Compound of Example 167 | 5.4 |
| Compound of Example 172 | 1.5 |
| Compound of Example 174 | 3.4 |
| Compound of Example 175 | 1.2 |
| Compound of Example 176 | 0.89 |
| Compound of Example 181 | 3.1 |
| Compound of Example 191 | 1.5 |
| Compound of Example 194 | 1.8 |
| Compound of Example 214 | 0.76 |
| Compound of Example 218 | 2.3 |
| Compound of Example 223 | 1.1 |

The invention claimed is:
1. A compound represented by the formula (1) or a salt of the compound:

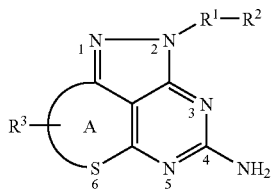

wherein in the formula (1),
R¹ represents a methylene group, an ethylene group or a propenylene group which may be substituted with 1 or 2 alkyl groups having 1 to 8 carbon atoms,
R² represents an phenyl group which may have a substituent(s) selected from the group consisting of
an alkyl group having 1 to 8 carbon atoms which may have a substituent(s) selected from c) to j) and l) to q) in the later-described Substituent Group, or
a pyridyl, quinolyl, or benzodioxin group which may have a substituent(s) selected from the group consisting of
an alkyl group having 1 to 8 carbon atoms which may have a substituent(s) selected from c) to j) and l) to q) in the later-described Substituent Group,
c), d), and f) to j) in the later described Substituent Group,
Ring A represents a 6- or 7-membered ring (wherein the ring constituent atoms of Ring A other than the sulfur atom at the 6-position are carbon atoms), and
R³ represents a hydrogen atom or 1 to 3 same or different substituents with which Ring A is substituted,
wherein
the same or different substituents
each independently represents a substituent selected from the group consisting of
a halogen atom,
a hydroxy group,
a carboxy group,
an alkyl group having 1 to 8 carbon atoms which may have a substituent(s) selected from c) to j) and l) to q) in the later-described Substituent Group,
an alkynyl group having 2 to 8 carbon atoms,
an alkoxy group having 1 to 8 carbon atoms,
a carbamoyl group which may have a substituent(s) selected from the group consisting of
an alkyl group having 1 to 8 carbon atoms which may have a substituent(s) selected from c) to j) and l) to q) in the later-described Substituent Group,
an alkenyl group having 2 to 8 carbon atoms,
an alkynyl group having 2 to 8 carbon atoms,
a phenyl group,
a heterocyclic group which may have a substituent(s) selected from the group consisting of
an alkyl group having 1 to 8 carbon atoms which may have a substituent(s) selected from c) to j) and l) to q) in the later-described Substituent Group,
c), d), f) to j), and l) to q) in the later described Substituent Group,
a carbamoyloxy group which may have a substituent(s) selected from the group consisting of
an alkyl group having 1 to 8 carbon atoms which may have a substituent(s) selected from c) to j) and l) to q) in the later-described Substituent Group,
an amino group which may have a substituent(s) selected from the group consisting of
an alkyl group having 1 to 8 carbon atoms which may have a substituent(s) selected from c) to j) and l) to q) in the later-described Substituent Groups,
an alkanoyl group having 1 to 8 carbon atoms,
a heterocyclic group which may have a substituent(s) selected from an alkyl group having 1 to 8 carbon atoms which may have a substituent(s) selected from c) to j) and l) to q) in the later-described Substituent Group,
an alkylsulfonyl group having 1 to 8 carbon atoms,
an arylsulfonyl group,
a heteroarylsulfonyl group, and
a carbamoyl group,
a cyano group,
a phenyl group,
a heterocyclic group which may have a substituent(s) selected from the group consisting of
a carbamoyl group,
an alkyl group having 1 to 8 carbon atoms which may have a substituent(s) selected from c) to j) and l) to q) in the later-described Substituent Groups,
an amino group which may have a substituent(s) selected from the group consisting of an alkyl group having 1 to 8 carbon atoms which may have a substituent(s) selected from c) to j) and l) to q) in the later-described Substituent Groups,
an alkanoyl group having 1 to 8 carbon atoms, and
a hydroxy group, and
an oxo group and
when there is a plurality of the same or different substituents, any two substituents of the indicated same or different substituents together with the carbon atom(s) on which they are substituted may form a saturated or unsaturated, condensed or spiro 3- to 8-membered ring which is attached to Ring A and which may contain one or more oxygen atoms as a cyclo constituent atom different from a carbon atom,
wherein Substituents Groups a)-q) are:
a) an alkyl group having 1 to 8 carbon atoms,
b) a halogenated alkyl group having from 1 to 8 carbon atoms,
c) a halogen atom,
d) a hydroxy group,
e) an oxo group,
f) a cyano group,
g) a carboxy group,
h) an alkoxy group having 1 to 8 carbon atoms,
i) a halogenated alkoxy group having 1 to 8 carbon atoms,
j) an alkoxycarbonyl group having 1 to 8 carbon atoms,
k) an alkanoyl group having 1 to 8 carbon atoms,
l) an alkanoyloxy group having 1 to 8 carbon atoms, m) an amino group which may be substituted with one or the same or different two alkyl groups having 1 to 8 carbon atoms, n) a carbamoyl group which may be substituted with one or the same or different two alkyl groups having 1 to 8 carbon atoms, o) an alkanoylamino group having from 1 to 8 carbon atoms, p) a phenyl group which may be substituted with one or the same or different 2 or 3 substituents selected from the Substituent Group consisting of a) to d) and f) to o), and q) a saturated or unsaturated 4- to 7-membered monocyclic heterocyclic group which may be substituted with one or the same or different 2 or 3 substituents selected from the Substituent Group consisting of a) to d) and f) to o).

2. The compound according to claim 1 or a salt of the compound, wherein $R^1$ in the formula (1) is a methylene group which may be substituted with 1 or 2 alkyl groups having 1 to 8 carbon atoms.

3. The compound according to claim 1 or a salt of the compound, wherein $R^2$ in the formula (1) is a pyridyl, quinolyl, or benzodioxin group which may have a substituent(s).

4. The compound according to claim 1 or a salt of the compound, wherein $R^2$ in the formula (1) is a pyridyl group which may have a substituent(s).

5. The compound according to claim 1 or a salt of the compound, wherein $R^3$ in the formula (1) is a hydrogen atom or 1 to 3 same or different substituents with which Ring A is substituted, wherein the same or different substituents are each independently a substituent selected from the group consisting of a hydroxy group, a carboxy group, an alkyl group having 1 to 8 carbon atoms which may have a substituent(s), an alkynyl group having 2 to 8 carbon atoms which may have a substituent(s), an alkoxy group having 1 to 8 carbon atoms which may have a substituent(s), a carbamoyl group which may have a substituent(s), a carbamoyloxy group which may have a substituent(s), an amino group which may have a substituent(s), a cyano group, a heterocyclic group which may have a substituent(s), and an oxo group, and when there is a plurality of the same or different substituents, any two substituents of the indicated same or different substituents together with the carbon atom(s) on which they are substituted may form the saturated or unsaturated, condensed or spiro 3- to 8-membered ring which may have a substituent(s).

6. The compound according to claim 1 or a salt of the compound, wherein the formula (1) is the following formula (1a):

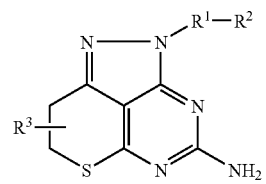

wherein in the formula (1a), $R^1$, $R^2$ and $R^3$ are as defined in claim 1.

7. The compound according to claim 1 or a salt of the compound, wherein the formula (1) is the following formula (1b):

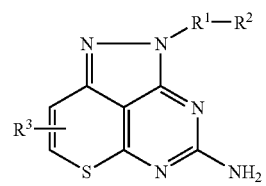

wherein in the formula (1b), $R^1$, $R^2$ and $R^3$ are as defined in claim 1.

8. The compound according to claim 1 or a salt of the compound, wherein the formula (1) is the following formula (1c):

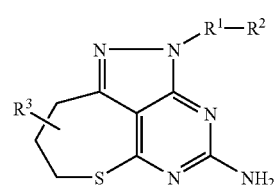

wherein in the formula (1c), $R^1$, $R^2$ and $R^3$ are as defined in claim 1.

9. The compound according to claim 1 or a salt of the compound, wherein the formula (1) is the following formula (1d):

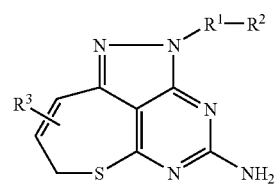

wherein in the formula (1d), $R^1$, $R^2$ and $R^3$ are as defined in claim 1.

10. A compound represented by the formula (2) or a salt of the compound:

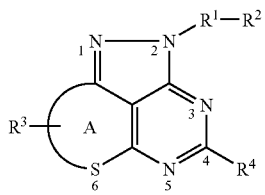

(2)

wherein in the formula (2),
$R^1$ represents a methylene group, an ethylene group or a propenylene group which may be substituted with 1 or 2 alkyl groups having 1 to 8 carbon atoms,
$R^2$ represents an phenyl group which may have a substituent(s) selected from the group consisting of
    an alkyl group having 1 to 8 carbon atoms which may have a substituent(s) selected from c) to j) and l) to q) in the later-described Substituent Group, or
a pyridyl, quinolyl, or benzodioxin group which may have a substituent(s) selected from the group consisting of
    an alkyl group having 1 to 8 carbon atoms which may have a substituent(s) selected from c) to j) and l) to q) in the later-described Substituent Group,
    c), d), and f) to j) in the later described Substituent Group,
Ring A represents a 6- or 7-membered ring (wherein the ring constituent atoms of Ring A other than the sulfur atom at the 6-position are carbon atoms), and
$R^3$ represents a hydrogen atom or 1 to 3 same or different substituents with which Ring A is substituted,
wherein
the same or different substituents
each independently represents a substituent selected from the group consisting of
a halogen atom,
a hydroxy group,
a carboxy group,
an alkyl group having 1 to 8 carbon atoms which may have a substituent(s) selected from c) to j) and l) to q) in the later-described Substituent Group,
an alkynyl group having 2 to 8 carbon atoms,
an alkoxy group having 1 to 8 carbon atoms,
a carbamoyl group which may have a substituent(s) selected from the group consisting of
    an alkyl group having 1 to 8 carbon atoms which may have a substituent(s) selected from c) to j) and l) to q) in the later-described Substituent Group,
    an alkenyl group having 2 to 8 carbon atoms,
    an alkynyl group having 2 to 8 carbon atoms,
    a phenyl group,
    a heterocyclic group which may have a substituent(s) selected from the group consisting of
        an alkyl group having 1 to 8 carbon atoms which may have a substituent(s) selected from c) to j) and l) to q) in the later-described Substituent Group,
        c), d), f) to j), and l) to q) in the later described Substituent Group,
a carbamoyloxy group which may have a substituent(s) selected from the group consisting of
    an alkyl group having 1 to 8 carbon atoms which may have a substituent(s) selected from c) to j) and l) to q) in the later-described Substituent Group,
an amino group which may have a substituent(s) selected from the group consisting of
    an alkyl group having 1 to 8 carbon atoms which may have a substituent(s) selected from c) to j) and l) to q) in the later-described Substituent Groups,
    an alkanoyl group having 1 to 8 carbon atoms,
    a heterocyclic group which may have a substituent(s) selected from an alkyl group having 1 to 8 carbon atoms which may have a substituent(s) selected from c) to j) and l) to q) in the later-described Substituent Group,
    an alkylsulfonyl group having 1 to 8 carbon atoms,
    an arylsulfonyl group,
    a heteroarylsulfonyl group, and
    a carbamoyl group,
a cyano group,
a phenyl group,
a heterocyclic group which relates to a group derived from a saturated or unsaturated monocyclic heterocyclic compound containing one or more nitrogen atoms and which may have a substituent(s) selected from the group consisting of
    a carbamoyl group,
    an alkyl group having 1 to 8 carbon atoms which may have a substituent(s) selected from c) to j) and l) to q) in the later-described Substituent Groups,
    an amino group which may have a substituent(s) selected from the group consisting of an alkyl group having 1 to 8 carbon atoms which may have a substituent(s) selected from c) to j) and l) to q) in the later-described Substituent Groups,
    an alkanoyl group having 1 to 8 carbon atoms, and
    a hydroxy group, and
an oxo group and
when there is a plurality of the same or different substituents, any two substituents of the indicated same or different substituents together with the carbon atom(s) on which they are substituted may form a saturated or unsaturated, condensed or spiro 3- to 8-membered ring which is attached to Ring A and which may contain one or more oxygen atoms as a cyclo constituent atom different from a carbon atom, and
$R^4$ represents an amino group having a protecting group selected from the group consisting of an alkanoylamino group 1 to 6 carbon atoms, a benzyloxycarbonyl group, and a methoxybenzyl group,
wherein Substituents Groups a)-q) are:
a) an alkyl group having 1 to 8 carbon atoms,
b) a halogenated alkyl group having from 1 to 8 carbon atoms,
c) a halogen atom,
d) a hydroxy group,
e) an oxo group, f) a cyano group,
g) a carboxy group,
h) an alkoxy group having 1 to 8 carbon atoms,
i) a halogenated alkoxy group having 1 to 8 carbon atoms,
j) an alkoxycarbonyl group having 1 to 8 carbon atoms,
k) an alkanoyl group having 1 to 8 carbon atoms,
l) an alkanoyloxy group having 1 to 8 carbon atoms,
m) an amino group which may be substituted with one or the same or different two alkyl groups having 1 to 8 carbon atoms,
n) a carbamoyl group which may be substituted with one or the same or different two alkyl groups having 1 to 8 carbon atoms,
o) an alkanoylamino group having from 1 to 8 carbon atoms,
p) a phenyl group which may be substituted with one or the same or different 2 or 3 substituents selected from the Substituent Group consisting of a) to d) and f) to o), and
q) a saturated or unsaturated 4- to 7-membered monocyclic heterocyclic group which may be substituted with one or the same or different 2 or 3 substituents selected from the Substituent Group consisting of a) to d) and f) to o).

11. A compound represented by the formula (3) or a salt of the compound:

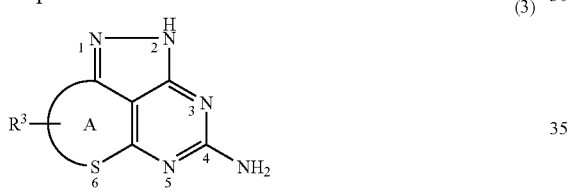

(3)

wherein in the formula (3),
Ring A represents a 5- to 8-membered ring (wherein the ring constituent atoms of Ring A other than the sulfur atom at the 6-position are carbon atoms), and
$R^3$ represents a hydrogen atom or 1 to 3 same or different substituents with which Ring A is substituted,
wherein
the same or different substituents
each independently represents a substituent selected from the group consisting of
a halogen atom,
a hydroxy group,
a carboxy group,
an alkyl group having 1 to 8 carbon atoms which may have a substituent(s) selected from c) to j) and l) to q) in the later-described Substituent Group,
an alkynyl group having 2 to 8 carbon atoms,
an alkoxy group having 1 to 8 carbon atoms,
a carbamoyl group which may have a substituent(s) selected from the group consisting of
an alkyl group having 1 to 8 carbon atoms which may have a substituent(s) selected from c) to j) and l) to q) in the later-described Substituent Group,
an alkenyl group having 2 to 8 carbon atoms,
an alkynyl group having 2 to 8 carbon atoms,
a phenyl group,
a heterocyclic group which may have a substituent(s) selected from the group consisting of
an alkyl group having 1 to 8 carbon atoms which may have a substituent(s) selected from c) to j) and l) to q) in the later-described Substituent Group,
c), d), f) to j), and l) to q) in the later described Substituent Group,
a carbamoyloxy group which may have a substituent(s) selected from the group consisting of
an alkyl group having 1 to 8 carbon atoms which may have a substituent(s) selected from c) to j) and l) to q) in the later-described Substituent Group,
an amino group which may have a substituent(s) selected from the group consisting of
an alkyl group having 1 to 8 carbon atoms which may have a substituent(s) selected from c) to j) and l) to q) in the later-described Substituent Groups,
an alkanoyl group having 1 to 8 carbon atoms,
a heterocyclic group which may have a substituent(s) selected from an alkyl group having 1 to 8 carbon atoms which may have a substituent(s) selected from c) to j) and l) to q) in the later-described Substituent Group,
an alkylsulfonyl group having 1 to 8 carbon atoms,
an arylsulfonyl group,
a heteroarylsulfonyl group, and
a carbamoyl group,
a cyano group,
a phenyl group,
a heterocyclic group which relates to a group derived from a saturated or unsaturated monocyclic heterocyclic compound containing one or more nitrogen atoms and which may have a substituent(s) selected from the group consisting of
a carbamoyl group,
an alkyl group having 1 to 8 carbon atoms which may have a substituent(s) selected from c) to j) and l) to q) in the later-described Substituent Groups,
an amino group which may have a substituent(s) selected from the group consisting of an alkyl group having 1 to 8 carbon atoms which may have a substituent(s) selected from c) to j) and l) to q) in the later-described Substituent Groups,
an alkanoyl group having 1 to 8 carbon atoms, and
a hydroxy group, and
an oxo group and
when there is a plurality of the same or different substituents, any two substituents of the indicated same or different substituents together with the carbon atom(s) on which they are substituted may form a saturated or unsaturated, condensed or spiro 3- to 8-membered ring which is attached to Ring A and which may contain one or more oxygen atoms as a cyclo constituent atom different from a carbon atom,
wherein Substituents Groups a)-q) are:
a) an alkyl group having 1 to 8 carbon atoms,
b) a halogenated alkyl group having from 1 to 8 carbon atoms,
c) a halogen atom,
d) a hydroxy group,
e) an oxo group,
f) a cyano group,
g) a carboxy group,
h) an alkoxy group having 1 to 8 carbon atoms, i) a halogenated alkoxy group having 1 to 8 carbon atoms, j) an alkoxycarbonyl group having 1 to 8 carbon atoms, k) an alkanoyl group having 1 to 8 carbon atoms, l) an alkanoyloxy group having 1 to 8 carbon atoms, m) an amino group which may be substituted with one or the same or different two alkyl groups having 1 to 8 carbon atoms, n) a carbamoyl group which may be substituted with one or the same or different two alkyl groups having 1 to 8 carbon atoms, o) an alkanoylamino group having from 1 to 8 carbon atoms, p) a phenyl group which may be substituted with one or the same or different 2 or 3 substituents selected from the Substituent Group consisting of a) to d) and f) to o), and q) a saturated or unsaturated 4- to 7-membered monocyclic heterocyclic group which may be substituted with one or the same or different 2 or 3 substituents selected from the Substituent Group consisting of a) to d) and f) to o).

12. A pharmaceutical composition comprising a pharmaceutically acceptable carrier and a compound according to claim 1 or a salt of the compound.

13. A method for treating cancer treatable by inhibiting HSP90, comprising administering an effective amount of the compound according to claim 1 or a salt of the compound to a subject in need thereof.

14. A method for inhibiting HSP90, comprising administering to a subject in need thereof an amount of a compound of claim 1 or a salt of the compound effective to inhibit HSP90.

15. A method for inhibiting the ATPase activity of HSP90, comprising administering to a subject in need thereof an amount of a compound of claim 1 or a salt of the compound effective to inhibit the ATPase activity of HSP90.

16. A method for inhibiting binding of HSP90 to ATP, comprising administering to a subject in need thereof an amount of a compound of claim 1 or a salt of the compound effective to inhibit binding of HSP90 to ATP.

17. A compound represented by the formula (1d-1y) or a salt of the compound:

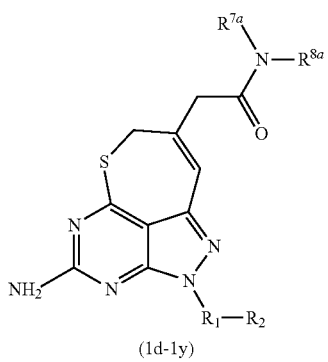

(1d-1y)

wherein $R^1$ represents a methylene group, an ethylene group or a propenylene group which may be substituted with 1 or 2 alkyl groups having 1 to 8 carbon atoms, $R^2$ represents a pyridyl group which may have a substituent(s) selected from the group consisting of an alkyl group having 1 to 8 carbon atoms which may have a substituent(s) selected from c) to j) and l) to q) in the later-described Substituent Group, c), d), and f) to j) in the later-described Substituent Group, and $R^{7a}$ and $R^{8a}$ are independently selected from the group consisting of hydrogen and alkyl, wherein Substituents Groups c), d), f) to j), and l) to q) are:

c) a halogen atom, d) a hydroxy group, f) a cyano group, g) a carboxy group, h) an alkoxy group having 1 to 8 carbon atoms, i) a halogenated alkoxy group having 1 to 8 carbon atoms, j) an alkoxycarbonyl group having 1 to 8 carbon atoms, l) an alkanoyloxy group having 1 to 8 carbon atoms, m) an amino group which may be substituted with one or the same or different two alkyl groups having 1 to 8 carbon atoms, n) a carbamoyl group which may be substituted with one or the same or different two alkyl groups having 1 to 8 carbon atoms, o) an alkanoylamino group having from 1 to 8 carbon atoms, p) a phenyl group which may be substituted with one or the same or different 2 or 3 substituents selected from the Substituent Group consisting of a) to d) and f) to o), and q) a saturated or unsaturated 4- to 7-membered monocyclic heterocyclic group which may be substituted with one or the same or different 2 or 3 substituents selected from the Substituent Group consisting of a) to d) and f) to o).

18. The compound of claim 17, wherein $R^1$ is methylene.

19. The compound of claim 17, wherein alkyl is methyl.

20. The compound of claim 17, wherein $R^{7a}$ is hydrogen and $R^{8a}$ is methyl.

21. The compound of claim 17, wherein $R^1$ is methylene, and $R^{7a}$ and $R^{8a}$ are independently selected from the group consisting of hydrogen and alkyl having 1 to 8 carbon atoms.

22. The compound of claim 21, wherein alkyl is methyl.

23. The compound of claim 21, wherein $R^{7a}$ is hydrogen and $R^{8a}$ is methyl.

24. A pharmaceutical composition comprising a pharmaceutically acceptable carrier and a compound according to claim 17 or a salt of the compound.

25. A method for treating cancer treatable by inhibiting HSP90, comprising administering an effective amount of a compound according to claim 17 or a salt of the compound to a subject in need thereof.

26. A method for inhibiting HSP90, comprising administering to a subject in need thereof an amount of a compound of claim 17 or a salt of the compound effective to inhibit HSP90.

27. A method for inhibiting the ATPase activity of HSP90, comprising administering to a subject in need thereof an amount of a compound of claim 17 or a salt of the compound effective to inhibit the ATPase activity of HSP90.

28. A pharmaceutical composition comprising a pharmaceutically acceptable carrier and a compound according to claim 23 or a salt of the compound.

29. A method for treating cancer treatable by inhibiting HSP90, comprising administering an effective amount of a compound according to claim 23 or a salt of the compound to a subject in need thereof.

30. A method for inhibiting HSP90, comprising administering to a subject in need thereof an amount of a compound of claim 23 or a salt of the compound effective to inhibit HSP90.

31. A method for inhibiting the ATPase activity of HSP90, comprising administering to a subject in need thereof an amount of a compound of claim 23 or a salt of the compound effective to inhibit the ATPase activity of HSP90.

* * * * *